United States Patent
Falotico et al.

(10) Patent No.: US 7,846,940 B2
(45) Date of Patent: Dec. 7, 2010

(54) SOLUTION FORMULATIONS OF SIROLIMUS AND ITS ANALOGS FOR CAD TREATMENT

(75) Inventors: Robert Falotico, Belle Mead, NJ (US); Jonathon Z. Zhao, Belle Mead, NJ (US)

(73) Assignee: Cordis Corporation, Bridgewater, NJ (US)

( * ) Notice: Subject to any disclaimer, the term of this patent is extended or adjusted under 35 U.S.C. 154(b) by 507 days.

(21) Appl. No.: 10/813,965

(22) Filed: Mar. 31, 2004

(65) Prior Publication Data

US 2005/0222191 A1   Oct. 6, 2005

(51) Int. Cl.
A61K 31/44   (2006.01)
(52) U.S. Cl. .................................. 514/291
(58) Field of Classification Search .............. 514/183, 514/291

See application file for complete search history.

(56) References Cited

U.S. PATENT DOCUMENTS

| | | |
|---|---|---|
| 3,576,886 A | 4/1971 | Neuworth |
| 3,862,332 A | 1/1975 | Barnhart et al. |
| 3,929,992 A | 12/1975 | Sehgal et al. |
| 3,959,078 A | 5/1976 | Guire et al. |
| 4,350,160 A | 9/1982 | Kolesov |
| 4,366,819 A | 1/1983 | Kaster |
| 4,368,736 A | 1/1983 | Kaster |
| 4,624,257 A | 11/1986 | Berggren et al. |
| 4,722,906 A | 2/1988 | Guire et al. |
| 4,733,665 A | 3/1988 | Palmaz |
| 4,739,762 A | 4/1988 | Palmaz |
| 4,776,337 A | 10/1988 | Palmaz |
| 4,814,470 A | 3/1989 | Colin et al. |
| 4,857,653 A | 8/1989 | Colin et al. |
| 4,917,090 A | 4/1990 | Berggren et al. |
| 4,917,091 A | 4/1990 | Berggren et al. |
| 4,942,184 A | 7/1990 | Haugwitz et al. |
| 4,984,060 A | 1/1991 | Ohmi et al. |
| 5,059,699 A | 10/1991 | Kingston et al. |
| 5,200,534 A | 4/1993 | Rao |
| 5,202,448 A | 4/1993 | Carver et al. |
| 5,229,172 A | 7/1993 | Cahalan et al. |
| 5,229,529 A | 7/1993 | Veno et al. |
| 5,234,447 A | 8/1993 | Kaster et al. |
| 5,248,796 A | 9/1993 | Chen et al. |
| 5,252,805 A | 10/1993 | Nakata et al. |
| 5,254,580 A | 10/1993 | Chen et al. |
| 5,272,171 A | 12/1993 | Ueda et al. |
| 5,274,137 A | 12/1993 | Nicolaou et al. |
| 5,278,324 A | 1/1994 | Kingston |
| 5,279,949 A | 1/1994 | Nair |
| 5,283,253 A | 2/1994 | Holton et al. |
| 5,294,637 A | 3/1994 | Chen et al. |
| 5,294,997 A | 3/1994 | Ogura et al. |
| 5,300,638 A | 4/1994 | Farina et al. |
| 5,308,641 A | 5/1994 | Cahalan et al. |
| 5,339,906 A | 8/1994 | Fox et al. |
| 5,350,800 A | 9/1994 | Verhoeven |
| 5,350,866 A | 9/1994 | Holton et al. |
| 5,362,831 A | 11/1994 | Mongelli et al. |
| 5,380,751 A | 1/1995 | Chen |
| 5,395,850 A | 3/1995 | Roth |
| 5,411,984 A | 5/1995 | Kingston et al. |
| 5,412,092 A | 5/1995 | Rey et al. |
| 5,415,938 A | 5/1995 | Cahalan et al. |
| 5,422,364 A | 6/1995 | Nicolaou |

(Continued)

FOREIGN PATENT DOCUMENTS

EP   0041795   * 12/1981

(Continued)

OTHER PUBLICATIONS

Ajroldi et al., "Fluoroelastomers-dependence of relaxation phenomena on compositions", *Polymer* 30, 2180 (1989).

(Continued)

*Primary Examiner*—Jennifer M Kim
(74) *Attorney, Agent, or Firm*—Carl Evens

(57) ABSTRACT

Medical devices, and in particular implantable medical devices, may be coated to minimize or substantially eliminate a biological organism's reaction to the introduction of the medical device to the organism. The medical devices may be coated with any number of biocompatible materials. Therapeutic drugs, agents or compounds may be mixed with the biocompatible materials and affixed to at least a portion of the medical device. These therapeutic drugs, agents or compounds may also further reduce a biological organism's reaction to the introduction of the medical device to the organism. In addition, these therapeutic drugs, agents and/or compounds may be utilized to promote healing, including the formation of blood clots. Therapeutic agents may also be delivered to the region of a disease site. In regional delivery, liquid formulations may be desirable to increase the efficacy and deliverability of the particular drug. Also, the devices may be modified to promote endothelialization. Various materials and coating methodologies may be utilized to maintain the drugs, agents or compounds on the medical device until delivered and positioned. In addition, the devices utilized to deliver the implantable medical devices may be modified to reduce the potential for damaging the implantable medical device during deployment. Medical devices include stents, grafts, anastomotic devices, perivascular wraps, sutures and staples. In addition, various polymer combinations may be utilized to control the elution rates of the therapeutic drugs, agents and/or compounds from the implantable medical devices.

3 Claims, 51 Drawing Sheets

U.S. PATENT DOCUMENTS

| | | | |
|---|---|---|---|
| 5,440,056 A | | 8/1995 | Klein et al. |
| 5,516,770 A | * | 5/1996 | Waranis et al. ............... 514/183 |
| 5,837,313 A | | 11/1998 | Ding et al. |
| 5,891,845 A | * | 4/1999 | Myers .......................... 514/11 |
| 5,924,997 A | | 7/1999 | Campbell |
| 6,099,562 A | | 8/2000 | Ding et al. |
| 6,120,536 A | | 9/2000 | Ding et al. |
| 6,153,252 A | | 11/2000 | Hossainy et al. |
| 6,241,762 B1 | | 6/2001 | Shanley |
| 6,293,967 B1 | | 9/2001 | Shanley |
| 6,425,898 B1 | | 7/2002 | Wilson et al. |
| 6,764,507 B2 | | 7/2004 | Shanley et al. |
| 7,060,709 B2 | * | 6/2006 | Cooperstone et al. ....... 514/291 |
| 2003/0170287 A1 | | 9/2003 | Prescott |
| 2004/0024003 A1 | | 2/2004 | Asmussen |
| 2004/0167152 A1 | * | 8/2004 | Rubino et al. ............... 514/291 |
| 2005/0222191 A1 | | 10/2005 | Falotico et al. |
| 2005/0272806 A1 | | 12/2005 | Falotico et al. |

FOREIGN PATENT DOCUMENTS

| | | |
|---|---|---|
| EP | 0041795 B1 | 12/1981 |
| EP | 590267 B1 | 7/1993 |
| EP | 0950386 A | 10/1999 |
| WO | WO 93/10076 A1 | 5/1993 |
| WO | WO 93/19763 A | 10/1993 |
| WO | 93/23555 | 11/1993 |
| WO | WO 93/23555 A1 | 11/1993 |
| WO | WO 93/24476 A1 | 12/1993 |
| WO | WO 94/00156 A1 | 1/1994 |
| WO | WO 94/07876 A1 | 4/1994 |
| WO | WO 94/07880 A1 | 4/1994 |
| WO | WO 94/07881 A1 | 4/1994 |
| WO | WO 94/07882 A1 | 4/1994 |
| WO | WO 94/20089 A1 | 9/1994 |
| WO | WO 98/33443 A1 | 8/1998 |
| WO | WO 2004/011000 A | 2/2004 |
| WO | WO 2004/026182 A2 | 4/2004 |
| WO | WO 2004/043510 A1 | 5/2004 |
| WO | WO 2004/110302 A2 | 12/2004 |

OTHER PUBLICATIONS

Arcella, V. et al., "Fluorocarbon Elastomers", *Modern Fluoropolymers*, (J. Shires ed.), John Wiley & Sons, New York, pp. 77-87 (1997).

Berk, B.C. et al., "Pharmacologic Roles of Heparin and Glucocorticoids to Prevent Restenosis After . . . ", *J. Am. College Cardiology* 17: 111B-117B (1991).

Carrera et al., "Potent Toxicity of 2-Chlorodeoxyadenosine toward Human Monocytes in Vitro and In Vivo" *J. Clin. Invest.* 86: 1480-1488 (1990).

Carson, D.A. et al., "Specific toxicity of 2-chlorodeoxyadenosine toward resting and proliferating human lymphocytes", *Blood* 62: 737-743 (1983).

Chang, M. W. et al., "Adenovirus-mediated Over-expression . . . " *J. Clin. Invest.* 96: 2260-2268 (1995).

Clowes, A. W. et al. "Suppression by heparin of smooth . . . " *Nature* 265: 625-626 (1977).

Clowes, A.W. et al. "Kinetics of Cellular Proliferation . . . " *Lab. Invest.* 52: 611-616 (1985).

Clowes, A.W. et al., "Kinetics of Cellular Proliferation . . . " *Circ. Res.* 58: 839-845 (1986).

Colburn, M.D. et al., "Done responsive suppression of . . . " *J. Vasc. Surg.* 15: 510-518 (1992).

Currier, J.W. et al., *Circ.* 80: 11-66 (1989).

Deroanne, C.F. et al., "Histone deacetylases inhibitors . . . ", *Oncogene* 21 (3): 427-436 (2002).

Farb, A. et al., "Vascular Smooth Muscle Cell Cytotoxicity . . . ", *Circ. Res.* 80: 542-550 (1997).

Ferns, G.A.A. et al., "Inhibition of Neointimal Smooth Muscle Accumulation after Angioplasty . . . ", *Science* 253: 1129-1132 (1991).

Fukuyama, J. et al., "Tranilast suppresses the vascular intimal hyperplasia after balloon injury . . . " *Eur. J. Pharmacol.* 318: 327-332 (1996).

Guyton, J.R. et al., "Inhibition of Rat Arterial Smooth Muscle . . . " *Circ. Res.* 46: 625-634 (1980).

Hanson, S.R. et al, "Interruption of acute platelet-dependent thrombosis by the synthetic . . . " *Proc. Natl. Acad. Sci. USA* 85: 3184-3188 (1988).

Hansson, G.K. et al., "Interferon-γ Inhibits Arterial Stenosis . . . " *Circ.* 84: 1266-1272 (1991).

Jonasson, L. et al., "Cyclosporin A inhibits smooth muscle proliferation in the vascular response to injury" *Proc. Natl. Acad. Sci.* 85: 2303 (1988).

Liu, M.W. et al., "Trapidil in Preventing Restenosis After Balloon Angioplasty in the Atherosclerotic Rabbit" *Circ.* 81: 1089-1093 (1990).

Lundergan, C.F. et al., "Peptide Inhibition of Myointimal Proliferation by Angiopeptin . . . " *Am. J. Cardiol.* 17 (Suppl. B): 132B-136B (1991).

Majesky, M.W. et al., "Heparin Regulates Smooth Muscle S Phase Entry In the Injured Rat Carotid Artery" *Circ. Res.* 61: 296-300 (1987).

Marx, S.O. et al., "Rapamycin-FKBP Inhibits Cell Cycle Regulators of Proliferation In Vascular Smooth Muscle Cells" Circ. Res. 76: 412-417 (1995).

Nemecek, G.M. et al., "Terbinafine Inhibits the Mitogenic Response to Platelet-Derived Growth Factor in Vitro and Neointimal Proliferation in Vivo" *J. Pharmacol. Exp. Thera.* 248: 1167-1174 (1989).

Okada, T. et al., "Localized Release of Perivascular Heparin Inhibits Intimal Proliferation After Endothelial Injury without Systemic Anticoagulation" *Neurosurgery* 25: 892-898 (1989).

Powell, J. S. et al., "Inhibitors of Angiotensin-Converting Enzyme Prevent Myointimal Proliferation After Vascular Injury" *Science*, 245: 186-188 (1989).

Simons, M. et al., "Antisense *c-myb* oligonucleotides inhibit intimal arterial smooth muscle sell accumulation in vivo" *Nature* 359: 67-70 (1992).

Snow, A.D. et al., "Heparin Modulates the Composition of the Extracellular Matrix Domain Surrounding . . . " *Am. J. Pathol.* 137: 313-330 (1990).

Sollot, S.J. et al., "Taxol Inhibits Neointimal Smooth Muscle Cell Accumulation After Angioplasty in the Rat" *J. Clin. Invest.* 95: 1869-1876 (1995).

Weinberger, J. et al., "Intracoronary Irradiation: Dose response For The Prevention of Restenosis in Swine" *Int. J. Rad. Onc. Biol. Phys.* 36: 767-775 (1996).

Woo, S.H. et al., "Structurally Simple Trichostatin A-Like Straight Chain Hydroxamates as Potent Histone Deacetylase Inhibitors" *J. Med Chem*, 45: 2877-2885 (2002).

Beutler, E. "Cladribine (2-chlorodeoxyadenosine)", The Lancet, vol. 340, p. 952 (Oct. 1992).

Campbell & Campbell, "Phenotypic Modulation of Smooth Muscle Cells in Primary Culture", (Table of Contents), Chapter 2, vol. 1, pp. 39-52 (1985).

Campbell & Campbell, "Cell Biology of Smooth Muscle in Culture: Implications for Atherogenesis", Inter. Angio, 6 pp. 73 (1987.

Clowes and Schwartz, "Significance of Quiescent Smooth Muscle Migration in the Injured Rat Carotid Artery", Cir. Res. 56: 139-145 (1985).

Edelman, E., et al. "Pathobiologic Responses to Stenting", American Journal of Cardiology vol. 91, Issue 7, Suppl. 1 (Apr. 1998) pp. 4E-6E.

Fischman, D., et al. "A Randomized Comparison of Coronary-Stent Placement and Balloon Angioplasty in the Treatment of Coronary Artery Disease", The New England Journal of Medicine, vol. 331 p. 496-501 (Aug. 1994).

Franklin, S., et al. "Pharmacologic Prevention of Restenosis After Coronary Angioplasty: Review of the Randomized Clinical Trials", Coronary Artery Disease, vol. 4, No. 3 (Mar. 1993).

Lang, R. J., et al. "Effects of Okadaic Acid and ATYPγS on Cell Length and $Ca^{2+}$-Channel Currents Recorded in Single Smooth Muscle Cells of the Guinea-Pig Taenia Caeci", Br. J. Pharmacol. (1991) 104, p. 331-336.

Mak, K., et al. "Clinical Trials to Prevent Restenosis after Percutaneous Coronary Revascularization", Department of Cardiolog, Cleveland Clinical Foundation, Ohio p. 255 (1991).

Pompa, J., et al. "Clinical Trials of Restenosis After Coronary Angioplasty", Journal of the American Heart Association (Circulation), 84:1426-1436 (1991).

Serruys, P., et al. "Evaluation of Ketanserin in the Prevention of Restenosis After Percutaneous Transuminal Coronary Angioplasty. A Multicenter Randomized Double-Blind Placebo-Controlled Trial", American Heart Association, Circulation, 88, p. 1588 (1993).

Serruys, P., et al., "A Comparison of Balloon-Expandable-Stent Implantation with Balloon Angioplasty in Patients with Coronary Artery Disease", New England Journal of Medicine, vol. 331, p. 489-495 (Aug. 1994).

Tanaka, H., et al. "Sustained Activation of Vascular Cells and Leukocytes in the Rabbit Aorta after Balloon Injury", Circulation vol. 88 p. 1788 (19930.

Tardif, J., et al. "Probucol and Multivitamins in the Prevention of Restenosis After coronary Angioplasty", The New England Journal of Medicine, vol. 337 p. 365 (Aug. 1997).

Teirstein, P., et al. "Catheter-Based Radiotherapy to Inhibit Restenosis after Coronary Stenting", New England Journal of Medicine, vol. 336, p. 1679 (1997).

Yokoi, H., et al. "Effectiveness of an Antioxidant in Preventing Restenosis After Percutaneous Transluminal Coronary Angioplasty: The Probucol Angioplasty Restenosis Trial", JACC vol. 30, No. 4 p. 855-862 (1997).

U.S. Appl. No. 09/948,987.

Ajroldi, G., et al. "Fluoroelastomers-Dependence of Relaxation Phenomena on Composition", Polymer (1989) vol. 30. p. 2180-2187.

Anderson, T., et al. "The Effect of Cholesterol-Lowering and Antioxidant Therapy on Endothelium-Dependent Coronary Vasomotion", The New England Journal of Medicine, vol. 332, No. 8, pp. 488-493 (Feb. 23, 1995).

Benedeck, M., et al. "Smooth Muscle Cell Migration and Matrix Metalloproteinase Expression After Arterial Injury in the Rat", Circulation Research pp. 539-545 (1994).

Berk, B., et al. "Pharmacologic Roles of Heparin and Gluocorticoids to Prevent Restenosis After Coronary Angioplasty", J. Am. Coll. Cardio. vol. 17 (Suppl B); pp. 111B-117B (1991).

Beutler, E., et al. "Cladribine (2-Chlorodeoxyadenoisine)", The Lancet (1992) vol. 340, pp. 952-956.

Brehm, B., et al. "β-Blockers of the Third Generation Inhibit Endothelin-1-Liberation, mRNA Production and Proliferation of Human Coronary Smooth Muscle and Endothelial Cells", Journal of Cardiovascular Pharmacology, (2000) Suppl. 1, vol. 36, pp. S401-S403.

Brehm, B., et al. "Chronically Elevated Endothelin-1 Concentrations Modulate the β-Adrenergic Receptor System in Vitro and in Vivo", Journal of Cardiovascular Pharmacology (2000) Suppl. 1 vol. 36, p. S157-S159.

Burton, G., et al. "β-Carotene: An Unusual Type of Lipid Antioxidant", Science, vol. 224 (1984) pp. 569-573.

Carrera, C., et al. "Potent Toxicity of 2-Chlorodeoxyadenoisine Toward Human Monocytes in Vitro and in Vito", J. Clinical Investigation vol. 86 pp. 1480-1488 (1990).

Carson, D., et al. "Specific Toxicity of 2-Chlorodeoxyadenosine Toward Resting and Proliferating Human Lymphocytes", Book 62 pp. 737-743 (1983).

Chang, M., et al. "Adenovirus-Mediated Over-Expression of the Cyclin/Cyclin-Dependent Kinase Inhibitor", J. Clinical Investigation, vol. 96, pp. 2260-2268 (1995).

Clowes, A., et al. "Kinetics of Cellular Proliferation After Arterial Injury, II. Inhibition", Lab. Invest. vol. 52(6) pp. 611-616 (1985).

Clowes, A., et al. "Kinetics of Cellular Proliferation After Arterial Injury, IV. Heparin", Circulation Research vol. 58, p. 839-845 (1986).

Clowes, A., et al. "Suppression of Heparin of Smooth Muscle Cell Proliferation in Injured Arteries", Nature vol. 265 pp. 25-26 (1977).

Colburn, M, et al. "Dose Responsive Suppression of Myointimal Hyperplasia by Dexamethasone", J. Vascular Surgery, vol. 15 pp. 510-518 (1992).

Currier, J., et al. "Restenosis After Percutaneous Transluminal Coronary Angioplasty: Have We Been Aiming at the Wrong Target?" JACC, vol. 25, No. 2, pp. 516-520 (1995).

Currier, J., et al. "Colchicine Inhibits Restenosis After Iliac Angioplasty in the Atherosclerotic Rabbit", Circulation 80, No. 4, pp. 11-66 (1989).

Deroanne, C., et al. "Histone Deacetylulases Inhibitors as Anti-Angiogenic Agents Altering Vascular Endothelial Growth Factor Signaling", Oncogene (2002) vol. 21, pp. 427-436.

Edelman, E. ,et al. "Pathobiologic Responses to Stenting", American Journal of Cardiology, Vol. 81, Issue 7, Suppl. 1 (Apr. 1998) pp. 4E-6E.

Farb, A., et al. "Vascular Smooth Muscle Cell Cytoxicity and Sustained Inhibition of Neointimal Formation by Fibroblast Growth Factor 2-Saporin Fusion Protein", Circulation Research vol. 80(4) pp. 542-550 (1997).

Ferns, G., et al. "Inhibition of Neointimal Smooth Muscle Accumulation After Angioplasty by an Antibody to PDGF", Reports p. 1129-1132 (1991).

Ferns, G., et al. "Probucol Inhibits Neointimal Thickening and Macrophage Accumulation After Balloon Injury in the Cholesterol-Fed Rabbit", Proc. National Academy Science, vol. 89, pp. 11312-11316 (1992).

Fleischman, L., et al. "Ras-Transformed Cells: Altered Levels of Phosphatidylinositol-4,5-Bisphosphate and Catabaolite", Reports (1986) pp. 407-410.

Franke, T. et al. "PI3K: Downstream AKTiion Blocks Apoptosis", Cell. vol. 88, pp. 435-437 (1997).

Fukuyama, J., et al. "Tranilast Suppresses Intimal Hyperplasia After Balloon Injury In Rabbits Fed On a high-Cholesterol Diet", European Journal of Pharmacology, vol. 318 pp. 327-332 (1996).

Galis, Z., et al. "Cytokine-Stimulated Human Vascular Smooth Muscle Cells Synthesize a Complement of Enzymes Required for Extracellular Matrix Digestion", Circulation Research vol. 75 pp. 181-189 (1994).

Georg, G., et al. "Synthesis of Biologically Active Taxol Analogues with Modified Phenylisoserine Side", J. Medical Chemistry, vol. 35 pp. 4230-4237 (1992).

Gimon, M., et al. "Matrix-Assisted Laser Desorption/Ionization Time-Of-Flight Mass Spectrometry of Paclitaxel and Related Taxanes", Journal of Natural Products, vol. 57(1) pp. 1404-1410 (1994).

Guieitte-Voegelein, F., et al. "Relationships Between The Structure of Taxol Analogues and Their Antimitotic Activity", J. Medical Chemistry, vol. 34 pp. 992-998 (1991).

Guyton, J., et al. "Inhibition of Rat Arterial Smooth Muscle Cell Proliferation by Heparin", Circulation Research, vol. 46(5) pp. 625-634 (1980).

Haas-Kogan, D., et al. "Protein Kinase B (PKB/akt) Activity is Elevated in Giloblastoma Cells Due to Mutation of the Tumor Suppressor PTEN/MMAC", Current Biology, vol. 8(21) pp. 1195-1198 (1998).

Hansson, G. ,et al. "Interferon-Gamma Inhibits Arterial Stenosis After Injury", Circulation 84 pp. 1266-1272 (1991).

Hanson, S., et al. "Interruption of Acute Platelet-Dependent Thrombosis by the Synthetic Antihrombin D-Penylalanyl-propyl-arginyl chloromethyl Ketone", Proc. Nat. Academy of Science, vol. 85 pp. 3184-3188 (1988).

Holton, R., et al. "A Synthesis of Taxusin", J. American Chemical Society, vol. 110 No. 19 pp. 6558-6560 (1988).

Ikada, Y., et al. "Sterocomplex Formulation Between Enantiometric Poly(lacides)", Macromolecules 20 pp. 904-906 (1987).

Jonasson, L., et al. "Cyclosporin A Inhibits Smooth Muscle Proliferation in the Vascular Response to Injury", Proc. Natl. Acad. Sci (USA) vol. 85 (Apr. 1988) pp. 2303-2306.

Ku, G., "Inhibition by Probucol of Interleukin 1 Secretion and Its implication in Atherosclerosis", American J. Cardiology vol. 62 pp. 77B-81B (1988).

Kugiyama, K., et al. "Impairment of Endotheliium-Dependent Arterial Relaxation by Lysolecithin in Modified Low-Density Lipoproteins", Nature, vol. 344 pp. 160-162.

Kunishima, T., et al. "A Randomized Trial of Aspirin Versus Cilostazol Therapy After Successful Coronary Stent Implantation", Clinical Therapeutics, vol. 19(5) pp. 1058-1066 (1997).

Kuzuya, M., et al. "Probucol Prevents Oxidative Injury to Endothellial Cells", Journal of Lipid Research, vol. 32 pp. 197-204 (1991).

Lang, R., et al. "Effects of Okadaic Acid and ATPγS on Cell Length and $CA^{2+}$ Channel Currents Recorded in Single Smooth Muscle Cells of the Guinea-pig Taenia Caeci", British J. pharmacol. (1991) pp. 331-336.

Langille, B., et al. "Reductions in Arterial Diameter Produced by Chronic Decreases in Blood Flow Are Endothelium-Dependent", Reports, Science, vol. 231 pp. 405-407 (1986).

Lee, Y., et al. "Effectiveness of Probucol in Preventing Restenosis After Percutaneous Transluminal Coronary Angioplasty", Japan Heart J. pp. 327-332 (1996).

Circulation: Lee 84: 11-299 Abstracts From the 64th Scientific Sessions (1991).

Leibel, S. et al. "Radiation Therapy for Neoplasms of the Brain", J. Neurosurgery vol. 66 pp. 1-22 (1987).

Liu, M., et al. "Trapidil in Preventing Restenosis After Balloon Angioplasty in the Atherosclerotic Rabbit", Circulation 81, No. 3 pp. 1089-1093 (1990).

Long, B., et al. "Pacitaxel Inhibits Progression of Mitotic Cells to G Phase by Interference With Spindle Formation Without Affecting Another Microbuble Functions During Anaphase and Telephase", Cancer Research vol. 54 pp. 4355-4361 (1994).

Lundergan, C., et al. "Peptide Inhibition of Myointimal Proliferation by Angiopeptin, A Somatostain Analogue", JACC, Vo. 17(6) pp. 132B-136B (1991).

Majesky, M., et al. "Heparin Regulates Smooth Muscle S Phase Entry in the Injured Rat Carotid Artery", Circulation Research, vol. 61(2) p. 296-300 (1987).

Marx, S., et al. "Rapamycin-FKBP Inhibits Cell Cycle Regulators of Proliferation in Vascular Smooth Muscle Cells", Circulation Research vol. 76(3) pp. 412-417 (1995).

Mintz, G., et al. "Limitations of Angiography in the Assessment of Plaque Distribution in Coronary Artery Disease", Circulation, vol. 93 pp. 924-932 (1996).

Mintz, G., et al. "Arterial Remodeling After Coronary Angioplasty: A Serial Intravascular Ultrasound Study", Circulation, vol. 94(1) pp. 35-43 (1996).

Mintz, G., et al. "Intravascular Ultrasound Predictors of Restenosis After Percutaneous Transcatheter Coronary Revascularization", JACC, vol. 27(7) p. 1678 (1996).

Morena, H., et al. "Comparison of the Effects of Regional Ischemia, Hypoxia, Hyperkalemia, and Acidosis on Intracellular and Extracellular Potentials and Metabolism in the Isolated Porcine Heart", Circulation Research, vol. 46(5) p. 634 (1980).

Nemecek, G., et al. "Terbinaine Inhibits the Mitogenic Response to Plalet-Derived Growth Factor in Vitro and Neotintimal Proliferation in Vivo", Journal of Pharmacology and Experimental Therapeutics, vol. 245(3) pp. 1167-1174.

Nunes, G., "Combination of Vitamins C and E Alters the Response to Coronary Balloon Injury in the Pig", Arteriscler. Thromb and Vascular Biol. vol. 15(1) pp. 156-165 (1995).

Okada, T., et al. "Localized Release of Perivascular Heparin Inhibits Intimal Proliferation After Endothelial Injury Without Systemic Anticoagulation", Neurosurgery(1989), vol. 25(6), pp. 892-898.

Orgill, D., et al. "Current Concepts and Approaches to Wound Healing", Critical Care Medicine, vol. 15(9) pp. 899-908 (1988).

Ozaki, H., et al. "Calcium-Independent Phosphorylation of Smooth Muscle Myosin Light Chain by Okadiac Acid Isolated From Black Sponge", Journal of Pharmacology and Experimenetal Therapeutics, vol. 243(3) pp. 1167-1173 (1987).

Parthasarathy, S., et al. "Probucol Inhibits Oxidative Modification of Low Density Lipopritein", J. Clinical Investigation, vol. 77 pp. 641-644 (1986).

Pazdur, R., et al. "The Taxoids" Paclitaxel (Taxol) and Docetaxel (Taxotere) Cancer Treatment Reviews, vol. 19 pp. 351-386 (1993).

Powell, J. "Inhibitors of Angiogenesis-Converting Enzyme Prevents Myointimal Proliferation After Vascular Injury" Science, vol. 245 (186-188 (1989).

Pozzati, E., "The Growth of Cerebral Cavernous Angiomas", Neurosurgery, vol. 25(10) pp. 92-97 (1989).

Pulcani, J., et al. Preparation of 7-Modified Docetaxel Analogs Using Electrochemistry, Tetrahedron Letters, vol. 35(52) p. 9709-9712 (1994).

Rajagopalan, S., et al. "Reactive Oxygen Species Produced by Macrophage-Derived Foam Cells Regulate the Activity of Vascular Matrix Metalloproteinases in Vitro", J. Clinical Investigation, vol. 98(11) pp. 2572-2579 (1996).

Reiser, K. et al. "Enzymatric and Nonenzymatric Cross-Linking of Collagen and Elastin", The FASAB Journal, vol. 6 pp. 2439-2449 (1992).

Ringel, I., et al. "Studies With RP 56976 (Taxotere): A Semisynthetic Analogue of Taxol", J. National Cancer Institute, vol. 83(4) pp. 288-291 (1991).

Saito, N., et al. "Intramedullary Cavernous Angioma With Trigeminal Neuralgia: A Case Report and Review of the Literature", Neurosurgery pp. 97-101 (1989).

Schiff, P., et al. "Promotion of Microbutule Assembly in Vitro by Taxol", Nature, vol. 277 p. 665-667 (1979).

Schneider, J., et al. "Probucol Deceases Neointimal Formation in a Swine Model of Coronary Artery Balloon Injury", Circulation, vol. 88 pp. 628-637 (1993).

Scully, R., et al. "Case Records of the Massachusetts General Hospital", The New England Journal of Medicine p. 924 (1989).

Serruys, P., et al. "Heparin-Coated Palmaz-Schartz Stents in Human Coronary Arteries: Early Outcome of the Benestent-II Pilot Study", Circulation vol. 93(3) pp. 412-422 (1996).

Setsuda, M., et al. "Probucol Therapy in the Prevention of Restenos After Successful Percutaneaous Transluminal Coronary Angioplasty", Clinical Therapeutics, vol. 15(2) pp. 374-382 (1993).

Shayesteh, L., et al. "PIK3CA is Implicated as an Oncogene in Ovarian Cancer", Nature Genetics, vol. 21 pp. 99-102 (1999).

Siddiqui, M., et al. "Isolation and Sequencing of a cDNA Coding for the Human DF3 Breast Carcinoma-Associated Antigen", Proc. National Academy of Science, vol. 85 pp. 2320-2323 (1989).

Simons, M., et al. "Antisense c-myb Oligonucleotides Inhibit Intimal Arterial Sooth Muscle Cell Accumulation in Vivo", Nature, vol. 359 pp. 67-70 (1992).

Snow, A., et al. "Heparin Modulates the Composition of the Extracellular Matrix Domain Surrounding Arterial Smooth Muscle Cells", American Journal of Pathology, vol. 73(2) pp. 313-330 (1990).

Sollott, S., et al. "Taxol Inhibits Neointimal Smooth Muscle Cell Accumulation After Angioplasty in the Rat", the Journal of Clinical Investigation, vol. 95 pp. 1869-1876 (1995).

Southgate, K., et al. "Involvement of Extracellular-Matrix-Degrading Metalloproteinases in Rabbit Aortic Smooth-Muscle Cell Proliferation" Biochem. J. vol. 288 pp. 93-99 (1992).

Southhorn, P., et al. "Free Radicals in Medicine: Chemical Nature and Biologic Reaction", Mayo Clin. Proc. vol. 63 pp. 381-389 (1988).

Steinberg, D., "Studies on the Mechanism of Action of Probucol", American J. Cardiology, vol. 57p. 16H-21H (1986).

Stierle, A., et al. "Taxol and Taxane Production by Taxomyces Andreanae, An Endophytic Fungus of Pacific Yew", Science, vol. 260 pp. 214-216 (1993).

Strauss, B., et al. "Extracellular Matrix Remodeling After Balloon Angioplasty Injury in a Rabbit Model of Restenosis" Circulation Research, vol. 75 pp. 650-658 (1994).

Take, S., et al. "Effect of Cilostazol in Preventing Restenosis After Percutaneous Transluminal Coronary Angioplasty", American J. of Cardiology, vol. 79 pp. 1097-1099 (1997).

Tanaka, H., et al., "Sustained Activation of Vascular Cells and Leukocytes in the Rabbit Aorta After Balloon Injury", Circulation, vol. 88, pp. 1788-1803 (1993).

Tsuchikane, E., et al. "Impact of Cilostazol in Restenosis After Percutaneous Coronary Balloon Angioplasty", Circulation, pp. 21-26 (1999).

Wani, M., et al. "Plant Anti-Tumor Agents, VI. The Isolation and Structure of Taxol, a Novel Antileukemic and Antitumor Agent from Taxus Brefolia", J. Am. Chem. Soc. (1971) vol. 93 pp. 2325-2327.

Watanabwe, K., et al. "Preventive Effects of Probucol on Restenosis After Percutaneous Transluminal Coronary Angioplasty", American Heart Journal, vol. 132 No. 1, Part 1 pp. 23-29 (1996).

Weinberger, J., et al. "Intracoronary Irradiation; Dose Response for the Prevention of Restenosis in Swine", International J. Radiation Oncology Biol. Phys. vol. 36(4) pp. 767-775 (1996).

Wiley and Sons, Chapter 2: "Modern Fluoropolymers—High Performance Polymers for Diverse Applications", pp. 71-90 (1997).

Woo, S., et al. "Structurally Simple Trichostatin A-Like Straight Chain Hydroxamates as Potent Histone Deacetylase Inhibitors", J. Med. Chemistry (2002) vol. 45, pp. 2877-2885.

Zhang, S., et al. "A New 11(1 1)-Abeo-Taxane from Taxus Yunnanensis," Journal of Natural Products, vol. 57(11) pp. 1580-1583 (1994).

Mak and Topol, K., et al. "Clinical Trials to Prevent Restenosis After Percutaneous Coronary Revascularization", Department of Cardiolg. Cleveland Clinical Foundation, Ohio pp. 255-288 (1991).

Carson, D.A., et al., "Specific Toxicity of 2-Chlorodeoxyadenosine Toward Resting and Proliferating Human Lymphocytes", Blood 62: 737-743 (1983).

Esterbauer, H., et al. "Continuous Monitoring of In Vitro Oxidation of Human Low Density Lipoprotein", Free Rad. Res. Comms., vol. 6, No. 1, pp. 67-75 (1989).

Lifu, M., et al., "Advances in Treatment of Coronary Restenosis using Rapamycin", Journal of Clinical Cardiology (2003) vol. 19, No. 9 5 pages total.

Seto, S., et al. "Mechanism of Deoxyadenosine and 2-Chlorodeoxyadenosine Toxicity to Nondividing Human Lymphocytes", J. Clinical Investigation, vol. 75 (Feb. 1985) pp. 377-383.

Siddiqui, J., et al. "Isolation and Sequencing of a cDNA Coding for the Human DF3 Breast Carcinoma-Associated Antigen", Proc. Nat. Acad. Sci, vol. 85, pp. 2320-2323 (1988).

Steinberg, D., et al. "Beyond Cholesterol, Modifications of Low-Density Lipoprotein That Increase Its Atherogenicity", vol. 320, No. 14, pp. 915-924 (1989).

Yan, J., et al. "Coated Stents in Blood Vessel", Advances in Cardiovascular Diseases (2002) Vo. 23, No. 6, 8 pages total.

Carson, *DNA Strand Breaks, NAD Metabolism, and Programmed Cell Death*, Experimental Cell Research 164 (1986) Special Article, 273-281.

* cited by examiner

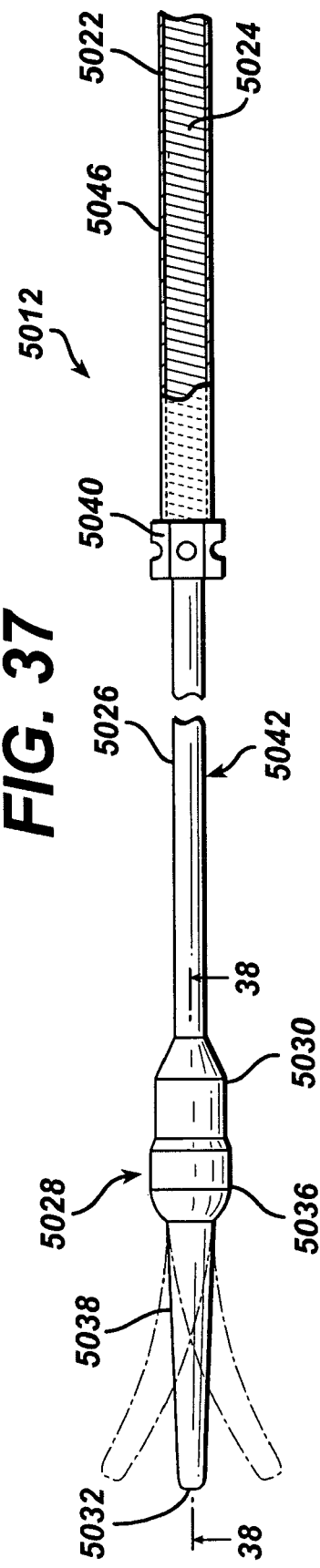

FIG. 57

Inhibition of CA-SMC proliferation by sirolimus

SOLUTION FORMULATIONS OF SIROLIMUS AND ITS ANALOGS FOR CAD TREATMENT

BACKGROUND OF THE INVENTION

1. Field of the Invention

The present invention relates to the local administration of drug/drug combinations for the prevention and treatment of vascular disease, and more particularly to intraluminal medical devices for the local delivery of drug/drug combinations for the prevention and treatment of vascular disease caused by injury and methods and devices for maintaining the drug/drug combinations on the intraluminal medical devices, as well as preventing damage to the medical device. The present invention also relates to medical devices, including stents, grafts, anastomotic devices, perivascular wraps, sutures and staples having drugs, agents and/or compounds affixed thereto to treat and prevent disease and minimize or substantially eliminate a biological organism's reaction to the introduction of the medical device to the organism. In addition, the drugs, agents and/or compounds may be utilized to promote healing and endothelialization. The present invention also relates to coatings for controlling the elution rates of drugs, agents and/or compounds from implantable medical devices. The present invention also relates to drugs and drug delivery systems for the regional delivery of drugs for treating vascular disease as well as liquid formulations of the drugs.

2. Discussion of the Related Art

Many individuals suffer from circulatory disease caused by a progressive blockage of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans, which are believed to be responsible for maintaining smooth muscle cells in the contractile phenotypic state (Campbell and Campbell, 1985).

Upon pressure expansion of an intracoronary balloon catheter during angioplasty, smooth muscle cells and endothelial cells within the vessel wall become injured, initiating a thrombotic and inflammatory response. Cell derived growth factors such as platelet derived growth factor, basic fibroblast growth factor, epidermal growth factor, thrombin, etc., released from platelets, invading macrophages and/or leukocytes, or directly from the smooth muscle cells provoke a proliferative and migratory response in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days' post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells adhere to the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25-26, 1977; Guyton, J. R. et al., Circ. Res., 46: 625-634, 1980; Clowes, A. W. and Clowes, M. M., Lab. Invest. 52: 611-616, 1985; Clowes, A. W. and Clowes, M. M., Circ. Res. 58: 839-845, 1986; Majesky et al., Circ. Res. 61: 296-300, 1987; Snow et al., Am. J. Pathol. 137: 313-330, 1990; Okada, T. et al., Neurosurgery 25: 92-98, 1989), colchicine (Currier, J. W. et al., Circ. 80: 11-66, 1989), taxol (Sollot, S. J. et al., J. Clin. Invest. 95: 1869-1876, 1995), angiotensin converting enzyme (ACE) inhibitors (Powell, J. S. et al., Science, 245: 186-188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129-1132, 1991), terbinafine (Nemecek, G. M. et al., J. Pharmacol. Exp. Thera. 248: 1167-1174, 1989), trapidil (Liu, M. W. et al., Circ. 81: 1089-1093, 1990), tranilast (Fukuyama, J. et al., Eur. J. Pharmacol. 318: 327-332, 1996), interferon-gamma (Hansson, G. K. and Holm, J., Circ. 84: 1266-1272, 1991), rapamycin (Marx, S. O. et al., Circ. Res. 76: 412-417, 1995), steroids (Colburn, M. D. et al., J. Vasc. Surg.

15: 510-518, 1992), see also Berk, B. C. et al., J. Am. Coll. Cardiol. 17: 111B-117B, 1991), ionizing radiation (Weinberger, J. et al., Int. J. Rad. One. Biol. Phys. 36: 767-775, 1996), fusion toxins (Farb, A. et al., Circ. Res. 80: 542-550, 1997) antisense oligionucleotides (Simons, M. et al., Nature 359: 67-70, 1992) and gene vectors (Chang, M. W. et al., J. Clin. Invest. 96: 2260-2268, 1995). Anti-proliferative action on smooth muscle cells in vitro has been demonstrated for many of these agents, including heparin and heparin conjugates, taxol, tranilast, colchicine, ACE inhibitors, fusion toxins, antisense oligionucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP $II_b/III_a$ receptor, antagonist, Reopro® is still under study but Reopro® has not shown definitive results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxident agent, probucol, may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

As stated above, the use of heparin coated stents demonstrates the feasibility and clinical usefulness of local drug delivery; however, the manner in which the particular drug or drug combination is affixed to the local delivery device will play a role in the efficacy of this type of treatment. For example, the processes and materials utilized to affix the drug/drug combinations to the local delivery device should not interfere with the operations of the drug/drug combinations. In addition, the processes and materials utilized should be biocompatible and maintain the drug/drug combinations on the local device through delivery and over a given period of time. For example, removal of the drug/drug combination during delivery of the local delivery device may potentially cause failure of the device.

Accordingly, there exists a need for drug/drug combinations and associated local delivery devices for the prevention and treatment of vascular injury causing intimal thickening which is either biologically induced, for example, atherosclerosis, or mechanically induced, for example, through percutaneous transluminal coronary angioplasty. In addition, there exists a need for maintaining the drug/drug combinations on the local delivery device through delivery and positioning as well as ensuring that the drug/drug combination is released in therapeutic dosages over a given period of time.

A variety of stent coatings and compositions have been proposed for the prevention and treatment of injury causing intimal thickening. The coatings may be capable themselves of reducing the stimulus the stent provides to the injured lumen wall, thus reducing the tendency towards thrombosis or restenosis. Alternately, the coating may deliver a pharmaceutical/therapeutic agent or drug to the lumen that reduces smooth muscle tissue proliferation or restenosis. The mechanism for delivery of the agent is through diffusion of the agent through either a bulk polymer or through pores that are created in the polymer structure, or by erosion of a biodegradable coating.

Both bioabsorbable and biostable compositions have been reported as coatings for stents. They generally have been polymeric coatings that either encapsulate a pharmaceutical/therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

One class of biostable materials that has been reported as coatings for stents is polyfluoro homopolymers. Polytetrafluoroethylene (PTFE) homopolymers have been used as implants for many years. These homopolymers are not soluble in any solvent at reasonable temperatures and therefore are difficult to coat onto small medical devices while maintaining important features of the devices (e.g. slots in stents).

Stents with coatings made from polyvinylidenefluoride homopolymers and containing pharmaceutical/therapeutic agents or drugs for release have been suggested. However, like most crystalline polyfluoro homopolymers, they are difficult to apply as high quality films onto surfaces without subjecting them to relatively high temperatures that correspond to the melting temperature of the polymer.

It would be advantageous to develop coatings for implantable medical devices that will reduce thrombosis, restenosis, or other adverse reactions, that may include, but do not require, the use of pharmaceutical or therapeutic agents or drugs to achieve such affects, and that possess physical and mechanical properties effective for use in such devices even when such coated devices are subjected to relatively low maximum temperatures. It would also be advantageous to develop implantable medical devices in combination with various drugs, agents and/or compounds which treat disease and minimize or substantially eliminate a living organisms' reaction to the implantation of the medical device. In certain circumstances, it may be advantageous to develop implantable medical devices in combination with various drugs, agents and/or compounds which promote wound healing and endothelialization of the medical device.

It would also be advantageous to develop delivery devices that provide for the delivery of the coated implantable medical devices without adversely affecting the coating or the medical device itself. In addition, such delivery devices should provide the physician with a means for easily and accurately positioning the medical device in the target area.

It would also be advantageous to develop coatings for implantable medical devices that allow for the precise control of the elution rate of drugs, agents and/or compounds from the implantable medical devices.

It would also be advantageous to develop delivery devices that provide for the release of one or more agents that act through different molecular mechanisms affecting cell proliferation.

It would also be advantageous to develop delivery devices that provide for the regional administration of one or more agents for the treatment of atherosclerotic plaque.

It would also be advantageous to develop liquid formulations of the drugs to increase the efficacy and deliverability thereof. Specifically, liquid solution dosage forms of water insoluble and lipohilic drugs are difficult to create without resorting to substantial quantities of surfactants, co-solvents and the like.

SUMMARY OF THE INVENTION

The liquid formulation of a therapeutic agent in accordance with the present invention overcomes the disadvantages associated with the local or regional delivery of water insoluble and lipohilic drugs as briefly described above.

In accordance with one aspect, the present invention is directed to a liquid formulation of a therapeutic agent. The liquid formulation comprises rapamycin in a pharmaceutically effective dosage and one or more pharmaceutically acceptable solubility enhancers.

In accordance with another aspect, the present invention is directed to a method for the treatment of vascular disease. The method comprises the administration of a liquid formulation of rapamycin proximate the disease site.

Various combinations of drugs, agents and/or compounds may be utilized to treat various conditions. For example, rapamycin and trichostatin A may be utilized to treat or prevent restenosis following vascular injury. As rapamycin and trichostatin A act through different molecular mechanisms affecting cell proliferation, it is possible that these agents, when combined on a drug eluting stent, may potentiate each other's anti-restenotic activity by downregulating both smooth muscle and immune cell proliferation (inflammatory cell proliferation) by distinct multiple mechanisms. This potentiation of sirolimus anti-proliferative activity by trichostatin A may translate to an enhancement in anti-restenotic efficacy following vascular injury during revascularization and other vascular surgical procedures and a reduction in the required amount of either agent to achieve the anti-restenotic effect.

Trichostatin A may block neointimal formation by local vascular application (e.g. via stent- or catheter-based delivery) by virtue of complete and potent blockade of human coronary artery smooth muscle cell proliferation. The combination of sirolimus and trichostatin A (and other agents within its pharmacologic class) represent a new therapeutic combination that may be more efficacious against restenosis/neointimal thickening than rapamycin alone. Different doses of the combination may lead to additional gains of inhibition of the neointimal growth than the simple additive effects of rapamycin plus trichostatin A. The combination of rapamycin and trichostatin A may be efficacious towards other cardiovascular diseases such as vulnerable atherosclerotic plaque.

In an alternate exemplary embodiment, rapamycin may be utilized in combination with mycophenolic acid. As rapamycin and mycophenolic acid act through different molecular mechanisms affecting cell proliferation at different phases of the cell cycle, it is possible that these agents, when combined on a drug eluting stent or any other medical device as defined herein, my potentiate each others anti-restenotic activity by down regulating both smooth muscle and immune cell proliferation by different mechanisms.

In yet another alternate exemplary embodiment, rapamycin may be utilized in combination with cladribine. As rapamycin and cladribine act through different molecular mechanisms affecting cell proliferation at different phases of the cell cycle, it is possible that these agents, when combined on a drug eluting stent or any other medical device as defined herein, may potentiate each others anti-restenotic activity by down regulating both smooth muscle and immune cell proliferation by different mechanisms. Essentially, the combination of rapamycin and cladribine represents a therapeutic combination that may be more efficacious than either agent alone or the simple sum of the effects of the two agents. In addition, different doses of the combination may lead to additional gains of inhibition of the neointimal growth than rapamycin or cladribine alone.

In yet still another alternate exemplary embodiment, rapamycin may be utilized in combination with topotecan or other topoisomerase I inhibitors, including irinotecan, camptothecin, camptosar and DX-8951f. As rapamycin and topotecan act through different molecular mechanisms affecting cell proliferation at different phases of the cell cycle, it is possible that these agents, when combined on a drug eluting stent or any other medical device as defined herein, may potentiate each other's anti-restenotic activity by downregulating both smooth muscle cell and immune cell proliferation (inflammatory cell proliferation) by distinct multiple mechanisms. Essentially, the combination of rapamycin and topotecan or other topoisomerase I inhibitors represents a therapeutic combination that may be more efficacious than either agent alone or the simple sum of the two agents. In addition, different doses of the combination may lead to additional gains of inhibition of the neointimal growth than rapamycin or topotecan alone.

In yet still another alternate exemplary embodiment, rapamycin may be utilized in combination with etoposide or other cytostatic glucosides, including podophyllotoxin and its derivatives and teniposide. As rapamycin and etoposide act through different molecular mechanisms affecting cell proliferation at different phases of the cell cycle, it is possible that these agents, when combined on a drug eluting stent or any other medical device as defined herein, may potentiate each other's anti-restenotic activity by downregulating both smooth muscle cell and immune cell proliferation (inflammatory cell proliferation) by distinct multiple mechanisms. Essentially, the combination of rapamycin and etoposide or other cytostatic glucosides, including podophyllotoxin and its derivatives and teniposide, represents a therapeutic combination that may be more efficacious than either agent alone or the simple sum of the two agents. In addition, different doses of the combination may lead to additional gains of inhibition of the neointimal growth than rapamycin or etoposide alone.

In yet still another alternate exemplary embodiment, 2-methoxyestradiol or Panzem® may be utilized alone or in combination with rapamycin to prevent restenosis following vascular injury. As rapamycin or sirolimus and Panzem® act to inhibit cell proliferation through different molecular mechanisms, it is possible that these agents, when combined on a drug eluting stent or any other medical device as described herein, may potentiate each other's anti-restenotic activity by downregulating both smooth muscle and immune cell proliferation by distinct multiple mechanisms. Essentially, the combination of rapamycin and Panzem® or other estrogen receptor modulators, represents a therapeutic combination that may be more efficacious than either agent alone or the simple sum of the two agents. In addition, different doses of the combination may lead to additional gains of inhibition of the neointimal growth than rapamycin or Panzem® alone.

The medical devices, drug coatings, delivery devices and methods for maintaining the drug coatings or vehicles thereon of the present invention utilizes a combination of materials to treat disease, and reactions by living organisms due to the implantation of medical devices for the treatment of disease or other conditions. The local delivery of drugs, agents or compounds generally substantially reduces the potential toxicity of the drugs, agents or compounds when compared to systemic delivery while increasing their efficacy.

Drugs, agents or compounds may be affixed to any number of medical devices to treat various diseases. The drugs, agents or compounds may also be affixed to minimize or substantially eliminate the biological organism's reaction to the introduction of the medical device utilized to treat a separate condition. For example, stents may be introduced to open coronary arteries or other body lumens such as biliary ducts. The introduction of these stents cause a smooth muscle cell proliferation effect as well as inflammation. Accordingly, the stents may be coated with drugs, agents or compounds to combat these reactions. Anastomosis devices, routinely utilized in certain types of surgery, may also cause a smooth muscle cell proliferation effect as well as inflammation. Stent-grafts and systems utilizing stent-grafts, for example, aneurysm bypass systems may be coated with drugs, agents and/or compounds which prevent adverse affects caused by the introduction of these devices as well as to promote healing and incorporation. Therefore, the devices may also be coated with drugs, agents and/or compounds to combat these reactions. In addition, devices such as aneurysm bypass systems may be coated with drugs, agents and/or compounds that promote would healing and endothelialization, thereby reducing the risk of endoleaks or other similar phenomena.

The drugs, agents or compounds will vary depending upon the type of medical device, the reaction to the introduction of the medical device and/or the disease sought to be treated.

The type of coating or vehicle utilized to immobilize the drugs, agents or compounds to the medical device may also vary depending on a number of factors, including the type of medical device, the type of drug, agent or compound and the rate of release thereof.

In order to be effective, the drugs, agents or compounds should preferably remain on the medical devices during delivery and implantation. Accordingly, various coating techniques for creating strong bonds between the drugs, agents or compounds may be utilized. In addition, various materials may be utilized as surface modifications to prevent the drugs, agents or compounds from coming off prematurely.

Alternately, the delivery devices for the coated implantable medical device may be modified to minimize the potential risk of damage to the coating or the device itself. For example, various modifications to stent delivery devices may be made in order to reduce the frictional forces associated with deploying self-expanding stents. Specifically, the delivery devices may be coated with various substances or incorporate features for reducing the forces acting upon specific areas of the coated stent.

The self-expanding stent delivery system of the present invention comprises a sheath coated with a layer of pyrolytic carbon or similar substance. The layer of pyrolytic carbon may be affixed to the inner lumen of the sheath in the region of the stent or along the entire length of the sheath. The pyrolytic carbon is hard enough to prevent the self-expanding stent from becoming embedded in the softer polymeric sheath. In addition, pyrolytic carbon is a lubricious material. These two properties reduce the change of damage to the stent during deployment, reduce the forces required for stent deployment, thereby making it easier for the physician to accomplish placement, and provide for more accurate stent deployment.

The pyrolytic carbon may be directly affixed to the inner lumen of the sheath or to a substrate which is then affixed to the inner lumen of the sheath. A variety of known techniques may be utilized in the manufacturing process. Pyrolytic carbon is biocompatible and is currently utilized in a number of implantable medical devices. The pyrolytic carbon layer is sufficiently thick to provide the above-described features and thin enough to maintain the overall profile and flexibility of the delivery system.

The lubricious nature of the pyrolytic carbon is particularly advantageous with drug coated stents. The drug coatings and polymer containing drugs, agents or compounds should preferably remain on the stent for best results. A lubricious coating on the sheath substantially reduces the risk of the drug or polymer from rubbing off during delivery.

The self-expanding stent delivery system of the present invention may also comprise a modified shaft. The modified shaft may include a plurality of elements which protrude from the shaft in the gaps between the stent elements. These elements may significantly reduce the forces acting upon the stent during deployment by preventing or substantially reducing the compression of the stent. Without the plurality of elements, the stent may move and compress against a stop on the inner shaft of the delivery system. Compression of the stent leads to higher deployment forces. Accordingly, a shaft comprising a plurality of elements eliminates or substantially reduces longitudinal movement of the stent, thereby eliminating or substantially reducing compression. In addition, the protruding elements distribute the total force acting upon the stent over the plurality of elements so that there is less localized stress on the stent and any coating thereon.

The composition for coating the surface of an implantable medical device of the present invention uses a combination of two chemically different polymers to achieve a coating that provides a chemical and physical barrier to drug release. This combination is durable, lubricious and provides control over the elution rate of any drugs, agents, and/or compounds contained in the coating.

Microneedles or other catheter-based delivery systems such as perfusion balloons may be utilized to deliver one or more drugs, agents and/or compounds, including rapamycin, to the site of atherosclerotic plaque. This type of regional delivery may be utilized alone or in combination with an implantable medical device with the same or different drugs affixed thereto. The one or more drugs, agents and/or compounds are preferably delivered to the adventitial space proximate the lesion.

A locally or regionally delivered solution of a potent therapeutic agent, such as rapamycin, offers a number of advantages over a systemically delivered agent or an agent delivered via an implantable medical device. For example, a relatively high tissue concentration may be achieved by the direct deposition of the pharmaceutical agent in the arterial wall. Depending on the location of the deposition, a different drug concentration profile may be achieved than through that of a drug eluting stent. In addition, with a locally or regionally delivered solution, there is no need for a permanently implanted device such as a stent, thereby eliminating the potential side affects associated therewith, such as inflammatory reaction and long term tissue damage. It is, however, important to note that the locally or regionally delivered solution may be utilized in combination with drug eluting stents or other coated implantable medical devices. Another advantage of solution or liquid formulations lies in the fact that the adjustment of the excipients in the liquid formulation would readily change the drug distribution and retention profiles. In addition, the liquid formulation may be mixed immediately prior to the injection through a pre-packaged multi-chamber injection device to improve the storage and shelf life of the dosage forms.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 37 is a simplified elevational view of the distal end of the inner shaft made in accordance with the present invention.

FIG. 38 is a cross-sectional view of FIG. 37 taken along lines 38-38.

FIG. 57 is a graphical representation of the anti-proliferative activity of rapamycin with varying concentrations of cladribine in non-synchronized cultured human coronary artery smooth muscle cells stimulated with two percent fetal bovine serum in accordance with the present invention.

DETAILED DESCRIPTION OF THE PREFERRED EMBODIMENTS

Figure 1:
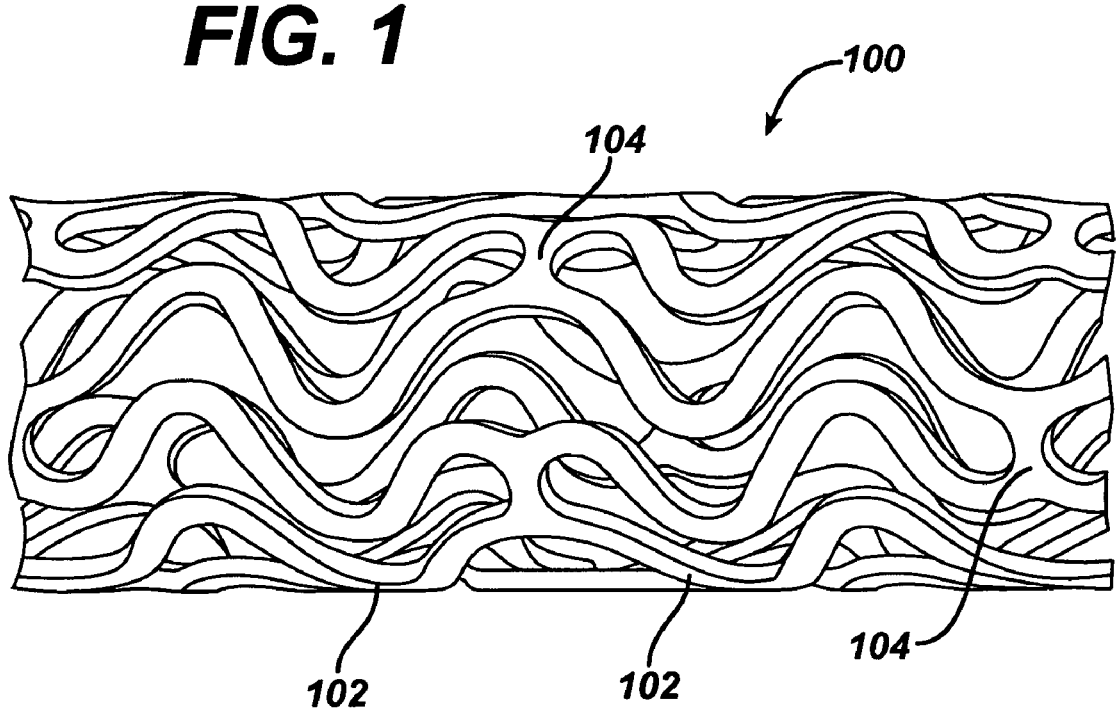
FIG. 1 is a view along the length of a stent (ends not shown) prior to expansion showing the exterior surface of the stent and the characteristic banding pattern.

The drug/drug combinations and delivery devices of the present invention may be utilized to effectively prevent and treat vascular disease, and in particular, vascular disease caused by injury. Various medical treatment devices utilized in the treatment of vascular disease may ultimately induce further complications. For example, balloon angioplasty is a procedure utilized to increase blood flow through an artery and is the predominant treatment for coronary vessel stenosis. However, as stated above, the procedure typically causes a certain degree of damage to the vessel wall, thereby potentially exacerbating the problem at a point later in time. Although other procedures and diseases may cause similar injury, exemplary embodiments of the present invention will be described with respect to the treatment of restenosis and related complications following percutaneous transluminal coronary angioplasty and other similar arterial/venous procedures, including the joining of arteries, veins and other fluid carrying conduits. In addition, various methods and devices will be described for the effective delivery of the coated medical devices.

While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b$/$III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, a combination of drugs, agents or compounds which prevents smooth muscle cell proliferation, reduces inflammation and reduces coagulation or prevents smooth muscle cell proliferation by multiple mechanisms, reduces inflammation and reduces coagulation combined with a stent may provide the most efficacious treatment for post-angioplasty restenosis. The systemic use of drugs, agents or compounds in combination with the local delivery of the same or different drug/drug combinations may also provide a beneficial treatment option.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents that may be utilized following percutaneous transluminal coronary angioplasty. Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

FIG. 1 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one exemplary embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 2:
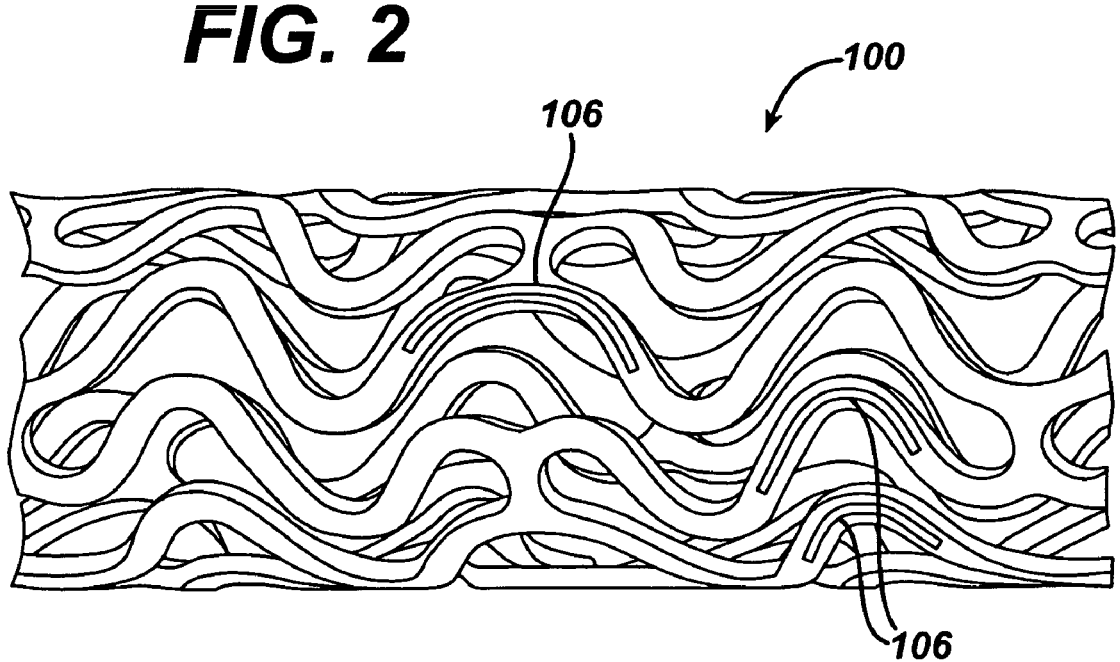
FIG. 2 is a perspective view along the length of the stent of FIG. 1 having reservoirs in accordance with the present invention.

FIG. 2 illustrates an exemplary embodiment of the present invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with drug/drug combinations in therapeutic dosage amounts. A detailed description of a drug for treating restenosis, as well as exemplary coating techniques, is described below. It is, however, important to note that the coating techniques may vary depending on the drug/drug combinations. Also, the coating techniques may vary depending on the material comprising the stent or other intraluminal medical device.

Rapamycin is a macrocyclic triene antibiotic produced by *Streptomyces hygroscopicus* as disclosed in U.S. Pat. No. 3,929,992. It has been found that rapamycin among other things inhibits the proliferation of vascular smooth muscle cells in vivo. Accordingly, rapamycin may be utilized in treating intimal smooth muscle cell hyperplasia, restenosis, and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin reduces vascular hyperplasia by antagonizing smooth muscle proliferation in response to mitogenic signals that are released during an angioplasty induced injury. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

As used herein, rapamycin includes rapamycin and all analogs, derivatives and conjugates that bind to FKBP12, and other immunophilins and possesses the same pharmacologic properties as rapamycin including inhibition of TOR.

Although the anti-proliferative effects of rapamycin may be achieved through systemic use, superior results may be achieved through the local delivery of the compound. Essentially, rapamycin works in the tissues, which are in proximity to the compound, and has diminished effect as the distance from the delivery device increases. In order to take advantage of this effect, one would want the rapamycin in direct contact with the lumen walls. Accordingly, in a preferred embodiment, the rapamycin is incorporated onto the surface of the stent or portions thereof. Essentially, the rapamycin is preferably incorporated into the stent 100, illustrated in FIG. 1, where the stent 100 makes contact with the lumen wall.

Rapamycin may be incorporated onto or affixed to the stent in a number of ways. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months, and more preferably between seven and thirty days.

Any number of non-erodible polymers may be utilized in conjunction with rapamycin. In one exemplary embodiment, the rapamycin or other therapeutic agent may be incorporated into a film-forming polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, wherein the relative amounts of the first moiety and the second moiety are effective to provide the coating and film produced therefrom with properties effective for use in treating implantable medical devices.

The present invention provides polymeric coatings comprising a polyfluoro copolymer and implantable medical devices, for example, stents coated with a film of the polymeric coating in amounts effective to reduce thrombosis and/or restenosis when such stents are used in, for example, angioplasty procedures. As used herein, polyfluoro copolymers means those copolymers comprising an amount of a first moiety selected from the group consisting of polymerized vinylidenefluoride and polymerized tetrafluoroethylene, and an amount of a second moiety other than the first moiety and which is copolymerized with the first moiety to produce the polyfluoro copolymer, the second moiety being capable of providing toughness or elastomeric properties to the polyfluoro copolymer, wherein the relative amounts of the first moiety and the second moiety are effective to provide coatings and film made from such polyfluoro copolymers with properties effective for use in coating implantable medical devices.

The coatings may comprise pharmaceutical or therapeutic agents for reducing restenosis, inflammation, and/or thrombosis, and stents coated with such coatings may provide sustained release of the agents. Films prepared from certain polyfluoro copolymer coatings of the present invention provide the physical and mechanical properties required of conventional coated medical devices, even where maximum temperature, to which the device coatings and films are exposed, are limited to relatively low temperatures. This is particularly important when using the coating/film to deliver pharmaceutical/therapeutic agents or drugs that are heat sensitive, or when applying the coating onto temperature-sensitive devices such as catheters. When maximum exposure temperature is not an issue, for example, where heat-stable agents such as itraconazole are incorporated into the coatings, higher melting thermoplastic polyfluoro copolymers may be used and, if very high elongation and adhesion is required, elastomers may be used. If desired or required, the polyfluoro elastomers may be crosslinked by standard methods described in, e.g., *Modern Fluoropolymers*, (J. Shires ed.), John Wiley & Sons, New York, 1997, pp. 77-87.

The present invention comprises polyfluoro copolymers that provide improved biocompatible coatings or vehicles for medical devices. These coatings provide inert biocompatible surfaces to be in contact with body tissue of a mammal, for example, a human, sufficient to reduce restenosis, or thrombosis, or other undesirable reactions. While many reported coatings made from polyfluoro homopolymers are insoluble and/or require high heat, for example, greater than about one hundred twenty-five degrees centigrade, to obtain films with adequate physical and mechanical properties for use on implantable devices, for example, stents, or are not particularly tough or elastomeric, films prepared from the polyfluoro copolymers of the present invention provide adequate adhesion, toughness or elasticity, and resistance to cracking when formed on medical devices. In certain exemplary embodiments, this is the case even where the devices are subjected to relatively low maximum temperatures.

The polyfluoro copolymers used for coatings according to the present invention are preferably film-forming polymers that have molecular weight high enough so as not to be waxy or tacky. The polymers and films formed therefrom should preferably adhere to the stent and not be readily deformable after deposition on the stent as to be able to be displaced by hemodynamic stresses. The polymer molecular weight should preferably be high enough to provide sufficient toughness so that films comprising the polymers will not be rubbed off during handling or deployment of the stent. In certain exemplary embodiments the coating will not crack where expansion of the stent or other medical devices occurs.

Coatings of the present invention comprise polyfluoro copolymers, as defined hereinabove. The second moiety polymerized with the first moiety to prepare the polyfluoro copolymer may be selected from those polymerized, biocompatible monomers that would provide biocompatible polymers acceptable for implantation in a mammal, while maintaining sufficient elastomeric film properties for use on medical devices claimed herein. Such monomers include, without limitation, hexafluoropropylene (HFP), tetrafluoroethylene (TFE), vinylidenefluoride, 1-hydropentafluoropropylene, perfluoro(methyl vinyl ether), chlorotrifluoroethylene (CTFE), pentafluoropropene, trifluoroethylene, hexafluoroacetone and hexafluoroisobutylene.

Polyfluoro copolymers used in the present invention typically comprise vinylidinefluoride copolymerized with hexafluoropropylene, in the weight ratio in the range of from about fifty to about ninety-two weight percent vinylidinefluoride to about fifty to about eight weight percent HFP. Preferably, polyfluoro copolymers used in the present invention comprise from about fifty to about eighty-five weight percent vinylidinefluoride copolymerized with from about fifty to about fifteen weight percent HFP. More preferably, the polyfluoro copolymers will comprise from about fifty-five to about seventy weight percent vinylidinefluoride copolymerized with from about forty-five to about thirty weight percent HFP. Even more preferably, polyfluoro copolymers comprise from about fifty-five to about sixty-five weight percent vinylidinefluoride copolymerized with from about forty-five to about thirty-five weight percent HFP. Such polyfluoro copolymers are soluble, in varying degrees, in solvents such as dimethylacetamide (DMAc), tetrahydrofuran, dimethyl formamide, dimethyl sulfoxide and n-methylpyrrolidone. Some are soluble in methylethylketone (MEK), acetone, methanol and other solvents commonly used in applying coatings to conventional implantable medical devices.

Conventional polyfluoro homopolymers are crystalline and difficult to apply as high quality films onto metal surfaces without exposing the coatings to relatively high temperatures that correspond to the melting temperature (Tm) of the polymer. The elevated temperature serves to provide films prepared from such PVDF homopolymer coatings that exhibit sufficient adhesion of the film to the device, while preferably maintaining sufficient flexibility to resist film cracking upon expansion/contraction of the coated medical device. Certain films and coatings according to the present invention provide these same physical and mechanical properties, or essentially the same properties, even when the maximum temperatures to which the coatings and films are exposed is less than about a maximum predetermined temperature. This is particularly important when the coatings/films comprise pharmaceutical or therapeutic agents or drugs that are heat sensitive, for example, subject to chemical or physical degradation or other heat-induced negative affects, or when coating heat sensitive substrates of medical devices, for example, subject to heat-induced compositional or structural degradation.

Depending on the particular device upon which the coatings and films of the present invention are to be applied and the particular use/result required of the device, polyfluoro copolymers used to prepare such devices may be crystalline, semi-crystalline or amorphous.

Where devices have no restrictions or limitations with respect to exposure of same to elevated temperatures, crystalline polyfluoro copolymers may be employed. Crystalline polyfluoro copolymers tend to resist the tendency to flow under applied stress or gravity when exposed to temperatures above their glass transition (Tg) temperatures. Crystalline polyfluoro copolymers provide tougher coatings and films than their fully amorphous counterparts. In addition, crystalline polymers are more lubricious and more easily handled through crimping and transfer processes used to mount self-expanding stents, for example, nitinol stents.

Semi-crystalline and amorphous polyfluoro copolymers are advantageous where exposure to elevated temperatures is an issue, for example, where heat-sensitive pharmaceutical or therapeutic agents are incorporated into the coatings and films, or where device design, structure and/or use preclude exposure to such elevated temperatures. Semi-crystalline polyfluoro copolymer elastomers comprising relatively high levels, for example, from about thirty to about forty-five weight percent of the second moiety, for example, HFP, copolymerized with the first moiety, for example, VDF, have the advantage of reduced coefficient of friction and self-blocking relative to amorphous polyfluoro copolymer elastomers. Such characteristics may be of significant value when processing, packaging and delivering medical devices coated with such polyfluoro copolymers. In addition, such polyfluoro copolymer elastomers comprising such relatively high content of the second moiety serves to control the solubility of certain agents, for example, rapamycin, in the polymer and therefore controls permeability of the agent through the matrix.

Polyfluoro copolymers utilized in the present inventions may be prepared by various known polymerization methods. For example, high pressure, free-radical, semi-continuous emulsion polymerization techniques such as those disclosed in *Fluoroelastomers-dependence of relaxation phenomena on compositions*, POLYMER 30, 2180, 1989, by Ajroldi, et al., may be employed to prepare amorphous polyfluoro copolymers, some of which may be elastomers. In addition, free-radical batch emulsion polymerization techniques disclosed herein may be used to obtain polymers that are semi-crystalline, even where relatively high levels of the second moiety are included.

As described above, stents may comprise a wide variety of materials and a wide variety of geometries. Stents may be made of biocomptible materials, including biostable and bioabsorbable materials. Suitable biocompatible metals include, but are not limited to, stainless steel, tantalum, titanium alloys (including nitinol), and cobalt alloys (including cobalt-chromium nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, ε-caprolactone, and blends thereof).

The film-forming biocompatible polymer coatings generally are applied to the stent in order to reduce local turbulence in blood flow through the stent, as well as adverse tissue reactions. The coatings and films formed therefrom also may be used to administer a pharmaceutically active material to the site of the stent placement. Generally, the amount of polymer coating to be applied to the stent will vary depending on, among other possible parameters, the particular polyfluoro copolymer used to prepare the coating, the stent design and the desired effect of the coating. Generally, the coated stent will comprise from about 0.1 to about fifteen weight percent of the coating, preferably from about 0.4 to about ten weight percent. The polyfluoro copolymer coatings may be applied in one or more coating steps, depending on the amount of polyfluoro copolymer to be applied. Different polyfluoro copolymers may be used for different layers in the stent coating. In fact, in certain exemplary embodiments, it is highly advantageous to use a diluted first coating solution comprising a polyfluoro copolymer as a primer to promote adhesion of a subsequent polyfluoro copolymer coating layer that may include pharmaceutically active materials. The individual coatings may be prepared from different polyfluoro copolymers.

Additionally, a top coating may be applied to delay release of the pharmaceutical agent, or they could be used as the matrix for the delivery of a different pharmaceutically active material. Layering of coatings may be used to stage release of the drug or to control release of different agents placed in different layers.

Blends of polyfluoro copolymers may also be used to control the release rate of different agents or to provide a desirable balance of coating properties, i.e. elasticity, toughness, etc., and drug delivery characteristics, for example, release profile. Polyfluoro copolymers with different solubilities in solvents may be used to build up different polymer layers that may be used to deliver different drugs or to control the release profile of a drug. For example, polyfluoro copolymers comprising 85.5/14.5 (wt/wt) of poly(vinylidinefluoride/HFP) and 60.6/39.4 (wt/wt) of poly(vinylidinefluoride/HFP) are both soluble in DMAc. However, only the 60.6/39.4 PVDF polyfluoro copolymer is soluble in methanol. So, a first layer of the 85.5/14.5 PVDF polyfluoro copolymer comprising a drug could be over coated with a topcoat of the 60.6/39.4 PVDF polyfluoro copolymer made with the methanol solvent. The top coating may be used to delay the drug delivery of the drug contained in the first layer. Alternately, the second layer could comprise a different drug to provide for sequential drug delivery. Multiple layers of different drugs could be provided by alternating layers of first one polyfluoro copolymer, then the other. As will be readily appreciated by those skilled in the art, numerous layering approaches may be used to provide the desired drug delivery.

Coatings may be formulated by mixing one or more therapeutic agents with the coating polyfluoro copolymers in a coating mixture. The therapeutic agent may be present as a liquid, a finely divided solid, or any other appropriate physical form. Optionally, the coating mixture may include one or more additives, for example, nontoxic auxiliary substances such as diluents, carriers, excipients, stabilizers or the like. Other suitable additives may be formulated with the polymer and pharmaceutically active agent or compound. For example, a hydrophilic polymer may be added to a biocompatible hydrophobic coating to modify the release profile, or a hydrophobic polymer may be added to a hydrophilic coating to modify the release profile. One example would be adding a hydrophilic polymer selected from the group consisting of polyethylene oxide, polyvinyl pyrrolidone, polyethylene glycol, carboxylmethyl cellulose, and hydroxymethyl cellulose to a polyfluoro copolymer coating to modify the release profile. Appropriate relative amounts may be determined by monitoring the in vitro and/or in vivo release profiles for the therapeutic agents.

The best conditions for the coating application are when the polyfluoro copolymer and pharmaceutic agent have a common solvent. This provides a wet coating that is a true solution. Less desirable, yet still usable, are coatings that contain the pharmaceutical agent as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that need to remain essentially free of coating. In cases where a dispersion is applied to the stent and the smoothness of the coating film surface requires improvement, or to be ensured that all particles of the drug are fully encapsulated in the polymer, or in cases where the release rate of the drug is to be slowed, a clear (polyfluoro copolymer only) topcoat of the same polyfluoro copolymer used to provide sustained release of the drug or another polyfluoro copolymer that further restricts the diffusion of the drug out of the coating may be applied. The topcoat may be applied by dip coating with mandrel to clear the slots. This method is disclosed in U.S. Pat. No. 6,153,252. Other methods for applying the topcoat include spin coating and spray coating. Dip coating of the topcoat can be problematic if the drug is very soluble in the coating solvent, which swells the polyfluoro copolymer, and the clear coating solution acts as a zero concentration sink and redissolves previously deposited drug. The time spent in the dip bath may need to be limited so that the drug is not extracted out into the drug-free bath. Drying should be rapid so that the previously deposited drug does not completely diffuse into the topcoat.

The amount of therapeutic agent will be dependent upon the particular drug employed and medical condition being treated. Typically, the amount of drug represents about 0.001 percent to about seventy percent of the total coating weight, more typically about 0.001 percent to about sixty percent of the total coating weight. It is possible that the drug may represent as little as 0.0001 percent to the total coating weight.

The quantity and type of polyfluoro copolymers employed in the coating film comprising the pharmaceutic agent will vary depending on the release profile desired and the amount of drug employed. The product may contain blends of the same or different polyfluoro copolymers having different molecular weights to provide the desired release profile or consistency to a given formulation.

Polyfluoro copolymers may release dispersed drug by diffusion. This can result in prolonged delivery (over, say approximately one to two-thousand hours, preferably two to eight-hundred hours) of effective amounts (0.001 $\mu g/cm^2$-min to 1000 $\mu g/cm^2$-min) of the drug. The dosage may be tailored to the subject being treated, the severity of the affliction, the judgment of the prescribing physician, and the like.

Individual formulations of drugs and polyfluoro copolymers may be tested in appropriate in vitro and in vivo models to achieve the desired drug release profiles. For example, a drug could be formulated with a polyfluoro copolymer, or blend of polyfluoro copolymers, coated onto a stent and placed in an agitated or circulating fluid system, for example, twenty-five percent ethanol in water. Samples of the circulating fluid could be taken to determine the release profile (such as by HPLC, UV analysis or use of radiotagged molecules). The release of a pharmaceutical compound from a stent coating into the interior wall of a lumen could be modeled in appropriate animal system. The drug release profile could then be monitored by appropriate means such as, by taking samples at specific times and assaying the samples for drug concentration (using HPLC to detect drug concentration). Thrombus formation can be modeled in animal models using the In-platelet imaging methods described by Hanson and Harker, Proc. Natl. Acad. Sci. USA 85:3184-3188 (1988). Following this or similar procedures, those skilled in the art will be able to formulate a variety of stent coating formulations.

While not a requirement of the present invention, the coatings and films may be crosslinked once applied to the medical devices. Crosslinking may be affected by any of the known crosslinking mechanisms, such as chemical, heat or light. In addition, crosslinking initiators and promoters may be used where applicable and appropriate. In those exemplary embodiments utilizing crosslinked films comprising pharmaceutical agents, curing may affect the rate at which the drug diffuses from the coating. Crosslinked polyfluoro copolymers films and coatings of the present invention also may be used without drug to modify the surface of implantable medical devices.

EXAMPLES

Example 1

A PVDF homopolymer (Solef® 1008 from Solvay Advanced Polymers, Houston, Tex., Tm about 175° C.) and polyfluoro copolymers of poly(vinylidenefluoride/HFP), 92/8 and 91/9 weight percent vinylidenefluoride/HFP as determined by $F^{19}$ NMR, respectively (e.g.: Solef® 11010 and 11008, Solvay Advanced Polymers, Houston, Tex., Tm about 159 degrees C. and 160 degrees C., respectively) were examined as potential coatings for stents. These polymers are soluble in solvents such as, but not limited to, DMAc, N,N-dimethylformamide (DMF), dimethyl sulfoxide (DMSO), N-methylpyrrolidone (NM P), tetrahydrofuran (TH F) and acetone. Polymer coatings were prepared by dissolving the polymers in acetone, at five weight percent as a primer, or by dissolving the polymer in 50/50 DMAc/acetone, at thirty weight percent as a topcoat. Coatings that were applied to the stents by dipping and dried at 60 degrees C. in air for several hours, followed by 60 degrees C. for three hours in a <100 mm Hg vacuum, resulted in white foamy films. As applied, these films adhered poorly to the stent and flaked off, indicating they were too brittle. When stents coated in this manner were heated above 175 degrees C., i.e. above the melting temperature of the polymer, a clear, adherent film was formed. Since coatings require high temperatures, for example, above the melting temperature of the polymer, to achieve high quality films. As mentioned above, the high temperature heat treatment is unacceptable for the majority of drug compounds due to their thermal sensitivity.

Example 2

A polyfluoro copolymer (Solef® 21508) comprising 85.5 weight percent vinylidenefluoride copolymerized with 14.5 weight percent HFP, as determined by $F^{19}$ NMR, was evaluated. This copolymer is less crystalline than the polyfluoro homopolymer and copolymers described in Example 1. It also has a lower melting point reported to be about 133 degrees C. Once again, a coating comprising about twenty weight percent of the polyfluoro copolymer was applied from a polymer solution in 50/50 DMAc/MEK. After drying (in air) at 60 degrees C. for several hours, followed by 60 degrees C. for three hours in a <100 mtorr Hg vacuum, clear adherent films were obtained. This eliminated the need for a high temperature heat treatment to achieve high quality films. Coatings were smoother and more adherent than those of Example 1. Some coated stents that underwent expansion show some degree of adhesion loss and "tenting" as the film pulls away from the metal. Where necessary, modification of coatings containing such copolymers may be made, e.g. by addition of plasticizers or the like to the coating compositions. Films prepared from such coatings may be used to coat stents or other medical devices, particularly where those devices are not susceptible to expansion to the degree of the stents.

The coating process above was repeated, this time with a coating comprising the 85.5/14.6 (wt/wt) (vinylidenefluoride/HFP) and about thirty weight percent of rapamycin (Wyeth-Ayerst Laboratories, Philadelphia, Pa.), based on total weight of coating solids. Clear films that would occasionally crack or peel upon expansion of the coated stents resulted. It is believed that inclusion of plasticizers and the like in the coating composition will result in coatings and films for use on stents and other medical devices that are not susceptible to such cracking and peeling.

Example 3

Polyfluoro copolymers of still higher HFP content were then examined. This series of polymers were not semicrystalline, but rather are marketed as elastomers. One such copolymer is Fluorel™ FC2261Q (from Dyneon, a 3M-Hoechst Enterprise, Oakdale, Minn.), a 60.6/39.4 (wt/wt) copolymer of vinylidenefluoride/HFP. Although this copolymer has a Tg well below room temperature (Tg about minus twenty degrees C.) it is not tacky at room temperature or even at sixty degrees C. This polymer has no detectable crystallinity when measured by Differential Scanning Calorimetry (DSC) or by wide angle X-ray diffraction. Films formed on stents as described above were non-tacky, clear, and expanded without incident when the stents were expanded.

The coating process above was repeated, this time with coatings comprising the 60.6/39.4 (wt/wt) (vinylidenefluoride/HFP) and about nine, thirty and fifty weight percent of rapamycin (Wyeth-Ayerst Laboratories, Philadelphia, Pa.), based on total weight of coating solids, respectively. Coatings comprising about nine and thirty weight percent rapamycin provided white, adherent, tough films that expanded without incident on the stent. Inclusion of fifty percent drug, in the same manner, resulted in some loss of adhesion upon expansion.

Changes in the comonomer composition of the polyfluoro copolymer also can affect the nature of the solid state coating, once dried. For example, the semicrystalline copolymer, Solef® 21508, containing 85.5 percent vinylidenefluoride polymerized with 14.5 percent by weight HFP forms homogeneous solutions with about 30 percent rapamycin (drug weight divided by total solids weight, for example, drug plus copolymer) in DMAc and 50/50 DMAc/MEK. When the film is dried (60 degrees C./16 hours followed by 60 degrees C./3 hours in vacuum of 100 mm Hg) a clear coating, indicating a solid solution of the drug in the polymer, is obtained. Conversely, when an amorphous copolymer, Fluorel™ FC2261Q, of PDVF/HFP at 60.6/39.5 (wt/wt) forms a similar thirty percent solution of rapamycin in DMAc/MEK and is similarly dried, a white film, indicating phase separation of the drug and the polymer, is obtained. This second drug containing film is much slower to release the drug into an in vitro test solution of twenty-five percent ethanol in water than is the former clear film of crystalline Solef® 21508. X-ray analysis of both films indicates that the drug is present in a non-crystalline form. Poor or very low solubility of the drug in the high HFP containing copolymer results in slow permeation of the drug through the thin coating film. Permeability is the product of diffusion rate of the diffusing species (in this case the drug) through the film (the copolymer) and the solubility of the drug in the film.

Example 4

In Vitro Release Results of Rapamycin from Coating

Figure 3:
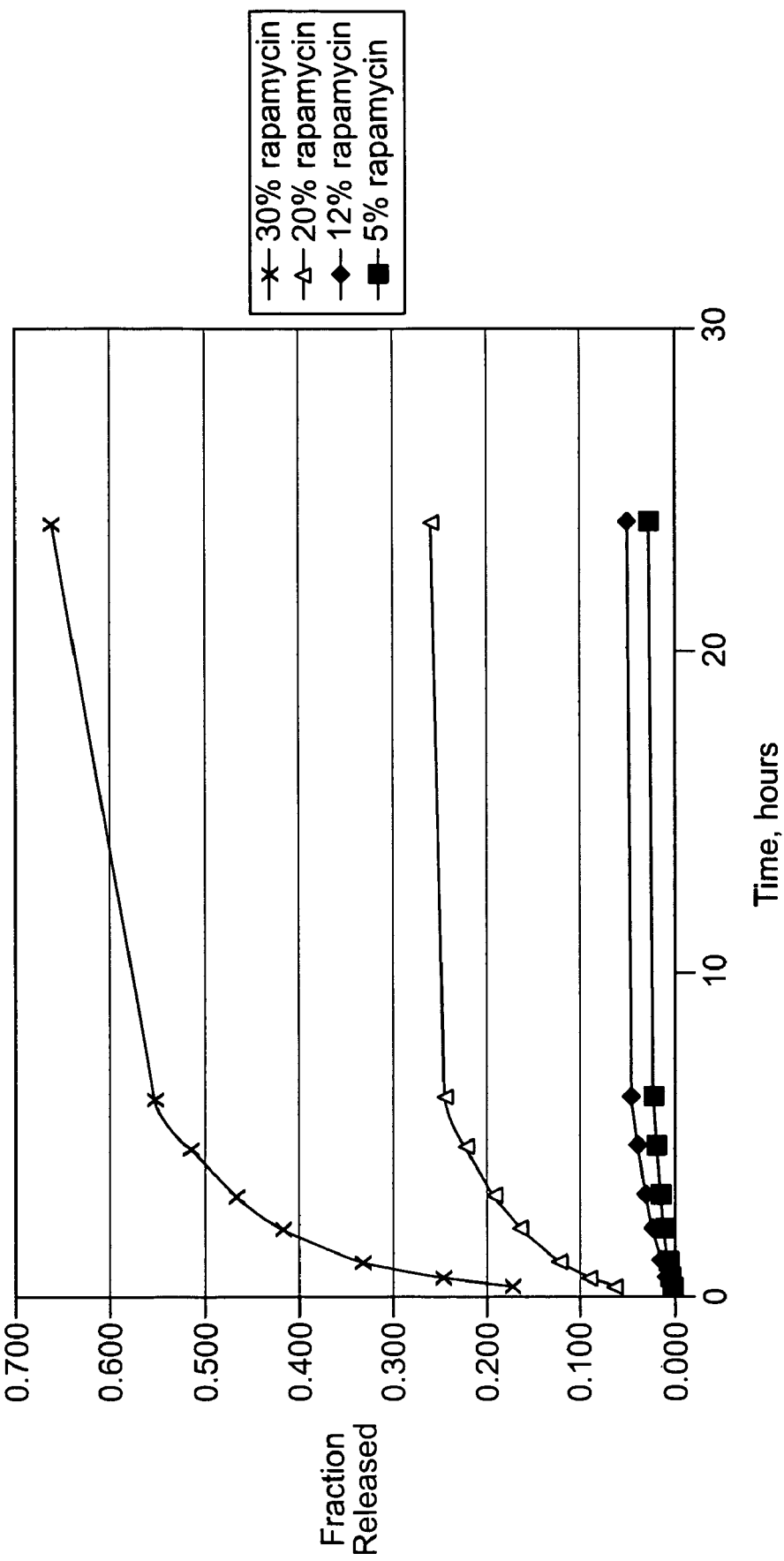
FIG. 3 indicates the fraction of drug released as a function of time from coatings of the present invention over which no topcoat has been disposed.
Figure 4:
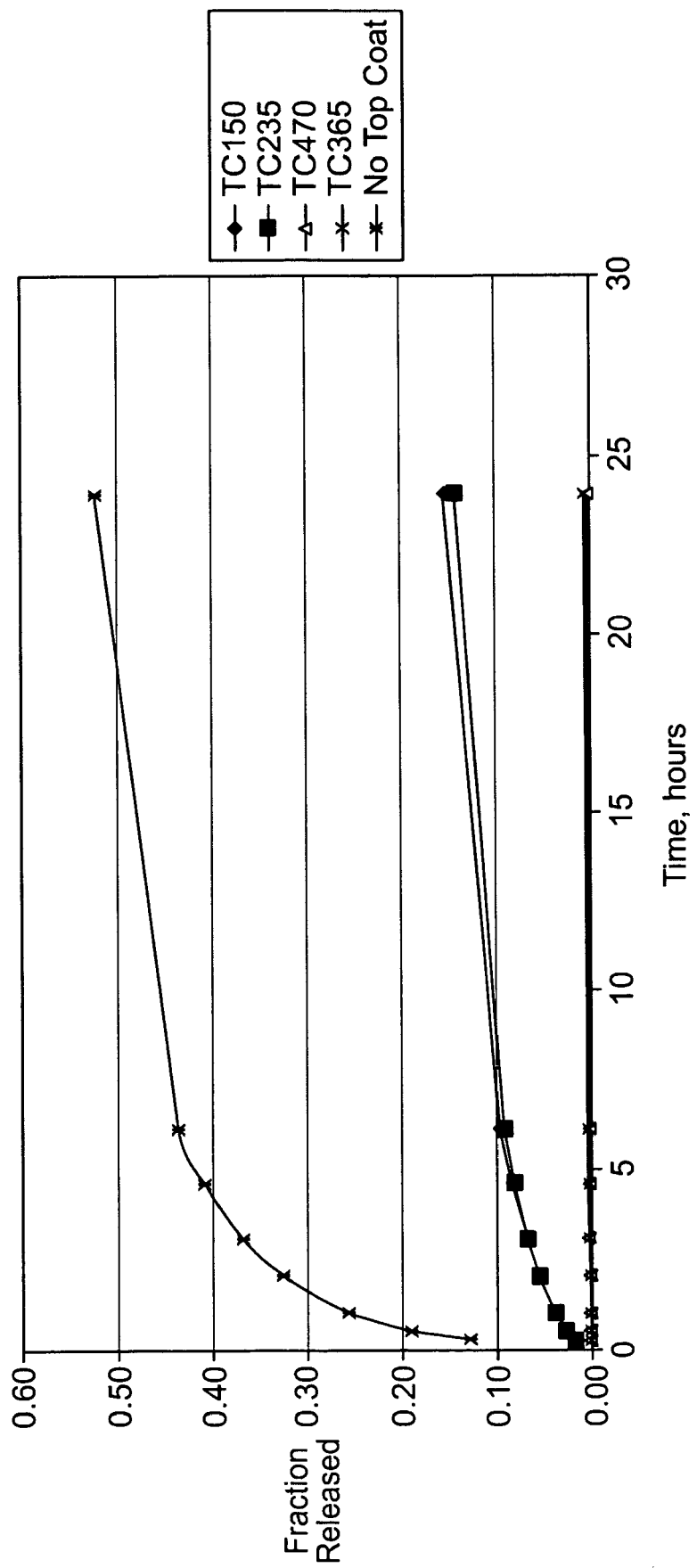
FIG. 4 indicates the fraction of drug released as a function of time from coatings of the present invention including a topcoat disposed thereon.
Figure 5:
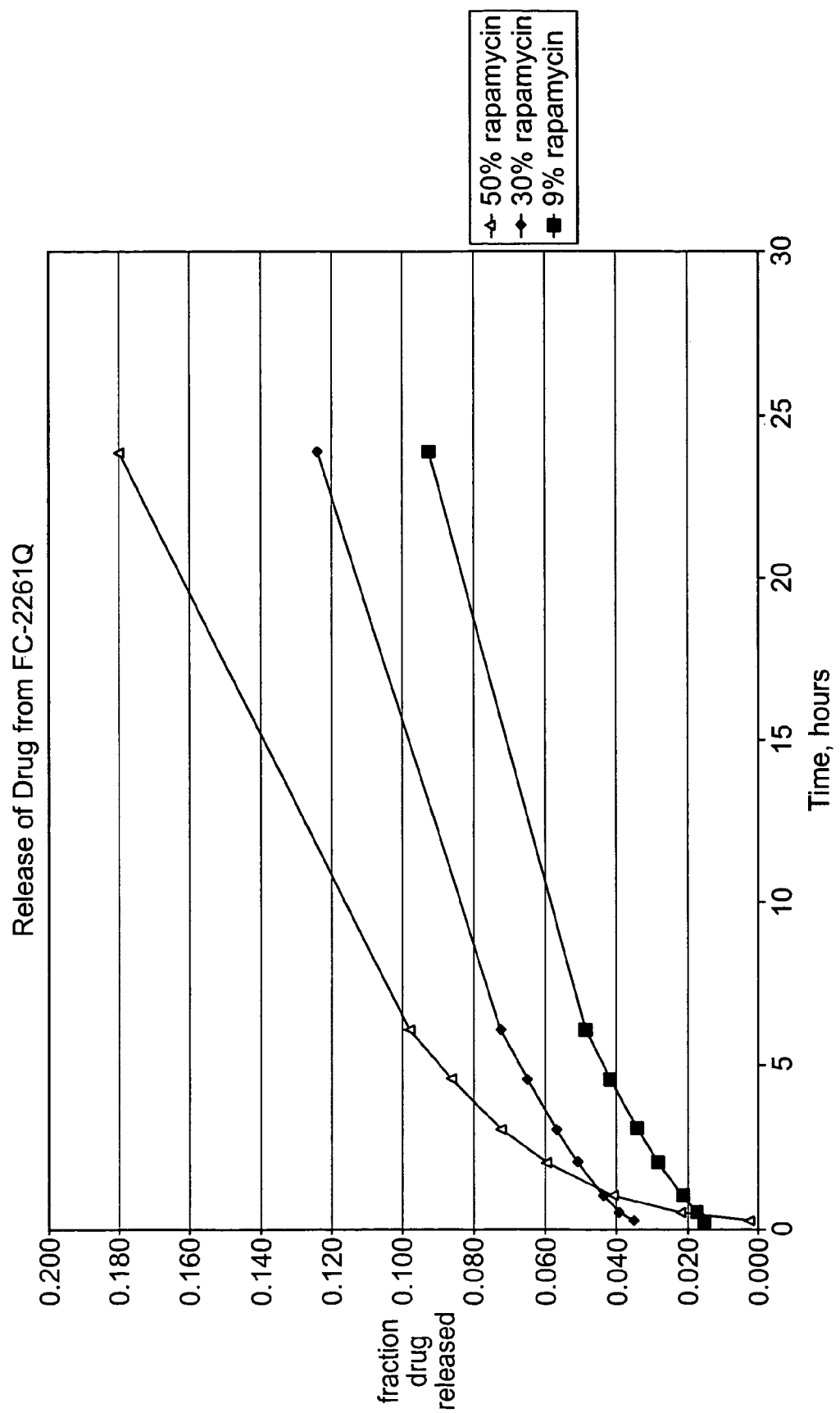
FIG. 5 indicates the fraction of drug released as a function of time from coatings of the present invention over which no topcoat has been disposed.
Figure 6:
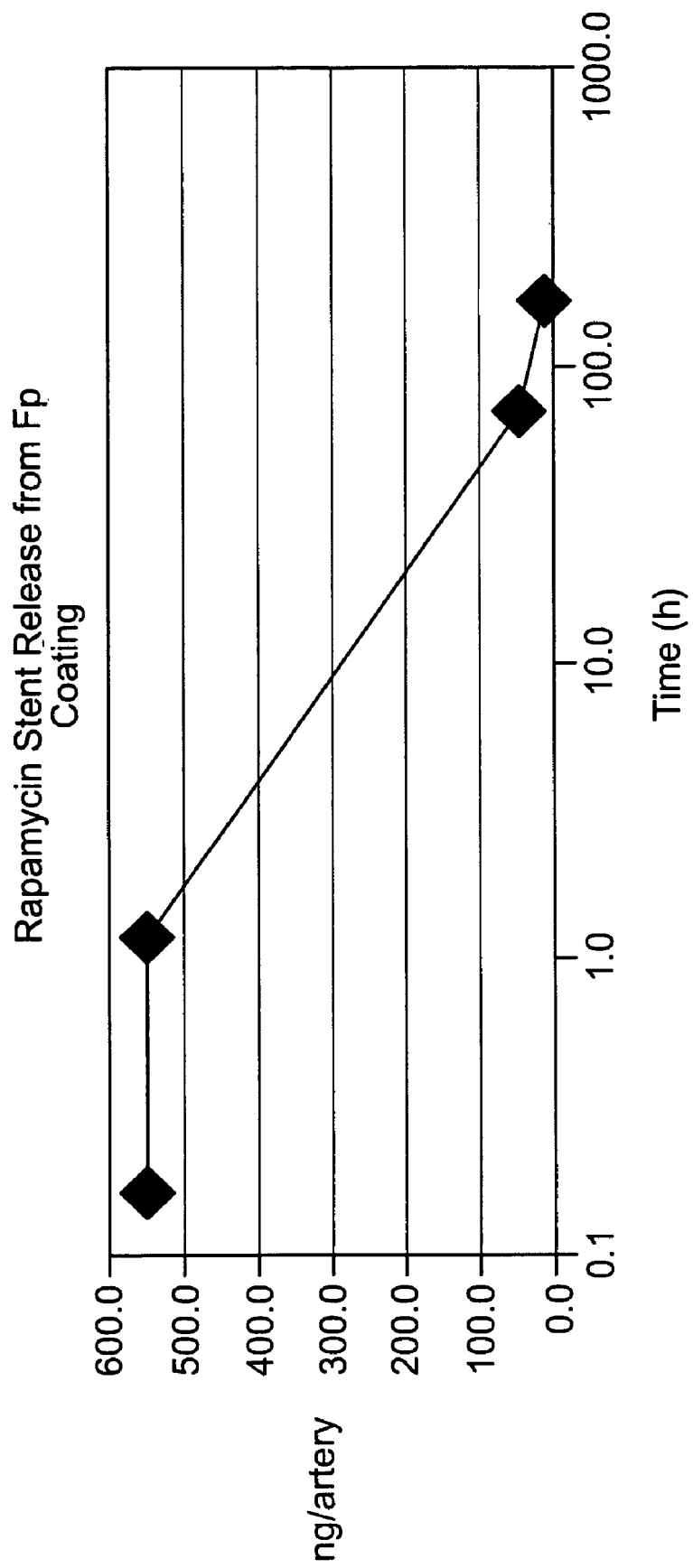
FIG. 6 indicates in vivo stent release kinetics of rapamycin from poly(VDF/HFP).

FIG. 3 is a plot of data for the 85.5/14.5 vinylidenefluoride/HFP polyfluoro copolymer, indicating fraction of drug released as a function of time, with no topcoat. FIG. 4 is a plot of data for the same polyfluoro copolymer over which a topcoat has been disposed, indicating that most effect on release rate is with a clear topcoat. As shown therein, TC150 refers to a device comprising one hundred fifty micrograms of topcoat, TC235 refers to two hundred thirty-five micrograms of topcoat, etc. The stents before topcoating had an average of seven hundred fifty micrograms of coating containing thirty percent rapamycin. FIG. 5 is a plot for the 60.6/39.4 vinylidenefluoride/HFP polyfluoro copolymer, indicating fraction of drug released as a function of time, showing significant control of release rate from the coating without the use of a topcoat. Release is controlled by loading of drug in the film.

Example 5

In Vivo Stent Release Kinetics of Rapamycin from Poly(VDF/HFP)

Nine New Zealand white rabbits (2.5-3.0 kg) on a normal diet were given aspirin twenty-four hours prior to surgery, again just prior to surgery and for the remainder of the study. At the time of surgery, animals were premedicated with Acepromazine (0.1-0.2 mg/kg) and anesthetized with a Ketamine/Xylazine mixture (40 mg/kg and 5 mg/kg, respectively). Animals were given a single intraprocedural dose of heparin (150 IU/kg, i.v.).

Arteriectomy of the right common carotid artery was performed and a 5 F catheter introducer (Cordis, Inc.) placed in the vessel and anchored with ligatures. Iodine contrast agent was injected to visualize the right common carotid artery, brachlocephalic trunk and aortic arch. A steerable guide wire (0.014 inch/180 cm, Cordis, Inc.) was inserted via the introducer and advanced sequentially into each iliac artery to a location where the artery possesses a diameter closest to 2 mm using the angiographic mapping done previously. Two stents coated with a film made of poly(VDF/HFP):(60.6/39.4) with thirty percent rapamycin were deployed in each animal where feasible, one in each iliac artery, using 3.0 mm balloon and inflation to 8-10 ATM for thirty seconds followed after a one minute interval by a second inflation to 8-10 ATM for thirty seconds. Follow-up angiographs visualizing both iliac arteries are obtained to confirm correct deployment position of the stent.

At the end of procedure, the carotid artery was ligated and the skin is closed with 3/0 vicryl suture using a one layered interrupted closure. Animals were given butoropanol (0.4 mg/kg, s.c.) and gentamycin (4 mg/kg, i.m.). Following recovery, the animals were returned to their cages and allowed free access to food and water.

Due to early deaths and surgical difficulties, two animals were not used in this analysis. Stented vessels were removed from the remaining seven animals at the following time points: one vessel (one animal) at ten minutes post implant; six vessels (three animals) between forty minutes and two hours post-implant (average, 1.2 hours); two vessels (two animals) at three days post implant; and two vessels (one animal) at seven days post-implant. In one animal at two hours, the stent was retrieved from the aorta rather than the iliac artery. Upon removal, arteries were carefully trimmed at both the proximal and distal ends of the stent. Vessels were then carefully dissected free of the stent, flushed to remove any residual blood, and both stent and vessel frozen immediately, wrapped separately in foil, labeled and kept frozen at minus eighty degrees C. When all samples had been collected, vessels and stents were frozen, transported and subsequently analyzed for rapamycin in tissue and results are illustrated in FIG. 4.

Example 6

Purifying the Polymer

The Fluorel™ FC2261Q copolymer was dissolved in MEK at about ten weight percent and was washed in a 50/50 mixture of ethanol/water at a 14:1 of ethanol/water to MEK solution ratio. The polymer precipitated out and was separated from the solvent phase by centrifugation. The polymer again was dissolved in MEK and the washing procedure repeated. The polymer was dried after each washing step at sixty degrees C. in a vacuum oven (<200 mtorr) over night.

Example 7

In Vivo Testing of Coated Stents in Porcine Coronary Arteries

CrossFlex® stents (available from Cordis, a Johnson & Johnson Company) were coated with the "as received" Fluorel™ FC2261 Q PVDF copolymer and with the purified polyfluoro copolymer of Example 6, using the dip and wipe approach. The coated stents were sterilized using ethylene oxide and a standard cycle. The coated stents and bare metal stents (controls) were implanted in porcine coronary arteries, where they remained for twenty-eight days.

Angiography was performed on the pigs at implantation and at twenty-eight days. Angiography indicated that the control uncoated stent exhibited about twenty-one percent restenosis. The polyfluoro copolymer "as received" exhibited about twenty-six percent restenosis (equivalent to the control) and the washed copolymer exhibited about 12.5 percent restenosis.

Histology results reported neointimal area at twenty-eight days to be $2.89\pm0.2$, $3.57\pm0.4$ and $2.75\pm0.3$, respectively, for the bare metal control, the unpurified copolymer and the purified copolymer.

Since rapamycin acts by entering the surrounding tissue, its preferably only affixed to the surface of the stent making contact with one tissue. Typically, only the outer surface of the stent makes contact with the tissue. Accordingly, in one exemplary embodiment, only the outer surface of the stent is coated with rapamycin.

The circulatory system, under normal conditions, has to be self-sealing, otherwise continued blood loss from an injury would be life threatening. Typically, all but the most catastrophic bleeding is rapidly stopped though a process known as hemostasis. Hemostasis occurs through a progression of steps. At high rates of flow, hemostasis is a combination of events involving platelet aggregation and fibrin formation. Platelet aggregation leads to a reduction in the blood flow due to the formation of a cellular plug while a cascade of biochemical steps leads to the formation of a fibrin clot.

Fibrin clots, as stated above, form in response to injury. There are certain circumstances where blood clotting or clotting in a specific area may pose a health risk. For example, during percutaneous transluminal coronary angioplasty, the endothelial cells of the arterial walls are typically injured, thereby exposing the sub-endothelial cells. Platelets adhere to these exposed cells. The aggregating platelets and the damaged tissue initiate further biochemical process resulting in blood coagulation. Platelet and fibrin blood clots may prevent the normal flow of blood to critical areas. Accordingly, there is a need to control blood clotting in various medical procedures. Compounds that do not allow blood to clot are called anti-coagulants. Essentially, an anti-coagulant is an inhibitor of thrombin formation or function. These compounds include drugs such as heparin and hirudin. As used herein, heparin includes all direct or indirect inhibitors of thrombin or Factor Xa.

In addition to being an effective anti-coagulant, heparin has also been demonstrated to inhibit smooth muscle cell growth in vivo. Thus, heparin may be effectively utilized in conjunction with rapamycin in the treatment of vascular disease. Essentially, the combination of rapamycin and heparin may inhibit smooth muscle cell growth via two different mechanisms in addition to the heparin acting as an anti-coagulant.

Because of its multifunctional chemistry, heparin may be immobilized or affixed to a stent in a number of ways. For example, heparin may be immobilized onto a variety of surfaces by various methods, including the photolink methods set forth in U.S. Pat. Nos. 3,959,078 and 4,722,906 to Guire et al. and U.S. Pat. Nos. 5,229,172; 5,308,641; 5,350,800 and 5,415,938 to Cahalan et al. Heparinized surfaces have also been achieved by controlled release from a polymer matrix, for example, silicone rubber, as set forth in U.S. Pat. Nos. 5,837,313; 6,099,562 and 6,120,536 to Ding et al.

Unlike rapamycin, heparin acts on circulating proteins in the blood and heparin need only make contact with blood to be effective. Accordingly, if used in conjunction with a medical device, such as a stent, it would preferably be only on the side that comes into contact with the blood. For example, if heparin were to be administered via a stent, it would only have to be on the inner surface of the stent to be effective.

Figure 7:
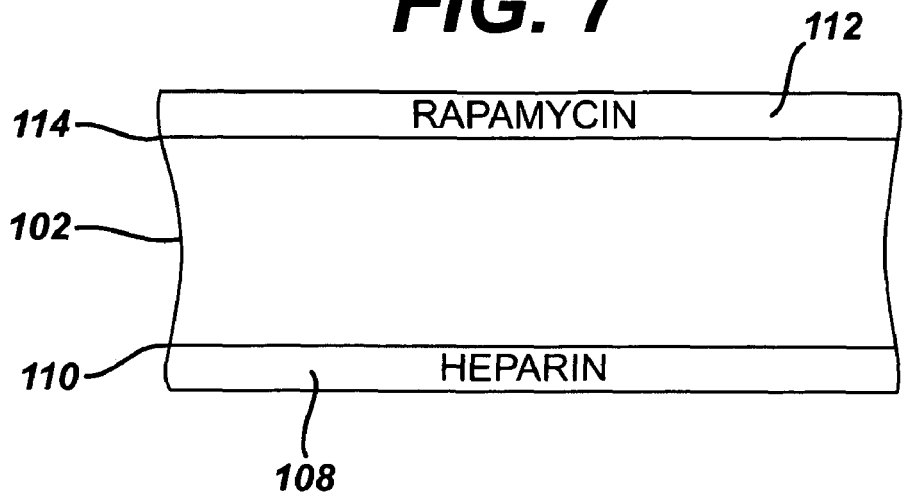
FIG. 7 is a cross-sectional view of a band of the stent of FIG. 1 having drug coatings thereon in accordance with a first exemplary embodiment of the invention.

In an exemplary embodiment of the invention, a stent may be utilized in combination with rapamycin and heparin to treat vascular disease. In this exemplary embodiment, the heparin is immobilized to the inner surface of the stent so that it is in contact with the blood and the rapamycin is immobilized to the outer surface of the stent so that it is in contact with the surrounding tissue. FIG. 7 illustrates a cross-section of a band 102 of the stent 100 illustrated in FIG. 1. As illustrated, the band 102 is coated with heparin 108 on its inner surface 110 and with rapamycin 112 on its outer surface 114.

Figure 8:
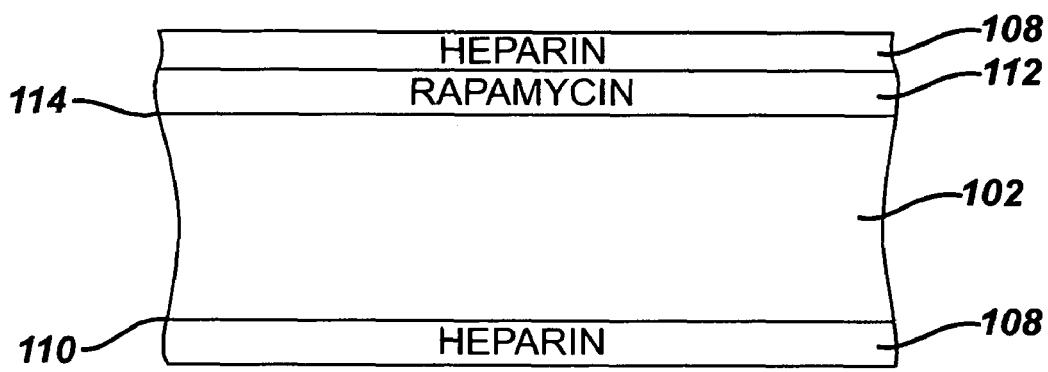
FIG. 8 is a cross-sectional view of a band of the stent of FIG. 1 having drug coatings thereon in accordance with a second exemplary embodiment of the invention.

In an alternate exemplary embodiment, the stent may comprise a heparin layer immobilized on its inner surface, and rapamycin and heparin on its outer surface. Utilizing current coating techniques, heparin tends to form a stronger bond with the surface it is immobilized to then does rapamycin. Accordingly, it may be possible to first immobilize the rapamycin to the outer surface of the stent and then immobilize a layer of heparin to the rapamycin layer. In this embodiment, the rapamycin may be more securely affixed to the stent while still effectively eluting from its polymeric matrix, through the heparin and into the surrounding tissue. FIG. 8 illustrates a cross-section of a band 102 of the stent 100 illustrated in FIG. 1. As illustrated, the band 102 is coated with heparin 108 on its inner surface 110 and with rapamycin 112 and heparin 108 on its outer surface 114.

Figure 9:
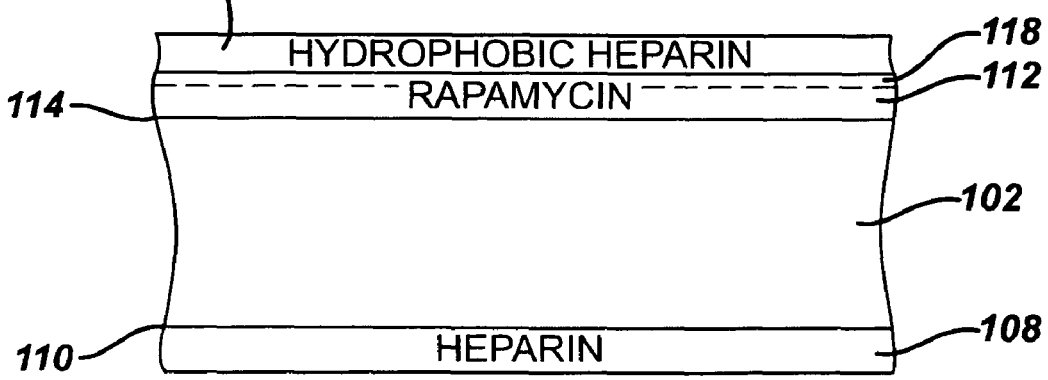
FIG. 9 is a cross-sectional view of a band of the stent of FIG. 1 having drug coatings thereon in accordance with a third exemplary embodiment of the present invention.
Figure 10:
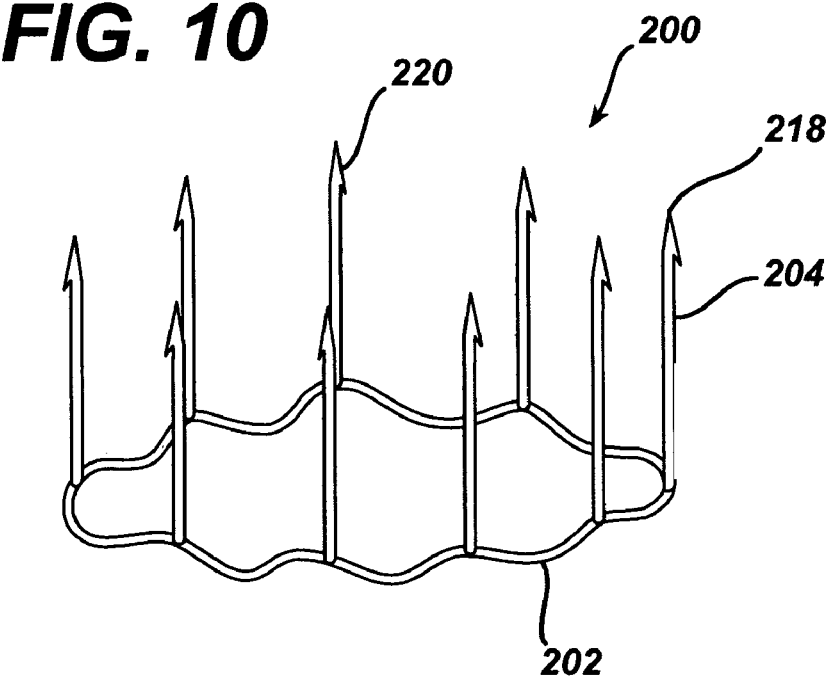
FIGS. 10-13 illustrate an exemplary one-piece embodiment of an anastomosis device having a fastening flange and attached staple members in accordance with the present invention.
Figure 11:
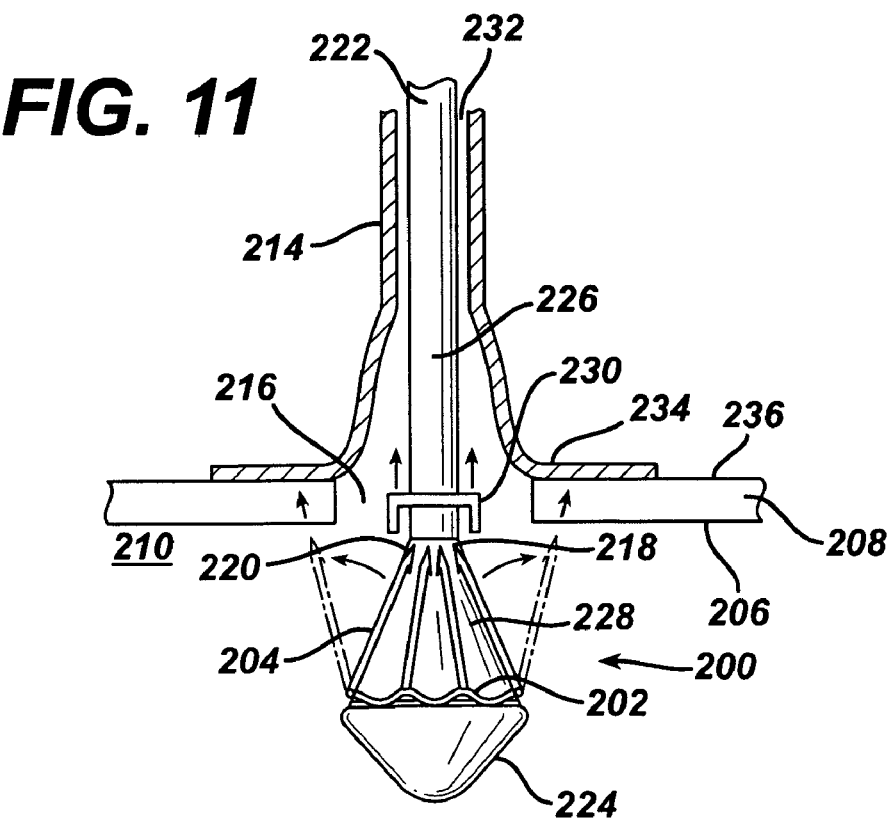
Figure 12:
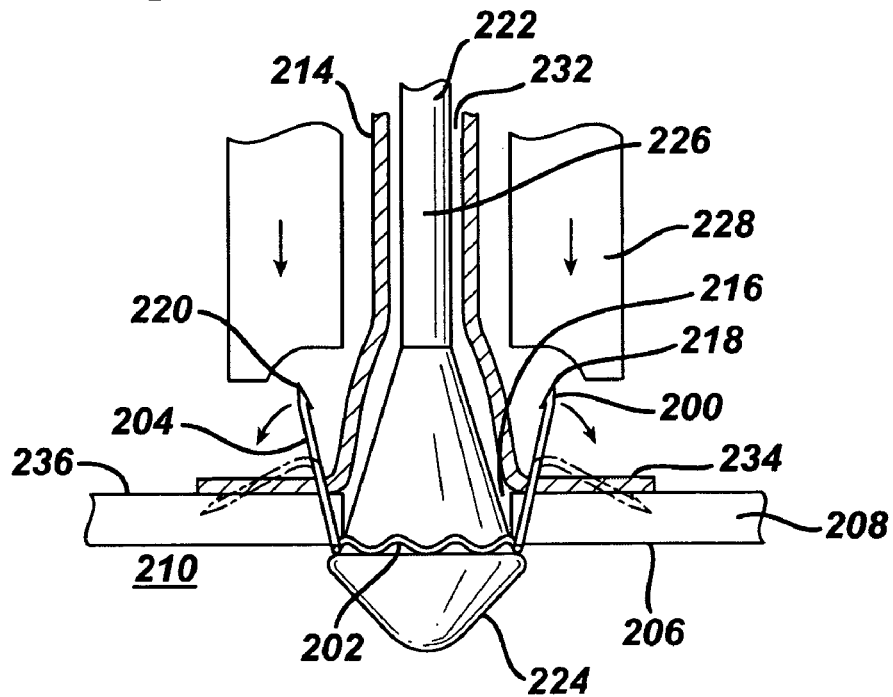
Figure 13:
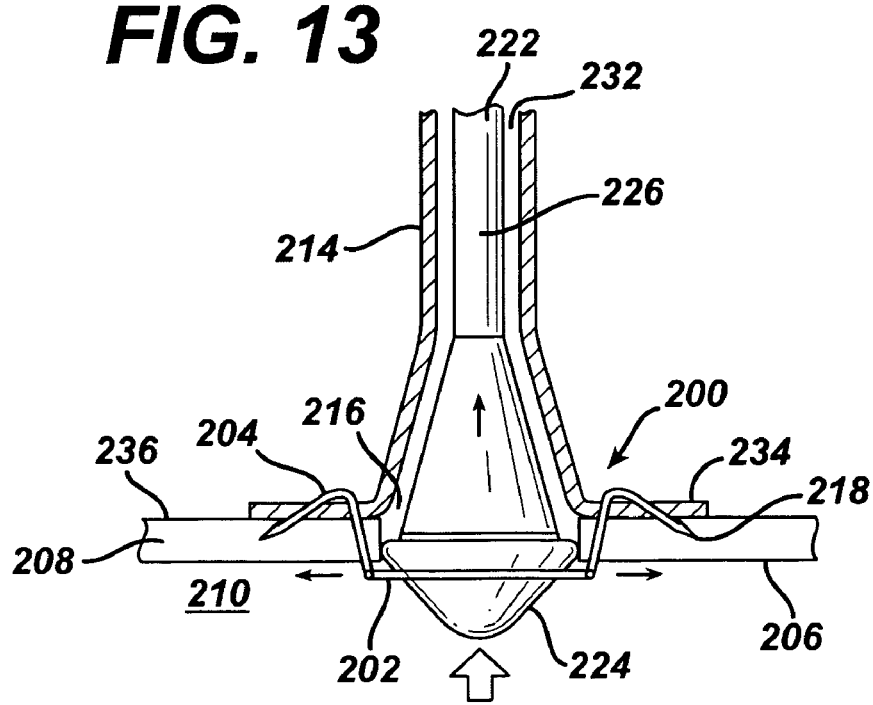

There are a number of possible ways to immobilize, i.e., entrapment or covalent linkage with an erodible bond, the heparin layer to the rapamycin layer. For example, heparin may be introduced into the top layer of the polymeric matrix. In other embodiments, different forms of heparin may be directly immobilized onto the top coat of the polymeric matrix, for example, as illustrated in FIG. 9. As illustrated, a hydrophobic heparin layer 116 may be immobilized onto the top coat layer 118 of the rapamycin layer 112. A hydrophobic form of heparin is utilized because rapamycin and heparin coatings represent incompatible coating application technologies. Rapamycin is an organic solvent-based coating and heparin, in its native form, is a water-based coating.

As stated above, a rapamycin coating may be applied to stents by a dip, spray or spin coating method, and/or any combination of these methods. Various polymers may be utilized. For example, as described above, poly(ethylene-co-vinyl acetate) and polybutyl methacrylate blends may be utilized. Other polymers may also be utilized, but not limited to, for example, polyvinylidene fluoride-co-hexafluoropropylene and polyethylbutyl methacrylate-co-hexyl methacrylate. Also as described above, barrier or top coatings may also be applied to modulate the dissolution of rapamycin from the polymer matrix. In the exemplary embodiment described above, a thin layer of heparin is applied to the surface of the polymeric matrix. Because these polymer systems are hydrophobic and incompatible with the hydrophilic heparin, appropriate surface modifications may be required.

The application of heparin to the surface of the polymeric matrix may be performed in various ways and utilizing various biocompatible materials. For example, in one embodiment, in water or alcoholic solutions, polyethylene imine may be applied on the stents, with care not to degrade the rapamycin (e.g., pH<7, low temperature), followed by the application of sodium heparinate in aqueous or alcoholic solutions. As an extension of this surface modification, covalent heparin may be linked on polyethylene imine using amide-type chemistry (using a carbondiimide activator, e.g. EDC) or reductive amination chemistry (using CBAS-heparin and sodium cyanoborohydride for coupling). In another exemplary embodiment, heparin may be photolinked on the surface, if it is appropriately grafted with photo initiator moieties. Upon application of this modified heparin formulation on the covalent stent surface, light exposure causes cross-linking and immobilization of the heparin on the coating surface. In yet another exemplary embodiment, heparin may be complexed with hydrophobic quaternary ammonium salts, rendering the molecule soluble in organic solvents (e.g. benzalkonium heparinate, troidodecylmethylammonium heparinate). Such a formulation of heparin may be compatible with the hydrophobic rapamycin coating, and may be applied directly on the coating surface, or in the rapamycin/hydrophobic polymer formulation.

It is important to note that the stent, as described above, may be formed from any number of materials, including various metals, polymeric materials and ceramic materials. Accordingly, various technologies may be utilized to immobilize the various drugs, agent, compound combinations thereon. Specifically, in addition to the polymeric matricies described above biopolymers may be utilized. Biopolymers may be generally classified as natural polymers, while the above-described polymers may be described as synthetic polymers. Exemplary biopolymers, which may be utilized include, agarose, alginate, gelatin, collagen and elastin. In addition, the drugs, agents or compounds may be utilized in conjunction with other percutaneously delivered medical devices such as grafts and profusion balloons.

In addition to utilizing an anti-proliferative and anti-coagulant, anti-inflammatories may also be utilized in combination therewith. One example of such a combination would be the addition of an anti-inflammatory corticosteroid such as dexamethasone with an anti-proliferative, such as rapamycin, cladribine, vincristine, taxol, or a nitric oxide donor and an anti-coagulant, such as heparin. Such combination therapies might result in a better therapeutic effect, i.e., less proliferation as well as less inflammation, a stimulus for proliferation, than would occur with either agent alone. The delivery of a stent comprising an anti-proliferative, anti-coagulant, and an anti-inflammatory to an injured vessel would provide the added therapeutic benefit of limiting the degree of local smooth muscle cell proliferation, reducing a stimulus for proliferation, i.e., inflammation and reducing the effects of coagulation thus enhancing the restenosis-limiting action of the stent.

In other exemplary embodiments of the inventions, growth factor inhibitor or cytokine signal transduction inhibitor, such as the ras inhibitor, R115777, or P38 kinase inhibitor, RWJ67657, or a tyrosine kinase inhibitor, such as tyrphostin, might be combined with an anti-proliferative agent such as taxol, vincristine or rapamycin so that proliferation of smooth muscle cells could be inhibited by different mechanisms. Alternatively, an anti-proliferative agent such as taxol, vincristine or rapamycin could be combined with an inhibitor of extracellular matrix synthesis such as halofuginone. In the above cases, agents acting by different mechanisms could act synergistically to reduce smooth muscle cell proliferation and vascular hyperplasia. This invention is also intended to cover other combinations of two or more such drug agents. As mentioned above, such drugs, agents or compounds could be administered systemically, delivered locally via drug delivery catheter, or formulated for delivery from the surface of a stent, or given as a combination of systemic and local therapy.

In addition to anti-proliferatives, anti-inflammatories and anti-coagulants, other drugs, agents or compounds may be utilized in conjunction with the medical devices. For example, immunosuppressants may be utilized alone or in combination with these other drugs, agents or compounds. Also gene therapy delivery mechanisms such as modified genes (nucleic acids including recombinant DNA) in viral vectors and non-viral gene vectors such as plasmids may also be introduced locally via a medical device. In addition, the present invention may be utilized with cell based therapy.

In addition to all of the drugs, agents, compounds and modified genes described above, chemical agents that are not ordinarily therapeutically or biologically active may also be utilized in conjunction with the present invention. These chemical agents, commonly referred to as pro-drugs, are agents that become biologically active upon their introduction into the living organism by one or more mechanisms. These mechanisms include the addition of compounds supplied by the organism or the cleavage of compounds from the agents caused by another agent supplied by the organism. Typically, pro-drugs are more absorbable by the organism. In addition, pro-drugs may also provide some additional measure of time release.

As stated above, rapamycin may be utilized alone or in combination with one or more drugs, agents and/or compounds for the prevention of restenosis following vascular injury.

Histone proteins are part of cellular chromatin that aid in the packaging of DNA and transcription of genes. Several histone proteins exist, each expressing net positive charges capable of interacting with anionic DNA. These histone proteins form nucleosome subunits around which DNA is wound. Chemical modification of the histones through acetylation/deacetylation by acetyltransferase and deacetylase enzymes as well as other post-translational modifications help regulate the shape of the histone proteins, and subsequently, the accessibility of DNA to transcription enzymes. In resting cells, gene transcription is, at least in part, regulated by a balance of acetylation (transcription ON) and deacetylation (transcription OFF) of histone proteins that bind to DNA. Therefore, affecting the balance between acetylation and deacetylation can ultimately impact gene transcription, and subsequently, cell proliferation as proliferative pathways depend to a significant degree on gene transcription. Histone deacetylase are of two general classes, RPd3-like and Hda1-like proteins.

Other drugs, agents and or compounds that may be utilized include other histone deacetylase inhibitors, which include trichostatin A, its analogs and derivatives as well as similar agents. These agents include short-chain fatty acids, such as butyrate, phenylbutyrate and valproate, hydroxamic acids, such as trichostatins, SAHA and its derivatives, oxamflatin, ABHA, scriptaid, pyroxamide, and propenamides, epoxyketone-containing cyclic tetrapeptides, such as trapoxins, HC-toxin, chlamydocin, diheteropeptin, WF-3161 and Cyl-1 and Cyl-2, non-epoxyketone-containing cyclic tetrapeptides such as, FR901228 and apicidin, benzamides, such as MS-275 (MS-27-275), CI-994 and other benzamide analogs, and various miscellaneous structures, such as depudecin and organosulfur compounds.

Trichostatin A is a histone deacetylase inhibitor that arrests tumor cell proliferation predominantly in the G1 and G2 phases of the cell cycle. The G1 and G2 phases of the cell cycle are the phases characterized by gene transcription. The anti-proliferative activity and point of cell cycle arrest profile of trichostatin A have been characterized primarily in tumor cell lines with anti-proliferative *IC50's in the low nM range* (Woo et al., *J. Med Chem,* 45:2877-2885, 2002). In addition, trichostatin A has been shown to have anti-angiogenic activity (Deroanne et al., Oncogene 21 (3): 427-436, 2002).

Figure 51:
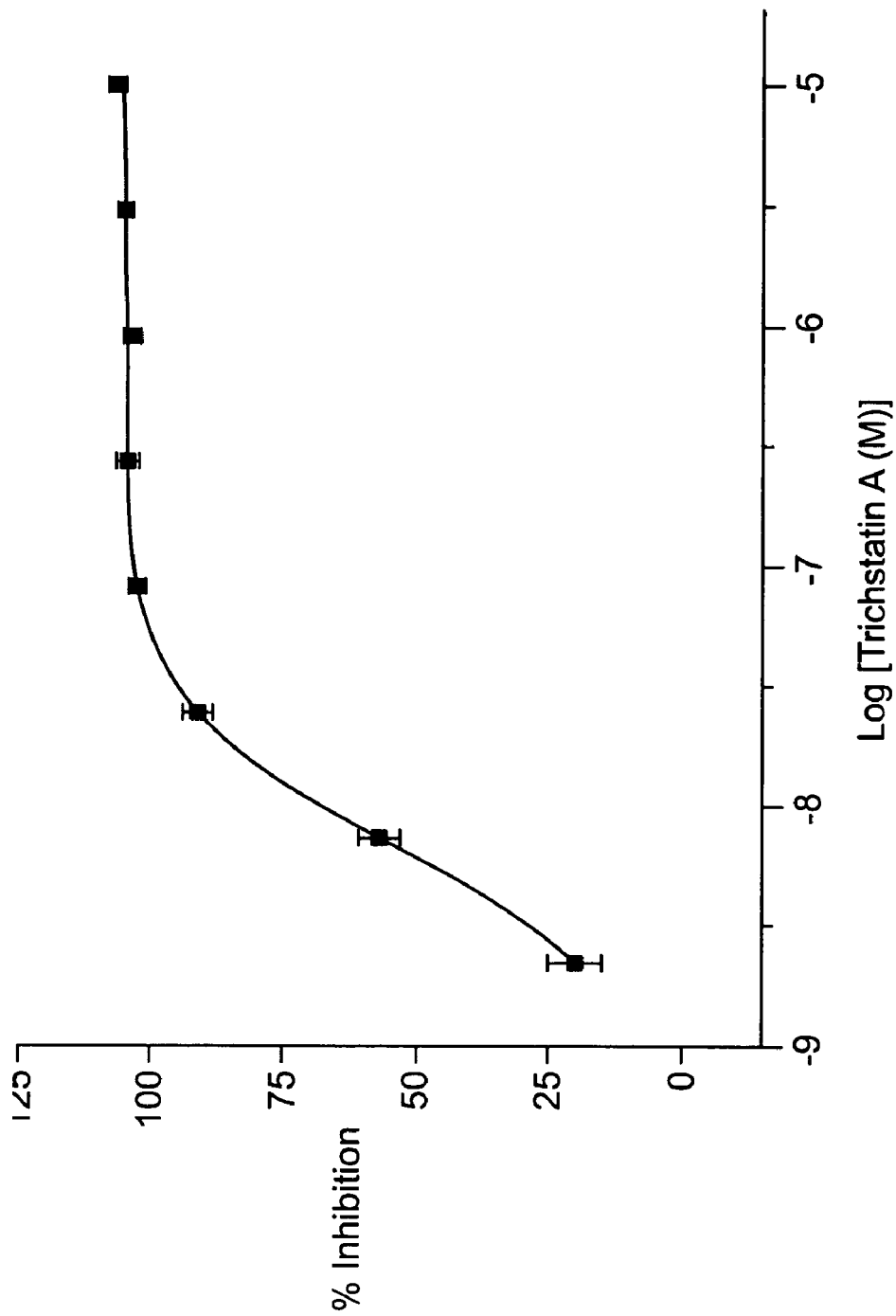
FIG. 51 is a graphical representation of the inhibition of coronary artery smooth muscle cell proliferation utilizing trichostatin A in an in vitro cell culture study.

In in vitro cell culture studies, trichostatin A has been shown to completely inhibit human coronary artery smooth muscle cell proliferation and has an anti-proliferative IC50 of approximately 6 nM. FIG. 51 is a graph of the inhibition of coronary artery smooth muscle cells by trichostatin A in a cell culture study. It is therefore possible that trichostatin A, delivered locally, may substantially inhibit neointimal formation following vascular injury.

Rapamycin, as described above, is a macroyclic triene antibiotic produced by *streptomyces hygroscopicus* as disclosed in U.S. Pat. No. 3,929,992. It has been found that rapamycin inhibits the proliferation of vascular smooth muscle cells in vivo. Accordingly, rapamycin may be utilized in treating intimal smooth muscle cell hyperplasia, restenosis and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin functions to inhibit smooth muscle cell proliferation through a number of mechanisms. In addition, rapamycin reduces the other effects caused by vascular injury, for example, inflammation. The mechanisms of action and various functions of rapamycin are described in detail below. Rapamycin as used throughout this application shall include rapamycin, rapamycin analogs, derivatives and congeners that bind FKBP12 and possess the same pharmacologic properties as rapamycin, as described in detail below.

Rapamycin reduces vascular hyperplasia by antagonizing smooth muscle proliferation in response to mitogenic signals that are released during angioplasty. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppressive activity and its ability to prevent graft rejection.

The molecular events that are responsible for the actions of rapamycin, a known anti-proliferative, which acts to reduce the magnitude and duration of neointimal hyperplasia, are still being elucidated. It is known, however, that rapamycin enters cells and binds to a high-affinity cytosolic protein called FKBP12. The complex of rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that rapamycin reduces restenosis by inhibiting neointimal hyperplasia. However, there is evidence that rapamycin may also inhibit the other major component of restenosis, namely, negative remodeling. Remodeling is a process whose mechanism is not clearly understood but which results in shrinkage of the external elastic lamina and reduction in lumenal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural timepoint to four-month and twelve-month follow-ups are reflective of remodeling changes.

Evidence that rapamycin exerts an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that rapamycin is preventing vascular remodeling.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

Angiographic In-Lesion Percent Diameter Stenosis
(%, mean ± SD and "n") In Patients Who Received a
Rapamycin-Coated Stent

| Coating Group | Post Placement | 4–6 month Follow Up | 12 month Follow Up |
|---|---|---|---|
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n=) | 4-Month Follow-Up (n=) | 12-Month Follow-Up (n=) |
|---|---|---|---|
| Mean proximal vessel area ($mm^2$) | 16.53 ± 3.53 (27) | 16.31 ± 4.36 (28) | 13.96 ± 2.26 (13) |
| Mean distal vessel area ($mm^2$) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycin may also affect the translation of key proteins involved in collagen formation or metabolism.

Rapamycin used in this context includes rapamycin and all analogs, derivatives and congeners that bind FKBP12 and possess the same pharmacologic properties as rapamycin.

In a preferred embodiment, the rapamycin is delivered by a local delivery device to control negative remodeling of an arterial segment after balloon angioplasty as a means of reducing or preventing restenosis. While any delivery device may be utilized, it is preferred that the delivery device comprises a stent that includes a coating or sheath which elutes or releases rapamycin. The delivery system for such a device may comprise a local infusion catheter that delivers rapamycin at a rate controlled by the administrator. In other embodiments, an injection need may be utilized.

Rapamycin may also be delivered systemically using an oral dosage form or a chronic injectible depot form or a patch to deliver rapamycin for a period ranging from about seven to forty-five days to achieve vascular tissue levels that are sufficient to inhibit negative remodeling. Such treatment is to be used to reduce or prevent restenosis when administered several days prior to elective angioplasty with or without a stent.

Data generated in porcine and rabbit models show that the release of rapamycin into the vascular wall from a nonerodible polymeric stent coating in a range of doses (35-430 ug/5-18 mm coronary stent) produces a peak fifty to fifty-five percent reduction in neointimal hyperplasia as set forth in Table 3 below. This reduction, which is maximal at about twenty-eight to thirty days, is typically not sustained in the range of ninety to one hundred eighty days in the porcine model as set forth in Table 4 below.

TABLE 3.0

Animal Studies with Rapamycin-coated stents.
Values are mean ± Standard Error of Mean

| Study | Duration | Stent[1] | Rapamycin | N | Neointimal Area (mm$^2$) | % Change From Polyme | Metal |
|---|---|---|---|---|---|---|---|
| Porcine | | | | | | | |
| 98009 | 14 days | Metal | | 8 | 2.04 ± 0.17 | | |
| | | 1X + rapamycin | 153 µg | 8 | 1.66 ± 0.17* | −42% | −19% |
| | | 1X + TC300 + rapamycin | 155 µg | 8 | 1.51 ± 0.19* | −47% | −26% |
| 99005 | 28 days | Metal | | 10 | 2.29 ± 0.21 | | |
| | | | | 9 | 3.91 ± 0.60** | | |
| | | 1X + TC30 + rapamycin | 130 µg | 8 | 2.81 ± 0.34 | | +23% |
| | | 1X + TC100 + rapamycin | 120 µg | 9 | 2.62 ± 0.21 | | +14% |
| 99006 | 28 days | Metal | | 12 | 4.57 ± 0.46 | | |
| | | EVA/BMA 3X | | 12 | 5.02 ± 0.62 | | +10% |
| | | 1X + rapamycin | 125 µg | 11 | 2.84 ± 0.31*** | −43% | −38% |
| | | 3X + rapamycin | 430 µg | 12 | 3.06 ± 0.17*** | −39% | −33% |
| | | 3X + rapamycin | 157 µg | 12 | 27.7 ± 0.41*** | −45% | −39% |
| 99011 | 28 days | Metal | | 11 | 3.09 ± 0.27 | | |
| | | | | 11 | 4.52 ± 0.37 | | |
| | | 1X + rapamycin | 189 µg | 14 | 3.05 ± 0.35 | | −1% |
| | | 3X + rapamycin/dex | 182/363 µg | 14 | 2.72 ± 0.71 | | −12% |
| 99021 | 60 days | Metal | | 12 | 2.14 ± 0.25 | | |
| | | 1X + rapamycin | 181 µg | 12 | 2.95 ± 0.38 | | +38% |
| 99034 | 28 days | Metal | | 8 | 5.24 ± 0.58 | | |
| | | 1X + rapamycin | 186 µg | 8 | 2.47 ± 0.33** | | −53% |
| | | 3X + rapamycin/dex | 185/369 µg | 6 | 2.42 ± 0.64** | | −54% |
| 20001 | 28 days | Metal | | 6 | 1.81 ± 0.09 | | |
| | | 1X + rapamycin | 172 µg | 5 | 1.66 ± 0.44 | | −8% |
| 20007 | | | | | | | |
| | 30 days | Metal | | 9 | 2.94 ± 0.43 | | |
| | | 1XTC + rapamycin | 155 µg | 10 | 1.40 ± 0.11* | | −52%* |
| Rabbit | | | | | | | |
| 99019 | 28 days | Metal | | 8 | 1.20 ± 0.07 | | |
| | | EVA/BMA 1X | | 10 | 1.26 ± 0.16 | | +5% |
| | | 1X + rapamycin | 64 µg | 9 | 0.92 ± 0.14 | −27% | −23% |
| | | 1X + rapamycin | 196 µg | 10 | 0.66 ± 0.12*** | −48% | −45% |
| 99020 | 28 days | Metal | | 12 | 1.18 ± 0.10 | | |
| | | EVA/BMA 1X + rapamycin | 197 µg | 8 | 0.81 ± 0.16 | | −32% |

[1]Stent nomenclature: EVA/BMA 1X, 2X, and 3X signifies approx. 500 µg, 1000 µg, and 1500 µg total mass (polymer + drug), respectively. TC, top coat of 30 µg, 100 µg, or 300 µg drug-free BMA; Biphasic: 2 × 1X layers of rapamycin in EVA/BMA spearated by a 100 µg drug-free BMA layer.
[2]0.25 mg/kg/d × 14 d preceeded by a loading dose of 0.5 mg/kg/d × 3 d prior to stent implantation.
*p < 0.05 from EVA/BMA control.
**p < 0.05 from Metal;
Inflammation score: (0 = essentially no intimal involvement; 1 = <25% intima involved; 2 = ≧25% intima involved; 3 = >50% intima involved).

TABLE 4.0

180 day Porcine Study with Rapamycin-coated stents.
Values are mean ± Standard Error of Mean

| Study | Duration | Stent[1] | Rapamycin | N | Neointimal Area (mm$^2$) | % Change From Polyme | Metal | Inflammation Score # |
|---|---|---|---|---|---|---|---|---|
| 20007 | 3 days | Metal | | 10 | 0.38 ± 0.06 | | | 1.05 ± 0.06 |
| (ETP-2-002233-P) | | 1XTC + rapamycin | 155 µg | 10 | 0.29 ± 0.03 | | −24% | 1.08 ± 0.04 |
| | 30 days | Metal | | 9 | 2.94 ± 0.43 | | | 0.11 ± 0.08 |
| | | 1XTC + rapamycin | 155 µg | 10 | 1.40 ± 0.11* | | −52%* | 0.25 ± 0.10 |
| | 90 days | Metal | | 10 | 3.45 ± 0.34 | | | 0.20 ± 0.08 |
| | | 1XTC + rapamycin | 155 µg | 10 | 3.03 ± 0.29 | | −12% | 0.80 ± 0.23 |
| | | 1X + rapamycin | 171 µg | 10 | 2.86 ± 0.35 | | −17% | 0.60 ± 0.23 |
| | 180 days | Metal | | 10 | 3.65 ± 0.39 | | | 0.65 ± 0.21 |
| | | 1XTC + rapamycin | 155 µg | 10 | 3.34 ± 0.31 | | −8% | 1.50 ± 0.34 |
| | | 1X + rapamycin | 171 µg | 10 | 3.87 ± 0.28 | | +6% | 1.68 ± 0.37 |

The release of rapamycin into the vascular wall of a human from a nonerodible polymeric stent coating provides superior results with respect to the magnitude and duration of the reduction in neointimal hyperplasia within the stent as compared to the vascular walls of animals as set forth above.

Humans implanted with a rapamycin coated stent comprising rapamycin in the same dose range as studied in animal models using the same polymeric matrix, as described above, reveal a much more profound reduction in neointimal hyperplasia than observed in animal models, based on the magnitude and duration of reduction in neointima. The human clinical response to rapamycin reveals essentially total abolition of neointimal hyperplasia inside the stent using both angiographic and intravascular ultrasound measurements. These results are sustained for at least one year as set forth in Table 5 below.

the polymer coating that controls the release of the drug is important in the effectiveness of the drug.

As stated above, rapamycin reduces vascular hyperplasia by antagonizing smooth muscle proliferation in response to mitogenic signals that are released during angioplasty injury. Also, it is known that rapamycin prevents T-cell proliferation and differentiation when administered systemically. It has also been determined that rapamycin exerts a local inflammatory effect in the vessel wall when administered from a stent in low doses for a sustained period of time (approximately two to six weeks). The local anti-inflammatory benefit is profound and unexpected. In combination with the smooth muscle anti-proliferative effect, this dual mode of action of rapamycin may be responsible for its exceptional efficacy.

Accordingly, rapamycin delivered from a local device platform, reduces neointimal hyperplasia by a combination of

TABLE 5.0

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| Procedure Success (QCA) | 100.0% (45/45) | [92.1%, 100.0%] |
| 4-month In-Stent Diameter Stenosis (%) | | |
| Mean ± SD (N) | 4.8% ± 6.1% (30) | [2.6%, 7.0%] |
| Range (min, max) | (−8.2%, 14.9%) | |
| 6-month In-Stent Diameter Stenosis (%) | | |
| Mean ± SD (N) | 8.9% ± 7.6% (13) | [4.8%, 13.0%] |
| Range (min, max) | (−2.9%, 20.4%) | |
| 12-month In-Stent Diameter Stenosis (%) | | |
| Mean ± SD (N) | 8.9% ± 6.1% (15) | [5.8%, 12.0%] |
| Range (min, max) | (−3.0%, 22.0%) | |
| 4-month In-Stent Late Loss (mm) | | |
| Mean ± SD (N) | 0.00 ± 0.29 (30) | [−0.10, 0.10] |
| Range (min, max) | (−0.51, 0.45) | |
| 6-month In-Stent Late Loss (mm) | | |
| Mean ± SD (N) | 0.25 ± 0.27 (13) | [0.10, 0.39] |
| Range (min, max) | (−0.51, 0.91) | |
| 12-month In-Stent Late Loss (mm) | | |
| Mean ± SD (N) | 0.11 ± 0.36 (15) | [−0.08, 0.29] |
| Range (min, max) | (−0.51, 0.82) | |
| 4-month Obstruction Volume (%) (IVUS) | | |
| Mean ± SD (N) | 10.48% ± 2.78% (28) | [9.45%, 11.51%] |
| Range (min, max) | (4.60%, 16.35%) | |
| 6-month Obstruction Volume (%) (IVUS) | | |
| Mean ± SD (N) | 7.22% ± 4.60% (13) | [4.72%, 9.72%], |
| Range (min, max) | (3.82%, 19.88%) | |
| 12-month Obstruction Volume (%) (IVUS) | | |
| Mean ± SD (N) | 2.11% ± 5.28% (15) | [0.00%, 4.78%], |
| Range (min, max) | (0.00%, 19.89%) | |
| 6-month Target Lesion Revascularization (TLR) | 0.0% (0/30) | [0.0%, 9.5%] |
| 12-month Target Lesion Revascularization (TLR) | 0.0% (0/15) | [0.0%, 18.1%] |

QCA = Quantitative Coronary Angiography
SD = Standard Deviation
IVUS = Intravascular Ultrasound Rapamycin produces an unexpected benefit in humans when delivered from a stent by causing a profound reduction in in-stent neointimal hyperplasia that is sustained for at least one year. The magnitude and duration of this benefit in humans is not predicted from animal model data. Rapamycin used in this context includes rapamycin and all analogs, derivatives and congeners that bind FKBP12 and possess the same pharmacologic properties as rapamycin.

These results may be due to a number of factors. For example, the greater effectiveness of rapamycin in humans is due to greater sensitivity of its mechanism(s) of action toward the pathophysiology of human vascular lesions compared to the pathophysiology of animal models of angioplasty. In addition, the combination of the dose applied to the stent and anti-inflammatory and smooth muscle anti-proliferative effects. Rapamycin used in this context means rapamycin and all analogs, derivatives and congeners that bind FKBP12 and possess the same pharmacologic properties as rapamycin. Local device platforms include stent coatings, stent sheaths, grafts and local drug infusion catheters or porous balloons or any other suitable means for the in situ or local delivery of drugs, agents or compounds.

The anti-inflammatory effect of rapamycin is evident in data from an experiment, illustrated in Table 6, in which rapamycin delivered from a stent was compared with dexamethasone delivered from a stent. Dexamethasone, a potent steroidal anti-inflammatory agent, was used as a reference standard. Although dexamethasone is able to reduce inflammation scores, rapamycin is far more effective than dexamethasone in reducing inflammation scores. In addition, rapamycin significantly reduces neointimal hyperplasia, unlike dexamethasone.

TABLE 6.0

| Group Rapamycin Rap | N = | Neointimal Area (mm²) | % Area Stenosis | Inflammation Score |
|---|---|---|---|---|
| Uncoated | 8 | 5.24 ± 1.65 | 54 ± 19 | 0.97 ± 1.00 |
| Dexamethasone (Dex) | 8 | 4.31 ± 3.02 | 45 ± 31 | 0.39 ± 0.24 |
| Rapamycin (Rap) | 7 | 2.47 ± 0.94* | 26 ± 10* | 0.13 ± 0.19* |
| Rap + Dex | 6 | 2.42 ± 1.58* | 26 ± 18* | 0.17 ± 0.30* |

*= significance level P < 0.05

Rapamycin has also been found to reduce cytokine levels in vascular tissue when delivered from a stent. The data in FIG. 1 illustrates that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycin may be shown to inhibit local inflammatory events in the vessel it is believed that this could explain the unexpected superiority of rapamycin in inhibiting neointima.

As set forth above, rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycin suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving rapamycin delivered locally from a stent. The present invention expands upon the mechanism of rapamycin to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs, agents or compounds that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as P27$^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

Any of the drugs, agents or compounds discussed above may be administered either systemically, for example, orally, intravenously, intramuscularly, subcutaneously, nasally or intradermally, or locally, for example, stent coating, stent covering or local delivery catheter. In addition, the drugs or agents discussed above may be formulated for fast-release or slow release with the objective of maintaining the drugs or agents in contact with target tissues for a period ranging from three days to eight weeks.

As set forth above, the complex of rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

The inhibitor may be a small organic molecule (approximate mw<1000), which is either a synthetic or naturally derived product. Wortmanin may be an agent which inhibits the function of this class of proteins. It may also be a peptide or an oligonucleotide sequence. The inhibitor may be administered either sytemically (orally, intravenously, intramuscularly, subcutaneously, nasally, or intradermally) or locally (stent coating, stent covering, local drug delivery catheter). For example, the inhibitor may be released into the vascular wall of a human from a nonerodible polymeric stent coating. In addition, the inhibitor may be formulated for fast-release or slow release with the objective of maintaining the rapamycin or other drug, agent or compound in contact with target tissues for a period ranging from three days to eight weeks.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

Further, insulin supplemented diabetic patients receiving rapamycin eluting vascular devices, such as stents, may exhibit a higher incidence of restenosis than their normal or non-insulin supplemented diabetic counterparts. Accordingly, combinations of drugs may be beneficial.

The local delivery of drugs, agents or compounds from a stent has the following advantages; namely, the prevention of vessel recoil and remodeling through the scaffolding action of the stent and the drugs, agents or compounds and the prevention of multiple components of neointimal hyperplasia. This local administration of drugs, agents or compounds to stented coronary arteries may also have additional therapeutic benefit. For example, higher tissue concentrations would be achievable than that which would occur with systemic administration, reduced systemic toxicity, and single treatment and ease of administration. An additional benefit of drug therapy may be to reduce the dose of the therapeutic compounds, thereby limiting their toxicity, while still achieving a reduction in restenosis.

As rapamycin and trichostatin A act through different molecular mechanisms affecting cell proliferation, it is possible that these agents, when combined on a medical device such as a drug eluting stent, may potentiate each other's anti-restenotic activity by downregulating both smooth muscle and immune cell proliferation (inflammatory cell proliferation) by distinct multiple mechanisms. This potentiation of rapamycin anti-proliferative activity by trichostatin A may translate to an enhancement in anti-restenotic efficacy following vascular injury during revascularization and other vascular surgical procedures and a reduction in the required amount of either agent to achieve the anti-restenotic effect.

Trichostatin A may be affixed to any of the medical devices described herein utilizing any of the techniques and materials described herein. For example, trichostatin A may be affixed to a stent, with or without polymers, or delivered locally via a catheter-based delivery system. The trichostatin A may substantially block neointimal formation by local vascular application by virtue of a substantially complete and potent blockade of human coronary artery smooth muscle cell proliferation. The combination of rapamycin and trichostatin A, as well as other agents within its pharmacologic class, represents a new therapeutic combination that may be more efficacious against restenosis/neointimal thickening then rapamycin alone. In addition, different doses of the combination may lead to additional gains of inhibition of the neointimal growth than the simple additive effects of rapamycin plus trichostatin A. The combination of rapamycin and trichostatin A may be efficacious towards other cardiovascular diseases such as vulnerable atherosclerotic plaque.

In yet another alternate exemplary embodiment, rapamycin may be utilized in combination with mycophenolic acid. Like rapamycin, mycophenolic acid is an antibiotic, an anti-inflammatory and an immunosuppressive agent. Rapamycin, as previously stated, acts to reduce lymphocyte proliferation by arresting cells in the G1 phase of the cell cycle through the inhibition of the mammalian target of rapamycin. The downstream effects of rapamycin on the mammalian target of rapamycin block subsequent activity of cell cycle associated protein kinases. In contrast, mycophenolic acid inhibits immune cell proliferation in the S phase of the cell cycle through the inhibition of inosine monophosphate dehydrogenase, an enzyme necessary for purine biosynthesis. In addition to their immunosuppressive and anti-inflammatory effects, rapamycin and mycophenolic acid are each potent inhibitors of human coronary artery smooth muscle cell proliferation.

As rapamycin and mycophenolic acid act through different molecular mechanisms affecting cell proliferation at different phases of the cell cycle, it is possible that these agents, when combined on a drug eluting stent or any other medical device as defined herein, my potentiate each others anti-restenotic activity by down regulating both smooth muscle and immune cell proliferation by different mechanisms.

Figure 52:
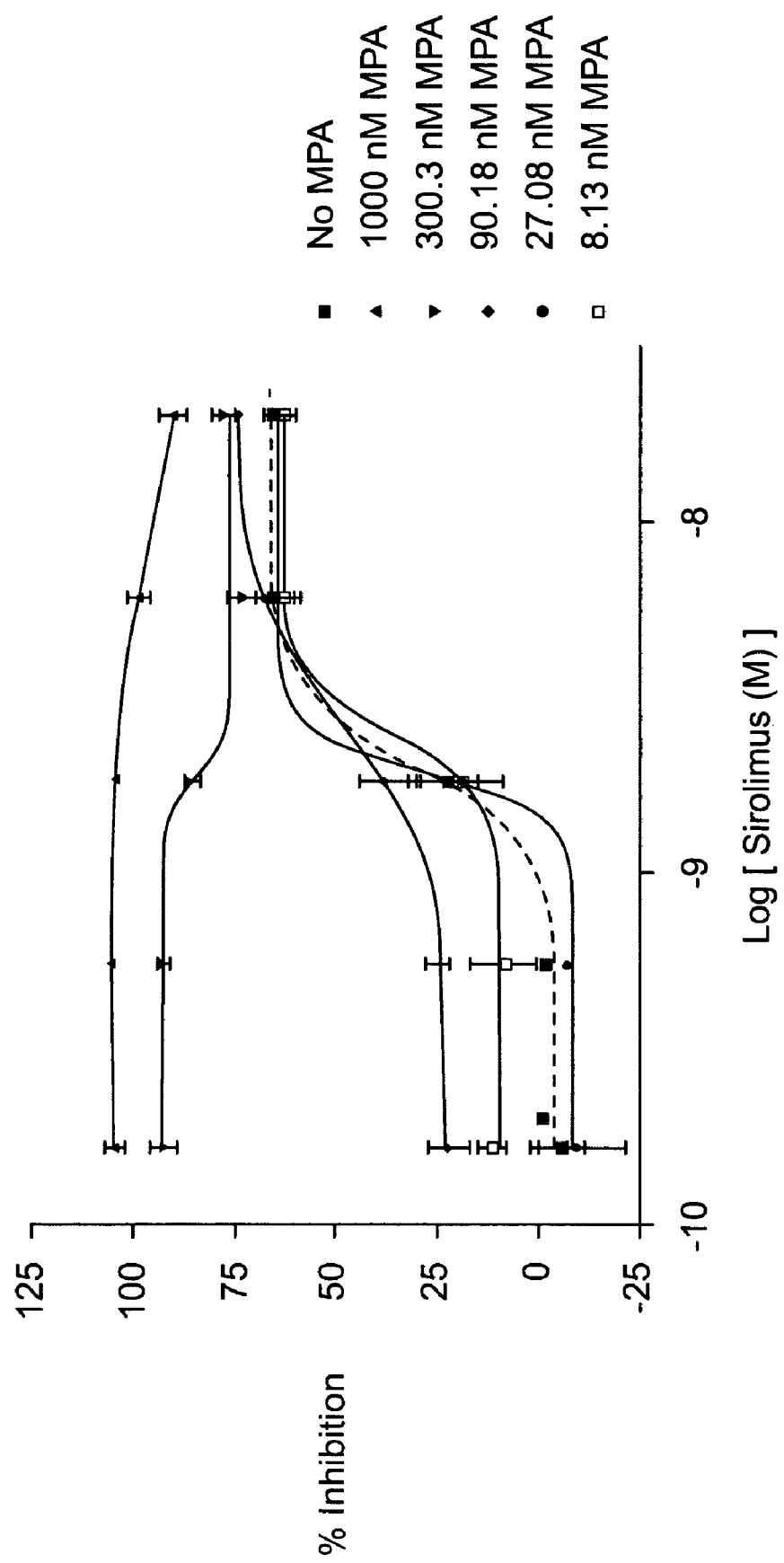
FIG. 52 is a graphical representation of the anti-proliferative activity of rapamycin with varying concentrations of mycophenolic acid in non-synchronized cultured human coronary artery smooth muscle cells stimulated with two percent fetal bovine serum in accordance with the present invention.

Referring to FIG. 52, there is illustrated, in graphical format, the anti-proliferative activity of rapamycin, with varying concentrations of mycophenolic acid in non-synchronized cultured human coronary artery smooth muscle cells stimulated with two percent fetal bovine serum. The multiple curves represent various concentrations of mycophenolic acid ranging from zero to one thousand nanomolar concentrations. As seen in FIG. 52, the addition of mycophenolic acid to cells treated with rapamycin resulted in a leftward and upward shift of the anti-proliferative rapamycin dose response curve, indicating that mycophenolic acid potentiates the anti-proliferative activity of rapamycin in coronary artery smooth muscle cells. This potentiation observed in cultured coronary artery smooth muscle cells preferably translates to an enhancement in anti-restenotic efficacy following vascular injury and a reduction in the required amount of either agent to achieve the desired anti-restenotic effect.

Figure 53:
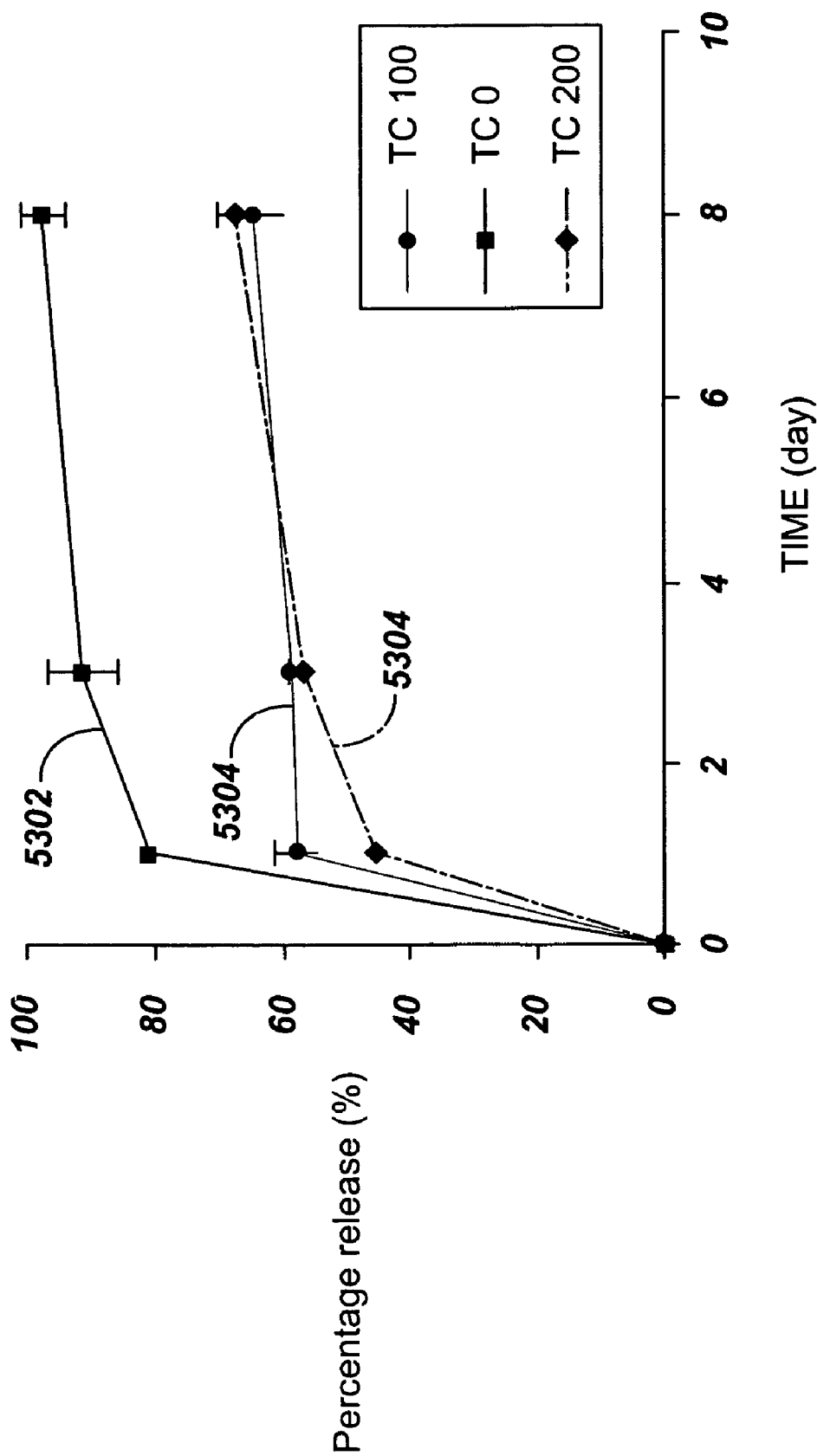
FIG. 53 is a graphical representation of the in vivo release kinetics of rapamycin from a combination of rapamycin, mycophenolic acid and a polymer in porcine pharmacokinetics studies in accordance with the present invention.

FIG. 53 is a graphical representation of the in vivo release kinetics of rapamycin from a combination of rapamycin, mycophenolic acid and a polymer in porcine pharmacokinetics studies. In the study, the rapamycin and mycophenolic acid are incorporated into an EVA/BMA polymer basecoat. The total weight of the basecoat is six hundred micro grams, with both the rapamycin and mycophenolic acid comprising thirty percent, by weight, of the basecoat (one hundred eighty micro grams rapamycin, one hundred eighty micro grams mycophenolic acid and two hundred forty micro grams EVA/BMA). Curve 5302 represents the release of rapamycin from the basecoat when no topcoat is utilized. Curve 5304 represents the release of rapamycin from the basecoat when a one hundred micro grams BMA topcoat is utilized. Curve 5306 represents the release of rapamycin from the basecoat when a two hundred micro grams BMA topcoat is utilized. The BMA topcoat does slow the release of rapamycin from the basecoat, which in turn provides a mechanism for greater drug release control.

Figure 54:
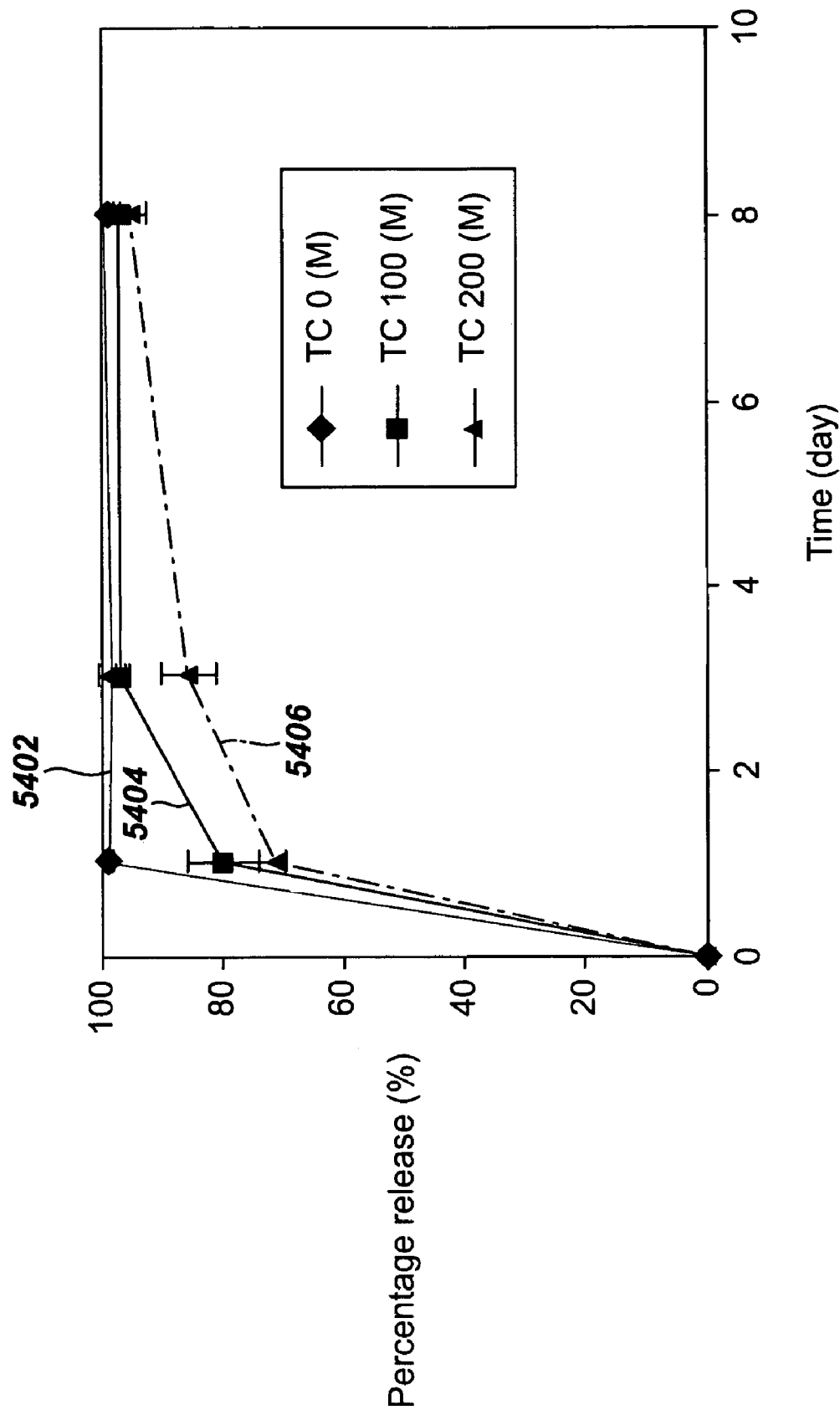
FIG. 54 is a graphical representation of the in vivo release kinetics of mycophenolic acid from a combination of rapamycin, mycophenolic acid and a polymer in porcine pharmacokinetics studies in accordance with the present invention.

FIG. 54 is a graphical representation of the in vivo release kinetics of mycophenolic acid from a combination of rapamycin, mycophenolic acid and a polymer in porcine pharmacokinetics studies. In the study, the rapamycin and mycophenolic acid are incorporated into an EVA/BMA polymer basecoat. The total weight of the basecoat is six hundred micro grams, with both the rapamycin and mycophenolic acid comprising thirty percent, by weight, of the basecoat (one hundred eighty micro grams rapamycin, one hundred eighty micro grams mycophenolic acid and two hundred forty micro grams EVA/BMA). Curve 5402 represents the release of mycophenolic acid from the basecoat when no topcoat is utilized. Curve 5404 represents the release of mycophenolic acid from the basecoat when a one hundred micro grams BMA topcoat is utilized. Curve 5406 represents the release of mycophenolic acid from the basecoat when a two hundred micro gram BMA topcoat is utilized. Similarly to the rapamycin pharmacokinetics, the BMA topcoat does slow the release of mycophenolic acid from the basecoat, which in turn provides a mechanism for greater drug release control. However, mycophenolic acid elutes more completely over a shorter duration than the rapamycin.

Figure 55:
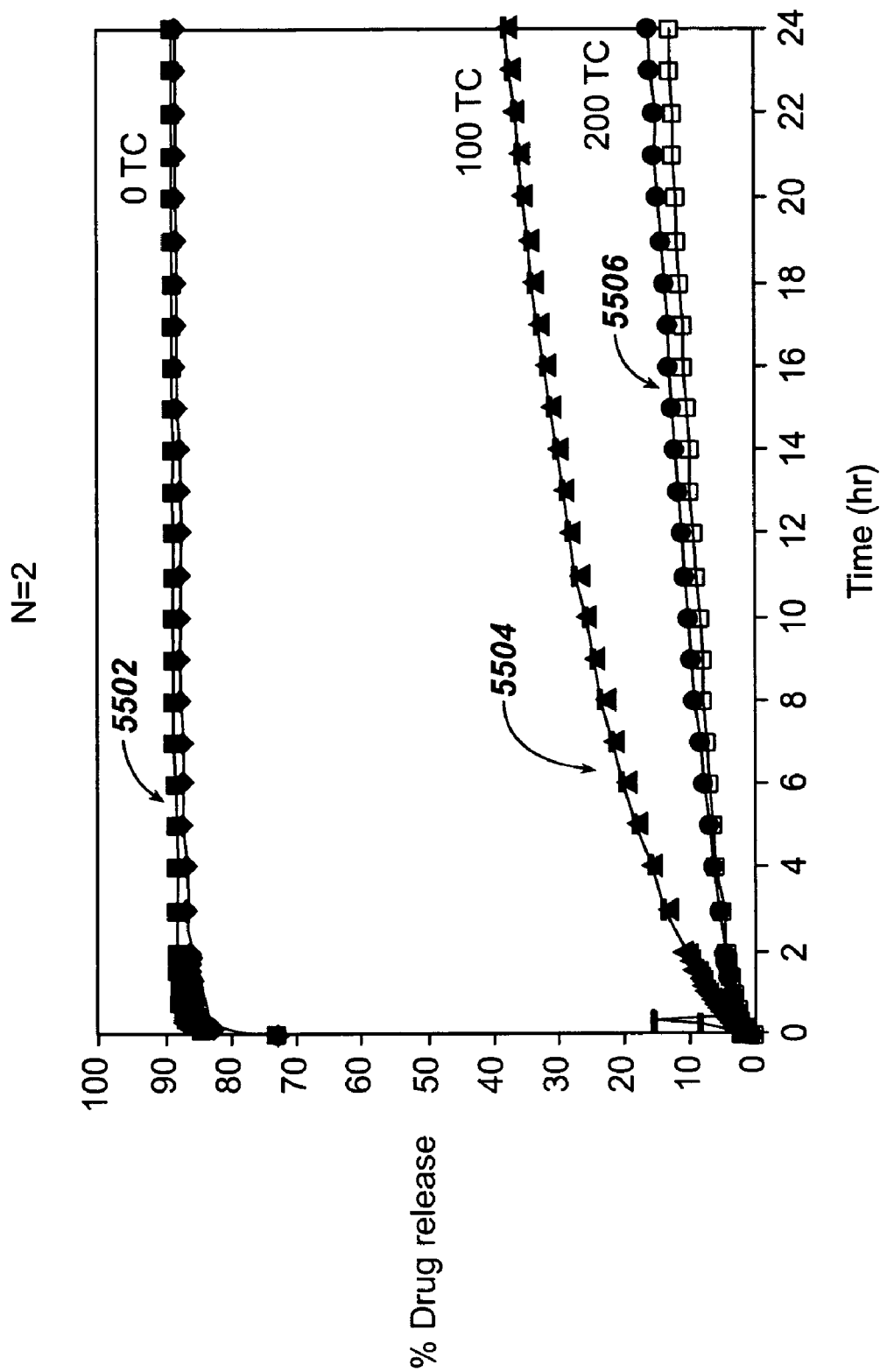
FIG. 55 is a graphical representation of the in vitro release kinetics of rapamycin from a combination of rapamycin and mycophenolic acid in accordance with the present invention.

FIG. 55 is a graphical representation of the in vitro release kinetics of rapamycin from a combination of rapamycin and mycophenolic acid. In the study, the rapamycin and mycophenolic acid are incorporated into an EVA/BMA polymer basecoat. The total weight of the basecoat is six hundred micro grams, with both the rapamycin and mycophenolic acid comprising thirty percent, by weight, of the basecoat (one hundred eighty micro grams rapamycin, one hundred eighty micro grams mycophenolic acid and two hundred forty micro grams EVA/BMA). The in vitro tests were run twice for each coating scenario. Curves 5502 represent the release of rapamycin from the basecoat when no topcoat is utilized. Curves 5504 represent the release of rapamycin from the basecoat when a one hundred micro grams BMA topcoat is utilized. Curves 5506 represent the release of rapamycin from the basecoat when a two hundred micro grams BMA topcoat is utilized. The BMA topcoat does slow the release of rapamycin from the basecoat in in vitro testing; however, the release rates are faster than in the in vivo testing.

Figure 56:
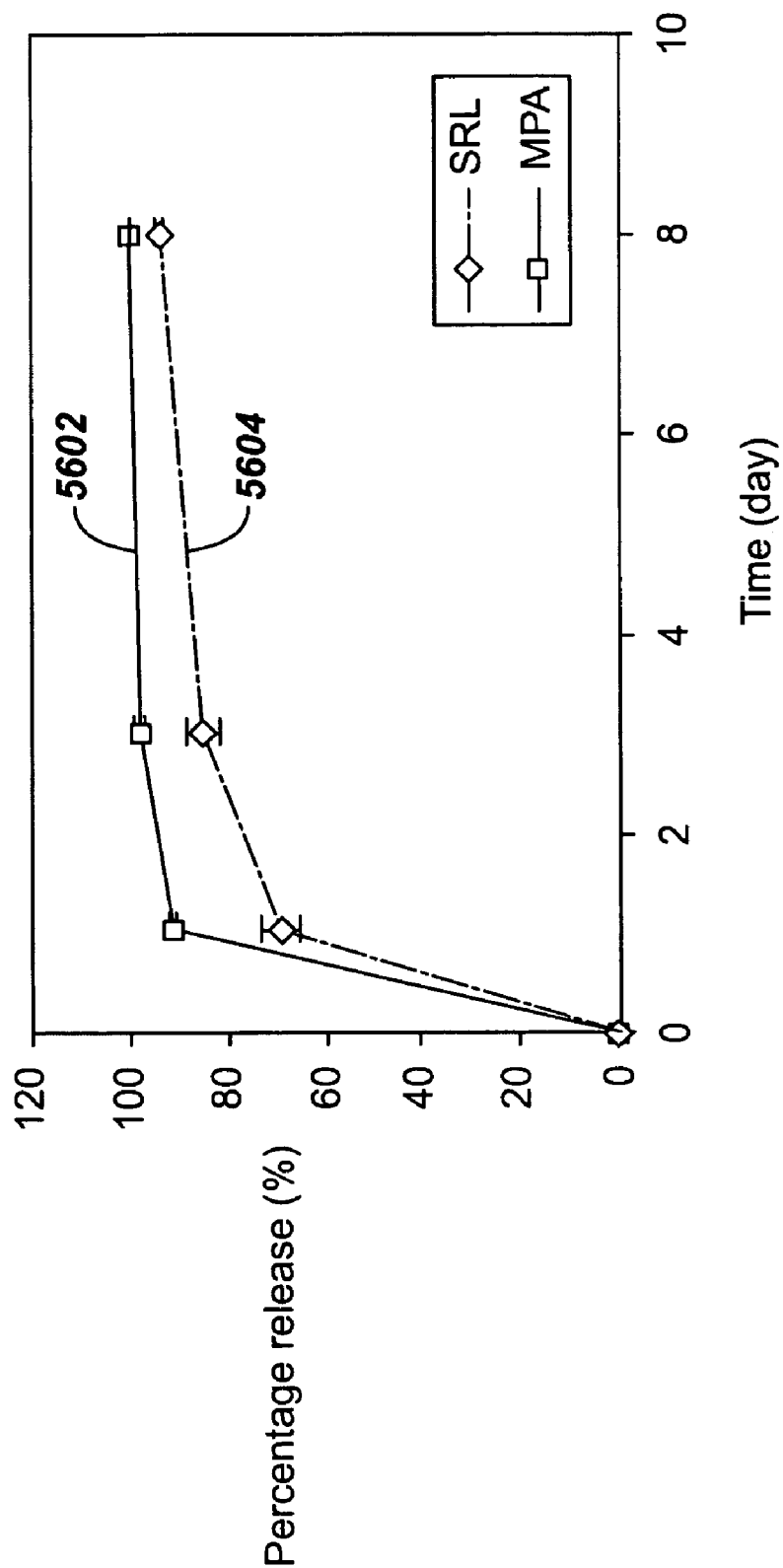
FIG. 56 is a graphical representation of the in vivo release kinetics of both rapamycin and mycophenolic acid in porcine pharmacokinetics studies in accordance with the present invention.

FIG. 56 is a graphical representation of the in vivo release kinetics of both rapamycin and mycophenolic acid in porcine pharmacokinetics studies. In this study, the rapamycin and mycophenolic acid are incorporated in a PVDF polymer basecoat with a PVDF topcoat. The total weight of the basecoat is six hundred micro grams with the rapamycin and mycophenolic acid equally comprising two thirds, by weight, of the basecoat. The topcoat is two hundred micro grams. Curve 5602 represents the release rate of mycophenolic acid and curve 5604 represents the release rate of rapamycin. As can be readily seen from the figure, rapamycin has a slower release rate than that of mycophenolic acid, which is consistent with the results found with an EVA/BMA basecoat and BMA topcoat. However, an EVA/BMA basecoat with a BMA topcoat appears to slow the release rate and thereby provide more control of the release rate or elution rate than a PVDF basecoat and PVDF topcoat.

In yet another alternate exemplary embodiment, rapamycin may be utilized in combination with cladribine. Cladribine (2-chlorodeoxyadenosine or 2-CdA) is the 2-chloro-2'-deoxy derivative of the purine nucleoside, adenosine. Cladribine is resistant to degradation by adenosine deaminase, one of two intracellular adenine nucleotide regulatory enzymes, found in most cells. The other enzyme, 5'-nucleotidase, is present in variable amounts in different cell types (Carson et al., 1983). After initial phosphorylation to its monophosphate derivative by the intracellular enzyme, deoxycytidine kinase, 2-CdA is converted to a 5'-triphosphate (2-CdATP) which accumulates in levels which may be fifty fold greater than normal dATP levels. Thus, in cells such as leukocytes, which contain a high ratio (>0.04) of deoxycytidine kinase to 5'-nucleotidase, 2-CdA and its subsequent metabolites will tend to accumulate in pharmacological concentrations (Carson et al., 1983). Such high levels of a nucleoside triphosphate are known to inhibit the enzyme ribonucleotide reductase in rapidly dividing cells, thus preventing synthesis of deoxynucleotides required for DNA synthesis.

In resting cells, 2-CdATP is incorporated into DNA which results in single strand breaks. Breaks in DNA results in the activation of poly (ADP-ribose) polymerase which in turn leads to a depletion of NAD, ATP and a disruption of cell metabolism (Carson et al., 1986; Seto et al., 1985). Further activation of a $Ca^{2+}/Mg^{2+}$-dependent endonuclease results in cleavage of the damaged DNA into fragments leading to programmed cell death (apoptosis). Thus, 2-CdA may be cytotoxic to both resting and dividing cells (Beutler, 1992). Cladribine has shown activity in other cell types known to play a role in the inflammatory process which accompanies restenosis. Additionally, data presented herein demonstrate that cladribine also possesses an ability to inhibit smooth muscle cell proliferation, an action previously unknown for cladribine (see Cladribine Example). Therefore, cladribine may possess a unique spectrum of therapeutic action, including the prevention of the leukocyte accumulation known to occur at sites of arterial injury and inflammation and the prevention of smooth muscle hyperplasia which results from angioplasty and stent implantation.

Cladribine Example

To assess the ability of cladribine to prevent cell proliferation, human smooth muscle or endothelial cells (Clonetics, Walkersville, Md.) were seeded at a density of 2000 cells/cm$^2$ (approximately 3600 cells/well) into each well of 12-well plates and cultured with 1.5 ml of growth medium containing five percent fetal calf serum (FCS). After twenty-four hours, the growth medium was changed and fresh medium containing 10 ng/ml platelet-derived growth factor AB (PDGF AB; LIFE Technologies), as well as various concentrations of cladribine (0.001-10,000 nM) were added with triplicate wells. Medium was replaced with fresh cladribine-containing medium after three days. On day six, cells were detached by trypsinization to yield a cell suspension, lightly centrifuged to pellet and then counted manually using a Neubauer hemocytometer system. Cell viability was assessed by trypan blue exclusion.

Table 7 provides the percent inhibition of the various tested concentrations of cladribine on human smooth muscle and endothelial cells in culture. Cladribine produced a concentration-related decrease in the proliferation of both smooth muscle and endothelial cells in this model system. IC$_{50}$ values (concentration required to produce a reduction in proliferation to 50 percent of the vehicle-treated cell count) for the inhibition of smooth muscle cell and endothelial cell growth were 23 nanomolar and 40 nanomolar, respectively. Cladribine was thus approximately twice as potent as an inhibitor of smooth muscle cells as it was as an inhibitor of endothelial cells. Both IC$_{50}$ values are within the range of inhibitory concentrations reported for cladribine on human monocytes (Carrera et al., J. Clin. Invest. 86:1480-1488, 1990) and normal bone marrow, lymphocytic and lymphoblastic cell lines (Carson, D. A. et al., Blood 62: 737-743, 1983). Thus, concentrations of cladribine known to be effective at inhibiting peripheral leukemic blood cell proliferation and bone marrow cells are also effective at inhibiting proliferating vascular smooth muscle and endothelial cells. Cladribine may therefore be therapeutically useful for inhibition of the intimal smooth muscle cell proliferation which accompanies stent implantation.

TABLE 7

Inhibition of human vascular cell proliferation with cladribine.

| | Con-trol | Vehi-cle | Cladribine (nM) | | | | | | | |
|---|---|---|---|---|---|---|---|---|---|---|
| | | | 0.001 | 0.01 | 0.1 | 1 | 10 | 100 | 1000 | 10,000 |
| SMC | 100 | 108 | — | 104 | 86 | 85 | 54 | 58 | 12 | −4 |
| EC | 100 | 100 | 100 | 90 | 79 | 75 | 59 | 57 | 35 | 10 |

Values represent % of PDGF-stimulated increase in cell count.
Each % is the mean of triplicate determinations.
SMC, smooth muscle cells;
EC, endothelial cells.

Cladribine or 2-chlorodeoxyadenosine is a purine antimetabolite prodrug that undergoes intracellular phosphorylation and incorporation into the DNA of proliferating cells. This leads to DNA strand breaks and inhibition of DNA synthesis. Cladribine is capable of arresting cells at the G1/S phase interface. Thus it is possible that cladribine may inhibit vascular smooth muscle cell proliferation and inhibit inflammatory cell function secondary to revascularization procedures.

Figure 58:
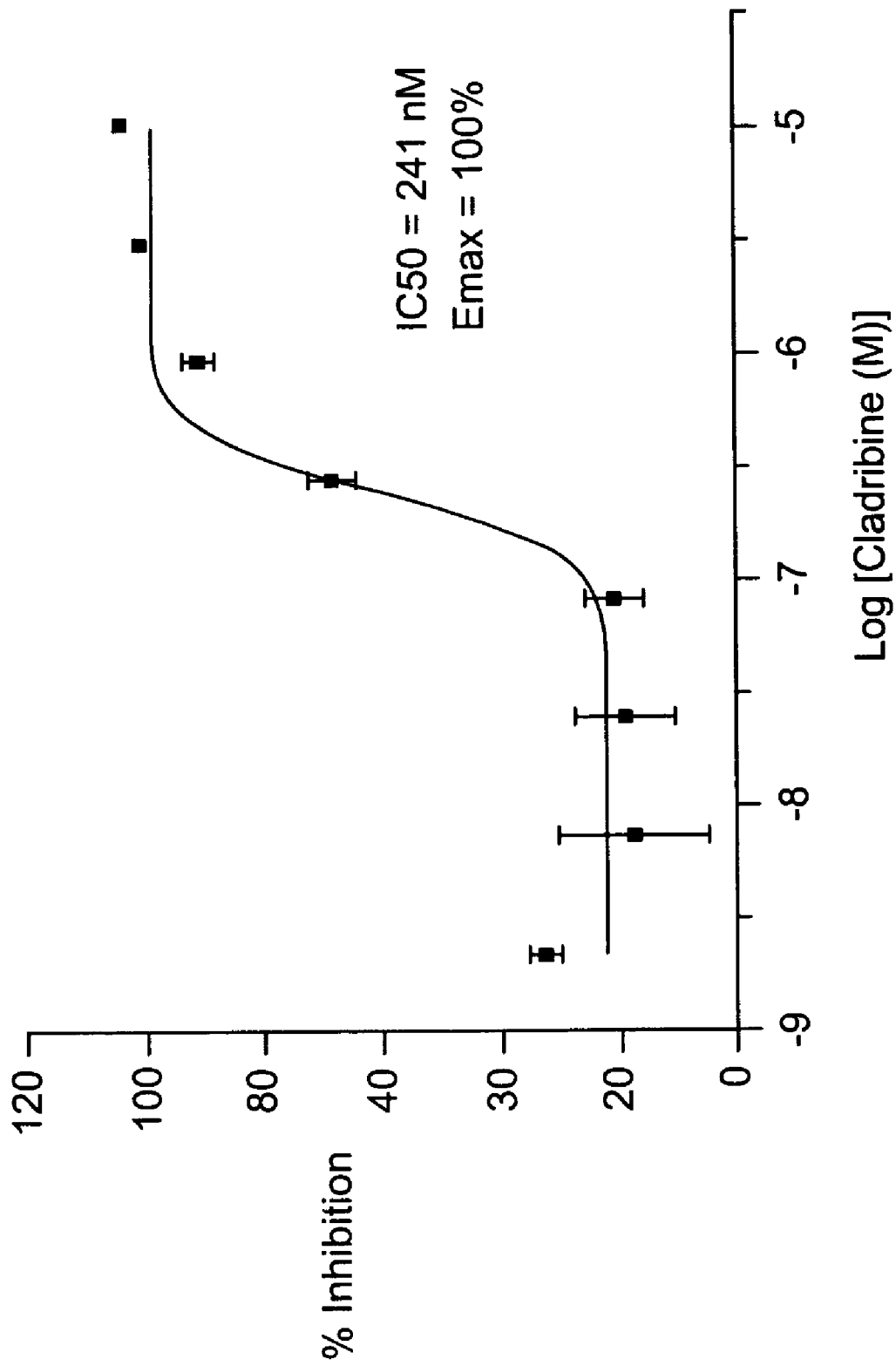
FIG. 58 is a graphical representation of the anti-proliferative activity of cladribine in non-synchronized cultured human coronary artery smooth muscle cells stimulated with two percent fetal bovine serum in accordance with the present invention.

FIG. 58 illustrates, in graphical format, the anti-proliferative activity of cladribine in non-synchronized cultured human coronary artery smooth muscle cells stimulated with two percent fetal bovine serum. As illustrated, cladribine completely inhibits human coronary artery smooth muscle cell proliferation and has an anti-proliferative IC50 of approximately 241 nanomolar. It is therefore possible that cladribine itself, delivered locally, may substantially inhibit neointimal formation following vascular injury.

As rapamycin and cladribine act through different molecular mechanisms affecting cell proliferation at different phases of the cell cycle, it is possible that these agents, when combined on a drug eluting stent or any other medical device as defined herein, may potentiate each other's anti-restenotic activity by downregulating both smooth muscle cell and immune cell proliferation by different mechanisms. In non-synchronized cultured human coronary artery smooth muscle cells studies, the addition of cladribine to cells treated with rapamycin resulted in a leftward and upward shift of the anti-proliferative rapamycin dose response curves, as set forth in detail below, suggesting that cladribine does in fact potentiate the anti-proliferative activity of rapamycin in coronary artery smooth muscle cells. The combination of rapamycin and cladribine may be utilized to enhance the anti-restenotic efficacy following vascular injury and a reduction in the required amount of either agent to achieve the anti-restenotic effect. The combination may be particularly relevant to the subpopulations of patients that are resistant to single drugs regimens such as rapamycin or paclitaxel coated stents.

Figure 57:
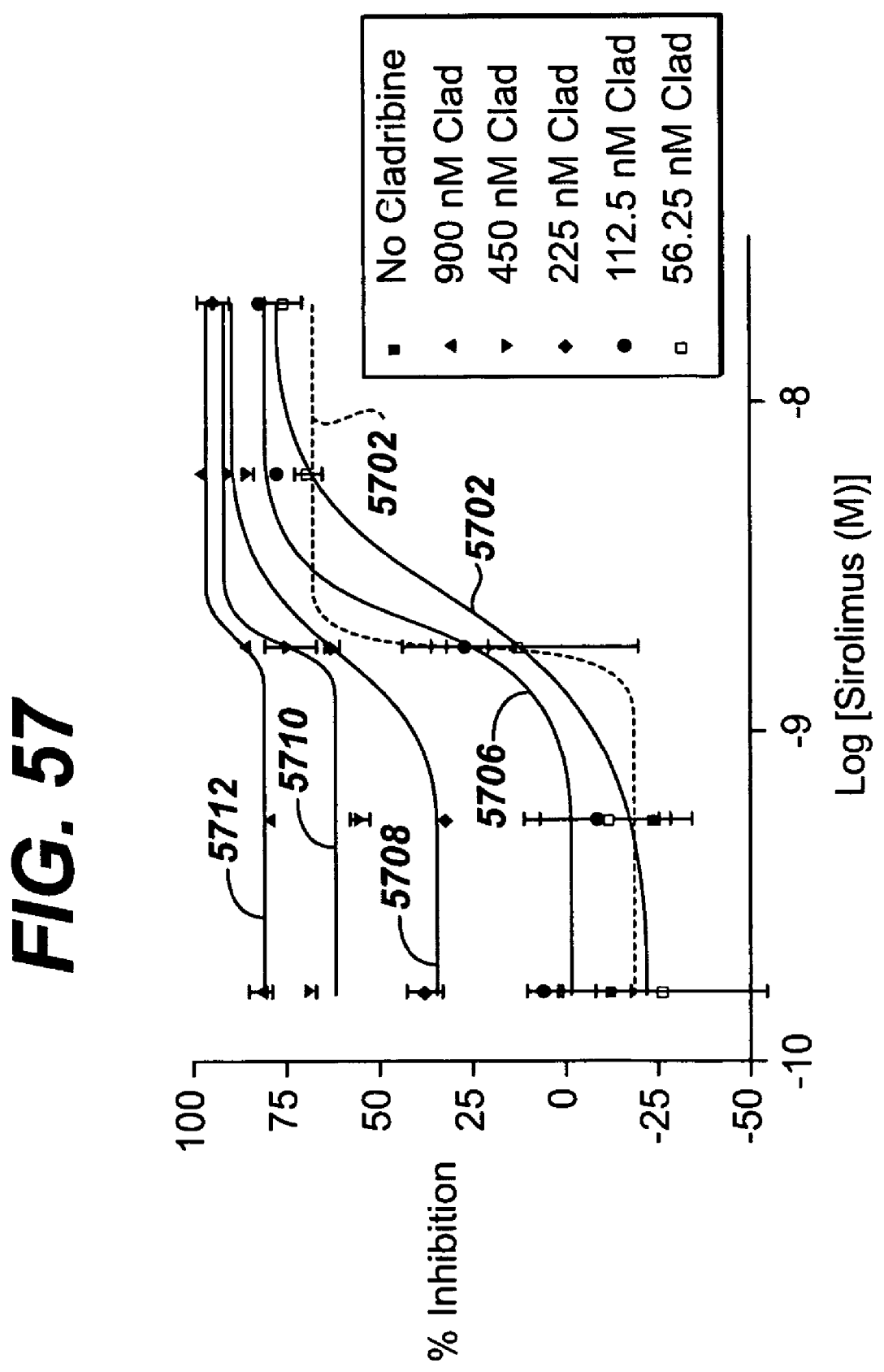

Referring to FIG. 57, there is illustrated, in graphical format, the anti-proliferative activity of rapamycin, with varying concentrations of cladribine in non-synchronized cultured human coronary artery smooth muscle cells stimulated with two percent fetal bovine serum. The multiple curves represent various concentrations of cladribine ranging from zero to nine hundred nanomolar concentrations. As seen in FIG. 57, the addition of cladribine to cells treated with rapamycin increases the percent inhibition of rapamycin alone. Curve 5702 represents the response of just rapamycin. Curve 5704 represents the response of rapamycin in combination with a 56.25 nanomolar concentration of cladribine. Curve 5706 represents the response of rapamycin in combination with a 112.5 nanomolar concentration of cladribine. Curve 5708 represents the response of rapamycin in combination with a 225 nanomolar concentration cladribine. Curve 5710 represents the response of rapamycin in combination with a 450 nanomolar concentration of cladribine. Curve 5712 represents the response of rapamycin in combination with a 900 nanomolar concentration of cladribine. As illustrated, the percent inhibition increases substantially as the dose of cladribine increases.

Figure 59:
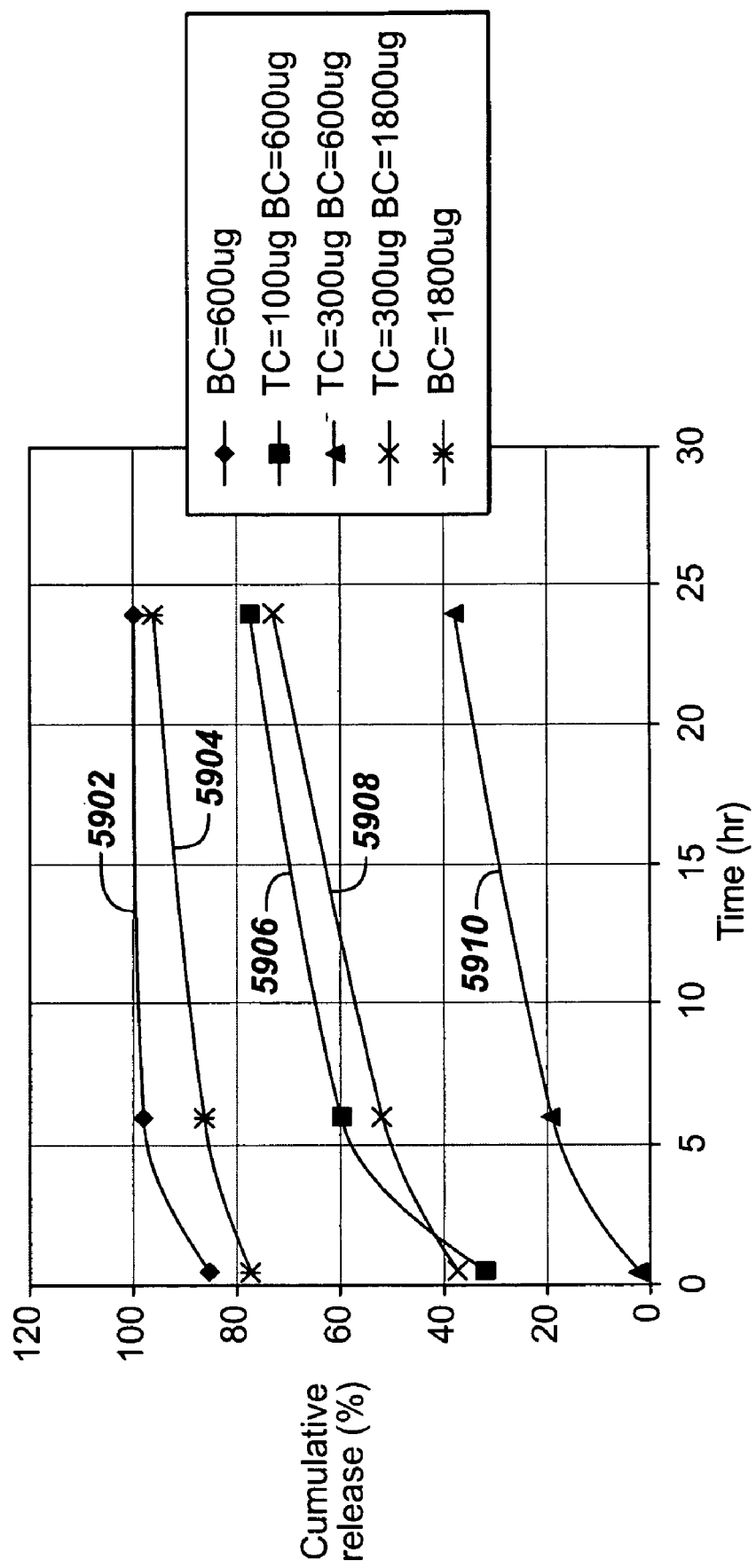
FIG. 59 is a graphical representation of the in vitro release kinetics of cladribine from non-sterile cladribine coatings in a PVDF/HFP basecoat incorporated in a twenty-five percent ethanol/water release medium at room temperature in accordance with the present invention.

FIG. 59 is a graphical representation of the in vitro release kinetics of cladribine from non-sterile cladribine coatings in a PVDF/HFP basecoat incorporated in a twenty-five percent ethanol/water release medium at room temperature. The basecoat comprises a ratio of PVDF/HFP (85/15) and cladribine. Cladribine comprises thirty percent of the basecoat. The topcoat also comprises an 85/15 ratio of PVDF and HFP, but no cladribine. Curve 5902 represents the release kinetics of cladribine wherein the basecoat weight is six hundred micrograms (one hundred eighty micrograms cladribine). Curve 5904 represents the release kinetics of cladribine wherein the basecoat weight is one thousand eight hundred micrograms (five hundred forty micrograms cladribine). Curve 5906 represents the release kinetics of cladribine wherein the basecoat weight is six hundred micrograms (one hundred eighty micrograms cladribine) and the topcoat weight is one hundred micrograms. Curve 5908 represents the release kinetics of cladribine wherein the basecoat weight is one thousand eight hundred micrograms (five hundred forty micrograms cladribine) and the topcoat is three hundred micrograms. Curve 5910 represents the release kinetic of cladribine wherein the basecoat weight is six hundred micrograms (one hundred eighty micrograms cladribine) and the topcoat is three hundred micrograms. As can be seen from the various curves, an increase in topcoat weight or thickness led to a decrease in the release rate of cladribine from the coating.

Figure 60:
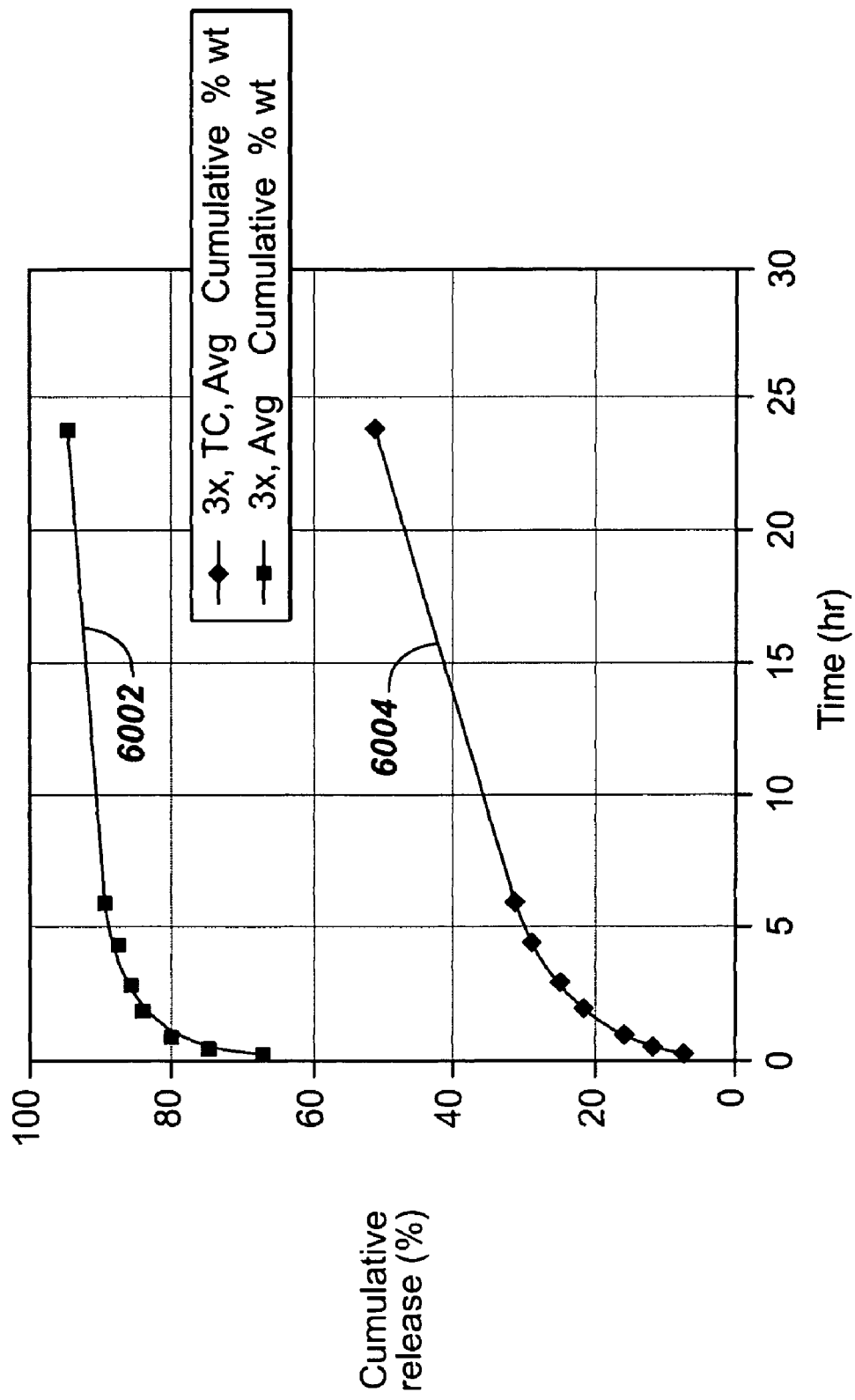
FIG. 60 is a graphical representation of the in vitro release kinetics of cladribine from sterile cladribine coatings in a PVDF/HFP basecoat incorporated in a twenty-five percent ethanol/water release medium at room temperature in accordance with the present invention.

FIG. 60 is a graphical representation of the in vitro release kinetics of cladribine from a sterile PVDF/HFP coating incorporated in a twenty-five percent ethanol/water release medium at room temperature. Curve 6002 represents the release kinetics where no topcoat is utilized and curve 6004 represents the release kinetics where a topcoat is utilized. As seen from the figure, a three-times topcoat led to a drastic decrease of release rate of cladribine.

Figure 61:
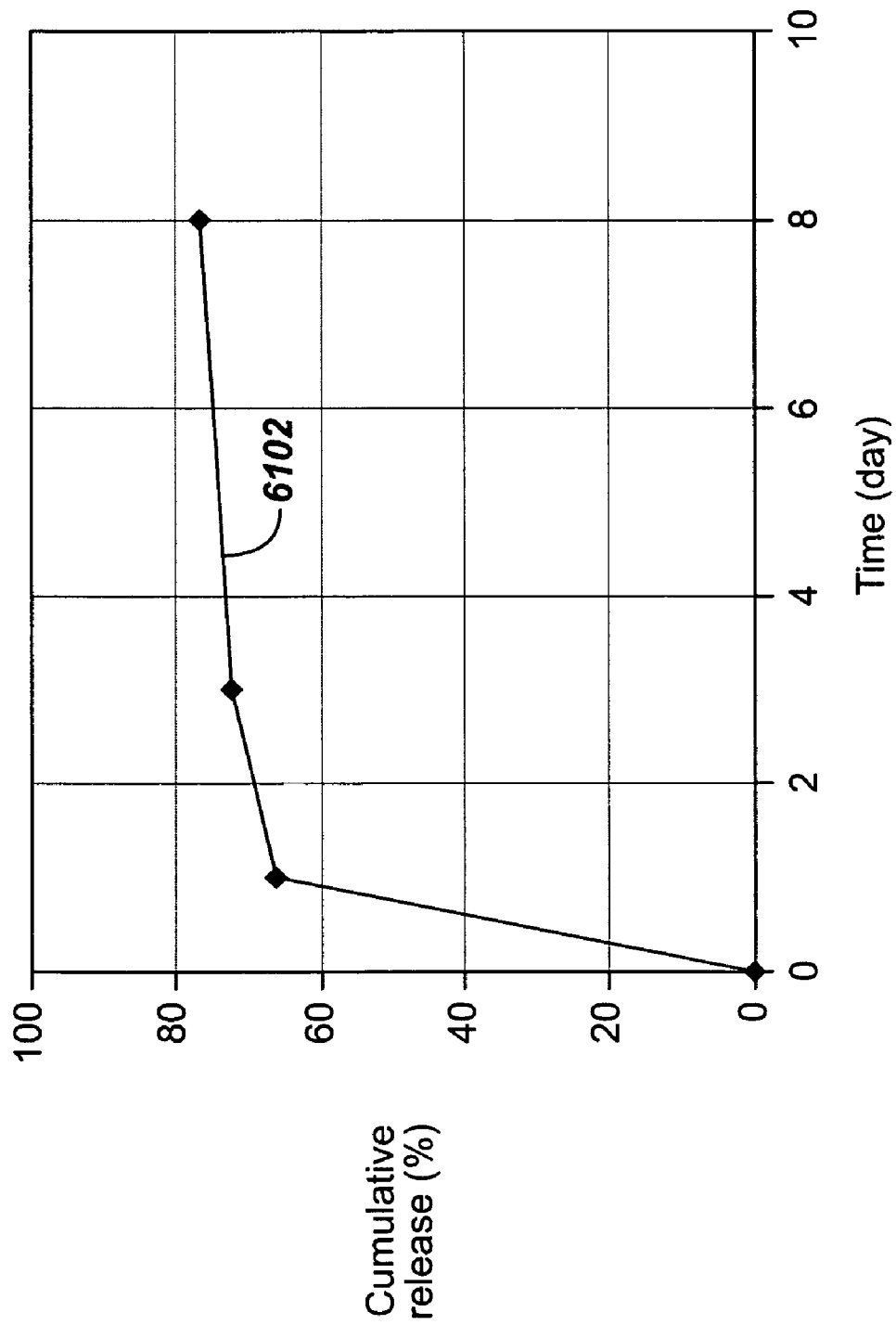
FIG. 61 is a graphical representation of the in vivo release kinetics of cladribine from a polymeric coating in porcine pharmacokinetics studies in accordance with the present invention.

FIG. 61 is a graphical representation of the in vivo release kinetics of cladribine from a polymeric coating on BxVelocity® stents, available from Cordis Corporation, implanted in a Yorkshire pig. The basecoat comprises an 85/15 ratio of PVDF and HFP and cladribine for a total combined weight of one thousand eight hundred micrograms (cladribine comprising thirty percent of the total weight). The topcoat comprises an 85/15 ratio of PVDF/HFP and no cladribine. The total weight of the topcoat is three hundred micrograms. As can be seen from curve 6102, after the first day, the elution of cladribine levels off significantly.

Figure 62:
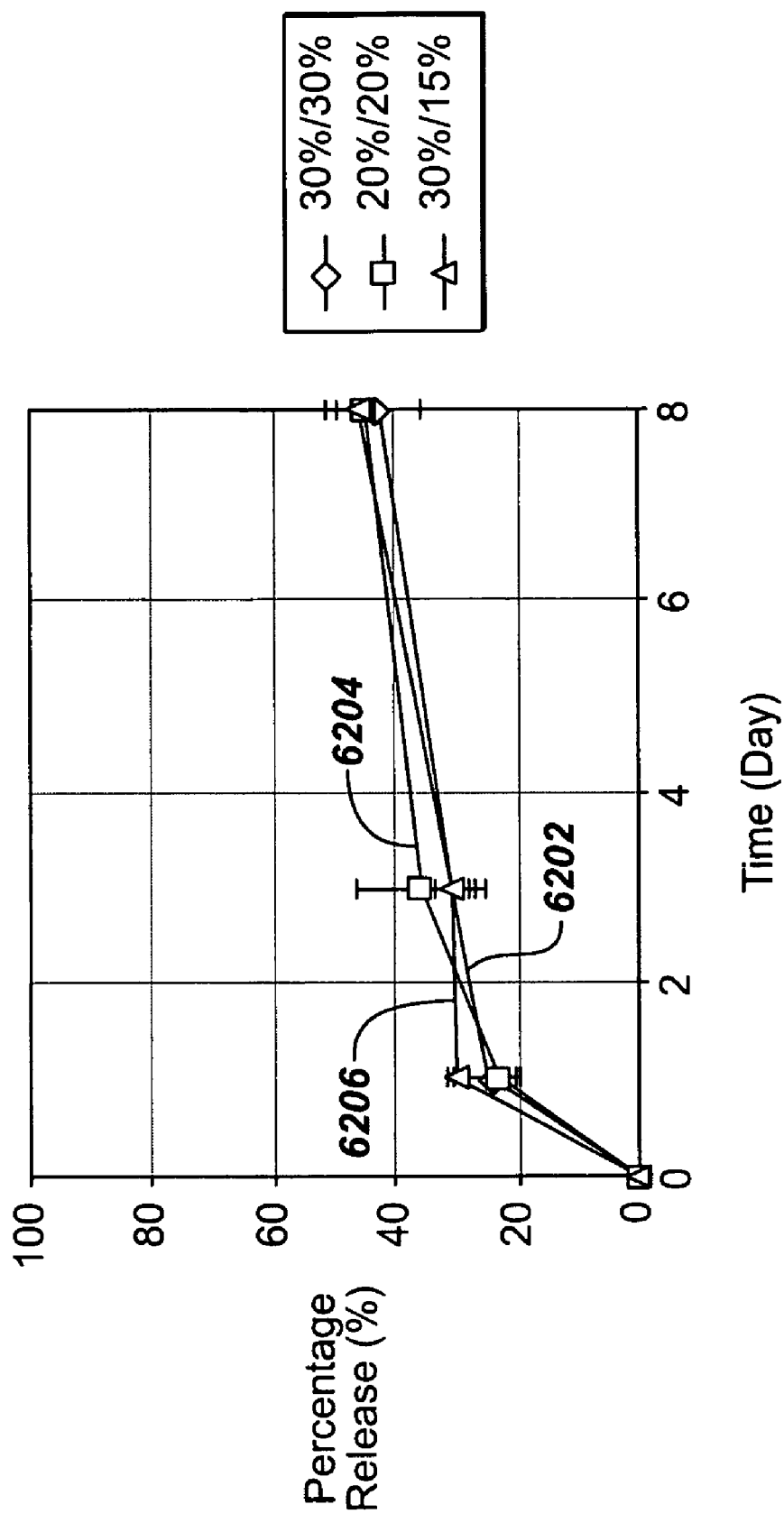
FIG. 62 is a graphical representation of the in vivo release kinetics of rapamycin from a combination of rapamycin, cladribine and a polymer in porcine pharmacokinetics studies in accordance with the present invention.

FIG. 62 is a graphical representation of the in vivo release kinetics of rapamycin from a combination of rapamycin, cladribine and a polymer in porcine pharmacokinetics studies. In the study, the rapamycin and cladribine are incorporated into an EVA/BMA (50/50) polymer basecoat. The basecoat is applied to Bx Velocity® stents and implanted into Yorkshire pigs. Curve 6202 represents the release kinetics of rapamycin from a six hundred microgram basecoat comprising one hundred eighty micrograms rapamycin, one hundred eighty micrograms cladribine and two hundred forty micrograms EVA/BMA with a two hundred microgram topcoat of BMA. Curve 6204 represents the release kinetics of rapamycin from a six hundred microgram basecoat comprising one hundred twenty micrograms rapamycin, one hundred twenty micrograms cladribine and three hundred sixty micrograms EVA/BMA with a two hundred microgram topcoat of BMA. Curve 6206 represents the release kinetics of rapamycin from a six hundred microgram basecoat comprising one hundred eighty micrograms rapamycin, ninety micrograms cladribine and three hundred thirty micrograms EVA/BMA with a two hundred microgram topcoat of BMA. The release rates of rapamycin from the polymeric coating are substantially similar to one another.

Figure 63:
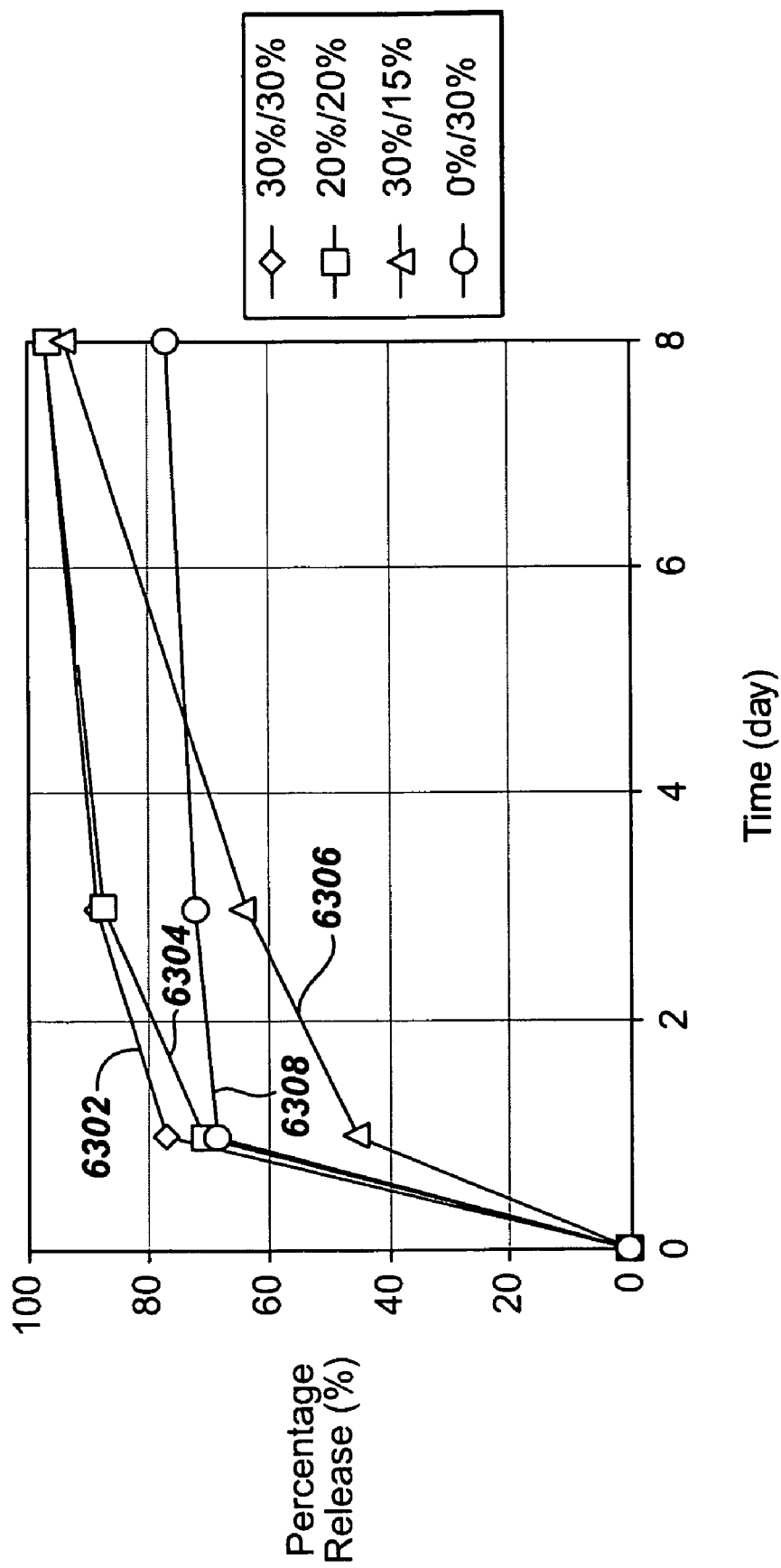
FIG. 63 is a graphical representation of the in vivo release kinetics of cladribine from a combination of rapamycin, cladribine and a polymer in porcine pharmacokinetics studies in accordance with the present invention.

FIG. 63 is a graphical representation of the in vivo release kinetics of cladribine from a combination of rapamycin, cladribine and a polymer in porcine pharmacokinetics studies. In the study, the rapamycin and cladribine are incorporated into an EVA/BMA polymer basecoat. The basecoat is applied to Bx Velocity® stents and implanted into Yorkshire pigs. Curve 6302 represents the release kinetics of cladribine from a six hundred microgram basecoat comprising one hundred eighty micrograms rapamycin, one hundred eighty micrograms cladribine and two hundred forty micrograms EVA/BMA with a two hundred microgram topcoat of BMA. Curve 6304 represents the release kinetics of cladribine from a six hundred microgram basecoat comprising one hundred twenty micrograms rapamycin, one hundred twenty micrograms cladribine and three hundred sixty micrograms EVA/BMA with a two hundred microgram topcoat of BMA. Curve 6306 represents the release kinetics of cladribine from a six hundred microgram basecoat comprising one hundred eighty micrograms rapamycin, ninety micrograms cladribine and three hundred thirty micrograms EVA/BMA with a two hundred microgram topcoat of BMA. Curve 6308 represents the release kinetics of cladribine from a six hundred microgram basecoat comprising no rapamycin, one hundred eighty micrograms of cladribine and four hundred micrograms EVA/BMA with a two hundred microgram BMA topcoat. As illustrated in FIG. 63, there appears to be some degree of controlled cladribine elution from the polymeric stent coating; however, it may be generally concluded that cladribine elutes more rapidly than rapamycin as is seen from a comparison to the results presented with respect to FIG. 62. In general, it appears that the thicker or heavier the topcoat, the slower the elution rate, regardless of the agent.

In yet another alternate exemplary embodiment, topotecan in combination with rapamycin may be utilized to prevent restenosis following vascular injury. Rapamycin acts to reduce lymphocyte and smooth muscle cell proliferation by arresting cells in the G1 phase of the cell cycle through the inhibition of the mammalian target of rapamycin. Subsequent activity of cell cycle associated protein kinases is blocked by the downstream effects of rapamycin on the mammalian target of rapamycin. Topotecan is an analog of camptothecin that interfaces with DNA synthesis through the inhibition of topoisomerase 1. This inhibition leads to an accumulation of DNA double strand breaks and an arrest of cell division at the S phase of the cell cycle. Topotecan has been shown to inhibit human coronary artery smooth muscle cell proliferation (Brehm et al., 2000).

Camptothecin is a quinoline-based alkaloid found in the barks of the Chinese camptotheca tree and the Asian nothapodytes tree. Camptothecin, aminocamptothecin, amerogentin, CPT-11 (irinotecan), DX-8951f and topotecan are all DNA topoisomerase I inhibitors. Topotecan, irinotecan and camptothecin belong to the group of medicines or agents generally referred to as anti-neoplastics and are utilized to treat various forms of cancer, including cancer of the ovaries and certain types of lung cancer. Camptothecin may be particularly advantageous in local delivery because of its high lipid solubility and poor water solubility. Poor water solubility may help retain the drug near the release site for a longer period of action time, potentially covering more cells as they cycle. High lipid solubility may lead to increased penetration of the drug through the lipid cellular membrane, resulting in better efficacy.

As rapamycin and topotecan (and the analogs camptothecin and irinotecan) act through different molecular mechanisms affecting cell proliferation at different phases of the cell cycle, it is possible that these agents, when combined on a drug eluting stent or any other medical device as defined herein, may potentiate each other's anti-restenotic activity by downregulating both smooth muscle cell and immune cell proliferation (inflammatory cell proliferation) by distinct multiple mechanisms. In synchronized cultured human coronary artery smooth muscle cells studies, the addition of topotecan to cells treated with rapamycin resulted in a leftward and upward shift of the anti-proliferative rapamycin dose response curves, as set forth in detail below, suggesting that topotecan, and by extension, other agents in the topoisomerase I inhibitor class, does in fact potentiate the anti-proliferative activity of rapamycin in coronary artery smooth muscle cells. The combination of rapamycin and topotecan may be utilized to enhance the anti-restenotic efficacy following vascular injury and a reduction in the required amount of either agent to achieve the anti-restenotic effect. The combination may be particularly relevant to the subpopulations of patients that are resistant to single drug regimens such as rapamycin or paclitaxel coated stents.

Figure 64:
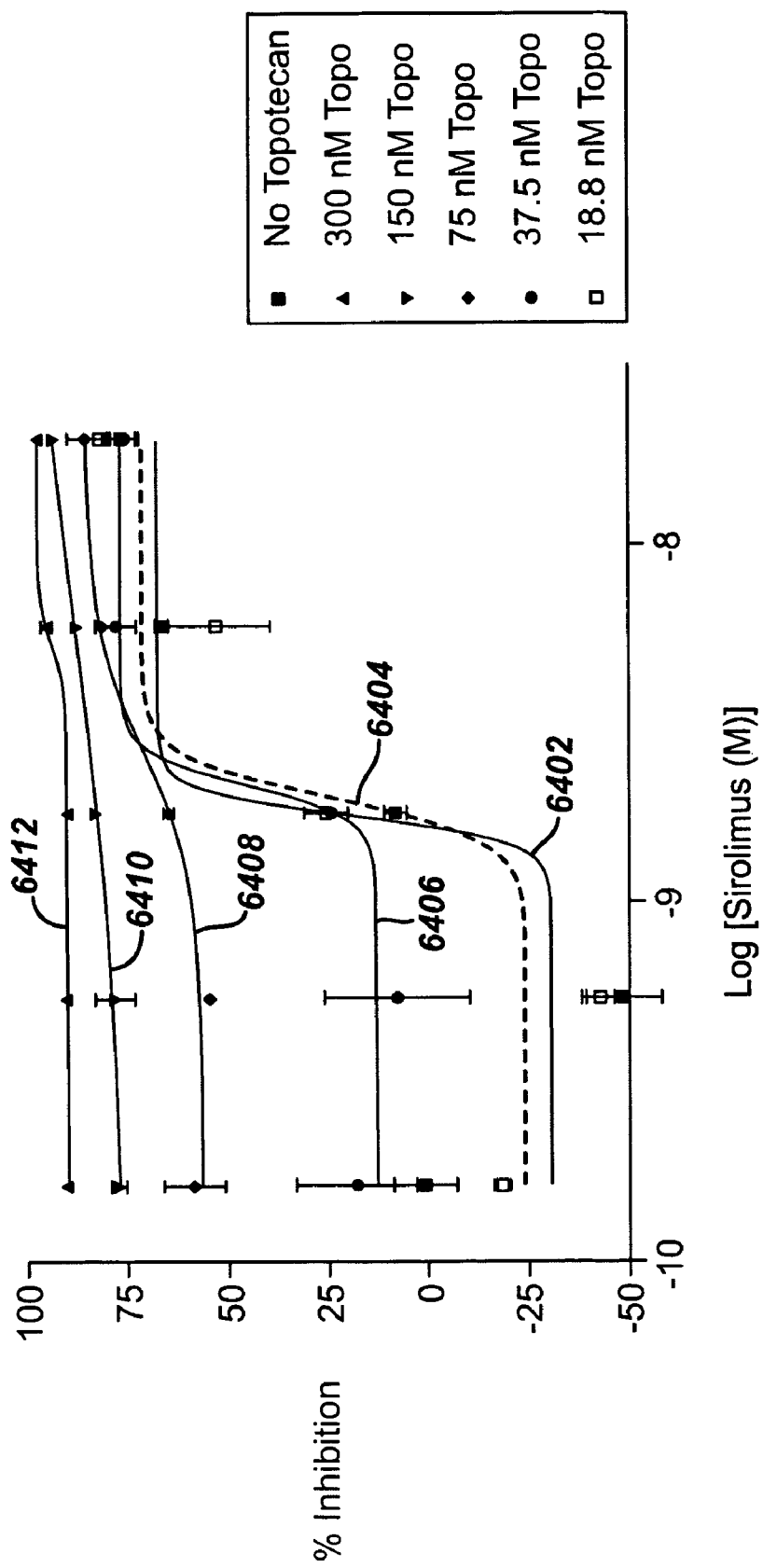
FIG. 64 is a graphical representation of the anti-proliferative activity of rapamycin with varying concentrations of topotecan in synchronized cultured human coronary artery smooth muscle cells stimulated with two percent fetal bovine serum in accordance with the present invention.

Referring to FIG. 64, there is illustrated, in graphical format, the anti-proliferative activity of rapamycin, with varying concentrations of topotecan in synchronized cultured human coronary artery smooth muscle cells stimulated with two percent fetal bovine serum. The multiple curves represent various concentrations of topotecan ranging from zero to three hundred nanomolar concentrations. Topotecan was found to be non-cytotoxic in a separate cell viability assay at concentrations up to one micromolar. As seen in FIG. 64, the addition of topotecan to cells treated with rapamycin increases the percent inhibition of rapamycin alone. Curve 6402 represents the response of just rapamycin. Curve 6404 represents the response of rapamycin in combination with a 18.8 nanomolar concentration of topotecan. Curve 6406 represents the response of rapamycin in combination with a 37.5 nanomolar concentration of topotecan. Curve 6408 represents the response of rapamycin in combination with a 75 nanomolar concentration of topotecan. Curve 6410 represents the response of rapamycin in combination with a 150 nanomolar concentration of topotecan. Curve 6412 represents the response of rapamycin in combination with a 300 nanomolar concentration of topotecan.

The combination of rapamycin and topotecan, as well as other topoisomerase I inhibitors, may provide a new therapeutic combination that may be more efficacious against restenosis/neointimal thickening than rapamycin alone. Different doses of rapamycin and topotecan, as well as other topoisomerase I inhibitors, may lead to additional gains of inhibition of the neointimal growth than the simple additive effects of rapamycin and topotecan. In addition, the combination of topotecan, as well as other topoisomerase I inhibitors, may be efficacious in the treatment of other cardiovascular diseases such as vulnerable atherosclerotic plaque.

The combination of rapamycin and topotecan, as well as other topoisomerase I inhibitors, may be delivered to the target tissue through any number of means including stents and catheters. The delivery of the drug combination may be achieved at different dose rates to achieve the desired effect, and as explained in more detail subsequently, each drug may be loaded into different levels of the polymeric matrix.

In yet another alternate exemplary embodiment, etoposide in combination with rapamycin may be utilized to prevent restenosis following vascular injury. Rapamycin acts to reduce smooth muscle cell proliferation and lymphocyte proliferation by arresting cells in the G1 phase of the cell cycle through inhibition of the mammalian target of rapamycin. Subsequent activity of cell cycle associated protein kinases is blocked by the downstream effects of rapamycin on the mammalian target of rapamycin. Etoposide is a cytostatic glucoside derivative of podophyllotoxin that interferes with DNA synthesis through inhibition of topoisomerase II. This inhibition leads to DNA strand breaks and an accumulation of cells in the G2/M phase of the cell cycle, G2/M checkpoint dysregulation and subsequent apoptosis.

Podophyllotoxin (podofilox) and its derivatives, etoposide and teniposide, are all cytostatic (antimitotic) glucosides.

Podofilox is an extract of the mayapple. Proliferating cells are particularly vulnerable to podofilox. Etoposide is utilized to treat cancer of the testicles, lungs and other kinds of cancer. Etoposide and teniposide both block the cell cycle in two specific places. Etoposide and teniposide block the phase between the last division and the start of DNA replication and also block the replication of DNA.

As rapamycin and etoposide act through different molecular mechanisms affecting cell proliferation at different phases of the cell cycle, it is likely that these agents, when combined on a drug eluting stent or any other medical device as defined herein may potentiate each other's anti-restenotic activity by downregulating both smooth muscle cell and immune cell proliferation (inflammatory cell proliferation) by distinct multiple mechanisms. In non-synchronized cultured human coronary artery smooth muscle cell studies, the addition of etoposide to cells treated with rapamycin resulted in a leftward and upward shift of the anti-proliferative rapamycin dose response curves, as set forth in detail below, suggesting that etoposide, and by extension, other agents in the topoisomerase II inhibitor class, potentiate the anti-proliferative activity of rapamycin in coronary artery smooth muscle cells. The combination of rapamycin and etoposide may be utilized to enhance the anti-restenotic efficacy following vascular injury and a reduction in the required amount of either agent to achieve the anti-restenotic effect. The combination may be particularly relevant to the subpopulation of patients that are resistant to single drug regimens such as rapamycin or paclitaxel coated stents.

Figure 65:
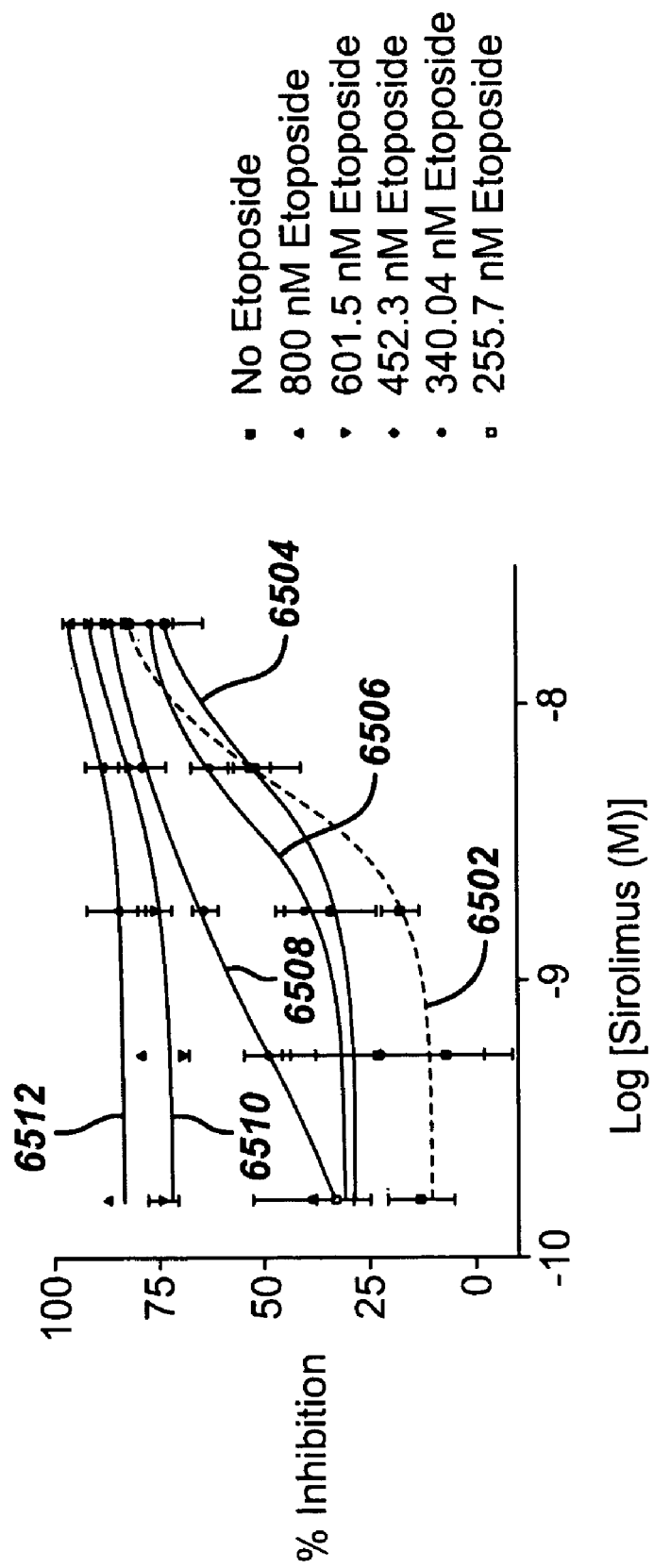
FIG. 65 is a graphical representation of the anti-proliferative activity of rapamycin with varying concentrations of etoposide in synchronized cultured human coronary smooth muscle cells stimulated with two percent fetal bovine serum in accordance with the present invention.

Referring to FIG. 65, there is illustrated, in graphical format, the anti-proliferative activity of rapamycin with varying concentrations of etoposide in synchronized cultured human coronary artery smooth muscle cells stimulated with two percent fetal bovine serum. The multiple curves represent various concentrations of etoposide ranging from zero to eight hundred nanomolar concentrations. Etoposide was found to be non-cytotoxic in a cell viability assay at concentrations up to ten micromolar. As seen in FIG. 65, the addition of etoposide to cells treated with rapamycin increases the percent inhibition of rapamycin alone. Curve 6502 represents the response of just rapamycin. Curve 6504 represents the response of rapamycin in combination with a 255.7 nanomolar concentration of etoposide. Curve 6506 represents the response of rapamycin in combination with a 340.04 nanomolar concentration of etoposide. Curve 6508 represents the response of rapamycin in combination with a 452.3 nanomolar concentration of etoposide. Curve 6510 represents the response of rapamycin in combination with a 601.5 nanomolar concentration of etoposide. Curve 6512 represents the response of rapamycin in combination with an eight-hundred nanomolar concentration of etoposide.

The combination of rapamycin and etoposide, as well as other cytostatic glucosides, including podophyllotoxin, its derivatives and teniposide, may provide a new therapeutic combination that may be more efficacious against restenosis/neointimal thickening than rapamycin alone. Different doses of rapamycin and etoposide, as well as other cytostatic glucosides, including podophyllotoxin, its derivatives and teniposide, may lead to additional gains of inhibition of the neointimal growth than the simple additive effects of rapamycin and etoposide. In addition, the combination of etoposide, as well as other cytostatic glucosides, including podophyllotoxin, its derivatives and teniposide, may be efficacious in the treatment of other cardiovascular diseases such as vulnerable atherosclerotic plaque.

The combination of rapamycin and etoposide, as well as other cytostatic glucosides, including podophyllotoxin, its derivatives and teniposide, may be delivered to the target tissue through any number of means including stents and catheters. The delivery of the drug combination may be achieved at different dose rates to achieve the desired effect, and as explained in more detail subsequently, each drug may be loaded into different levels of the polymeric matrix.

In yet another alternate exemplary embodiment, Panzem® may be utilized alone or in combination with rapamycin to prevent restenosis following vascular injury. Rapamycin or sirolimus acts to reduce lymphocyte and smooth muscle cell proliferation by arresting cells in the G1 phase of the cell cycle through the inhibition of the mammalian target of rapamycin (mTOR). Rapamycin or sirolimus has shown excellent anti-restenotic effects when administered during revascularization procedures using drug eluting stents. In recent clinical trials, the Cypher® stent, available from Cordis Corporation, which contains rapamycin or sirolimus in a polymer coating, consistently demonstrated superior efficacy against restenosis after the implantation of the stent as compared to a bare metal stent. Although the local delivery of rapamycin from a drug eluting stent or other medical device is effective in reducing restenosis, further reductions in neointimal hyperplasia would benefit certain patient populations. Thus, the combination of rapamycin with another agent, for example, another anti-proliferative agent from a stent or other medical device may further reduce fibroproliferative vascular responses secondary to procedures involving vascular injury.

Panzem®, or 2-methoxyestradiol (2ME2) is a naturally occurring metabolite of endogenous estrogen. Its many properties provide for a wide range of potential formulations for drug delivery to treat numerous indications. Panzem® has been shown to exhibit anti-cancer activity in patients with breast cancer, prostate cancer and multiple myeloma. Panzem® is a by-product of the metabolism estrogen and is normally present in the body in small amounts. Panzem®; however, does not act like a hormone. Panzem® is a potent inhibitor of angiogenesis, which is what makes it such an effective anti-tumor agent. Essentially, Panzem® inhibits the formation of new blood vessels that supply oxygen and nutrients to tumor cells. Panzem® also appears to have multiple direct and indirect anti-myeloma effects as briefly described above.

Panzem®, 2-methoxyestradiol (2ME2) or methoxy-β-estradiol is, as described above, a product of estrogen metabolism and is currently being evaluated clinically for a variety of oncologic indications. Panzem® has anti-angiogenic activity, blocks the production of vascular endothelial growth factor and directly inhibits the growth of a number of tumor cell types. Panzem® is also proapoptotic (programmed cell death) to myeloma cells. Panzem® has been found to upregulate the DR-5 receptor (of the TNF receptor family) number responsible for TRAIL-mediated apoptosis (AACR, 2003) and has microtubule stabilizing properties and reduces hypoxia-inducible factor-1 (MCR, 2003). In addition, as illustrated in detail below, Panzem® reduces human coronary artery smooth muscle cell proliferation without negatively impacting coronary artery smooth muscle cell viability.

Figure 66:
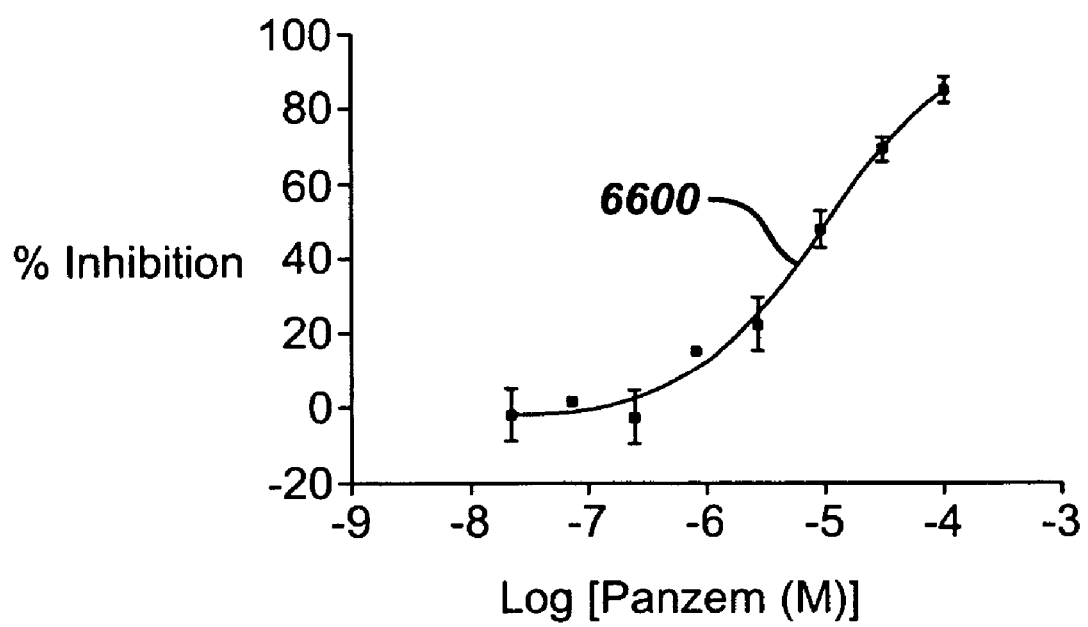
FIG. 66 is a graphical representation of the anti-proliferative activity of Panzem® in synchronized cultured human coronary artery smooth muscle cells stimulated with two percent fetal bovine serum in accordance with the present invention.
Figure 67:
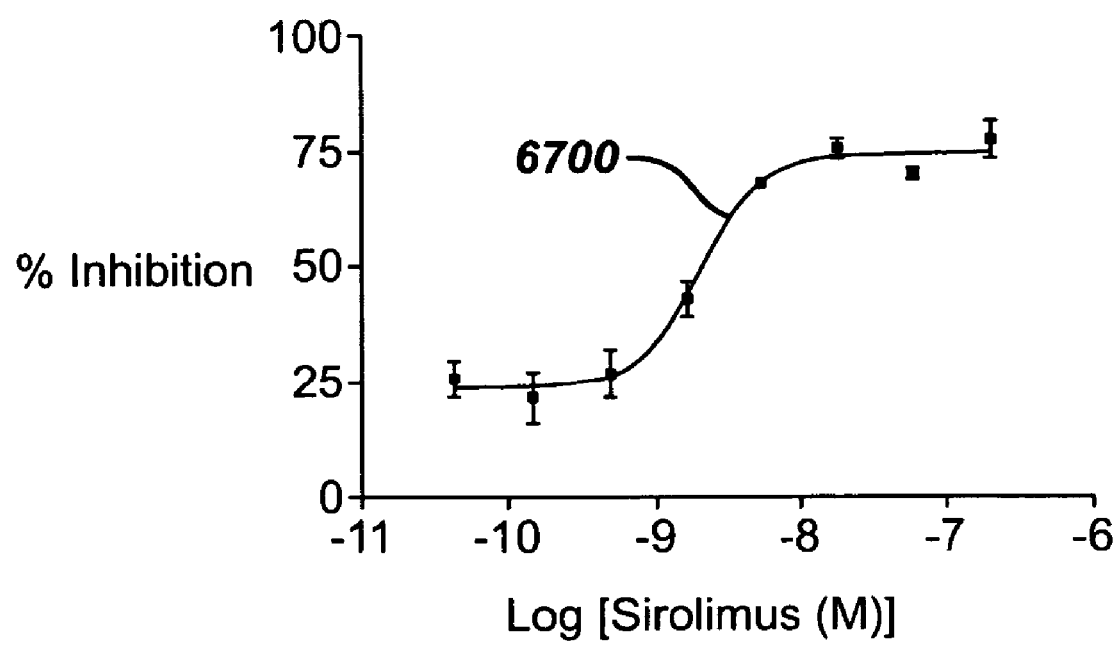
FIG. 67 is a graphical representation of the anti-proliferative activity of rapamycin in synchronized cultured human coronary artery smooth muscle cells stimulated with two percent fetal bovine serum in accordance with the present invention.

Referring to FIG. 66, there is illustrated, in graphical format, the anti-proliferative activity of Panzem® in synchronized cultured human coronary artery smooth muscle cells stimulated with two percent fetal bovine serum. As illustrated by curve 6600, Panzem® is an extremely effective inhibitor of human coronary artery smooth muscle cell proliferation in vitro. FIG. 67 illustrates, in graphical format, the anti-proliferative activity of rapamycin or sirolimus in synchronized cultured human coronary artery smooth muscle cells stimulated with two percent fetal bovine serum. As can be seen between a comparison between curves 6700 and 6600, both agents are effective in the in vitro studies.

Figure 68:
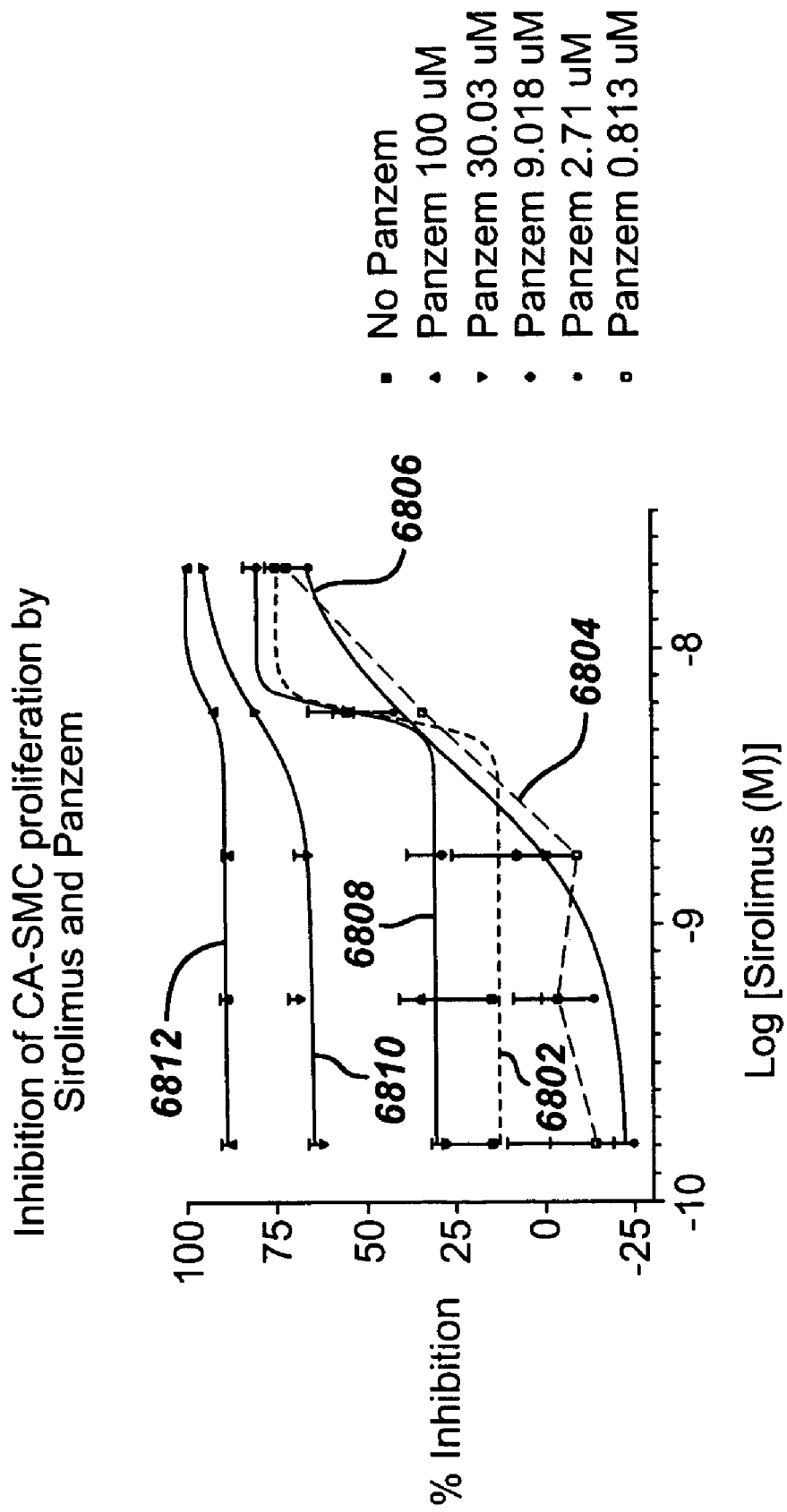
FIG. 68 is a graphical representation of the anti-proliferative activity of rapamycin with varying concentrations of Panzem® in synchronized cultured human coronary artery smooth muscle cells stimulated with two percent fetal bovine serum in accordance with the present invention.

As rapamycin or sirolimus and Panzem® or other estrogen receptor modulators act to inhibit cell proliferation through different molecular mechanisms, it is possible that these agents, when combined on a drug eluting stent or other medical device as defined herein, may potentiate each other's anti-restenotic activity by downregulating both smooth muscle and immune cell proliferation (inflammatory cell proliferation) by distinct multiple mechanisms. FIG. 68 illustrates the potentiation of rapamycin by Panzem® on the anti-proliferative effects of rapamycin in coronary artery smooth muscle cells. This potentiation of rapamycin anti-proliferative activity by Panzem® and related compounds may translate into an enhancement in anti-restenotic efficacy following vascular injury during revascularization and other vascular surgical procedures and a reduction in the required amount of either agent to achieve the anti-restenotic effect. In addition, the local application of Panzem® and related compounds, alone or in combination with rapamycin may be therapeutically useful in treating vulnerable plaque.

Referring to FIG. 68, there is illustrated, in graphical format, the anti-proliferative activity of rapamycin with varying concentrations of Panzem® in synchronized cultured human coronary artery smooth muscle cells stimulated with two percent fetal bovine serum. The multiple curves represent various concentrations of Panzem® ranging from zero to 100 micromolar concentrations. As seen in FIG. 68, the addition of Panzem® to cells treated with rapamycin increases the percent of inhibition of rapamycin alone. Curve 6802 represents the response of just rapamycin. Curve 6804 represents the response of rapamycin in combination with a 0.813 micromolar concentration of Panzem®. Curve 6806 represents the response of rapamycin in combination with a 2.71 micromolar concentration of Panzem®. Curve 6808 represents the response of rapamycin in combination with a 9.018 micromolar concentration of Panzem®. Curve 6810 represents the response of rapamycin in combination with a 30.03 micromolar concentration of Panzem®. Curve 6812 represents the response of rapamycin in combination with a 100 micromolar concentration of Panzem®.

Figure 69:
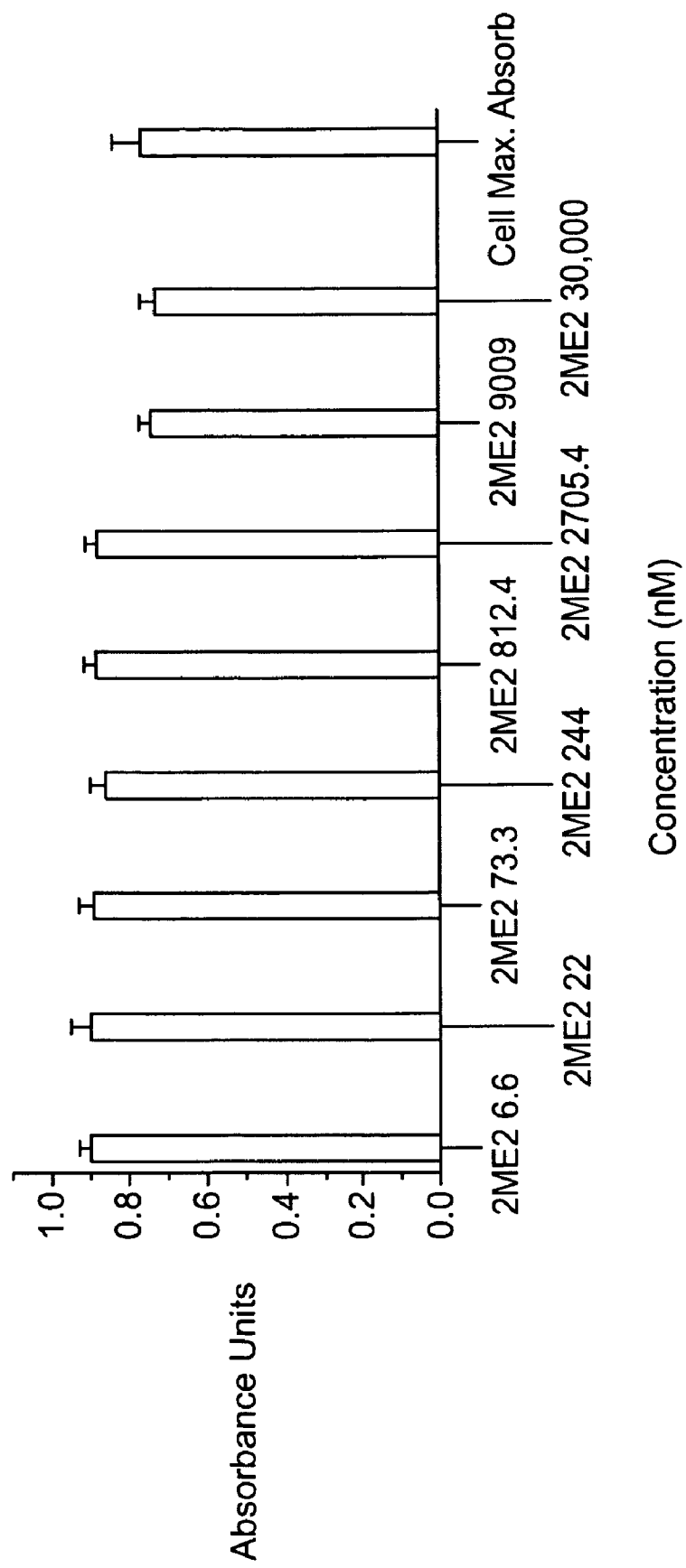
FIG. 69 is a graphical representation of a MTS assay of Panzem® in accordance with the present invention.

In vitro cytotoxicity tests or assays may be utilized to determine if drugs, agents and/or compounds are potentially toxic and the level of toxicity. Essentially, in vitro cytotoxicity assays determine acute necrotic effects by a drug causing direct cellular damage. The idea behind these assays is that toxic chemicals affect basic functions of cells which are common to all cells. Typically, a control is utilized to determine baseline toxicity. There are a number of different assays that may be utilized. In the present invention, the cytotoxicity assay utilized is based upon the measurement of cellular metabolic activity. A reduction in metabolic activity is an indication of cellular damage. Tests that can measure metabolic function measure cellular ATP levels or mitochondrial activity via MTS metabolism. FIG. 69 is a graphical representation of the results of an MTS assay of Panzem®. As illustrated, concentrations of Panzem® ranging from 6.6 nanomolar to 30,000.00 nanomolar concentrations were tested without any significant fluctuations in cytotoxicity. The results of the assay indicate that Panzem® concentrations up to 30,000.00 nanomolar do not reduce human coronary artery smooth muscle cell survival.

Figure 70:
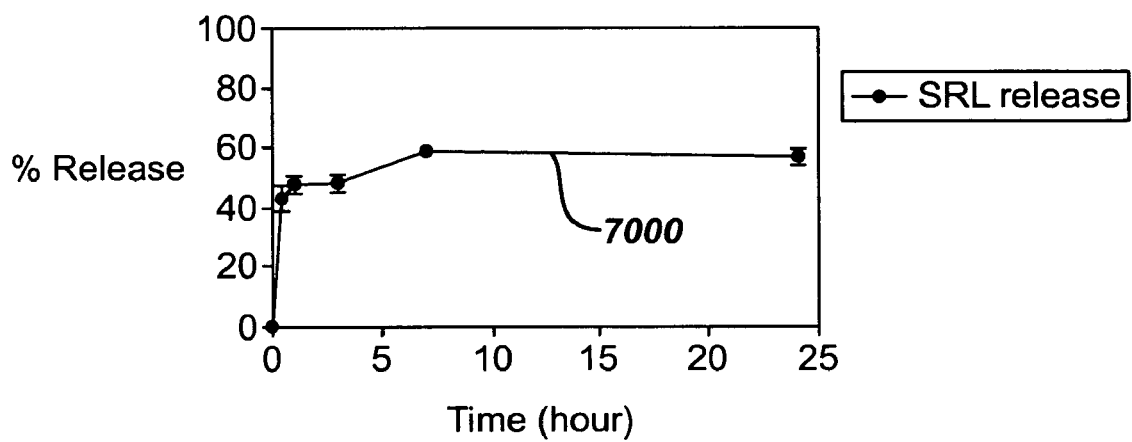
FIG. 70 is a graphical representation of the in vitro release kinetics of rapamycin from a layered rapamycin, Panzem® and polymeric coating in accordance with the present invention.

FIG. 70 is a graphical representation of the in vitro release kinetics of rapamycin or sirolimus from a combination of rapamycin and Panzem®. In the study, the rapamycin and Panzem® are incorporated into different layers of a polymeric coating. In this study, a Bx Velocity stent is coated with a four hundred microgram inner layer and a three hundred microgram outer layer. The inner layer comprises forty-five percent Panzem® and fifty-five percent EVA/BMA (50/50). The outer layer comprises forty percent rapamycin and sixty percent EVA/BMA (50/50). There is no topcoat of just polymer in this study. Curve 7000 illustrates the release kinetics of rapamycin from the combination.

Figure 71:
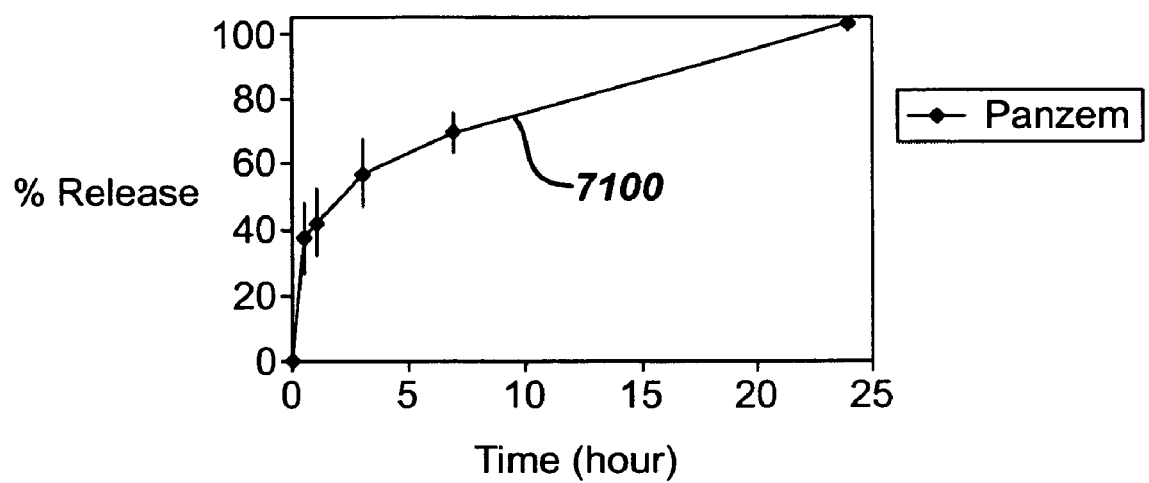
FIG. 71 is a graphical representation of the in vitro release kinetics of Panzem® from a layered rapamycin, Panzem® and polymeric coating in accordance with the present invention.
Figure 72A:
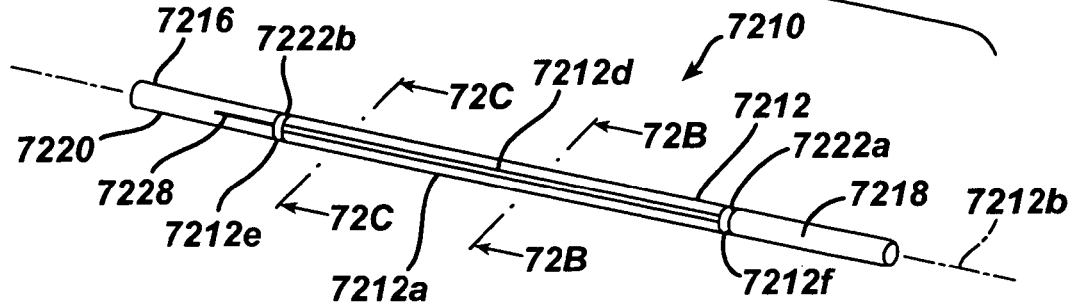
FIG. 72A is a schematic, perspective view of a microfabricated surgical device for interventional procedures in an unactuated condition in accordance with the present invention.
Figure 72B:
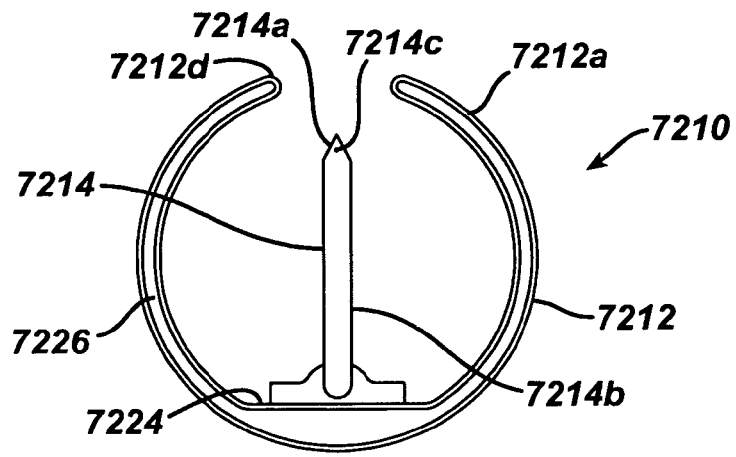
FIG. 72B is a schematic view along line 72B-72B of FIG. 72A.
Figure 72C:
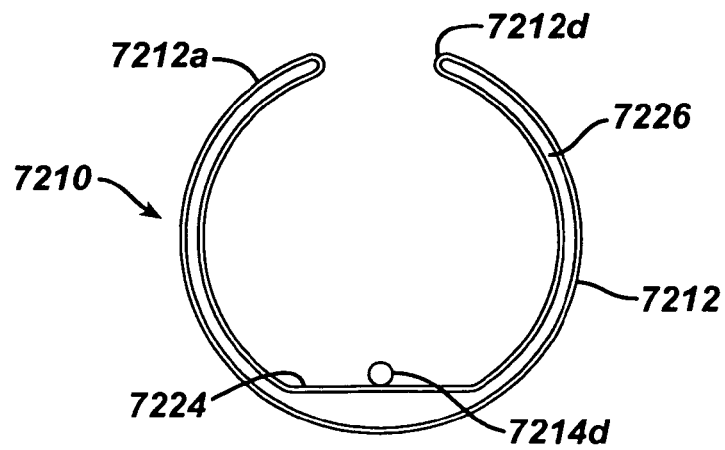
FIG. 72C is a schematic view along line 72C-72C of FIG. 72A.

FIG. 71 is a graphical representation of the in vitro release kinetics of Panzem® from a combination of rapamycin or sirolimus and Panzem®. In the study, the rapamycin and Panzem® are incorporated into different layers of a polymeric coating. In this study, a Bx Velocity stent is coated with a four hundred microgram inner layer and a three hundred microgram outer layer. The inner layer comprises forty-five percent Panzem® and fifty-five percent EVA/BMA (50/50). The outer layer comprises forty percent rapamycin and sixty percent EVA/BMA (50/50). There is no topcoat of just polymer in this study. Curve 7100 illustrates the release kinetics of Panzem® from the coating. As may be seen from a comparison of FIGS. 70 and 71, rapamycin elutes more slowly than Panzem® under the conditions of the test.

As is explained in more detail subsequently, a combination of incompatible polymers may be utilized in combination with rapamycin and mycophenolic acid, rapamycin and trichostatin A, rapamycin and cladribine, rapamycin and topotecan, rapamycin and etoposide, rapamycin and Panzem and/or any of the drugs, agents and/or compounds described herein to provide for the controlled local delivery of these drugs, agents and/or compounds or combinations thereof from a medical device. In addition, these incompatible polymers may be utilized in various combinations to control the release rates of individual agents from combinations of agents. For example, from the tests described above, it is seen that mycophenolic acids elute more quickly than rapamycin. Accordingly, the correct combination of incompatible polymers may be utilized to ensure that both agents elute at the same rate if so desired.

The coatings and drugs, agents or compounds described above may be utilized in combination with any number of medical devices, and in particular, with implantable medical devices such as stents and stent-grafts. Other devices such as vena cava filters and anastomosis devices may be used with coatings having drugs, agents or compounds therein. The exemplary stent illustrated in FIGS. 1 and 2 is a balloon expandable stent. Balloon expandable stents may be utilized in any number of vessels or conduits, and are particularly well suited for use in coronary arteries. Self-expanding stents, on the other hand, are particularly well suited for use in vessels where crush recovery is a critical factor, for example, in the carotid artery. Accordingly, it is important to note that any of the drugs, agents or compounds, as well as the coatings described above, may be utilized in combination with self-expanding stents which are known in the art.

Surgical anastomosis is the surgical joining of structures, specifically the joining of tubular organs to create an intercommunication between them. Vascular surgery often involves creating an anastomosis between blood vessels or between a blood vessel and a vascular graft to create or restore a blood flow path to essential tissues. Coronary artery bypass graft surgery (CABG) is a surgical procedure to restore blood flow to ischemic heart muscle whose blood supply has been compromised by occlusion or stenosis of one or more of the coronary arteries. One method for performing CABG surgery involves harvesting a saphenous vein or other venous or arterial conduit from elsewhere in the body, or using an artificial conduit, such as one made of Dacron® or GoreTex® tubing, and connecting this conduit as a bypass graft from a viable artery, such as the aorta, to the coronary artery downstream of the blockage or narrowing. It is preferable to utilize natural grafts rather than synthetic grafts. A graft with both the proximal and distal ends of the graft detached is known as a "free graft." A second method involves rerouting a less essential artery, such as the internal mammary artery, from its native location so that it may be connected to the coronary artery downstream of the blockage. The proximal end of the graft vessel remains attached in its native position. This type of graft is known as a "pedicled graft." In the first case, the bypass graft must be attached to the native arteries by an end-to-side anastomosis at both the proximal and distal ends of the graft. In the second technique at least one end-to-side anastomosis must be made at the distal end of the artery used for the bypass. In the description of the exemplary embodiment given below reference will be made to the anastomoses on a free graft as the proximal anastomosis and the distal anastomosis. A proximal anastomosis is an anastomosis on the end of the graft vessel connected to a source of blood, for example, the aorta and a distal anastomosis is an anastomosis on the end of the graft vessel connected to the destination of the blood flowing through it, for example, a coronary artery. The anastomoses will also sometimes be called the first anastomosis or second anastomosis, which refers to the order in which the anastomoses are performed regardless of whether the anastomosis is on the proximal or distal end of the graft.

At present, essentially all vascular anastomoses are performed by conventional hand suturing. Suturing the anastomoses is a time-consuming and difficult task, requiring much skill and practice on the part of the surgeon. It is important that each anastomosis provide a smooth, open flow path for the blood and that the attachment be completely free of leaks. A completely leak-free seal is not always achieved on the very first try. Consequently, there is a frequent need for resuturing of the anastomosis to close any leaks that are detected.

The time consuming nature of hand sutured anastomoses is of special concern in CABG surgery for several reasons. Firstly, the patient is required to be supported on cardiopulmonary bypass (CPB) for most of the surgical procedure, the heart must be isolated from the systemic circulation (i.e. "cross-clamped"), and the heart must usually be stopped, typically by infusion of cold cardioplegia solution, so that the anastomosis site on the heart is still and blood-free during the suturing of the anastomosis. Cardiopulminary bypass, circulatory isolation and cardiac arrest are inherently very traumatic, and it has been found that the frequency of certain post-surgical complications varies directly with the duration for which the heart is under cardioplegic arrest (frequently referred to as the "crossclamp time"). Secondly, because of the high cost of cardiac operating room time, any prolongation of the surgical procedure can significantly increase the cost of the bypass operation to the hospital and to the patient. Thus, it is desirable to reduce the duration of the crossclamp time and of the entire surgery by expediting the anastomosis procedure without reducing the quality or effectiveness of the anastomoses.

The already high degree of manual skill required for conventional manually sutured anastomoses is even more elevated for closed-chest or port-access thoracoscopic bypass surgery, a newly developed surgical procedure designed to reduce the morbidity of CABG surgery as compared to the standard open-chest CABG procedure. In the closed-chest procedure, surgical access to the heart is made through narrow access ports made in the intercostal spaces of the patient's chest, and the procedure is performed under thoracoscopic observation. Because the patient's chest is not opened, the suturing of the anastomoses must be performed at some distance, using elongated instruments positioned through the access ports for approximating the tissues and for holding and manipulating the needles and sutures used to make the anastomoses. This requires even greater manual skill than the already difficult procedure of suturing anastomoses during open-chest CABG surgery.

In order to reduce the difficulty of creating the vascular anastomoses during either open or closed-chest CABG surgery, it would be desirable to provide a rapid means for making a reliable end-to-side anastomosis between a bypass graft or artery and the aorta or the native vessels of the heart. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery. Various surgical stapling instruments have been developed for end-to-end, side-to-side, and end-to-side anastomoses of hollow or tubular organs, such as the bowel. These instruments, unfortunately, are not easily adaptable for use in creating vascular anastomoses. This is partially due to the difficulty in miniaturizing the instruments to make them suitable for smaller organs such as blood vessels. Possibly even more important is the necessity of providing a smooth, open flow path for the blood. Known gastrointestinal stapling instruments for end-to-side or end-to-end anastomosis of tubular organs are designed to create an inverted anastomosis, that is, one where the tissue folds inward into the lumen of the organ that is being attached. This is acceptable in gastrointestinal surgery, where it is most important to approximate the outer layers of the intestinal tract (the serosa). This is the tissue which grows together to form a strong, permanent connection. However, in vascular surgery this geometry is unacceptable for several reasons. Firstly, the inverted vessel walls would cause a disruption in the blood flow. This could cause decreased flow and ischemia downstream of the disruption, or, worse yet, the flow disruption or eddies created could become a locus for thrombosis which could shed emboli or occlude the vessel at the anastomosis site. Secondly, unlike the intestinal tract, the outer surfaces of the blood vessels (the adventitia) will not grow together when approximated. The sutures, staples, or other joining device may therefore be needed permanently to maintain the structural integrity of the vascular anastomosis. Thirdly, to establish a permanent, nonthrombogenic vessel, the innermost layer (the endothelium) should grow together for a continuous, uninterrupted lining of the entire vessel. Thus, it would be preferable to have a stapling instrument that would create vascular anastomoses that are everted, that is folded outward, or which create direct edge-to-edge coaptation without inversion.

At least one stapling instrument has been applied to performing vascular anastomoses during CABG surgery. This device, first adapted for use in CABG surgery by Dr. Vasilii I. Kolesov and later refined by Dr. Evgenii V. Kolesov (U.S. Pat. No. 4,350,160), was used to create an end-to-end anastomosis between the internal mammary artery (IMA) or a vein graft and one of the coronary arteries, primarily the left anterior descending coronary artery (LAD). Because the device could only perform end-to-end anastomoses, the coronary artery first had to be severed and dissected from the surrounding myocardium, and the exposed end everted for attachment. This technique limited the indications of the device to cases where the coronary artery was totally occluded, and therefore there was no loss of blood flow by completely severing the coronary artery downstream of the blockage to make the anastomosis. Consequently, this device is not applicable where the coronary artery is only partially occluded and is not at all applicable to making the proximal side-to-end anastomosis between a bypass graft and the aorta.

One attempt to provide a vascular stapling device for end-to-side vascular anastomoses is described in U.S. Pat. No. 5,234,447, issued to Kaster et al. for a Side-to-end Vascular Anastomotic Staple Apparatus. Kaster et al. provide a ring-shaped staple with staple legs extending from the proximal and distal ends of the ring to join two blood vessels together in an end-to-side anastomosis. However, Kaster et al. does not provide a complete system for quickly and automatically performing an anastomosis. The method of applying the anastomosis staple disclosed by Kaster et al. involves a great deal of manual manipulation of the staple, using hand operated tools to individually deform the distal tines of the staple after the graft has been attached and before it is inserted into the opening made in the aortic wall. One of the more difficult maneuvers in applying the Kaster et al. staple involves carefully everting the graft vessel over the sharpened ends of the staple legs, then piercing the evened edge of the vessel with the staple legs. Experimental attempts to apply this technique have proven to be very problematic because of difficulty in manipulating the graft vessel and the potential for damage to the graft vessel wall. For speed, reliability and convenience, it is preferable to avoid the need for complex maneuvers while performing the anastomosis. Further bending operations must then be performed on the staple legs. Once the distal tines of the staple have been deformed, it may be difficult to insert the staple through the aortotomy opening. Another disadvantage of the Kaster et al. device is that the distal tines of the staple pierce the wall of the graft vessel at the point where it is evened over the staple. Piercing the wall of the graft vessel potentially invites leaking of the anastomosis and may compromise the structural integrity of the graft vessel wall, serving as a locus for a dissection or even a tear, which could lead to catastrophic failure. Because the Kaster et al staple legs only apply pressure to the anastomosis at selected points, there is a potential for leaks between the staple legs. The distal tines of the staple are also exposed to the blood flow path at the anastomotic site where it is most critical to avoid the potential for thrombosis. There is also the potential that exposure of the medial layers of the graft vessel where the staple pierces the wall could be a site for the onset of intimal hyperplasia, which would compromise the long-term patency of the graft as described above. Because of these potential drawbacks, it is desirable to make the attachment to the graft vessel as atraumatic to the vessel wall as possible and to eliminate as much as possible the exposure of any foreign materials or any vessel layers other than a smooth uninterrupted intimal layer within the anastomosis site or within the graft vessel lumen.

A second approach to expediting and improving anastomosis procedures is through the use of anastomotic fittings for joining blood vessels together. One attempt to provide a vascular anastomotic fitting device for end-to-side vascular anastomoses is described in U.S. Pat. No. 4,366,819, issued to Kaster for an Anastomotic Fitting. This device is a four-part anastomotic fitting having a tubular member over which the graft vessel is evened, a ring flange which engages the aortic wall from within the aortic lumen, and a fixation ring and a locking ring which engage the exterior of the aortic wall. Another similar Anastomotic Fitting is described in U.S. Pat. No. 4,368,736, also issued to Kaster. This device is a tubular fitting with a flanged distal end that fastens to the aortic wall with an attachment ring, and a proximal end with a graft fixation collar for attaching to the graft vessel. These devices have a number of drawbacks. Firstly, the anastomotic fittings described expose the foreign material of the anastomotic device to the blood flow path within the arteries. This is undesirable because foreign materials within the blood flow path can have a tendency to cause hemolysis, platelet deposition and thrombosis. Immune responses to foreign material, such as rejection of the foreign material or auto-immune responses triggered by the presence of foreign material, tend to be stronger when the material is exposed to the bloodstream. As such, it is preferable that as much as possible of the interior surfaces of an anastomotic fitting that will be exposed to the blood flow path be covered with vascular tissue, either from the target vessel or from the graft vessel, so that a smooth, continuous, hemocompatible endothelial layer will be presented to the bloodstream. The anastomotic fitting described by Kaster in the '819 patent also has the potential drawback that the spikes that hold the graft vessel onto the anastomotic fitting are very close to the blood flow path, potentially causing trauma to the blood vessel that could lead to leaks in the anastomosis or compromise of the mechanical integrity of the vessels. Consequently, it is desirable to provide an anastomosis fitting that is as atraumatic to the graft vessel as possible. Any sharp features such as attachment spikes should be placed as far away from the blood flow path and the anastomosis site as possible so that there is no compromise of the anastomosis seal or the structural integrity of the vessels.

Another device, the 3M-Unilink device for end-to-end anastomosis (U.S. Pat. Nos. 4,624,257; 4,917,090; 4,917,091) is designed for use in microsurgery, such as for reattaching vessels severed in accidents. This device provides an anastomosis clamp that has two eversion rings which are locked together by a series of impaling spikes on their opposing faces. However, this device is awkward for use in end-to-side anastomosis and tends to deform the target vessel; therefore it is not currently used in CABG surgery. Due to the delicate process needed to insert the vessels into the device, it would also be unsuitable for port-access surgery.

In order to solve these and other problems, it is desirable to provide an anastomosis device which performs an end-to-side anastomosis between blood vessels or other hollow organs and vessels. It is also desirable to provide an anastomosis device which minimizes the trauma to the blood vessels while performing the anastomosis, which minimizes the amount of foreign materials exposed to the blood flow path within the blood vessels and which avoids leakage problems, and which promotes rapid endothelialization and healing. It is also desirable that the invention provide a complete system for quickly and automatically performing an anastomosis with a minimal amount of manual manipulation.

Anastomosis devices may be utilized to join biological tissues, and more particularly, joining tubular organs to create a fluid channel. The connections between the tubular organs or vessels may be made side to side, end to end and/or end to side. Typically, there is a graft vessel and a target vessel. The target vessel may be an artery, vein or any other conduit or fluid carrying vessel, for example, coronary arteries. The graft vessel may comprise a synthetic material, an autologus vessel, a homologus vessel or a xenograft. Anastomosis devices may comprise any suitable biocompatible materials, for example, metals, polymers and elastomers. In addition, there are a wide variety of designs and configurations for anastomosis devices depending on the type of connection to be made. Similarly to stents, anastomosis devices cause some injury to the target vessel, thereby provoking a response from the body. Therefore, as in the case with stents, there is the potential for smooth muscle cell proliferation which can lead to blocked connections. Accordingly, there is a need to minimize or substantially eliminate smooth muscle cell proliferation and inflammation at the anastomotic site. Rapamycin and/or other drugs, agents or compounds may be utilized in a manner analogous to stents as described above. In other words, at least a portion of the anastomosis device may be coated with rapamycin or other drug, agent and/or compound.

FIGS. 10-13 illustrate an exemplary anastomosis device 200 for an end to side anastomosis. The exemplary anastomosis device 200 comprises a fastening flange 202 and attached staple members 204. As stated above, the anastomosis device may comprise any suitable biocompatible material. Preferably, the anastomosis device 200 comprises a deformable biocompatible metal, such as a stainless steel alloy, a titanium alloy or a cobalt alloy. Also as stated above, a surface coating or surface coating comprising a drug, agent or compound may be utilized to improve the biocompatibility or other material characteristics of the device as well as to reduce or substantially eliminate the body's response to its placement therein.

In the exemplary embodiment, the fastening flange 202 resides on the interior surface 206 of the target vessel wall 208 when the anastomosis is completed. In order to substantially reduce the risk of hemolysis, thrombogenesis or foreign body reactions, the total mass of the fastening flange 202 is preferably as small as possible to reduce the amount of foreign material within the target vessel lumen 210.

The fastening flange 202 is in the form of a wire ring with an internal diameter, which when fully expanded, is slightly greater than the outside diameter of the graft vessel wall 214 and of the opening 216 made in the target vessel wall 208. Initially, the wire ring of the fastening flange 202 has a rippled wave-like shape to reduce the diameter of the ring so that it will easily fit through the opening 216 in the target vessel wall 208. The plurality of staple members 204 extend substantially perpendicular from the wire ring in the proximal direction. In the illustrative exemplary embodiment, there are nine staple members 204 attached to the wire ring fastening flange 202. Other variations of the anastomosis device 200 might typically have from four to twelve staple members 204 depending on the size of the vessels to be joined and the security of attachment required in the particular application. The staple members 204 may be integrally formed with the wire ring fastening flange 202 or the staple members 204 may be attached to the fastening flange 202 by welding, brazing or any other suitable joining method. The proximal ends 218 of the staple members 204 are sharpened to easily pierce the target vessel wall 208 and the graft vessel wall 214. Preferably, the proximal ends 218 of the staple members 204 have barbs 220 to improve the security of the attachment when the anastomosis device 200 is deployed. The anastomosis device 200 is prepared for use by mounting the device onto the distal end of an application instrument 222. The fastening flange 202 is mounted on an anvil 224 attached to the distal end of the elongated shaft 226 of the application instrument 222. The staple members 204 are compressed inward against a conical holder 228 attached to the instrument 222 proximal to the anvil 224. The staple members 204 are secured in this position by a cap 230 which is slidably mounted on the elongated shaft 226. The cap 230 moves distally to cover the sharpened, barbed proximal ends 218 of the staple members 204 and to hold them against the conical holder 228. The application instrument 222 is then inserted through the lumen 232 of the graft vessel 214. This may be done by inserting the application instrument 222 through the graft vessel lumen 232 from the proximal to the distal end of the graft vessel 214, or it may be done by back loading the elongated shaft 226 of the application instrument 222 into the graft vessel lumen 232 from the distal end to the proximal end, whichever is most convenient in the case. The anvil 224 and conical holder 228 on the distal end of the application instrument 222 with the anastomosis device 200 attached is extended through the opening 216 into the lumen 210 of the target vessel.

Next, the distal end 234 of the graft vessel wall 214 is everted against the exterior surface 236 of the target vessel wall 208 with the graft vessel lumen 232 centered over the opening 216 in the target vessel wall 208. The cap 230 is withdrawn from the proximal ends 218 of the staple members 204, allowing the staple members 204 to spring outward to their expanded position. The application instrument 222 is then drawn in the proximal direction so that the staple members pierce the target vessel wall 208 surrounding the opening 216 and the everted distil end 234 of the graft vessel 214.

The application instrument 222 has an annular staple former 238 which surrounds the outside of the graft vessel 214. Slight pressure on the everted graft vessel wall from the annular staple former 238 during the piercing step assists in piercing the staple members 204 through the graft vessel wall 214. Care should be taken not to apply too much pressure with the annular staple former 238 at this point in the process because the staple members 204 could be prematurely deformed before they have fully traversed the vessel walls. If desired, an annular surface made of a softer material, such as an elastomer, can be provided on the application instrument 222 to back up the vessel walls as the staple members 204 pierce through them.

Once the staple members 204 have fully traversed the target vessel wall 208 and the graft vessel wall 214, the staple former 238 is brought down with greater force while supporting the fastening flange 202 with the anvil 224. The staple members 204 are deformed outward so that the sharpened, barbed ends 218 pierce back through the everted distil end 234 and into the target vessel wall 208 to form a permanent attachment. To complete the anastomosis, the anvil 224 is withdrawn through the graft vessel lumen 232. As the anvil 224 passes through the wire ring fastening flange 202, it straightens out the wave-like ripples so that the wire ring flange 202 assumes its full expanded diameter. Alternately, the wire ring fastening flange 202 may be made of a resilient material so that the flange 202 may be compressed and held in a rippled or folded position until it is released within the target vessel lumen 210, whereupon it will resume its full expanded diameter. Another alternate construction would be to move the anastomosis device of a shape-memory alloy so that the fastening flange may be compressed and inserted through the opening in the target vessel, whereupon it would be returned to its full expanded diameter by heating the device 200 to a temperature above the shape-memory transition temperature.

In the above-described exemplary embodiment, the staple members 204 and/or the wire ring fastening flange 202 may be coated with any of the above-described agents, drugs or compounds such as rapamycin to prevent or substantially reduce smooth muscle wall proliferation.

Figure 14:
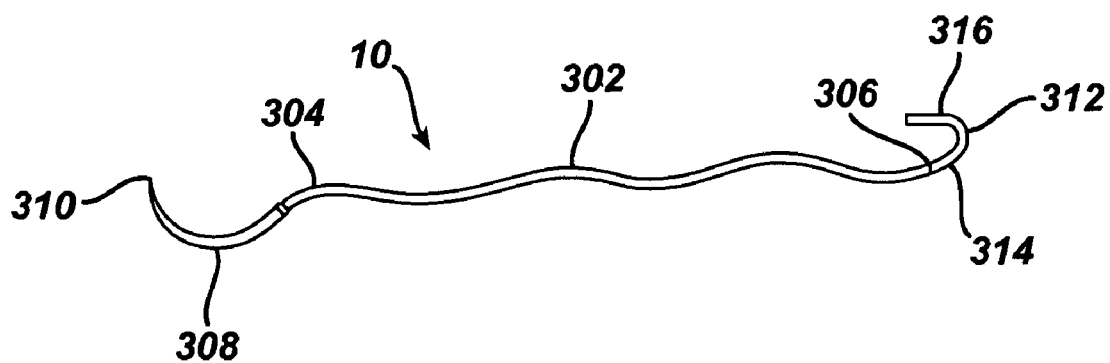
FIG. 14 is a side view of an apparatus for joining anatomical structures together, according to an exemplary embodiment of the invention.

FIG. 14 illustrates an alternate exemplary embodiment of an anastomosis device. FIG. 14 is a side view of an apparatus for joining at least two anatomical structures, according to another exemplary embodiment of the present invention. Apparatus 300 includes a suture 302 having a first end 304 and a second end 306, the suture 302 being constructed for passage through anatomical structures in a manner to be described subsequently. Suture 302 may be formed from a wide variety of materials, for example, monofilament materials having minimal memory, including polypropylene or polyamide. Any appropriate diameter size may be used, for example, through 8-0. Other suture types and sizes are also possible, of course, and are equally contemplated by the present invention.

A needle 308 preferably is curved and is disposed at the first end 304 of the suture 302. A sharp tip 310 of needle 308 enables easy penetration of various anatomical structures and enables the needle 308 and the suture 302 to readily pass therethrough. The needle 308 may be attached to the suture 302 in various ways, for example, by swedging, preferably substantially matching the outer diameter of the needle 308 and the suture 302 as closely as possible.

Apparatus 300 also includes a holding device 312 disposed at the second end 306 of the suture 302. The holding device 312 includes first and second limbs 314, 316, according to the illustrated exemplary embodiment, and preferably is of greater stiffness than the suture 302. The first limb 314 may be connected to suture 302 in a number of ways, for example, by swedging, preferably substantially matching the outside diameter of the suture 302 and the holding device 312 as closely as possible. The holding device 312 includes a staple structure comprising a bendable material that preferably is soft and malleable enough to crimp and hold its crimped position on the outside of an anastomosis. Such materials may include titanium or stainless steel. The holding device 312 may be referred to as a staple, according to the illustrated embodiment, and the suture 302 and the needle 308 a delivery system for staple 312.

FIG. 14 illustrates one of the many possible initial configurations of holding device 312, i.e. the configuration the holding device 312 is in upon initial passage through the anatomical structures and/or at a point in time beforehand. As will be described, the holding device 312 is movable from the initial configuration to a holding configuration, in which holding device 312 holds the anatomical structures together. According to the illustrated exemplary embodiments, the holding device 312 assumes the holding configuration when it is bent or crimped, as shown in FIG. 19 (further described below).

The holding device 312 preferably is substantially V-shaped or substantially U-shaped, as illustrated, but may assume a wide variety of shapes to suit particular surgical situations and/or surgeon preference. For example, one of limbs 314, 316 may be straight and the other curved, or limbs 314, 316 may be collinear. The holding device 312 preferably is as smooth and round in cross-section as the needle 308. Further, the diameters of the needle 308, the suture 302, and the holding device 312 preferably are substantially identical, especially the needle 308 and the holding device 312, to avoid creating holes in the anatomical structures that are larger than the diameter of the staple 312. Such holes likely would cause bleeding and/or leakage.

Figure 15:
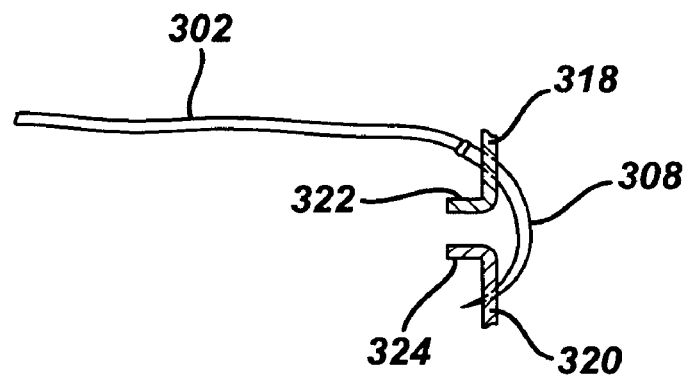
FIG. 15 is a cross-sectional view showing a needle portion of the FIG. 14 apparatus passing through edges of anatomical structures, according to an exemplary embodiment of the invention.
Figure 16:
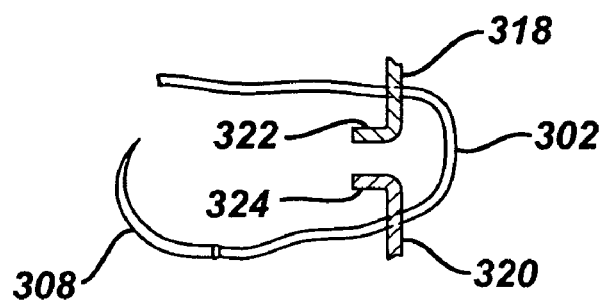
FIG. 16 is a cross-sectional view showing the FIG. 14 apparatus pulled through an anastomosis, according to an exemplary embodiment of the invention.
Figure 17:
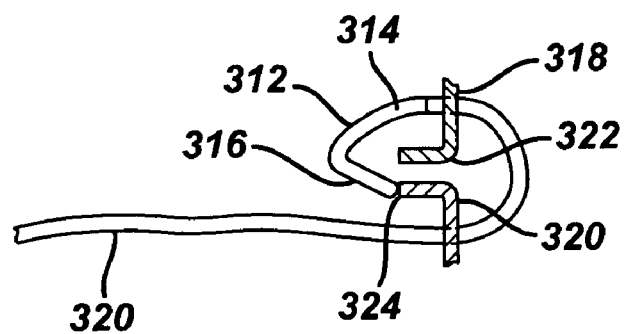
FIG. 17 is a cross-sectional view showing a staple of the FIG. 14 apparatus being placed into proximity with the anatomical structures, according to an exemplary embodiment of the invention
Figure 18:
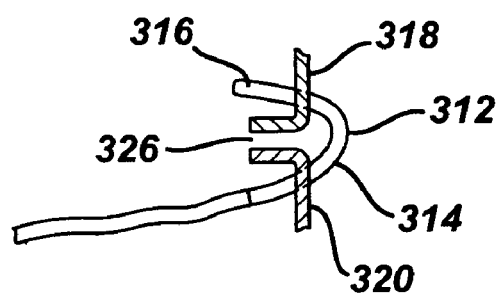
FIG. 18 is a cross-sectional view showing a staple of the FIG. 14 apparatus being engaged on both sides of the anastomosis, according to an exemplary embodiment of the invention.
Figure 19:
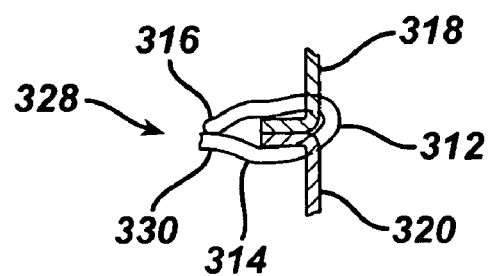
FIG. 19 is a cross-sectional view showing a staple after it has been crimped to join the anatomical structures, according to an exemplary embodiment of the invention.

A method of using apparatus 300 is illustrated in FIGS. 15-19. First, as illustrated in FIG. 15, the needle 308 passes through anatomical structures 318, 320, which are, for example, vascular structures. Specifically, according to the illustrated exemplary embodiment, the needle 308 passes through the edges 322, 324 of vascular structures 318, 320. Then, as shown in FIG. 16, the needle 308 pulls suture 302 into and through both structures 318, 320. The staple 312 then is pulled into desired proximity with structures 318, 320, as shown in FIGS. 17-19, such that it is engaged on both sides of the illustrated anastomosis and associated lumen 326. According to one exemplary embodiment, traction is placed on suture 302 to hook staple 312 into position.

As illustrated in FIG. 19 and as referenced earlier, the staple 312 then is moved from its initial configuration to a holding or crimped configuration 328, in which anatomical structures 318, 320 are joined together to effect an anastomosis between them. The staple 312 creates a substantially three hundred sixty-degree loop at the edge of the anastomosis, with crimped portion 330 outside lumen 321. A wide variety of tools and/or mechanisms may be used to crimp the staple 312 into its holding configuration, for example, in the manner of closure of a vascular clip. The same tool, or an alternative tool, may then be used to separate the staple 312 from the suture 302, for example, by cutting.

Thus, the staple 312 holds vascular structures 318, 320 together from inside the vascular structures, as well as from outside, unlike the many prior art staples that secure opposed structures only externally. This achieves a number of advantages, as described above. Not only does a better approximation result, but crimping a staple is simpler than tying one or more knots and is also less likely traumatic on tissue. Staple closure with a single crimp provides less tension on an anastomosis, for example, than a knot requiring several throws. Embodiments of the invention are especially advantageous in minimally invasive surgical situations, as knot-tying with, for example, a knot pusher in a minimally invasive setting through a small port is particularly tedious and can require up to four or five throws to prevent slippage. Crimping a staple through the port, as with embodiments of the invention, is far simpler and eliminates much of the difficulty.

According to one exemplary embodiment, the surgeon achieves a precise approximation of the vascular or other structures with preferably a limited number of staples or other holding devices, and then completes the anastomosis with biologic glue or laser techniques. The holding devices, for example, two or more in number, may be used to orient or line up the structures initially and thus used as a "pilot" for guiding the completion of the anastomosis.

In the above described exemplary embodiment, the holding device 312 may be coated with any of the above-described drugs, agents or compounds such as rapamycin to prevent or substantially reduce smooth muscle cell proliferation.

As described above, various drugs, agents or compounds may be locally delivered via medical devices. For example, rapamycin and heparin may be delivered by a stent to reduce restenosis, inflammation, and coagulation. Various techniques for immobilizing the drugs, agents or compounds are discussed above, however, maintaining the drugs, agents or compounds on the medical devices during delivery and positioning is critical to the success of the procedure or treatment. For example, removal of the drug, agent or compound coating during delivery of the stent can potentially cause failure of the device. For a self-expanding stent, the retraction of the restraining sheath may cause the drugs, agents or compounds to rub off the stent. For a balloon expandable stent, the expansion of the balloon may cause the drugs, agents or compounds to simply delaminate from the stent through contact with the balloon or via expansion. Therefore, prevention of this potential problem is important to have a successful therapeutic medical device, such as a stent.

There are a number of approaches that may be utilized to substantially reduce the above-described concern. In one exemplary embodiment, a lubricant or mold release agent may be utilized. The lubricant or mold release agent may comprise any suitable biocompatible lubricious coating. An exemplary lubricious coating may comprise silicone. In this exemplary embodiment, a solution of the silicone base coating may be introduced onto the balloon surface, onto the polymeric matrix, and/or onto the inner surface of the sheath of a self-expanding stent delivery apparatus and allowed to air cure. Alternately, the silicone based coating may be incorporated into the polymeric matrix. It is important to note, however, that any number of lubricious materials may be utilized, with the basic requirements being that the material be biocompatible, that the material not interfere with the actions/effectiveness of the drugs, agents or compounds and that the material not interfere with the materials utilized to immobilize the drugs, agents or compounds on the medical device. It is also important to note that one or more, or all of the above-described approaches may be utilized in combination.

Figure 20:
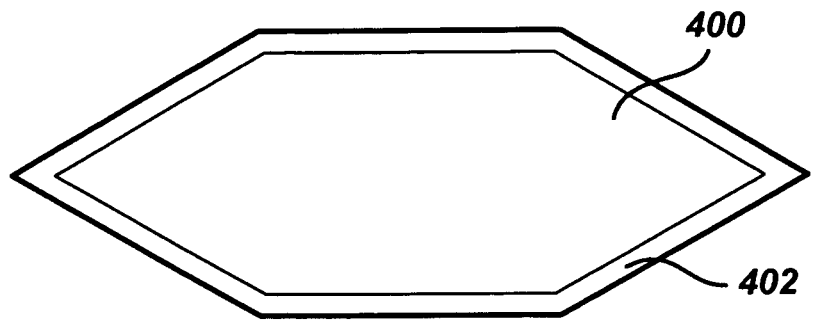
FIG. 20 is a cross-sectional view of a balloon having a lubricious coating affixed thereto in accordance with the present invention.

Referring now to FIG. 20, there is illustrated a balloon 400 of a balloon catheter that may be utilized to expand a stent in situ. As illustrated, the balloon 400 comprises a lubricious coating 402. The lubricious coating 402 functions to minimize or substantially eliminate the adhesion between the balloon 400 and the coating on the medical device. In the exemplary embodiment described above, the lubricious coating 402 would minimize or substantially eliminate the adhesion between the balloon 400 and the heparin or rapamycin coating. The lubricious coating 402 may be attached to and maintained on the balloon 400 in any number of ways including but not limited to dipping, spraying, brushing or spin coating of the coating material from a solution or suspension followed by curing or solvent removal step as needed.

Materials such as synthetic waxes, e.g. diethyleneglycol monostearate, hydrogenated castor oil, oleic acid, stearic acid, zinc stearate, calcium stearate, ethylenebis (stearamide), natural products such as paraffin wax, spermaceti wax, carnuba wax, sodium alginate, ascorbic acid and flour, fluorinated compounds such as perfluoroalkanes, perfluorofatty acids and alcohol, synthetic polymers such as silicones e.g. polydimethylsiloxane, polytetrafluoroethylene, polyfluoroethers, polyalkylglycol e.g. polyethylene glycol waxes, and inorganic materials such as talc, kaolin, mica, and silica may be used to prepare these coatings. Vapor deposition polymerization e.g. parylene-C deposition, or RF-plasma polymerization of perfluoroalkenes and perfluoroalkanes can also be used to prepare these lubricious coatings.

Figure 21:
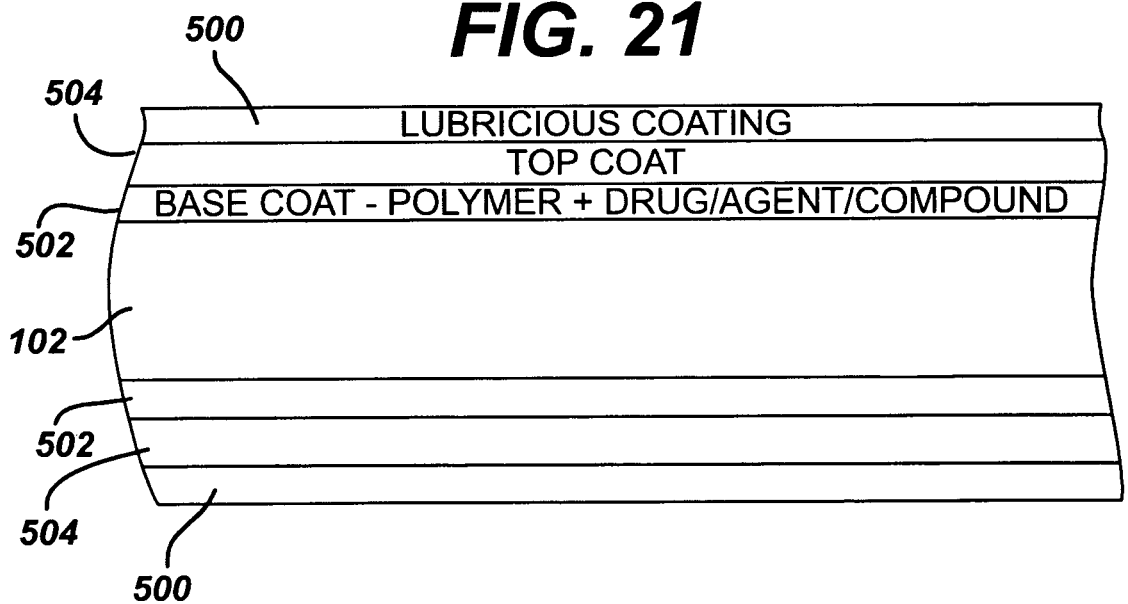
FIG. 21 is a cross-sectional view of a band of the stent in FIG. 1 having a lubricious coating affixed thereto in accordance with the present invention.

FIG. 21 illustrates a cross-section of a band 102 of the stent 100 illustrated in FIG. 1. In this exemplary embodiment, the lubricious coating 500 is immobilized onto the outer surface of the polymeric coating. As described above, the drugs, agents or compounds may be incorporated into a polymeric matrix. The stent band 102 illustrated in FIG. 21 comprises a base coat 502 comprising a polymer and rapamycin and a top coat 504 or diffusion layer 504 also comprising a polymer. The lubricious coating 500 is affixed to the top coat 502 by any suitable means, including but not limited to spraying, brushing, dipping or spin coating of the coating material from a solution or suspension with or without the polymers used to create the top coat, followed by curing or solvent removal step as needed. Vapor deposition polymerization and RF-plasma polymerization may also be used to affix those lubricious coating materials that lend themselves to this deposition method, to the top coating. In an alternate exemplary embodiment, the lubricious coating may be directly incorporated into the polymeric matrix.

Figure 22:
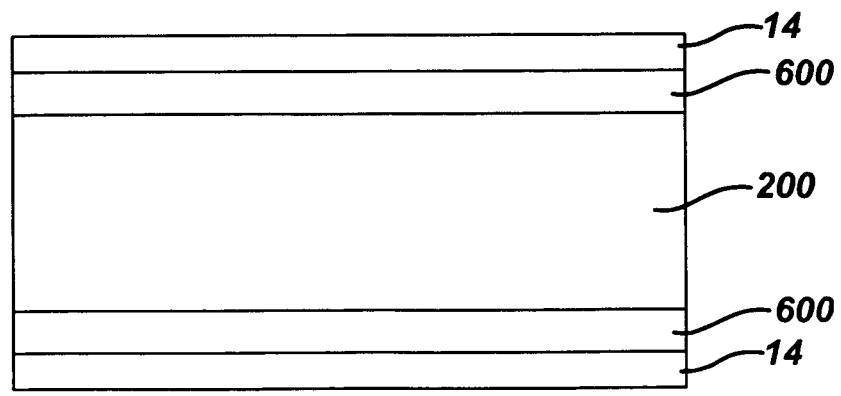
FIG. 22 is a partial cross-sectional view of a self-expanding stent in a delivery device having a lubricious coating in accordance with the present invention.

If a self-expanding stent is utilized, the lubricious coating may be affixed to the inner surface of the restraining sheath. FIG. 22 illustrates a partial cross-sectional view of self-expanding stent 200 within the lumen of a delivery apparatus sheath 14. As illustrated, a lubricious coating 600 is affixed to the inner surfaces of the sheath 14. Accordingly, upon deployment of the stent 200, the lubricious coating 600 preferably minimizes or substantially eliminates the adhesion between the sheath 14 and the drug, agent or compound coated stent 200.

Figure 23:
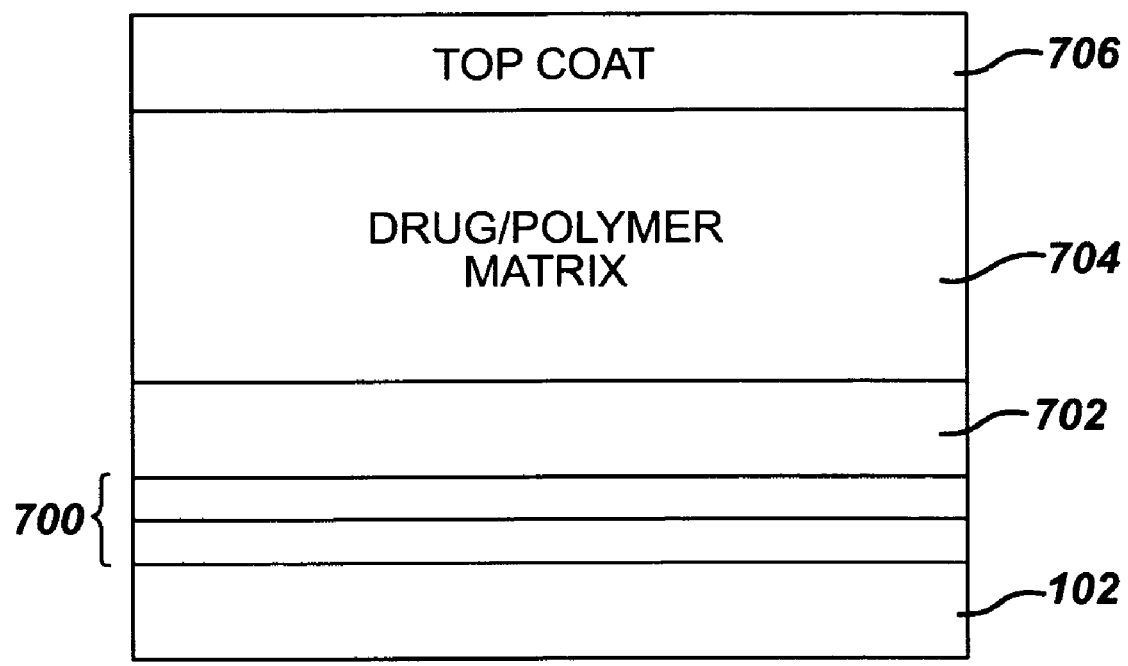
FIG. 23 is a cross-sectional view of a band of the stent in FIG. 1 having a modified polymer coating in accordance with the present invention.

In an alternate approach, physical and/or chemical cross-linking methods may be applied to improve the bond strength between the polymeric coating containing the drugs, agents or compounds and the surface of the medical device or between the polymeric coating containing the drugs, agents or compounds and a primer. Alternately, other primers applied by either traditional coating methods such as dip, spray or spin coating, or by RF-plasma polymerization may also be used to improve bond strength. For example, as shown in FIG. 23, the bond strength can be improved by first depositing a primer layer 700 such as vapor polymerized parylene-C on the device surface, and then placing a secondary layer 702 which comprises a polymer that is similar in chemical composition to the one or more of the polymers that make up the drug-containing matrix 704, e.g., polyethylene-co-vinyl acetate or polybutyl methacrylate but has been modified to contain cross-linking moieties. This secondary layer 702 is then cross-linked to the primer after exposure to ultraviolet light. It should be noted that anyone familiar with the art would recognize that a similar outcome could be achieved using cross-linking agents that are activated by heat with or without the presence of an activating agent. The drug-containing matrix 704 is then layered onto the secondary layer 702 using a solvent that swells, in part or wholly, the secondary layer 702. This promotes the entrainment of polymer chains from the matrix into the secondary layer 702 and conversely from the secondary layer 702 into the drug-containing matrix 704. Upon removal of the solvent from the coated layers, an interpenetrating or interlocking network of the polymer chains is formed between the layers thereby increasing the adhesion strength between them. A top coat 706 is used as described above.

A related difficulty occurs in medical devices such as stents. In the drug-coated stents crimped state, some struts come into contact with each other and when the stent is expanded, the motion causes the polymeric coating comprising the drugs, agents or compounds to stick and stretch. This action may potentially cause the coating to separate from the stent in certain areas. The predominant mechanism of the coating self-adhesion is believed to be due to mechanical forces. When the polymer comes in contact with itself, its chains can tangle causing the mechanical bond, similar to Velcro®. Certain polymers do not bond with each other, for example, fluoropolymers. For other polymers, however, powders may be utilized. In other words, a powder may be applied to the one or more polymers incorporating the drugs, agents or other compounds on the surfaces of the medical device to reduce the mechanical bond. Any suitable biocompatible material which does not interfere with the drugs, agents, compounds or materials utilized to immobilize the drugs, agents or compounds onto the medical device may be utilized. For example, a dusting with a water soluble powder may reduce the tackiness of the coatings surface and this will prevent the polymer from sticking to itself thereby reducing the potential for delamination. The powder should be water-soluble so that it does not present an emboli risk. The powder may comprise an anti-oxidant, such as vitamin C, or it may comprise an anti-coagulant, such as aspirin or heparin. An advantage of utilizing an anti-oxidant may be in the fact that the anti-oxidant may preserve the other drugs, agents or compounds over longer periods of time.

It is important to note that crystalline polymers are generally not sticky or tacky. Accordingly, if crystalline polymers are utilized rather than amorphous polymers, then additional materials may not be necessary. It is also important to note that polymeric coatings without drugs, agents and/or compounds may improve the operating characteristics of the medical device. For example, the mechanical properties of the medical device may be improved by a polymeric coating, with or without drugs, agents and/or compounds. A coated stent may have improved flexibility and increased durability. In addition, the polymeric coating may substantially reduce or eliminate galvanic corrosion between the different metals comprising the medical device. The same holds true for anastomosis devices.

As stated above, for a self-expanding stent, the retraction of the restraining sheath may cause the drugs, agents or compounds to rub off the stent. Accordingly, in an alternate exemplary embodiment, the stent delivery device may be modified to reduce the potential of rubbing off the coating. This is especially important for long stents, for example, long rapamycin coated stents. In addition, there is also the potential of damaging the stent itself when the delivery sheath is retracted during stent deployment. Accordingly, the stent delivery device may be modified to substantially reduce the forces acting on certain areas of the stent by distributing the forces to more areas of the stent. The stent and stent delivery system described herein are intended to be merely illustrative in nature and those skilled in the art will recognize that the designs disclosed may be incorporated into any number of stents and stent delivery systems.

Figure 35:
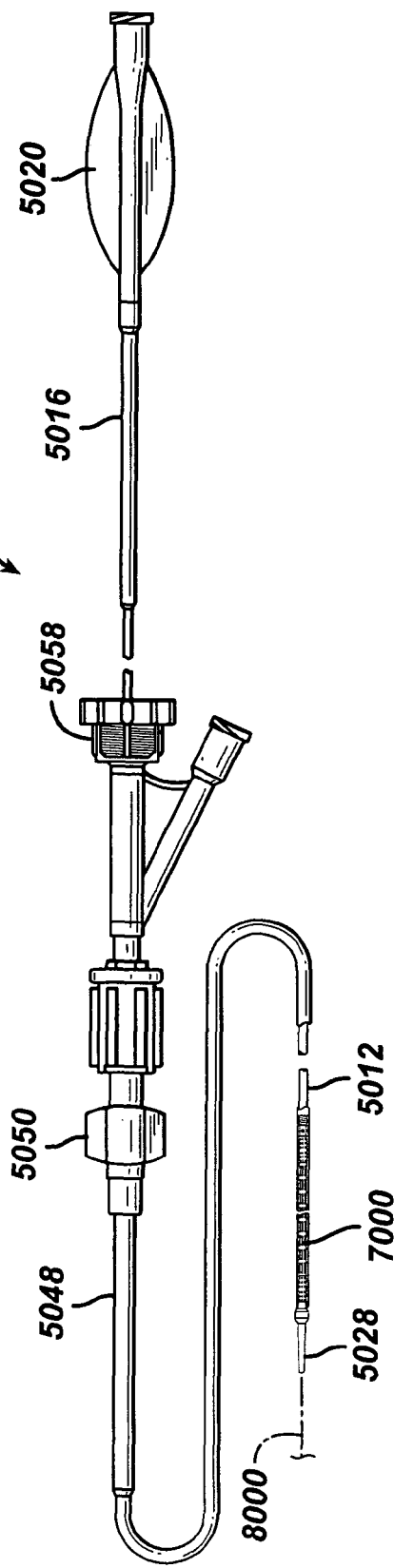
FIG. 35 is a simplified elevational view of a stent delivery apparatus made in accordance with the present invention.
Figure 36:
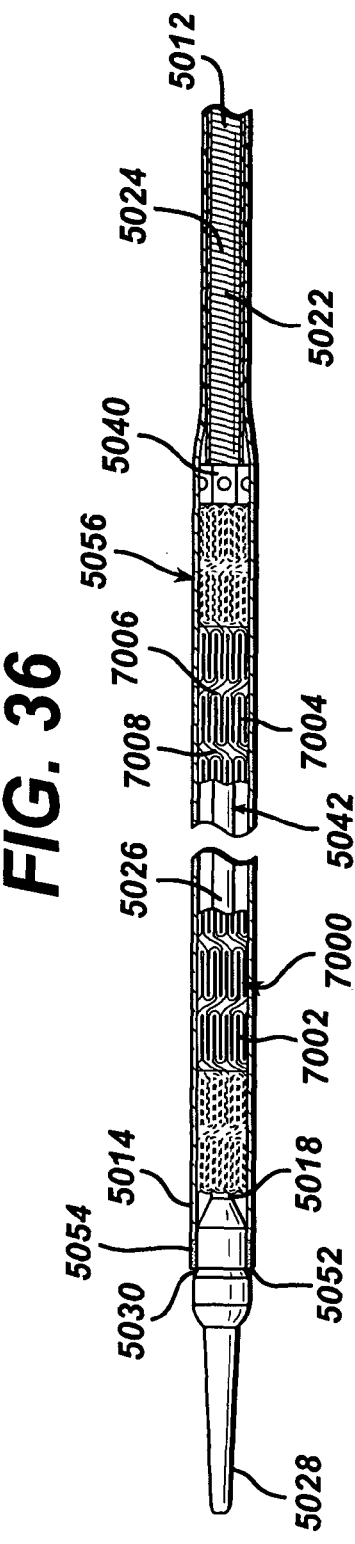
FIG. 36 is a view similar to that of FIG. 35 but showing an enlarged view of the distal end of the apparatus having a section cut away to show the stent loaded therein.

FIGS. 35 and 36 illustrate an exemplary self-expanding stent delivery apparatus 5010 in accordance with the present invention. Apparatus 5010 comprises inner and outer coaxial tubes. The inner tube is called the shaft 5012 and the outer tube is called the sheath 5014. A self-expanding stent 7000 is located within the sheath 5014, wherein the stent 7000 makes frictional contact with the sheath 5014 and the shaft 5012 is disposed coaxially within a lumen of the stent 7000.

Shaft 5012 has proximal and distal ends 5016 and 5018 respectively. The proximal end 5016 of the shaft 5012 has a Luer guidewire hub 5020 attached thereto. As seen best from FIG. 44, the proximal end 5016 of the shaft 5012 is preferably a ground stainless steel hypotube. In one exemplary embodiment, the hypotube is stainless steel and has a 0.042 inch outside diameter at its proximal end and then tapers to a 0.036 inch outside diameter at its distal end. The inside diameter of the hypotube is 0.032 inch throughout its length. The tapered outside diameter is utilized to gradually change the stiffness of the hypotube along its length. This change in the hypotube stiffness allows for a more rigid proximal end or handle end that is needed during stent deployment. If the proximal end is not stiff enough, the hypotube section extending beyond the Tuohy Borst valve described below could buckle as the deployment forces are transmitted. The distal end of the hypotube is more flexible allowing for better track-ability in tortuous vessels. The distal end of the hypotube also needs to be flexible to minimize the transition between the hypotube and the coil section described below.

As will be described in greater detail below, shaft 5012 has a body portion 5022, wherein at least a section thereof is made from a flexible coiled member 5024, looking very much like a compressed or closed coil spring. Shaft 5012 also includes a distal portion 5026, distal to body portion 5022, which is preferably made from a coextrusion of high-density polyethylene and Nylon®. The two portions 5022 and 5026 are joined together by any number of means known to those of ordinary skill in the art including heat fusing, adhesive bonding, chemical bonding or mechanical attachment.

As best seen from FIG. 37, the distal portion 5026 of the shaft 5012 has a distal tip 5028 attached thereto. Distal tip 5028 may be made from any number of suitable materials known in the art including polyamide, polyurethane, polytetrafluoroethylene, and polyethylene including multi-layer or single layer construction. The distal tip 5028 has a proximal end 5030 whose diameter is substantially the same as the outer diameter of the sheath 5014 which is immediately adjacent thereto. The distal tip 5028 tapers to a smaller diameter from its proximal end 5030 to its distal end 5032, wherein the distal end 5032 of the distal tip 5028 has a diameter smaller than the inner diameter of the sheath 5014.

The stent delivery apparatus 5010 glides over a guide wire 8000 (shown in FIG. 35) during navigation to the stent deployment site. As used herein, guidewire may also refer to similar guiding devices which have a distal protection apparatus incorporated herein. One preferred distal protection device is disclosed in published PCT Application 98/33443, having an international filing date of Feb. 3, 1998. As discussed above, if the distal tip 5028 is too stiff it will overpower the guide wire path and push the guide wire 8000 against the lumen wall and in some very tortuous settings the stent delivery apparatus 5010 could prolapse the wire. Overpowering of the wire and pushing of the apparatus against the lumen wall can prevent the device from reaching the target area because the guide wire will no longer be directing the device. Also, as the apparatus is advanced and pushed against the lumen wall, debris from the lesion can be dislodged and travel upstream causing complications to distal vessel lumens. The distal tip 5028 is designed with an extremely flexible leading edge and a gradual transition to a less flexible portion. The distal tip 5028 may be hollow and may be made of any number of suitable materials, including 40D Nylon®. Its flexibility may be changed by gradually increasing the thickness of its cross-sectional diameter, whereby the diameter is thinnest at its distal end, and is thickest at its proximal end. That is, the cross-sectional diameter and wall thickness of the distal tip 5028 increases as you move in the proximal direction. This gives the distal end 5032 of the distal tip 5028 the ability to be directed by the guidewire prior to the larger diameter and thicker wall thickness, less flexible portion, of the distal tip 5028 over-powering the guidewire. Over-powering the wire, as stated above, is when the apparatus, due to its stiffness, dictates the direction of the device instead of following the wire.

The guidewire lumen 5034 has a diameter that is matched to hug the recommended size guide wire so that there is a slight frictional engagement between the guidewire 8000 and the guidewire lumen 5034 of distal tip 5028. The distal tip 5028 has a rounded section 5036 between its distal portion 5032 and its proximal portion 5030. This helps prevent the sheath 5014 from slipping distally over the distal tip 5028, and thereby exposing the squared edges of the sheath 5014 to the vessel, which could cause damage thereto. This improves the device's "pushability." As the distal tip 5028 encounters resistance it does not allow the sheath 5014 to ride over it thereby exposing the sheath's 5014 square cut edge. Instead the sheath 5014 contacts the rounded section 5036 of the distal tip 5028 and thus transmits the forces applied to the distal tip 5028. The distal tip 5028 also has a proximally tapered section 5038 which helps guide the distal tip 5028 through the deployed stent 7000 without providing a sharp edge that could grab or hang up on a stent strut end or other irregularity in the lumen inner diameter.

Attached to distal portion 5026 of shaft 5012 is a stop 5040, which is proximal to the distal tip 5028 and stent 7000. Stop 5040 may be made from any number of suitable materials known in the art, including stainless steel, and is even more preferably made from a highly radio-opaque material such as platinum, gold tantalum, or radio-opaque filled polymer. The stop 5040 may be attached to shaft 5012 by any suitable means, including mechanical or adhesive bonding, or by any other means known to those skilled in the art. Preferably, the diameter of stop 5040 is large enough to make sufficient contact with the loaded stent 7000 without making frictional contact with the sheath 5014. As will be explained subsequently, the stop 5040 helps to "push" the stent 7000 or maintain its relative position during deployment, by preventing the stent 7000 from migrating proximally within the sheath 5014 during retraction of the sheath 5014 for stent deployment. The radio-opaque stop 5040 also aides in positioning the stent 7000 within the target lesion area during deployment within a vessel, as is described below.

A stent bed 5042 is defined as being that portion of the shaft 5012 between the distal tip 5028 and the stop 5040 (FIG. 36). The stent bed 5042 and the stent 7000 are coaxial so that the distal portion 5026 of the shaft 5012 comprising the stent bed 5042 is located within the lumen of stent 7000. The stent bed 5042 makes minimal contact with the stent 7000 because of the space which exists between the shaft 5012 and the sheath 5014. As the stent 7000 is subjected to temperatures at the austenite phase transformation it attempts to recover to its programmed shape by moving outwardly in a radial direction within the sheath 5014. The sheath 5014 constrains the stent 7000 as will be explained in detail subsequently. Distal to the distal end of the loaded stent 7000 attached to the shaft 5012 is a radio-opaque marker 5044 which may be made of platinum, iridium coated platinum, gold tantalum, stainless steel, radio-opaque filled polymer or any other suitable material known in the art.

Figure 44:
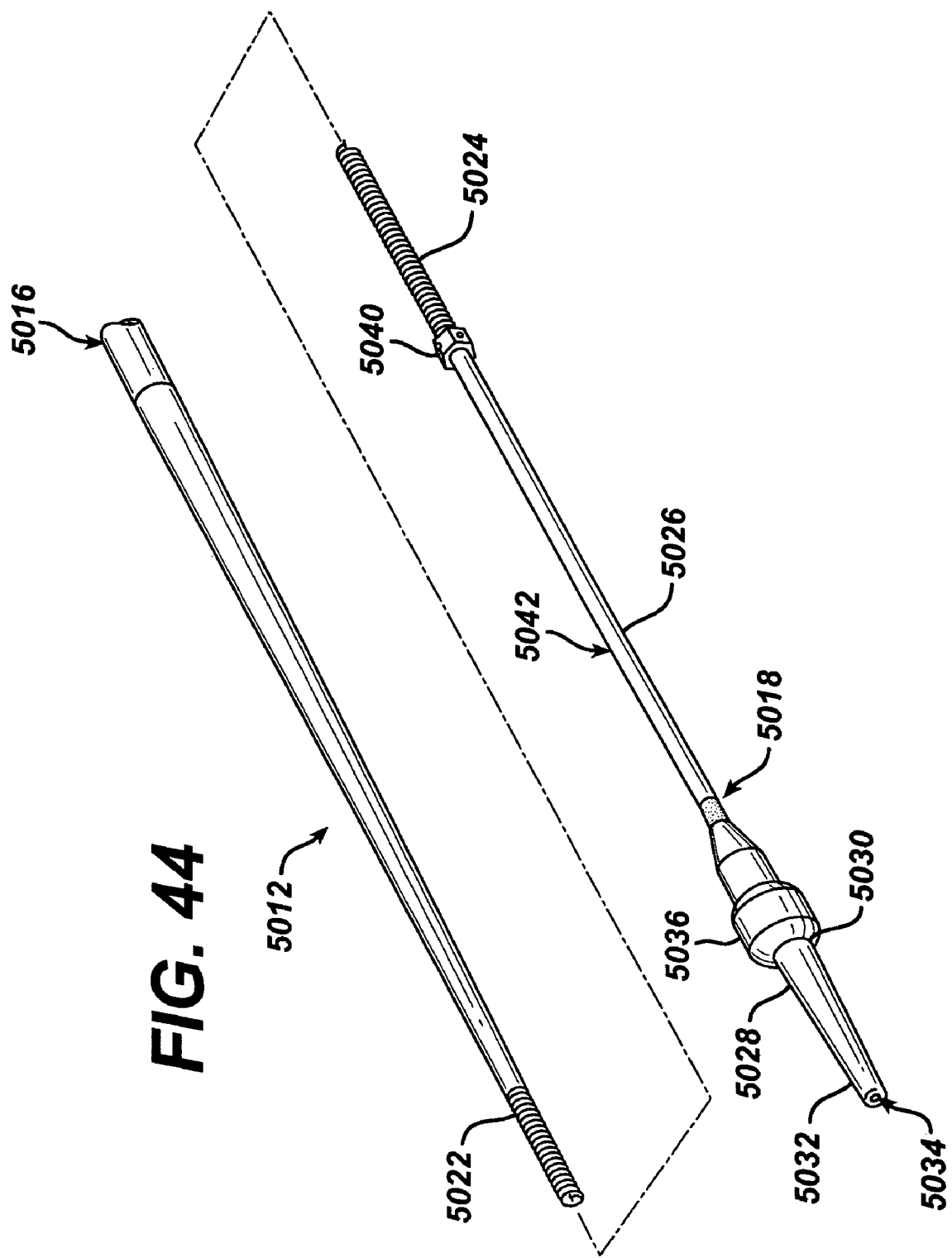
FIG. 44 is a simplified elevational view of a shaft for a stent delivery apparatus made in accordance with the present invention.

As seen from FIGS. 36, 37 and 44, the body portion 5022 of the shaft 5012 is made from a flexible coiled member 5024, similar to a closed coil or compressed spring. During deployment of the stent 7000, the transmission of compressive forces from the stop 5040 to the Luer guidewire hub 5020 is an important factor in deployment accuracy. A more compressive shaft 5012 results in a less accurate deployment because the compression of the shaft 5012 is not taken into account when visualizing the stent 7000 under fluoroscopic imaging. However, a less compressive shaft 5012 usually means less flexibility, which would reduce the ability of the apparatus 5010 to navigate through tortuous vessels. A coiled assembly allows both flexibility and resistance to compression. When the apparatus 5010 is being navigated through the arteries, the shaft 5012 is not in compression and therefore the coiled member 5024 is free to bend with the delivery path. As one deploys the stent 7000, tension is applied to the sheath 5014 as the sheath 5014 is retracted over the encapsulated stent 7000. Because the stent 7000 is self-expanding it is in contact with the sheath 5014 and the forces are transferred along the stent 7000 and to the stop 5040 of the shaft 5012. This results in the shaft 5012 being under compressive forces. When this happens, the flexible coiled member 5024, no gaps between the coil members, transfers the compressive force from one coil to the next.

The flexible coiled member 5024 further includes a covering 5046 that fits over the flexible coiled member 5024 to help resist buckling of the coiled member 5024 in both bending and compressive modes. The covering 5046 is an extruded polymer tube and is preferably a soft material that can elongate slightly to accommodate bending of the flexible coiled member 5024, but does not allow the coils to ride over each other. Covering 5046 may be made from any number of suitable materials including coextrusions of Nylons and high-density polyethylene, polyurethane, polyamide, polytetrafluoroethylene, etc. The extrusion is also attached to the stop 5040. Flexible coiled member 5024 may be made of any number of materials known in the art including stainless steel, Nitinol, and rigid polymers. In one exemplary embodiment, flexible coiled member 5024 is made from a 0.003 inch thick by 0.010 inch wide stainless steel ribbon wire. The wire may be round, or more preferably flat to reduce the profile of the flexible coiled member 5024.

Sheath 5014 is preferably a polymeric catheter and has a proximal end 5048 terminating at a sheath hub 5050 (FIG. 35). Sheath 5014 also has a distal end 5052 which terminates at the proximal end 5030 of distal tip 5028 of the shaft 5012, when the stent 7000 is in an un-deployed position as shown in FIG. 36. The distal end 5052 of sheath 5014 includes a radio-opaque marker band 5054 disposed along its outer surface (FIG. 35). As will be explained below, the stent 7000 is fully deployed when the marker band 5054 is proximal to radio-opaque stop 5040, thus indicating to the physician that it is now safe to remove the delivery apparatus 5010 from the body.

As detailed in FIG. 36, the distal end 5052 of sheath 5014 includes an enlarged section 5056. Enlarged section 5056 has larger inside and outside diameters than the inside and outside diameters of the sheath 5014 proximal to enlarged section 5056. Enlarged section 5056 houses the pre-loaded stent 7000, the stop 5040 and the stent bed 5042. The outer sheath 5014 tapers proximally at the proximal end of enlarged section 5056 to a smaller size diameter. This design is more fully set forth in co-pending U.S. application Ser. No. 09/243,750 filed on Feb. 3, 1999, which is hereby incorporated herein by reference. One particular advantage to the reduction in the size of the outer diameter of sheath 5014 proximal to enlarged section 5056 is in an increase in the clearance between the delivery apparatus 5010 and the guiding catheter or sheath that the delivery apparatus 5010 is placed through. Using fluoroscopy, the physician will view an image of the target site within the vessel, before and after deployment of the stent, by injecting a radio-opaque solution through the guiding catheter or sheath with the delivery apparatus 5010 placed within the guiding catheter. Because the clearance between the sheath 5014, and the guiding catheter is increased by tapering or reducing the outer diameter of the sheath 5014 proximal to enlarged section 5056, higher injection rates may be achieved, resulting in better images of the target site for the physician. The tapering of sheath 5014 provides for higher injection rates of radio-opaque fluid, both before and after deployment of the stent.

Figure 45:
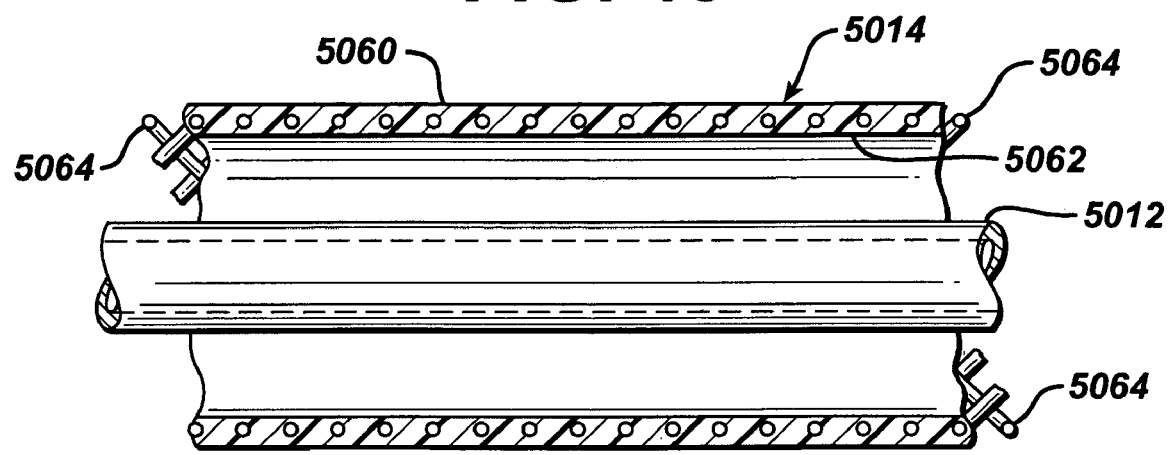
FIG. 45 is a partial cross-sectional view of the shaft and sheath of the stent delivery apparatus in accordance with the present invention.

A problem encountered with earlier self-expanding stent delivery systems is that of the stent becoming embedded within the sheath in which it is disposed. Referring to FIG. 45, there is illustrated a sheath construction which may be effectively utilized to substantially prevent the stent from becoming embedded in the sheath as well as provide other benefits as described in detail below. As illustrated, the sheath 5014 comprises a composite structure of at least two layers and preferably three layers. The outer layer 5060 may be formed from any suitable biocompatible material. Preferably, the outer layer 5060 is formed from a lubricious material for ease of insertion and removal of the sheath 5014. In a preferred embodiment, the outer layer 5060 comprises a polymeric material such as Nylon®. The inner layer 5062 may also be formed from any suitable biocompatible material. For example, the inner layer 5062 may be formed from any number of polymers including polyethylene, polyamide or polytetrafluroethylene. In a preferred embodiment, the inner layer 5062 comprises polytetrafluroethylene. Polytetrafluroethylene is also a lubricious material which makes stent delivery easier, thereby preventing damage to the stent 7000. The inner layer 5062 may also be coated with another material to increase the lubricity thereof for facilitating stent deployment. Any number of suitable biocompatible materials may be utilized. In an exemplary embodiment, silicone based coatings may be utilized. Essentially, a solution of the silicone based coating may be injected through the apparatus and allowed to cure at room temperature. The amount of silicone based coating utilized should be minimized to prevent transference of the coating to the stent 7000. Sandwiched between the outer and inner layers 5060 and 5062, respectively, is a wire reinforcement layer 5064. The wire reinforcement layer 5064 may take on any number of configurations. In the exemplary embodiment, the wire reinforcement layer 5064 comprises a simple under and over weave or braiding pattern. The wire used to form the wire reinforcement layer 5064 may comprise any suitable material and any suitable cross-sectional shape. In the illustrated exemplary embodiment, the wire forming the wire reinforcement layer 5064 comprises stainless steel and has a substantially circular cross-section. In order to function for its intended purpose, as described in detail below, the wire has a diameter of 0.002 inches.

The three layers 5060, 5062, and 5064 comprising the sheath 5014 collectively enhance stent deployment. The outer layer 5060 facilitates insertion and removal of the entire apparatus 5010. The inner layer 5062 and the wire reinforcement layer 5064 function to prevent the stent 7000 from becoming embedded in the sheath 5014. Self-expanding stents such as the stent 7000 of the present invention tend to expand to their programmed diameter at a given temperature. As the stent attempts to undergo expansion, it exerts a radially outward directed force and may become embedded in the sheath 5014 restraining it from expanding. Accordingly, the wire reinforcing layer 5064 provides radial or hoop strength to the inner layer 5062 thereby creating sufficient resistance to the outwardly directed radial force of the stent 7000 within the sheath 5014. The inner layer 5062, also as discussed above, provides a lower coefficient of friction surface to reduce the forces required to deploy the stent 7000 (typically in the range from about five to eight pounds). The wire reinforcement layer 5064 also provides tensile strength to the sheath 5014. In other words, the wire reinforcement layer 5064 provides the sheath 5014 with better pushability, i.e., the ability to transmit a force applied by the physician at a proximal location on the sheath 5014 to the distal tip 5028, which aids in navigation across tight stenotic lesions within the vasculature. Wire reinforcement layer 5064 also provides the sheath 5014 with better resistance to elongation and necking as a result of tensile loading during sheath retraction for stent deployment.

The sheath 5014 may comprise all three layers along its entire length or only in certain sections, for example, along the length of the stent 7000. In a preferred embodiment, the sheath 5014 comprises all three layers along its entire length.

Prior art self-expanding stent delivery systems did not utilize wire reinforcement layers. Because the size of typical self-expanding stents is relatively large, as compared to balloon expandable coronary stents, the diameter or profile of the delivery devices therefore had to be large as well. However, it is always advantageous to have delivery systems which are as small as possible. This is desirable so that the devices can reach into smaller vessels and so that less trauma is caused to the patient. However, as stated above, the advantages of a thin reinforcing layer in a stent delivery apparatus outweighs the disadvantages of slightly increased profile.

Figure 46:
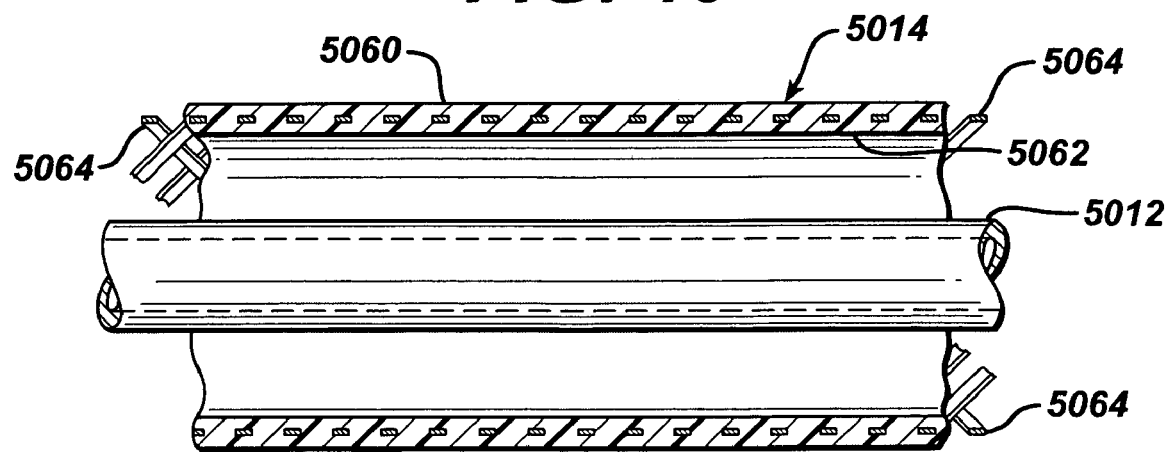
FIG. 46 is a partial cross-sectional view of the shaft and modified sheath of the stent delivery system in accordance with the present invention.

In order to minimize the impact of the wire reinforcement layer on the profile of the apparatus 5010, the configuration of the wire reinforcement layer 5064 may be modified. For example, this may be accomplished in a number of ways, including changing the pitch of the braid, changing the shape of the wire, changing the wire diameter and/or changing the number of wires utilized. In a preferred embodiment, the wire utilized to form the wire reinforcement layer comprises a substantially rectangular cross-section as illustrated in FIG. 46. In utilizing a substantially rectangular cross-section wire, the strength features of the reinforcement layer 5064 may be maintained with a significant reduction in the profile of the delivery apparatus. In this preferred embodiment, the rectangular cross-section wire has a width of 0.003 inches and a height of 0.001 inches. Accordingly, braiding the wire in a similar manner to FIG. 45, results in a fifty percent decrease in the thickness of the wire reinforcement layer 5064 while maintaining the same beneficial characteristics as the 0.002 round wire. The flat wire may comprise any suitable material, and preferably comprises stainless steel.

In another alternate exemplary embodiment, the sheath of the delivery system may comprise an inner layer or coating on its inner surface which substantially prevents the stent from becoming embedded therein while increasing the lubricity thereof. This inner layer or coating may be utilized with the sheaths illustrated in FIGS. 45 and 46 or as an alternative means to decrease the stent deployment forces. Given the thinness of the coating, as described in more detail below, the overall profile of the delivery system will be minimally impacted if at all. In addition to increasing the strength of the sheath and making it more lubricious, the coating is extremely biocompatible which is important since it does make contact with blood, albeit at least temporarily.

Essentially, in the exemplary embodiment, a hard and lubricious coating is applied to or affixed to the inner surface of the sheath of the self-expanding delivery system. The coating provides a number of advantages over currently utilized self-expanding stent delivery systems. For example, the coating provides a hard surface against which the stent exerts a radially outward directed force. As described above, self-expanding stents have a constant outward force of expansion when loaded into the delivery system. This constant and relatively high radially outward directed force can force the polymeric materials that comprise the sheath of the delivery system to creep and allow the stent to become embedded into the polymer surface. As stent platforms are developed with larger diameter stents and subsequently higher radially outward directed forces, the occurrence of this phenomenon will increase. Consequently, embedding increases the force required to deploy the stent because it causes mechanical resistance to the movement of the stent inside the delivery system, thereby preventing accurate deployment and causing potential damage to the stent. In addition, the coating is lubricious, i.e. it has a low coefficient of friction. A lubricious coating, as stated above, functions to further reduce the force required to deploy the stent, thereby increasing the facility by which the stents are delivered and deployed by physicians. This is especially important with respect to newer larger diameter stent designs and/or drug/polymer coated stent designs that have either increased radial forces, increased profile or increased overall diameter. A lubricious coating is particularly advantageous with respect to drug/polymer coated stents. Accordingly, the coating functions to prevent the stent from embedding in the sheath of the delivery system prior to deployment and reducing the friction between the sheath and the stent, both of which will reduce the deployment forces.

Various drugs, agents or compounds may be locally delivered via medical devices such as stents. For example, rapamycin and/or heparin may be delivered by a stent to reduce restenosis, inflammation and coagulation. Various techniques for immobilizing the drugs, agents or compounds onto the stent are known; however, maintaining the drugs, agents or compounds on the stent during delivery and positioning is critical to the success of the procedure or treatment. For example, removal of the drug, agent or compound during delivery of the stent can potentially cause failure of the device. For a self-expanding stent, the retraction of the restraining sheath may cause the drugs, agents or compounds to rub off the stent. Therefore, prevention of this potential problem is important to have successful therapeutic medical devices such as stents.

Figure 47:
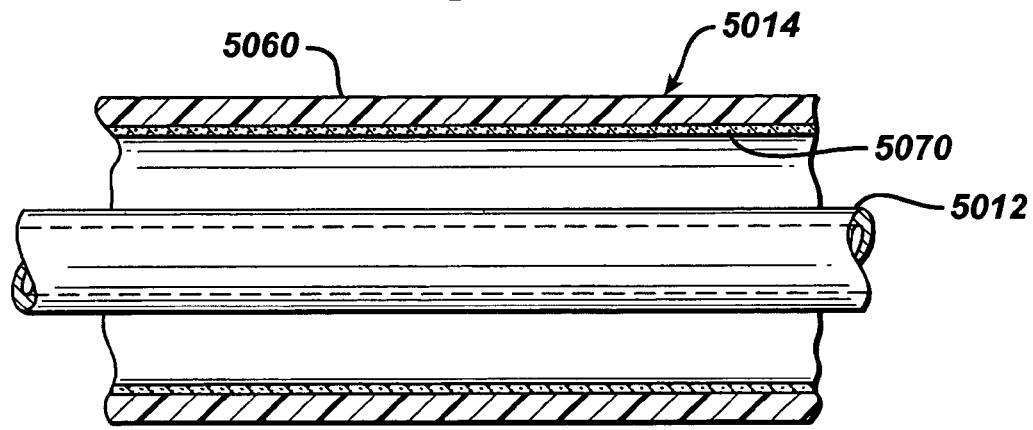
FIG. 47 is a partial cross-sectional view of the shaft and modified sheath of the stent delivery system in accordance with the present invention.

FIG. 47 illustrates a partial cross-sectional view of the shaft and modified sheath of the stent delivery system in accordance with an exemplary embodiment of the present invention. As shown, a coating or layer of material 5070 is affixed or otherwise attached to the inner circumference of the sheath 5014. As stated above, the coating or layer of material 5070 comprises a hard and lubricious substance. In a preferred embodiment, the coating 5070 comprises pyrolytic carbon. Pyrolytic carbon is a well-known substance that is utilized in a wide variety of implantable medical prostheses and is most commonly utilized in cardiac valves, as it combines high strength with excellent tissue and blood compatibility.

Pyrolytic carbon's usefulness in the implantable medical device area is a result of its unique combination of physical and chemical characteristics, including chemical inertness, isotrophy, low weight, compactness and elasticity. Pyrolytic carbon belongs to a specific family of turbostratic carbons which are similar to the structure of graphite. In graphite, the carbon atoms are covalently bonded in planar hexagonal arrays that are stacked in layers with relatively weak interlayer bonding. In turbostratic carbons, the stacking sequence is disordered and distortions may exist within each of the layers. These structural distortions in the layers are responsible for the superior ductility and durability of pyrolytic carbon. Essentially, the microstructure of pyrolytic carbon makes the material durable, strong and wear resistant. In addition, pyrolytic carbon is highly thromboresistant and has inherent cellular biocompatability with blood and soft tissue.

The pyrolytic carbon layer 5070 may be deposited along the entire length of the sheath 5014 or only in proximity to the stent bed 5042, illustrated in FIGS. 36 and 37. In a preferred embodiment, the pyrolytic carbon layer 5070 is affixed to the sheath 5014 in the region of the stent bed 5042. The pyrolytic carbon layer 5070 may be deposited or affixed to the inner circumference utilizing any number of known techniques that are compatible or usable with the polymeric materials comprising the sheath 5014. The thickness of the pyrolytic carbon layer 5070 is selected such that it prevents or substantially reduces the possibility of the stent becoming embedded in the sheath 5014 without decreasing the flexibility of the sheath 5014 or increasing the profile of the self-expanding stent delivery system. As described above, it is important that the sheath be both flexible and pushable to navigate tortuous pathways within the body. In addition, it is always desirable to reduce the profile of percutaneously delivered devices.

As stated above, pyrolytic carbon surfaces are recognized as biocompatible, especially with respect to blood contact applications. This is, however, only a minor benefit in terms of stent delivery applications because the location of the pyrolytic carbon layer 5070 within the sheath 5014 is only minimally exposed to blood and is only within the body for a duration sufficient to deliver a stent.

The pyrolytic carbon layer 5070 may be affixed to the lumen of the sheath in any number of ways as mentioned above. In one exemplary embodiment, the pyrolytic carbon layer 5070 may be directly affixed to the lumen of the sheath 5014. In another exemplary embodiment, the pyrolytic carbon layer 5070 may be indirectly applied to the lumen of the sheath 5014 by first applying it to a variety of substrates, also utilizing any number of known techniques. Regardless of whether the pyrolytic carbon layer 5070 is deposited directly onto the sheath 5014 or first onto a substrate, any number of known techniques may be utilized, for example, chemical vapor deposition. In chemical vapor deposition, the carbon material is deposited from gaseous hydrocarbon compounds on suitable underlying substrates, e.g. carbon materials, metals, ceramics as well as other materials, at temperatures ranging from about 1000K to about 2500K. At these temperatures, one can understand the need to possibly utilize substrates. Any suitable biocompatible, durable and flexible substrate may be utilized and then affixed to the lumen of the sheath 5014 utilizing well-known techniques such as adhesives. As stated above, profile and flexibility are important design characteristics; accordingly, the type of substrate material chosen and/or its thickness should be considered. It is important to note that a wide range of microstructures, e.g. isotropic, lamellor, substrate-nucleated and a varied content of remaining hydrogen can occur in pyrolytic carbons, depending on the deposition conditions, including temperature, type, concentration and flow rates of the source gas and surface area of the underlying substrate.

Other techniques which may be utilized to affix the pyrolytic carbon layer 5070 directly onto the sheath 5014 or onto a substrate include pulsed laser ablation deposition, radio frequency plasma modification, physical vapor deposition as well as other known techniques. In addition to pyrolytic carbon, other materials that might be beneficial in providing similar properties include diamond-like carbon coatings, silane/silicon glass like surfaces and thin ceramic coatings such as alumina, hydroxyapatite and titania.

In an alternate exemplary embodiment, the pyrolytic carbon coating may be applied with a controlled finite porosity as briefly described above. This controlled finite porosity provides two distinct advantages. First, the porosity may serve to reduce the contact surface area if the stent with the pyrolytic carbon coating 5070, thereby reducing the friction between the stent and the inner lumen of the sheath 5014. Second, lubricious materials such as biocompatible oils, waxes and powders could be infused or impregnated within the porous surface of the coating thereby providing a reservoir of lubricious material further reducing the frictional coefficient.

FIGS. 35 and 36 show the stent 7000 as being in its fully un-deployed position. This is the position the stent is in when the apparatus 5010 is inserted into the vasculature and its distal end is navigated to a target site. Stent 7000 is disposed around the stent bed 5042 and at the distal end 5052 of sheath 5014. The distal tip 5028 of the shaft 5012 is distal to the distal end 5052 of the sheath 5014. The stent 7000 is in a compressed state and makes frictional contact with the inner surface of the sheath 5014.

When being inserted into a patient, sheath 5014 and shaft 5012 are locked together at their proximal ends by a Tuohy Borst valve 5058. This prevents any sliding movement between the shaft 5012 and sheath 5014, which could result in a premature deployment or partial deployment of the stent 7000. When the stent 100 reaches its target site and is ready for deployment, the Tuohy Borst valve 5058 is opened so that the sheath 5014 and shaft 5012 are no longer locked together.

Figure 39:
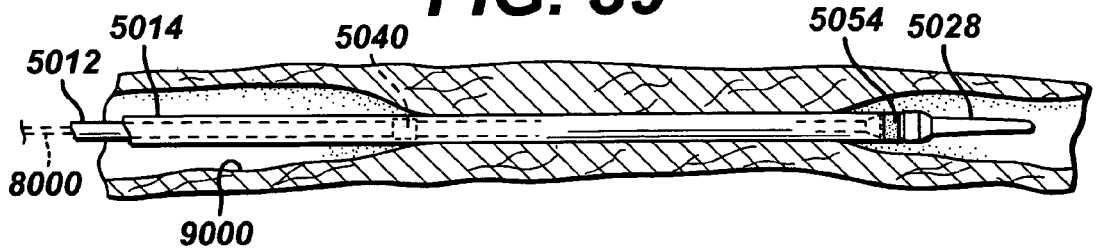
FIG. 39 through 43 are partial cross-sectional views of the apparatus of the present invention sequentially showing the deployment of the self-expanding stent within the vasculature.
Figure 40:
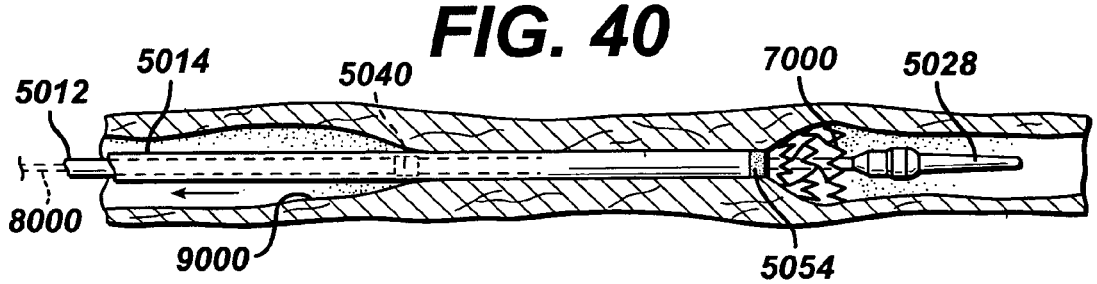
Figure 41:
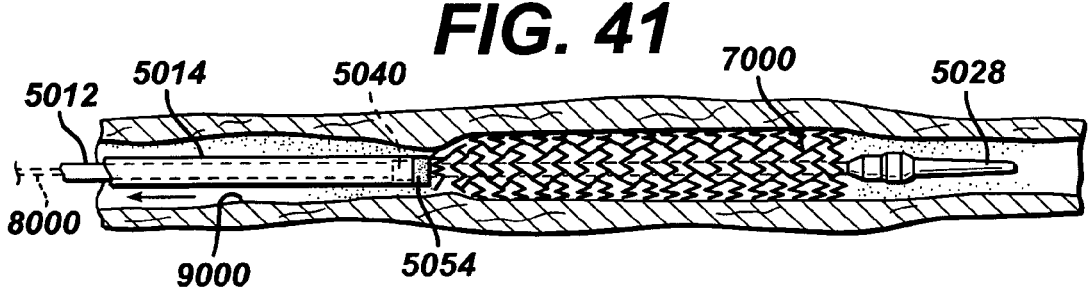
Figure 42:
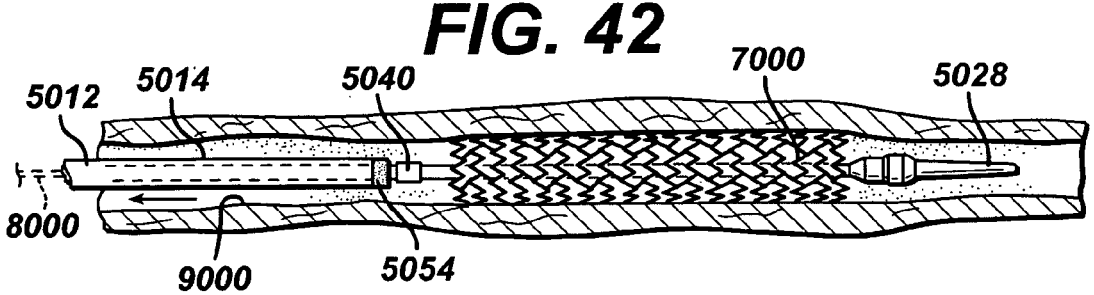

The method under which delivery apparatus 5010 deploys stent 7000 may best be described by referring to FIGS. 39-43. In FIG. 39, the delivery apparatus 5010 has been inserted into a vessel 9000 so that the stent bed 5042 is at a target diseased site. Once the physician determines that the radio-opaque marker band 5054 and stop 5040 on shaft 5012 indicating the ends of stent 7000 are sufficiently placed about the target disease site, the physician would open Tuohy Borst valve 5058. The physician would then grasp the Luer guidewire hub 5020 of shaft 5012 so as to hold shaft 5012 in a fixed position. Thereafter, the physician would grasp the Tuohy Borst valve 5058, attached proximally to sheath 5014, and slide it proximal, relative to the shaft 5012 as shown in FIGS. 40 and 41. Stop 5040 prevents the stent 7000 from sliding back with sheath 5014, so that as the sheath 5014 is moved back, the stent 7000 is effectively "pushed" out of the distal end 5052 of the sheath 5014, or held in position relative to the target site. Stent 7000 should be deployed in a distal to proximal direction to minimize the potential for creating emboli with the diseased vessel 9000. Stent deployment is complete when the radio-opaque band 5054 on the sheath 5014 is proximal to radio-opaque stop 5040, as shown in FIG. 42. The apparatus 5010 can now be withdrawn through stent 7000 and removed from the patient.

Figure 43:
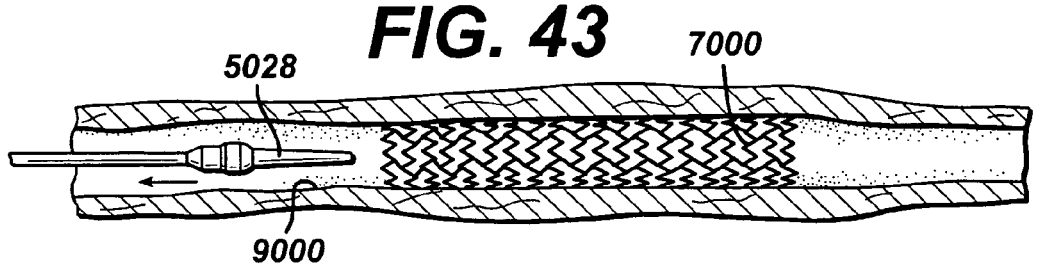

FIGS. 36 and 43 show a preferred embodiment of a stent 7000, which may be used in conjunction with the present invention. Stent 7000 is shown in its unexpanded compressed state, before it is deployed, in FIG. 36. Stent 7000 is preferably made from a superelastic alloy such as Nitinol. Most preferably, the stent 7000 is made from an alloy comprising from about 50.5 percent (as used herein these percentages refer to atomic percentages) Ni to about 60 percent Ni, and most preferably about 55 percent Ni, with the remainder of the alloy Ti. Preferably, the stent 7000 is such that it is superelastic at body temperature, and preferably has an Af in the range from about twenty-one degrees C. to about thirty-seven degrees C. The superelastic design of the stent makes it crush recoverable which, as discussed above, can be used as a stent or frame for any number of vascular devices for different applications.

Stent 7000 is a tubular member having front and back open ends a longitudinal axis extending there between. The tubular member has a first smaller diameter, FIG. 30, for insertion into a patient and navigation through the vessels, and a second larger diameter for deployment into the target area of a vessel. The tubular member is made from a plurality of adjacent hoops 7002 extending between the front and back ends. The hoops 7002 include a plurality of longitudinal struts 7004 and a plurality of loops 7006 connecting adjacent struts, wherein adjacent struts are connected at opposite ends so as to form a substantially S or Z shape pattern. Stent 7000 further includes a plurality of curved bridges 7008, which connect adjacent hoops 7002. Bridges 7008 connect adjacent struts together at bridge to loop connection points which are offset from the center of a loop.

The above described geometry helps to better distribute strain throughout the stent, prevents metal to metal contact when the stent is bent, and minimizes the opening size between the features, struts, loops and bridges. The number of and nature of the design of the struts, loops and bridges are important factors when determining the working properties and fatigue life properties of the stent. Preferably, each hoop has between twenty-four to thirty-six or more struts. Preferably the stent has a ratio of number of struts per hoop to strut length (in inches) which is greater than two hundred. The length of a strut is measured in its compressed state parallel to the longitudinal axis of the stent.

In trying to minimize the maximum strain experienced by features, the stent utilizes structural geometries which distribute strain to areas of the stent which are less susceptible to failure than others. For example, one vulnerable area of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge to loop connection points. One way to accomplish this is to utilize the largest possible radii while maintaining feature widths, which are consistent with applied forces. Another consideration is to minimize the maximum open area of the stent. Efficient utilization of the original tube from which the stent is cut increases stent strength and it's ability to trap embolic material.

As set forth above, stents coated with combinations of polymers and drugs, agents and/or compounds may potentially increase the forces acting on the stent during stent deployment. This increase in forces may in turn damage the stent. For example, as described above, during deployment, the stent is forced against a stop to overcome the force of sliding the outer sheath back. With a longer stent, e.g. greater than 200 mm, the forces exerted on the end of the stent during sheath retraction may be excessive and could potentially cause damage to the end of the stent or to other sections of the stent. Accordingly, a stent delivery device which distributes the forces over a greater area of the stent would be beneficial.

Figure 48:
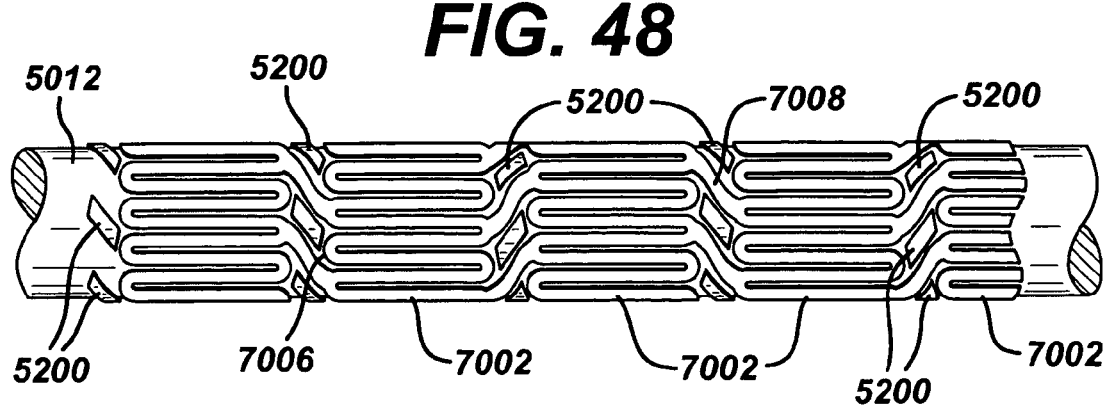
FIG. 48 is a partial cross-sectional view of a modified shaft of the stent delivery system in accordance with the present invention.

FIG. 48 illustrates a modified shaft 5012 of the stent delivery section. In this exemplary embodiment, the shaft 5012 comprises a plurality of raised sections 5200. The raised sections 5200 may comprise any suitable size and geometry and may be formed in any suitable manner. The raised sections 5200 may comprise any suitable material, including the material forming the shaft 5012. The number of raised sections 5200 may also be varied. Essentially, the raised sections 5200 may occupy the open spaces between the stent 7000 elements. All of the spaces may be filled or select spaces may be filled. In other words, the pattern and number of raised sections 5200 is preferably determined by the stent design. In the illustrated embodiment, the raised sections or protrusions 5200 are arranged such that they occupy the spaces formed between adjacent loops 7006 on adjacent hoops 7002 and between the bridges 7008.

The raised sections 5200 may be formed in any number of ways. For example, the raised sections 5200 may be formed using a heated clamshell mold or a waffle iron heated die approach. Either method allows for the low cost mass production of inner shafts comprising protrusions.

The size, shape and pattern of the raised sections 5200 may be modified to accommodate any stent design. The height of each of the raised sections 5200 is preferably large enough to compensate for the slight gap that exists between the inner shaft 5012 and the outer sheath 5014. The height, H, of the raised sections or protrusions 5200 on the shaft 5012 should preferably be, at a minimum, greater than the difference in radius between the outside diameter of the shaft 5012, IM(r), and the inside diameter of the sheath 5014, OM(r), minus the wall thickness of the device or stent 7000, WT. The equation representing this relationship is given by $H > (OM(r) - IM(r)) - WT.$ For example, if the shaft 5012 has an outside diameter of 0.08 inches, the sheath 5014 has an inside diameter of 0.1 inches, and the wall thickness of the stent 7000 is 0.008 inches, then the height of the raised sections or protrusions 5200 is $$H > \left(\frac{0.100}{2} - \frac{0.080}{2}\right) - 0.008, \text{ or}$$

$$H > 0.002 \text{ inches.}$$

It is important to note that the height of the raised sections 5200 should preferably be less than the difference between the radius of the sheath and the radius of the shaft unless the protrusions 5200 are compressible.

Although each raised section 5200 is small, the number of raised sections 5200 may be large and each of the raised sections 5200 apply a small amount of force to different parts of the stent 7002, thereby distributing the force to deploy the stent 7000 and preventing damage to the stent 7000 particularly at its proximal end. The raised sections 5200 also protect the stent 7000 during loading of the stent 7000 into the delivery system. Essentially, the same forces that act on the stent 7000 during deployment act on the stent 7000 during loading. The longitudinal flexibility of the stent necessitates that as little force as possible is placed on the stent as it is released or deployed to ensure repeatable foreshortening and accurate placement. Essentially, it is preferable that longitudinal movement of the stent 7000 be eliminated or substantially reduced during deployment thereby eliminating or substantially reducing compression of the stent. Without the raised sections 5200, as the stent 7000 is being deployed, the compressive forces will compress the delivery system as well as the stent 7000. This compressive energy will be released upon deployment, reducing the chances of accurate placement of the stent 7000 and contributing to the possibility of stent "jumping." With the raised sections 5200, the stent 7000 is less likely to move, thereby eliminating or substantially reducing compression.

In an alternate exemplary embodiment, once the stent is positioned on the shaft of the delivery device, the stent may be heated and externally pressurized to make a mirror-like imprint in the inner shaft of the delivery system. The imprint provides a three-dimensional surface which allows the stent to maintain its position as the sheath is retracted. The three-dimensional imprint may be made using heat alone, pressure alone or with a separate device.

Any of the above-described medical devices may be utilized for the local delivery of drugs, agents and/or compounds to other areas, not immediately around the device itself. In order to avoid the potential complications associated with systemic drug delivery, the medical devices of the present invention may be utilized to deliver therapeutic agents to areas adjacent to the medical device. For example, a rapamycin coated stent may deliver the rapamycin to the tissues surrounding the stent as well as areas upstream of the stent and downstream of the stent. The degree of tissue penetration depends on a number of factors, including the drug, agent or compound, the concentrations of the drug and the release rate of the agent. The same holds true for coated anastomosis devices.

The drug, agent and/or compound/carrier or vehicle compositions described above may be formulated in a number of ways. For example, they may be formulated utilizing additional components or constituents, including a variety of excipient agents and/or formulary components to affect manufacturability, coating integrity, sterilizability, drug stability, and drug release rate. Within exemplary embodiments of the present invention, excipient agents and/or formulary components may be added to achieve both fast-release and sustained-release drug elution profiles. Such excipient agents may include salts and/or inorganic compounds such as acids/bases or buffer components, anti-oxidants, surfactants, polypeptides, proteins, carbohydrates including sucrose, glucose or dextrose, chelating agents such as EDTA, glutathione or other excipients or agents.

It is important to note that any of the above-described medical devices may be coated with coatings that comprise drugs, agents or compounds or simply with coatings that contain no drugs, agents or compounds. In addition, the entire medical device may be coated or only a portion of the device may be coated. The coating may be uniform or non-uniform. The coating may be discontinuous.

As described above, any number of drugs, agents and/or compounds may be locally delivered via any number of medical devices. For example, stents and anastomosis devices may incorporate coatings comprising drugs, agents and/or compounds to treat various disease states and reactions by the body as described in detail above. Other devices which may be coated with or otherwise incorporate therapeutic dosages of drugs, agents and/or compounds include stent-grafts, which are briefly described above, and devices utilizing stent-grafts, such as devices for treating abdominal aortic aneurysms as well as other aneurysms, e.g. thoracic aorta aneurysms.

Figure 24:
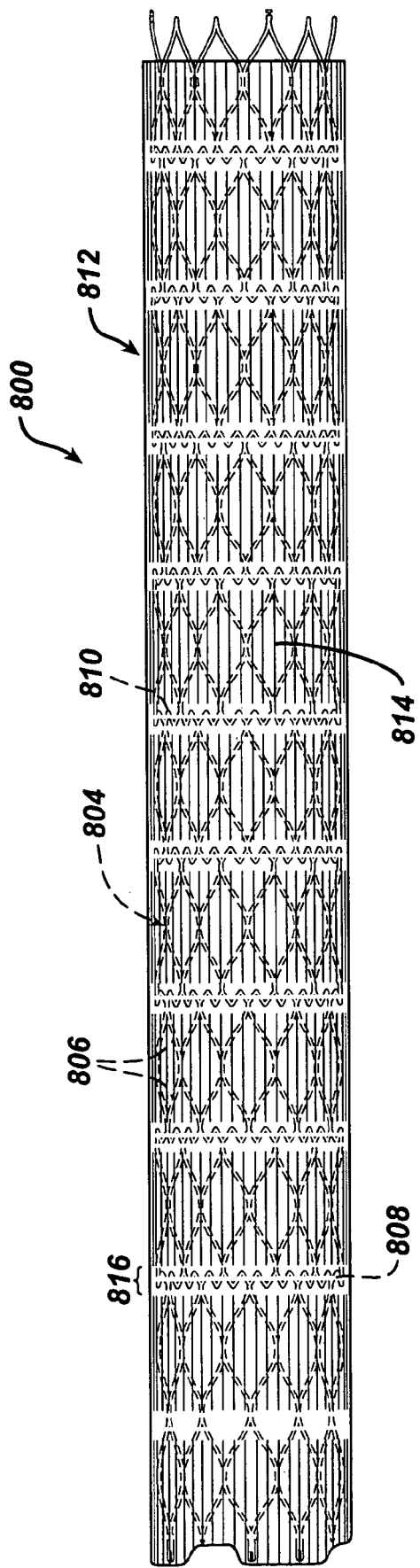
FIG. 24 is a side elevation of an exemplary stent-graft in accordance with the present invention.

Stent-grafts, as the name implies, comprise a stent and a graft material attached thereto. FIG. 24 illustrates an exemplary stent-graft 800. The stent-graft 800 may comprise any type of stent and any type of graft material as described in detail subsequently. In the illustrated exemplary embodiment, the stent 802 is a self-expanding device. A typical self-expanding stent comprises an expandable lattice or network of interconnected struts. In preferred embodiments of the invention, the lattice is fabricated, e.g. laser cut, from an integral tube of material.

In accordance with the present invention, the stent may be variously configured. For example, the stent may be configured with struts or the like that form repeating geometric shapes. One skilled in the art will readily recognize that a stent may be configured or adapted to include certain features and/or to perform a certain function(s), and that alternate designs may be used to promote that feature or function.

In the exemplary embodiment of the invention illustrated in FIG. 24, the matrix or struts of stent 802 may be configured into at least two hoops 804, each hoop 804 comprising a number of struts 806 formed into a diamond shape, having approximately nine diamonds. The stent 802 may further include a zigzag shaped ring 808 for connecting adjacent hoops to one another. The zigzag shaped rings 808 may be formed from a number of alternating struts 810, wherein each ring has fifty-four struts.

An inner or outer surface of the stent 802 may be covered by or support a graft material. Graft material 812 may be made from any number of materials known to those skilled in the art, including woven or other configurations of polyester, Dacron®, Teflon®, polyurethane porous polyurethane, silicone, polyethylene, terephthalate, expanded polytetrafluoroethylene (ePTFE) and blends of various materials.

The graft material 812 may be variously configured, preferably to achieve predetermined mechanical properties. For example, the graft material may incorporate a single or multiple weaving and/or pleating patterns, or may be pleated or unpleated. For example, the graft material may be configured into a plain weave, a satin weave, include longitudinal pleats, interrupted pleats, annular or helical pleats, radially oriented pleats, or combinations thereof. Alternately, the graft material may be knitted or braided. In the embodiments of the invention in which the graft material is pleated, the pleats may be continuous or discontinuous. Also, the pleats may be oriented longitudinally, circumferentially, or combinations thereof.

As illustrated in FIG. 24, the graft material 812 may include a plurality of longitudinal pleats 814 extending along its surface, generally parallel to the longitudinal axis of the stent-graft 800. The pleats 814 allow the stent-graft 800 to collapse around its center, much as it would be when it is delivered into a patient. This provides a relatively low profile delivery system, and provides for a controlled and consistent deployment therefrom. It is believed that this configuration minimizes wrinkling and other geometric irregularities. Upon subsequent expansion, the stent-graft 800 assumes its natural cylindrical shape, and the pleats 814 uniformly and symmetrically open.

In addition, the pleats 814 help facilitate stent-graft manufacture, in that they indicate the direction parallel to the longitudinal axis, allowing stent to graft attachment along these lines, and thereby inhibiting accidental twisting of the graft relative to the stent after attachment. The force required to push the stent-graft 800 out of the delivery system may also be reduced, in that only the pleated edges of the graft make frictional contact with the inner surface of the delivery system. One further advantage of the pleats 814 is that blood tends to coagulate generally uniformly in the troughs of the pleats 814, discouraging asymmetric or large clot formation on the graft surface, thereby reducing embolus risk.

As shown in FIG. 24, the graft material 812 may also include one or more, and preferably a plurality of, radially oriented pleat interruptions 816. The pleat interruptions 816 are typically substantially circular and are oriented perpendicular to longitudinal axis. Pleat interruptions 816 allow the graft and stent to bend better at selective points. This design provides for a graft material that has good crimpability and improved kink resistance.

The foregoing graft materials may be braided, knitted or woven, and may be warp or weft knitted. If the material is warp knitted, it may be provided with a velour, or towel like surface; which is believed to speed the formation of blood clots, thereby promoting the integration of a stent-graft or stent-graft component into the surrounding cellular structure.

A graft material may be attached to a stent or to another graft material by any number of structures or methods known to those skilled in the art, including adhesives, such as polyurethane glue; a plurality of conventional sutures of polyvinylidene fluoride, polypropylene, Dacron®, or any other suitable material; ultrasonic welding; mechanical interference fit; and staples.

The stent 802 and/or graft material 812 may be coated with any of the above-described drugs, agents and/or compounds. In one exemplary embodiment, rapamycin may be affixed to at least a portion of the graft material 812 utilizing any of the materials and processes described above. In another exemplary embodiment, rapamycin may be affixed to at least a portion of the graft material 812 and heparin or other anti-thrombotics may be affixed to at least a portion of the stent 802. With this configuration, the rapamycin coated graft material 812 may be utilized to minimize or substantially eliminate smooth muscle cell hyperproliferation and the heparin coated stent may substantially reduce the chance of thrombosis.

The particular polymer(s) utilized depends on the particular material upon which it is affixed. In addition, the particular drug, agent and/or compound may also affect the selection of polymer(s). As set forth above, rapamycin may be affixed to at least a portion of the graft material 812 utilizing the polymer(s) and processes described above. In another alternate exemplary embodiment, the rapamycin or any other drug, agent and/or compound may be directly impregnated into the graft material 812 utilizing any number of known techniques.

Figure 25:
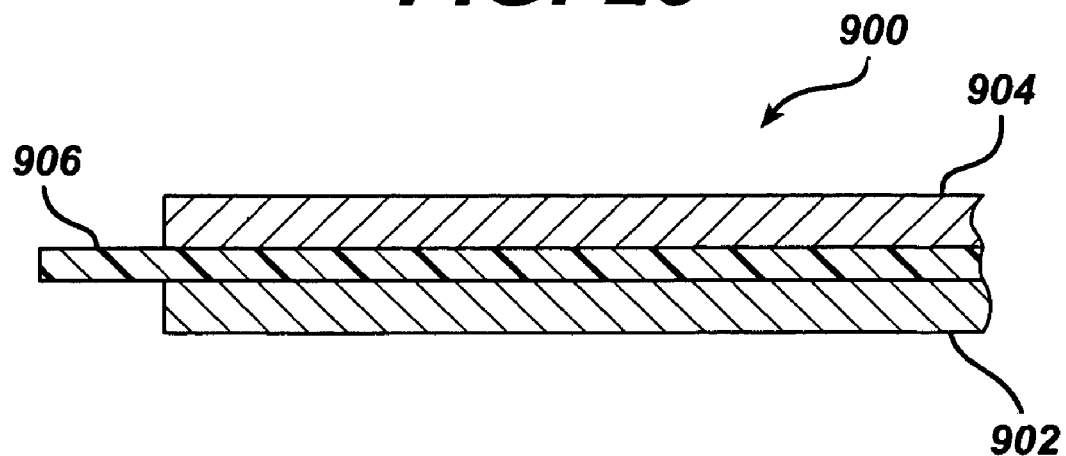
FIG. 25 is a fragmentary cross-sectional view of another alternate exemplary embodiment of a stent-graft in accordance with the present invention.

In yet another alternate exemplary embodiment, the stent-graft may be formed from two stents with the graft material sandwiched therebetween. FIG. 25 is a simple illustration of a stent-graft 900 formed from an inner stent 902, an outer stent 904 and graft material 906 sandwiched therebetween. The stents 902, 904 and graft material 906 may be formed from the same materials as described above. As before, the inner stent 902 may be coated with an anti-thrombotic or anti-coagulant such as heparin while the outer stent 904 may be coated with an anti-proliferative such as rapamycin. Alternately, the graft material 906 may be coated with any of the above described drugs, agents and/or compounds, as well as combinations thereof, or all three elements may be coated with the same or different drugs, agents and/or compounds.

Figure 26:
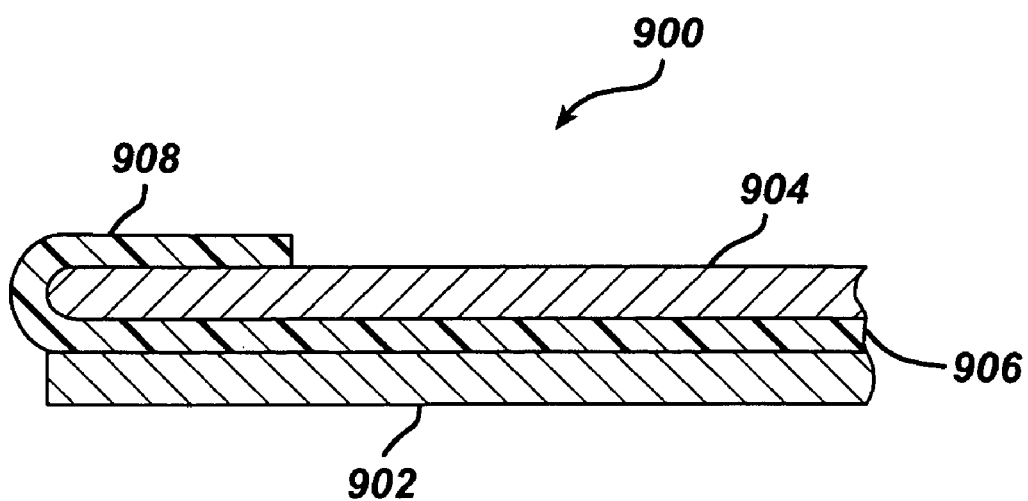
FIG. 26 is a fragmentary cross-sectional view of another alternate exemplary embodiment of a stent-graft in accordance with the present invention.

In yet another alternate exemplary embodiment, the stent-graft design may be modified to include a graft cuff. As illustrated in FIG. 26, the graft material 906 may be folded around the outer stent 904 to form cuffs 908. In this exemplary embodiment, the cuffs 908 may be loaded with various drugs, agents and/or compounds, including rapamycin and heparin. The drugs, agents and/or compounds may be affixed to the cuffs 908 utilizing the methods and materials described above or through other means. For example, the drugs, agents and/or compounds may be trapped in the cuffs 908 with the graft material 906 acting as the diffusion barrier through which the drug, agent and/or compound elutes. The particular material selected as well as its physical characteristics would determine the elution rate. Alternately, the graft material 906 forming the cuffs 908 may be coated with one or more polymers to control the elution rate as described above.

Stent-grafts may be utilized to treat aneurysms. An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type 1 aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal approach has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital, and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, percutaneous, e.g., catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. The delivery procedure typically involves advanced angiographic techniques performed through vascular accesses gained via surgical cutdown of a remote artery, such as the common femoral or brachial arteries. Over a guidewire, the appropriate size introducer will be placed. The catheter and guidewire are passed through the aneurysm, and, with the appropriate size introducer housing a stent-graft, the stent-graft will be advanced along the guidewire to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure requires surgical repair. Some procedures may require additional surgical techniques, such as hypogastric artery embolization, vessel ligation, or surgical bypass, in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and re-configurable while maintaining acute and long term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

Figure 27:
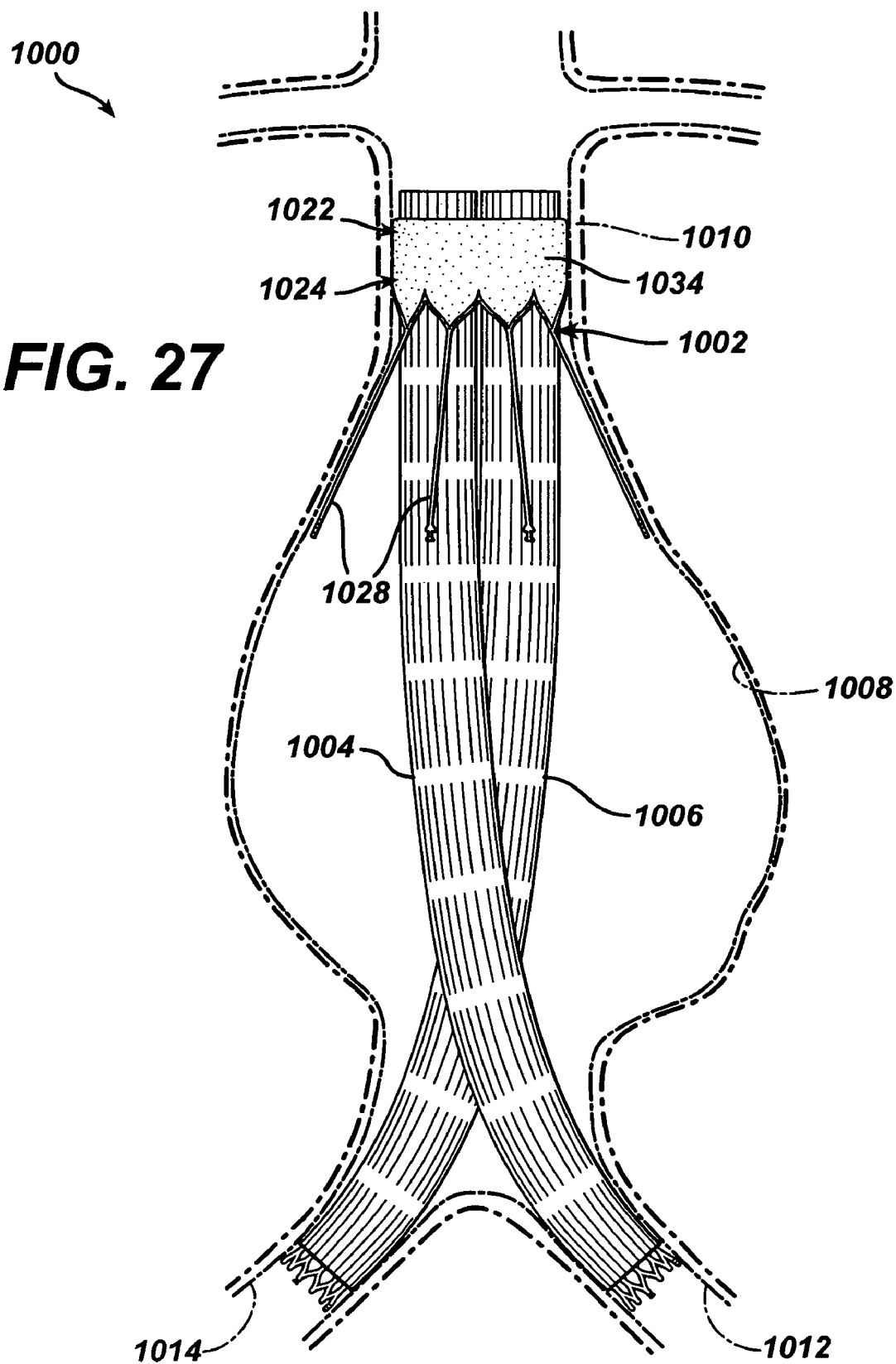
FIG. 27 is an elevation view of a fully deployed aortic repair system in accordance with the present invention.

As stated above, one or more stent-grafts may be utilized to treat aneurysms. These stent-grafts or endoprostheses may comprise any number of materials and configurations. FIG. 27 illustrates an exemplary system for treating abdominal aortic aneurysms. The system 1000 includes a first prosthesis 1002 and two second prostheses 1004 and 1006, which in combination, bypass an aneurysm 1008. In the illustrated exemplary embodiment, a proximal portion of the system 1000 may be positioned in a section 1010 of an artery upstream of the aneurysm 1008, and a distal portion of the system 1000 may be positioned in a downstream section of the artery or a different artery such as iliacs 1012 and 1014.

A prosthesis used in a system in accordance with the present invention typically includes a support, stent or lattice of interconnected struts defining an interior space or lumen having an open proximal end and an open distal end. The lattice also defines an interior surface and an exterior surface. The interior and/or exterior surfaces of the lattice, or a portion of the lattice, may be covered by or support at least one gasket material or graft material.

In preferred embodiments of the invention, a prosthesis is moveable between an expanded or inflated position and an unexpanded or deflated position, and any position therebetween. In some exemplary embodiments of the invention, it may be desirable to provide a prosthesis that moves only from fully collapsed to fully expanded. In other exemplary embodiments of the invention, it may be desirable to expand the prosthesis, then collapse or partially collapse the prosthesis. Such capability is beneficial to the surgeon to properly position or re-position the prosthesis. In accordance with the present invention, the prosthesis may be self-expanding, or may be expandable using an inflatable device, such as a balloon or the like.

Referring back to FIG. 27, the system 1000 is deployed in the infrarenal neck 1010 of the abdominal aorta, upstream of where the artery splits into first and second common iliac arteries 1012, 1014. FIG. 27 shows the first prosthesis or stent gasket 1002 positioned in the infrarenal neck 1010; two second prostheses, 1004, 1006, the proximal ends of which matingly engage a proximal portion of stent gasket 1002, and the distal ends of which extend into a common iliac artery 1012 or 1014. As illustrated, the body of each second prosthesis forms a conduit or fluid flow path that passes through the location of the aneurysm 1008. In preferred embodiments of the invention, the components of the system 1000 define a fluid flow path that bypasses the section of the artery where the aneurysm is located.

The first prosthesis includes a support matrix or stent that supports a sealing material or foam, at least a portion of which is positioned across a biological fluid flow path, e.g., across a blood flow path. In preferred embodiments of the invention, the first prosthesis, the stent, and the sealing material are radially expandable, and define a hollow space between a proximal portion of the prosthesis and a distal portion of the prosthesis. The first prosthesis may also include one or more structures for positioning and anchoring the prosthesis in the artery, and one or more structures for engaging and fixing at least one second prosthesis in place, e.g., a bypass prosthesis.

The support matrix or stent of the first prosthesis may be formed of a wide variety of materials, may be configured in a wide variety of shapes, and their shapes and uses are well known in the art. Exemplary prior art stents are disclosed in U.S. Pat. No. 4,733,665 (Palmaz); U.S. Pat. No. 4,739,762 (Palmaz); and U.S. Pat. No. 4,776,337 (Palmaz), each of the foregoing patents being incorporated herein by reference.

In preferred embodiments of the invention, the stent of the first prosthesis is a collapsible, flexible, and self-expanding lattice or matrix formed from a metal or metal alloy, such as nitinol or stainless steel. Structures formed from stainless steel may be made self-expanding by configuring the stainless steel in a predetermined manner, for example, by twisting it into a braided configuration. More preferably, the stent is a tubular frame that supports a sealing material. The term tubular, as used herein, refers to any shape having a sidewall or sidewalls defining a hollow space or lumen extending therebetween; the cross-sectional shape may be generally cylindrical, elliptic, oval, rectangular, triangular, or any other shape. Furthermore, the shape may change or be deformable as a consequence of various forces that may press against the stent or prosthesis.

The sealing material or gasket member supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The sealing material or gasket member may comprise any suitable material. Exemplary materials preferably comprise a biodurable and biocompatible material, including but are not limited to, open cell foam materials and closed cell foam materials. Exemplary materials include polyurethane, polyethylene, polytetrafluoroethylene; and other various polymer materials, preferably woven or knitted, that provide a flexible structure, such as Dacron®. Highly compressible foams are particularly preferred, preferably to keep the crimped profile low for better delivery. The sealing material or foam is preferably substantially impervious to blood when in a compressed state.

The sealing material may cover one or more surfaces of the stent i.e., may be located along an interior or exterior wall, or both, and preferably extends across the proximal end or a proximal portion of the stent. The sealing material helps impede any blood trying to flow around the first prosthesis, e.g., between the first prosthesis and the arterial wall, and around one or more bypass prostheses after they have been deployed within the lumen of the first prosthesis (described in more detail below).

In preferred embodiments of the invention, the sealing material stretches or covers a portion of the proximal end of the stent and along at least a portion of the outside wall of the stent.

In some embodiments of the invention, it may be desirable for the portion of the sealing material covering the proximal portion of the stent to include one or more holes, apertures, points, slits, sleeves, flaps, weakened spots, guides, or the like for positioning a guidewire, for positioning a system component, such as a second prosthesis, and/or for engaging, preferably matingly engaging, one or more system components, such as a second prosthesis. For example, a sealing material configured as a cover or the like, and having a hole, may partially occlude the stent lumen.

These openings may be variously configured, primarily to conform to its use. These structures promote proper side by side placement of one or more, preferably multiple, prostheses within the first prosthesis, and, in some embodiments of the invention, the sealing material may be configured or adapted to assist in maintaining a certain shape of the fully deployed system or component. Further, these openings may exist prior to deployment of the prosthesis, or may be formed in the prosthesis as part of a deployment procedure. The various functions of the openings will be evident from the description below. In exemplary embodiments of the invention, the sealing material is a foam cover that has a single hole.

The sealing material may be attached to the stent by any of a variety of connectors, including a plurality of conventional sutures of polyvinylidene fluoride, polypropylene, Dacron®, or any other suitable material and attached thereto. Other methods of attaching the sealing material to the stent include adhesives, ultrasonic welding, mechanical interference fit and staples.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

First prosthesis is typically deployed in an arterial passageway upstream of an aneurysm, and functions to open and/or expand the artery, to properly position and anchor the various components of the system, and, in combination with other components, seal the system or portions thereof from fluid leaks. For example, the sealing prosthesis may be deployed within the infrarenal neck, between an abdominal aortic aneurysm and the renal arteries of a patient, to assist in repairing an abdominal aortic aneurysm.

Figure 28:
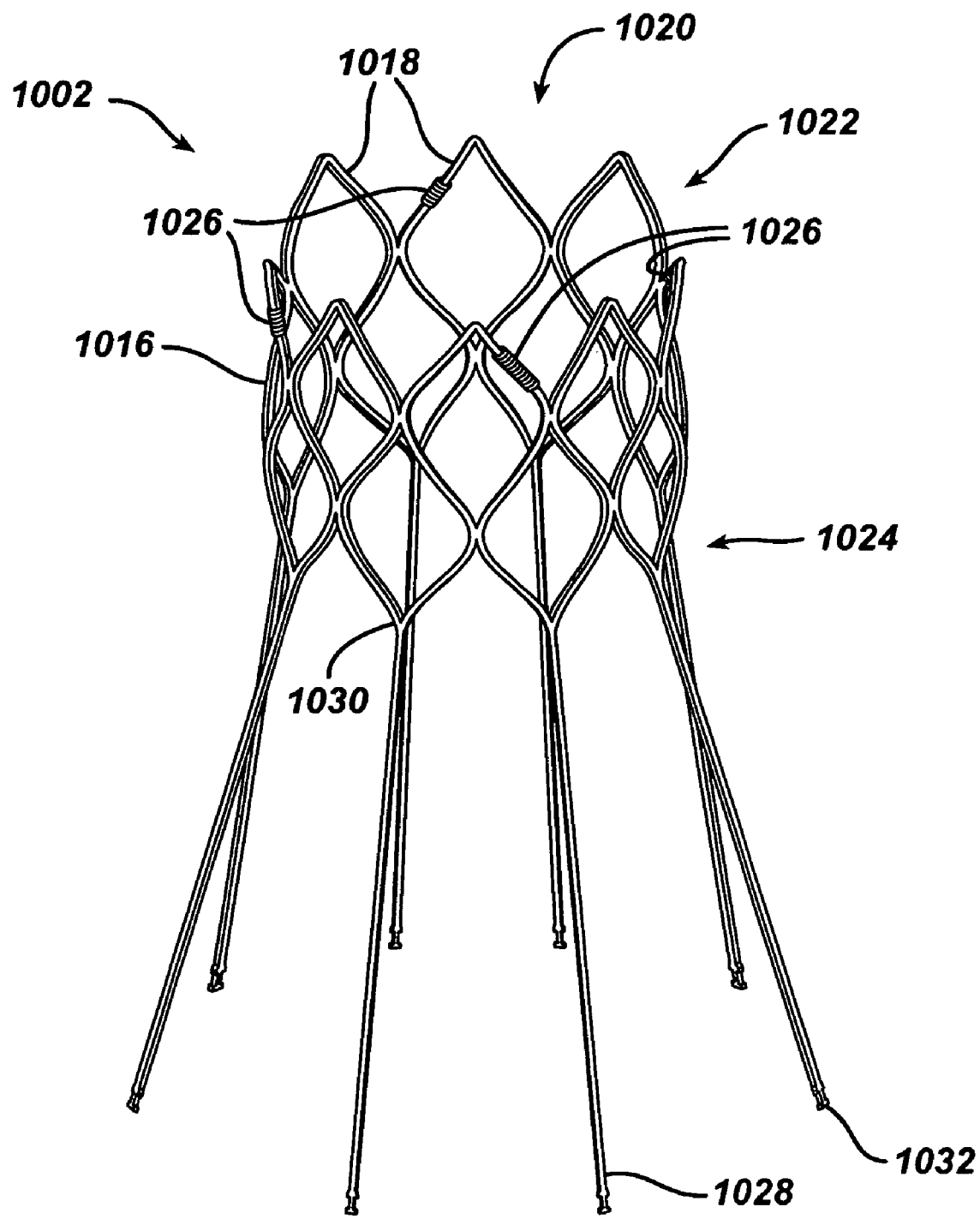
FIG. 28 is a perspective view of a stent for a first prosthesis, shown for clarity in an expanded state, in accordance with the present invention.
Figure 29:
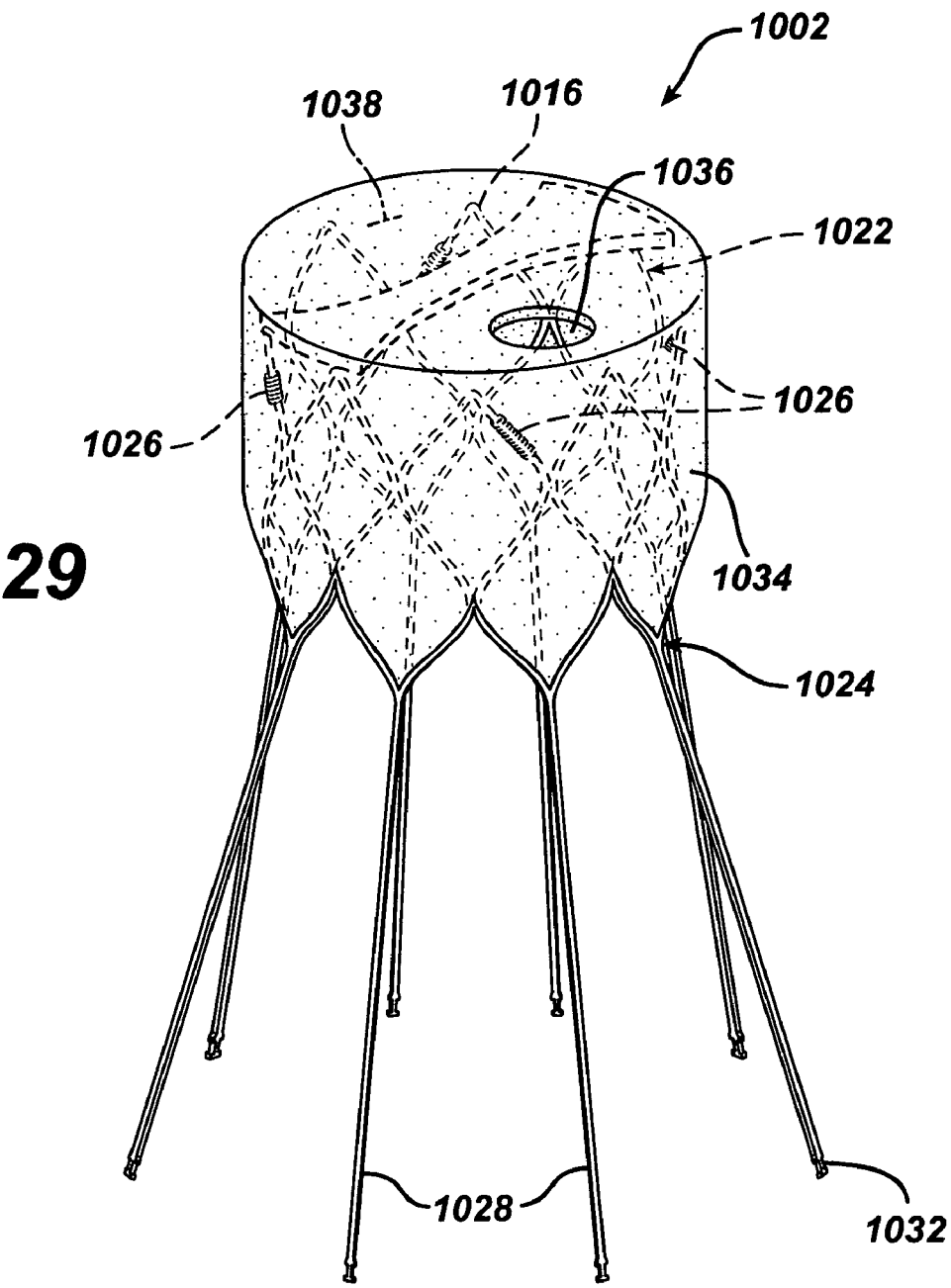
FIG. 29 is a perspective view of a first prosthesis having a stent covered by a gasket material in accordance with the present invention.

FIGS. 27-29 show an exemplary sealing prosthesis of the present invention. Sealing prosthesis 1002 includes a cylindrical or oval self-expanding lattice, support, or stent 1016, typically made from a plurality of interconnected struts 1018. Stent 1016 defines an interior space or lumen 1020 having two open ends, a proximal end 1022 and a distal end 1024. One or more markers 1026 may be optionally disposed in or on the stent between the proximal end 1022 and the distal end 1024.

Stent 1016 may further include at least two but preferably eight (as shown in FIG. 28) spaced apart longitudinal legs 1028. Preferably, there is a leg extending from each apex 1030 of diamonds formed by struts 1018. At least one leg, but preferably each leg, includes a flange 1032 adjacent its distal end which allows for the stent 1016 to be retrievable into its delivery apparatus after partial or nearly full deployment thereof so that it can be turned, or otherwise repositioned for proper alignment.

FIG. 29 shows the sealing material 1034 covering the proximal end 1022 of stent gasket 1002. In the exemplary embodiment shown in FIG. 29, sealing prosthesis 1002 includes a sealing material 1034 having a first opening or hole 1036 and a second opening or slit 1038. The gasket material covers at least a portion of the interior or exterior of the stent, and most preferably covers substantially all of the exterior of the stent. For example, gasket material 1034 may be configured to cover stent 1016 from the proximal end 1022 to the distal end 1024, but preferably not covering longitudinal legs 1028.

The sealing material 1034 helps impede any blood trying to flow around bypass prostheses 1004 and 1006 after they have been deployed (as shown in FIG. 27) and from flowing around the stent gasket 1002 itself. For this embodiment, sealing material 1034 is a compressible member or gasket located along the exterior of the stent 1016 and at least a portion of the interior of the stent 1016.

The second prostheses 1004 and 1006 may comprise stent-grafts such as described with respect to FIG. 24 and may be coated with any of the drugs, agents and/or compounds as described above. In other words, the stent and/or the graft material may be coated with any of the above-described drugs, agents and/or compounds utilizing any of the above-described polymers and processes. The stent gasket 1002 may also be coated with any of the above-described drugs, agents and/or compounds. In other words, the stent and/or sealing material may be coated with any of the above-described drugs, agents and/or compounds utilizing any of the above-described polymers and processes. In particular, rapamycin and heparin may be of importance to prevent smooth muscle cell hyperproliferation and thrombosis. Other drugs, agents and/or compounds may be utilized as well. For example drugs, agents and/or compounds which promote re-endothelization may be utilized to facilitate incorporation of the prosthesis into the living organism. Also, embolic material may be incorporated into the stent-graft to reduce the likelihood of endo leaks.

It is important to note that the above-described system for repairing abdominal aortic aneurysms is one example of such a system. Any number of aneurysmal repair systems comprising stent-grafts may be coated with the appropriate drugs, agents and/or compounds, as well as combinations thereof. For example, thoracic aorta aneurysms may be repaired in a similar manner. Regardless of the type of aneurysm or its position within the living organism, the components comprising the repair system may be coated with the appropriate drug, agent and/or compound as described above with respect to stent-grafts.

A difficulty associated with the treatment of aneurysms, specifically abdominal aortic aneurysms, is endoleaks. An endoleak is generally defined as the persistence of blood flow outside of the lumen of the stent-graft, but within the aneurysmal sac or adjacent vascular segment being treated with the stent-graft. Essentially, endoleaks are caused by one of two primary mechanisms, wherein each mechanism has a number of possible modalities. The first mechanism involves the incomplete sealing or exclusion of the aneurysmal sac or vessel segment. The second mechanism involves retrograde flow. In this type of endoleak, blood-flow into the aneurysmal sac is reversed due to retrograde flow from patent collateral vessels, particularly the lumbar arteries or the inferior mesenteric artery. This type of endoleak may occur even when a complete seal has been achieved around the stent-grafts. It is also possible that an endoleak may develop due to stent-graft failure, for example, a tear in the graft fabric.

Endoleaks may be classified by type. A type I endoleak is a perigraft leak at the proximal or distal attachment sites of the stent-grafts. Essentially, this type of endoleak occurs when a persistent perigraft channel of blood flow develops due to an ineffective or inadequate seal at the ends of the stent-graft. There are a number of possible causes of a type I endoleak, including improper sizing of the stent-graft, migration of the stent-graft, incomplete stent-graft expansion and an irregular shape of the arterial lumen. A type II endoleak is persistent collateral blood flow into the aneurysmal sac from a patent branch of the aorta. Essentially, the pressure in the aneurysmal sac is lower than the collateral branches, thereby causing a retrograde blood flow. Sources of type II endoleaks include the accessory renal arteries, the testicular arteries, the lumbar arteries, the middle sacral artery, the inferior mesenteric artery and the spinal artery. A type III endoleak may be caused by a structural failure of the abdominal aortic aneurysm repair system or its components, for example, the stent-grafts. A type III endoleak may also be caused by a junction failure in systems employing modular components. Sources of type III endoleaks include tears, rips or holes in the fabric of the stent-graft, improper sizing of the modular components and limited overlap of the modular components. A type IV endoleak is blood flow through the graft material itself. The blood flow through the pores of the graft material or through small holes in the fabric caused by the staples or sutures attaching the graft material to the stent. Blood flow through the pores typically occurs with highly porous graft fabrics. A type V endoleak or endotension is a persistent or recurrent pressurization of the aneurysmal sac without any radiologically detectable endoleak. Possible causes of a type V endoleak include pressure transmission by thrombus, highly porous graft material, or the adjacent aortic lumen.

There are a number of possible treatment options for each type of endoleak described above. The particular treatment option depends mainly upon the cause of endoleak and the options are not always successful. The present invention is directed to a modification of existing endovascular abdominal aortic aneurysm repair systems or devices, such as the exemplary devices described herein, that is intended to eliminate or substantially reduce the incidence of endoleaks.

The modification comprises coating at least a portion of the various components comprising an abdominal aortic aneurysm repair system with drugs, agents and/or compounds which promote wound healing as described below. For example, portions of the exemplary system 1000, illustrated in FIG. 27, may be coated with one or more drugs, agents and/or compounds that induce or promote the wound healing process, thereby reducing or substantially reducing the risk of endoleaks. It may be particularly advantageous to coat the ends of the two second prostheses 1004 and 1006 and the entire first prosthesis 1002, as these are the most likely regions for endoleaks. However, coating the entire stent-graft, i.e. graft material and stent, may prove beneficial depending upon the type of endoleak. Since it is not always possible to stop endoleaks utilizing currently available methods, the use of wound healing agents, delivered locally, in accordance with the present invention may serve to effectively stop or prevent acute and chronic endoleaks. It is important to note that the present invention may be utilized in combination with any abdominal aortic aneurysm repair system, or with any other type of graft component where leakage is a potential problem. The present invention may be utilized in conjunction with type I, III, IV and V endoleaks.

Normal wound healing essentially occurs in three stages or phases, which have a certain degree of overlap. The first phase is cellular migration and inflammation. This phase lasts for several days. The second phase is the proliferation of fibroblasts for two to four weeks with new collagen synthesis. The third phase is remodeling of the scar and typically lasts from one month to a year. This third phase includes collagen cross linking and active collagen turnover.

As stated above, there are certain drugs, agents and/or compounds that may be delivered locally to the repair site, via the repair system, that promotes wound healing which in turn may eliminate or substantially reduce the incidence of endoleaks. For example, increased collagen production early in wound healing leads to greater wound strength. Accordingly, collagen may be combined with the repair system to increase wound strength and promote platelet aggregation and fibrin formation. In addition, certain growth factors may be combined with the repair system to promote platelet aggregation and fibrin formation as well as to increase wound strength.

Platelet-derived Growth Factor induces mitoses and is the major mitogen in serum for growth in connective tissue. Platelet Factor 4 is a platelet released protein that promotes blood clotting by neutralizing heparin. Platelet-derived Growth Factor and Platelet Factor 4 are important in inflammation and repair. They are active for human monocytes, neutrophils, smooth muscle cells, fibroblasts and inflammation cells. Transforming Growth Factor-$\beta$ is a part of a complex family of polypeptide hormones or biological factors that are produced by the body to control growth, division and maturation of blood cells by the bone marrow. Transforming Growth Factor-$\beta$ is found in tissues and platelets, and is known to stimulate total protein, collagen and DNA content in wound chambers implanted in vivo. Transforming Growth Factor-$\beta$ in combination with collagen has been shown to be extremely effective in wound healing.

A series of reactions take place in the body whenever a blood clot begins to form. A major initiator of these reactions is an enzyme system called the Tissue Factor/VIIa complex. Accordingly, Tissue Factor/VIIa may be utilized to promote blood clot formation and thus enhance wound healing. Other agents which are known to initiate thrombus formation include thrombin, fibrin, plasminogin-activator initiator, adenosine diphosphate and collagen.

The use of these drugs, agents and/or compounds in conjunction with the various components of the repair system may be used to eliminate or substantially reduce the incidence of endoleaks through the formation of blood clots and wound healing.

The stent and/or graft material comprising the components of the system 1000 may be coated with any of the above-described drugs, agents and/or compounds. The above-described drugs, agents and/or compounds may be affixed to a portion of the components or to all of the components utilizing any of the materials and processes described above. For example, the drugs, agents and/or compounds may be incorporated into a polymeric matrix or affixed directly to various portions of the components of the system.

The particular polymer(s) utilized depends on the particular material upon which it is affixed. In addition, the particular drug, agent and/or compound may also affect the selection of polymer(s).

As described above, other implantable medical devices that may be coated with various drugs, agents and/or compounds include surgical staples and sutures. These medical devices may be coated with any of the above-described drugs, agents and/or compounds to treat various conditions and/or to minimize or substantially eliminate the organisms' reaction to the implantation of the device.

Figure 30:
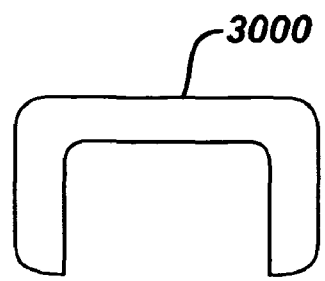
FIG. 30 is a diagrammatic representation of an uncoated surgical staple in accordance with the present invention.
Figure 31:
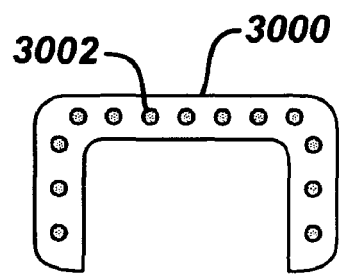
FIG. 31 is a diagrammatic representation of a surgical staple having a multiplicity of through-holes in accordance with the present invention.

FIG. 30 illustrates an uncoated or bare surgical staple 3000. The staple 3000 may be formed from any suitable biocompatible material having the requisite strength requirements for a given application. Generally, surgical staples comprise stainless steel. FIG. 31 illustrates an exemplary embodiment of a surgical staple 3000 comprising a multiplicity of through-holes 3002, which preferably contain one or more drugs, agents and/or compounds as described above. The one or more drugs, agents and/or compounds may be injected into the through-holes 3002 with or without a polymeric mixture. For example, in one exemplary embodiment, the through-holes 3002 may be sized such that the one or more drugs, agents and/or compounds may be injected directly therein and elute at a specific rate based upon the size of the through-holes 3002. In another exemplary embodiment, the one or more drugs, agents and/or compounds may be mixed with the appropriate polymer, which controls the elution rate, and injected into or loaded into the through-holes 3002. In yet another alternate exemplary embodiment, the one or more drugs, agents and/or compounds may be injected into or loaded into the though-holes 3002 and then covered with a polymer to control the elution rate.

Figure 32:
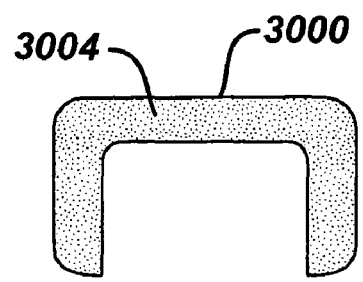
FIG. 32 is a diagrammatic representation of a surgical staple having a coating on the outer surface thereof in accordance with the present invention.

FIG. 32 illustrates an exemplary embodiment of a surgical staple 3000 comprising a coating 3006 covering substantially the entire surface thereof. In this embodiment, the one or more drugs, agents and/or compounds may be directly affixed to the staple 3000 utilizing any number of known techniques including spraying or dipping, or the one or more drugs, agents and/or compounds may be mixed with or incorporated into a polymeric matrix and then affixed to the staple 3000. Alternately, the one or more drugs, agents and/or compounds may be directly affixed to the surface of the staple 3000 and then a diffusion barrier may be applied over the layer of one or more drugs, agents and/or compounds.

Although any number of drugs, agents and/or compounds may be used in conjunction with the surgical staple 3000 to treat a variety of conditions and/or to minimize or substantially eliminate the organisms' reaction to the implantation of the staple 3000, in a preferred embodiment, the surgical staple 3000 is coated with an anti-proliferative. The advantage of such a device is that the anti-proliferative coating would function as a prophylactic defense against neo-intimal hyperplasia. As described above, neo-intimal hyperplasia often happens at the site of what the body perceives to be injuries, for example, anastomatic sites, either tissue to tissue or tissue to implant, which are often sites of hyperplastic events. By utilizing a staple that comprises an anti-proliferative agent, the incidence of neo-intimal hyperplasia may be substantially reduced or eliminated.

Rapamycin is a known anti-proliferative that may be utilized on or in the surgical staple 3000 and may be incorporated into any of the above-described polymeric materials. An additional benefit of utilizing rapamycin is its action as an anti-inflammatory. The dual action not only functions to reduce neo-intimal hyperplasia but inflammation as well. As used herein, rapamycin includes rapamycin, sirolimus, everolimus and all analogs, derivatives and conjugates that bind FKBP12, and other immunophilins and possesses the same pharmacologic properties as rapamycin including inhibition of MTOR.

In yet another alternate exemplary embodiment, the surgical staple 3000 may be fabricated from a material, such as a polymeric material, which incorporates the one or more drugs, agents, and/or compounds. Regardless of the particular embodiment, the elution rate of the one or more drugs, agents and/or compounds may be controlled as described above.

Figure 33:
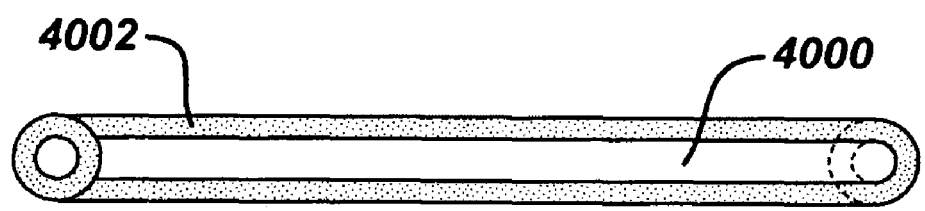
FIG. 33 is a diagrammatic representation of a section of suture material having a coating thereon in accordance with the present invention.

Referring now to FIG. 33, there is illustrated a section of suture material 4000. The suture 4000 may comprise any suitable material commonly utilized in the fabrication of both absorbable or non-absorbable sutures. As illustrated, the suture 4000 comprises a coating 4002 of one or more drugs, agents and/or compounds. As in the coating on the surgical staple 3000, the one or more drugs, agents and/or compounds may be applied directly to the suture 4000 or it may be mixed or incorporated into a polymeric matrix and then affixed to the suture 4000. Also as described above, the one or more drugs, agents and/or compounds may be affixed to the suture 4000 and then a diffusion barrier or top coating may be affixed to the one or more drugs, agents and/or compounds to control the elution or release rate.

Figure 34:
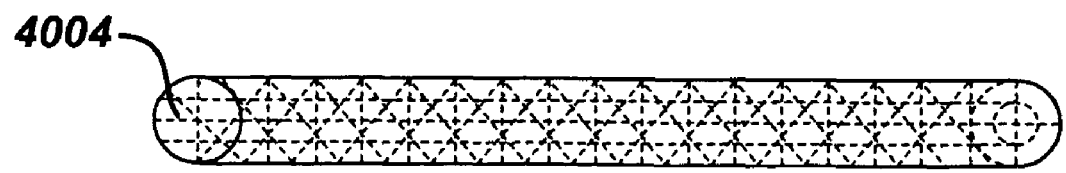
FIG. 34 is a diagrammatic representation of a section of suture material having a coating impregnated into the surface thereof in accordance with the present invention.

FIG. 34 illustrates a section of suture material 4000 impregnated with one or more drugs, agents and/or compounds 4004. The one or more drugs, agents, and/or compounds may be directly impregnated into the suture material 4000, incorporated into a polymeric matrix and then impregnated into the suture material 4000. Alternately, the one or more drugs, agents and/or compounds may be impregnated into the suture material 4000 and then covered with a polymeric material.

In yet another alternate exemplary embodiment, the suture 4000 may be formed from a material, for example, a polymeric material that incorporates the one or more drugs, agents and/or compounds. For example, the one or more drugs, agents, and/or compounds may be mixed within the polymer matrix and then extruded and/or formed by a dip method to form the suture material.

The particular polymer(s) utilized depend on the particular material upon which it is affixed. In addition, the particular drug, agent, and/or compound may also affect the selection of polymers. Rapamycin may be utilized with poly(vinylidene-fluoride)/hexafluoropropylene.

The introduction of medical devices into a living organism, and more particularly into the vasculature of a living organism, provokes a response by the living organism. Typically the benefit provided by the medical device far exceeds any complications associated with the living organism's response. Endothelialization is one preferable manner or means for making devices fabricated from synthetic materials more blood compatible. The endothelium is a single layer of endothelial cells that forms the lining of all blood vessels. The endothelium regulates exchanges between blood and surrounding tissues and is surrounded by a basal lamina, i.e. extracellular matrix that separates epithelia layers and other cell types, including fat and muscle cells from connective tissue.

Endothelial cells cover or line the inner surface of the entire vascular system, including the heart, arteries, veins, capillaries and everything in between. Endothelial cells control the passage of materials and the transit of white blood cells into and out of the blood stream. While the larger blood vessels comprise multiple layers of different tissues, the smallest blood vessels consist essentially of endothelial cells and a basal lamina. Endothelial cells have a high capacity to modify or adjust their numbers and arrangement to suit local requirements. Essentially, if it were not for endothelial cells multiplying and remodeling, the network of blood vessel/tissue growth and repair would be impossible.

Even in an adult living organism, endothelial cells throughout the vascular system retain a capacity for cell division and movement. For example, if one portion of a vein or artery is missing endothelial cells through damage or disease, neighboring endothelial cells proliferate and migrate to the affected area in order to cover the exposed surface. Endothelial cells not only repair areas of missing endothelial cells, they are capable of creating new blood vessels. In addition, and directly related to the present invention, newly formed endothelial cells will cover implantable medical devices, including stents and other similar devices.

As stated above, endothelialization is a means for making devices fabricated from synthetic materials more blood compatible and thus more acceptable to the living organism. For the introduction of certain medical devices anywhere in the vasculature, one goal is the reduction of the thrombogenicity of the medical device. This is device specific, for example, certain medical devices would require thrombus formation for healing and fixation. Therefore, the endothelialization of these specific medical devices is preferable. The source of autologous endothelial cells is crucial and thus an amplification step is preferable to obtain enough cells to cover the entire exposed surface of the medical device regardless of the complexity of design of the medical device. Accordingly, it would be preferable to coat the medical device or provide some localized means for the introduction of a chemical, agent, drug, compound and/or biological element for the promotion or proliferation of endothelial cells at the site of the implant.

In accordance with one exemplary embodiment, implantable intraluminal medical devices, such as stents, may be affixed with, in any of the above described manners, with vascular endothelial growth factor, VEGF, which acts selectively on endothelial cells. Vascular endothelial growth factor and its various related isoforms may be affixed directly to any of the medical devices illustrated and described herein by any of the means described herein. For example, VEGF may be incorporated into a polymeric matrix or affixed directly to the medical device.

Other factors that promote the stimulation of endothelial cells include members of the fibroblast growth factor family. Various agents that accelerate cellular migration may increase endothelialization, including agents that upregulate integrins. Nitric oxide may promote endothelialization. In addition, pro-angiogenic agents may stimulate endothelialization.

Alternately, the medical device may be fabricated from a material which by its physical material characteristics promotes the migration of endothelial towards the device. Essentially, since the living organism creates endothelial cells, any material or coating that attracts endothelial cells would be preferable.

It is generally known in the art that the application of a topcoat of a biocompatible material, for example, a polymer, may be utilized to control the elution of a therapeutic dosage of a pharmaceutical drug, agent and/or compound, or combinations thereof, from a medical device base coating, for example, a stent base coating. The basecoat generally comprises a matrix of one or more drugs, agents and/or compounds and a biocompatible material such as a polymer. The control over elution results from either a physical barrier, a chemical barrier, or a combination physical and chemical barrier supplied by the topcoat material. When the topcoat material acts as a physical barrier, the elution is controlled by varying the thickness of the topcoat, thereby changing the diffusion path length for the drugs, agents and/or compounds to diffuse out of the basecoat matrix. Essentially, the drugs, agents and/or compounds in the basecoat matrix diffuse through the interstitial spaces in the topcoat. Accordingly, the thicker the topcoat, the longer the diffusion path, and conversely, the thinner the topcoat, the shorter the diffusion path. It is important to note that both the basecoat and the topcoat thickness may be limited by the desired overall profile of the medical device. For action as a chemical barrier, the topcoat preferably comprises a material that is less compatible with the drugs, agents and/or compounds to substantially prevent or slow the diffusion, or is less compatible with the basecoat matrix to provide a chemical barrier the drugs, agents and/or compounds must cross prior to being released. It is important to note that the concentration of the drugs, agents and/or compounds may affect diffusion rate; however, the concentration of the drugs, agents and/or compounds is dictated to a certain extent by the required therapeutic dosage as described herein.

In one exemplary embodiment, a medical device such as a stent, may utilize a polymeric material that acts primarily as a chemical barrier for the control of elution of rapamycin from the stent. As used herein, rapamycin includes rapamycin, sirolimus, everolimus and all analogs, derivatives and conjugates that bind FKBP12, and other immunophilins and possesses the same pharmacologic properties as rapamycin including inhibition of mTOR. In this exemplary embodiment, the coating comprises a basecoat drug, agent and/or compound and polymer matrix with a topcoat that includes only a polymer. The topcoat polymer and the basecoat polymer are immiscible or incompatible, thereby creating the chemical barrier. Comparisons, however, are made with basecoat and topcoats comprising the exact same polymers or with polymers containing the same constituents in different ratios. Although the primary control mechanism is the chemical barrier, the topcoat also provides a limited physical barrier, as will be described subsequently.

In this exemplary embodiment, the basecoat may comprise any suitable fluoropolymer and the topcoat may comprise any suitable acrylate or methacrylate. In preferred embodiments, the basecoat drugs, agent and/or compound/polymer matrix comprises the copolymer polyvinylidenefluoride-co-hexafluoropropylene (PVDF/HFP) as described above in detail. The copolymers utilized in this exemplary basecoat embodiment comprises vinylidenefluoride copolymerized with hexafluoropropylene in the weight ratio of sixty weight percent vinyldenefluoride to forty weight percent hexafluoropropylene. The topcoat polymer may, as described above, comprise any suitable acrylate or methacrylate. In the preferred embodiment, the topcoat polymer comprises poly(n-butylmethacrylate) or BMA.

PVDF/HFP and BMA are immiscible or incompatible polymers that when mixed and precipitated from solution utilizing known techniques will undergo phase separation. It is this incompatibility that allows a topcoat of an acrylic polymer to act as both a chemical barrier (primary mechanism) and physical barrier (secondary mechanism) to the release of a drug, agent and/or compound, such as rapamycin, from the basecoat matrix.

The combination of a PVDF/HFP basecoat and a BMA topcoat offers a number advantages over other combinations, including increased durability, increased lubriciousness and increased elution rate control. PVDF/HFP is a flexible polymer. Flexible polymers result in more durable medical device coatings as they tend to move or give as the stent or other device undergoes deformations. Poly(n-butylmethacrylate) or BMA is a more thermoplastic polymer rather than a more elastomeric polymer, and therefore more rigid than PVDF/HFP. A more rigid polymer equates to a harder surface and a harder surface is a more lubricious surface. The lubriciousness of the polymer topcoat is important during device delivery and deployment as described in detail herein. A lubricious coating is particularly advantageous in the delivery of self-expanding stents which typically require the retraction of a delivery sheath. If the coating were not lubricious, the retraction of the delivery sheath may remove a position of the coating, including the drugs, agents and/or compounds contained therein. Lubricious coatings are also advantageous for balloon expandable stents where stent/balloon separation during deployment may also remove coating. Acrylic polymers utilized in conjunction with fluoropolymers are excellent chemical and physical barriers as described above and thus provide increase elution rate control.

Although the coatings in this exemplary embodiment may be utilized on any number of implantable medical devices as described herein, the exemplary coating embodiments described below are utilized in conjunction with nickel-titanium self-expanding stents.

Figure 49:
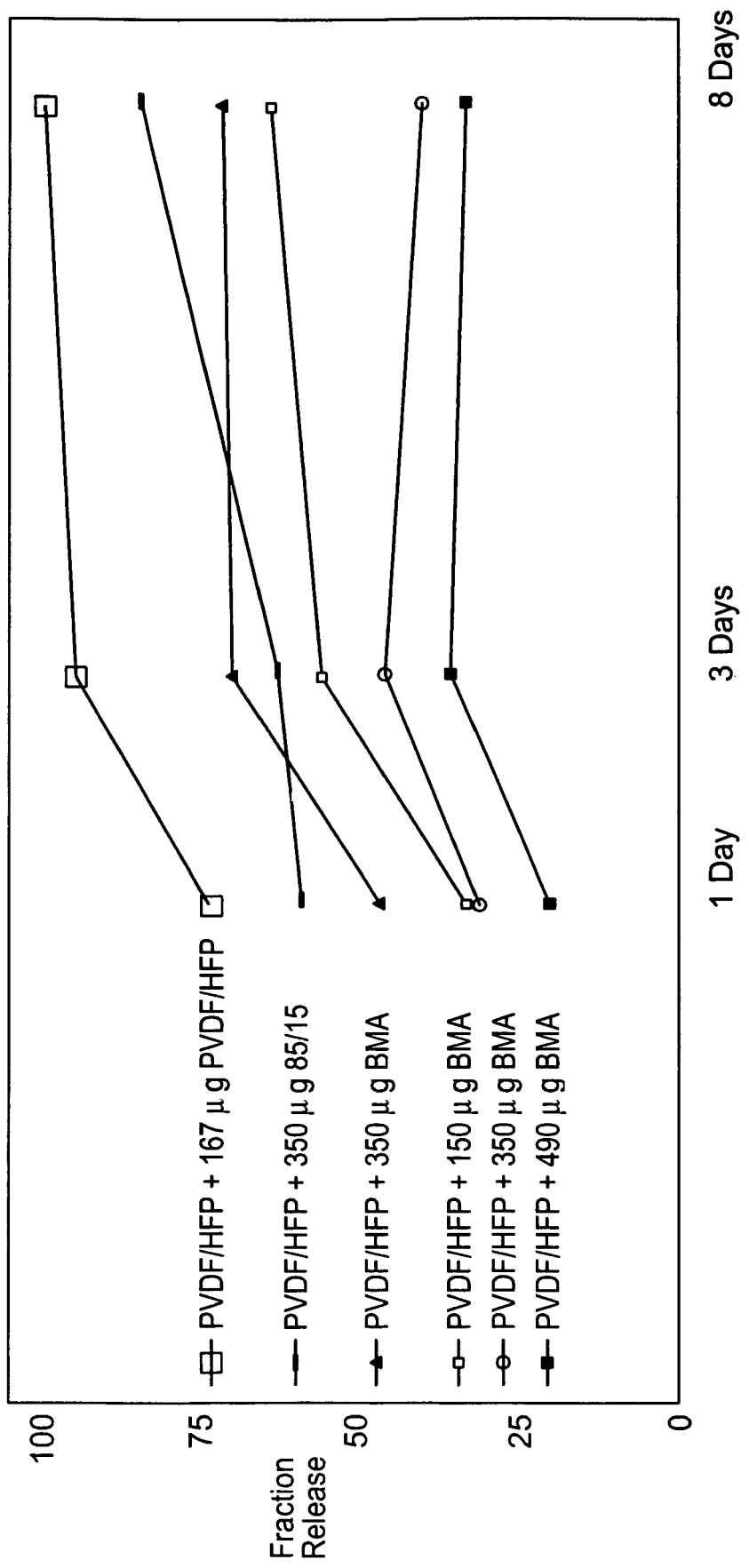
FIG. 49 indicates the fraction or percentage of rapamycin released over time from various polymeric coatings during in vivo testing in accordance with the present invention.

Referring now to FIG. 49, there is illustrated in vivo drug release curves for a number of fluoropolymer/fluoropolymer and fluoropolymer/acrylic coating formulations. The in vivo procedure involved evaluating the elution characteristics of rapamycin eluting stents with a number of polymer coating formulations for both the basecoat and the topcoat. Pigs are an established animal species for intravascular stent studies and accepted for such studies by the appropriate regulatory agencies. This in vivo study utilized male pigs of the species Sus Scrofa and strain Yoorkshire pigs. S.M.A.R.T.™ stents, available from Cordis Corporation, were placed into the iliac and femoral arteries, PALMAZ® GENESIS™ stents, available from Cordis Corporation, were placed in the renal arteries and CYPHER™ stents, available from Cordis Corporation, were placed in the coronary arteries. Once third of the pigs were euthanized on each of days 2, 4 and 8 and the stents and surrounding vessels were explanted and analyzed for drug content.

The data presented in FIG. 49 represents the release of rapamycin in vivo from coated S.M.A.R.T.™ stents, which as described herein, are nickel-titanium stents twenty millimeters in length. The ratio by weight of rapamycin to polymer is thirty/seventy for each PVDF/HFP basecoat and thirty-three/sixty-seven for the polyethylene-co-vinylacetate/poly(n-butylmethacrylate) (EVA/BMA) basecoat. Curve 4902 represents the elution release rate for a stent coated with a PVDF/HFP (sixty/forty weight ratio of VDF:HFP) and rapamycin basecoat with a one hundred sixty-seven microgram PVDF/HFP (sixty/forty weight ratio of VDF:HFP) topcoat. Curve 4904 represents the elution release rate for a stent coated with a PVDF/HFP (sixty/forty weight ratio of VDF:HFP) and rapamycin basecoat with a three hundred fifty microgram PVDF/HFP (eighty-five/fifteen weight ratio of VDF:HFP) topcoat. Curve 4906 represents the elution release rate for a stent coated with an EVA/BMA and rapamycin basecoat (thirty-three percent EVA, thirty-three percent BMA and thirty-three percent rapamycin) with a three hundred fifty microgram BMA topcoat. Curve 4908 represents the elution release rate for a stent coated with a PVDF/HFP (sixty/forty weight ratio of VDF:HFP) and rapamycin basecoat with a one hundred fifty microgram BMA topcoat. Curve 4910 represents the elution release rate for a stent coated with a PVDF/HFP (sixty/forty weight ratio of VDF:HFP) and rapamycin basecoat with a three-hundred fifty microgram BMA topcoat. Curve 4912 represents the elution release rate for a stent coated with a PVDF/HFP (sixty/forty weight ratio of VDF:HFP) and rapamycin basecoat with a four hundred ninety microgram BMA topcoat.

The data represented in FIG. 49 provides an understanding of the elution rate of rapamycin from various coating combinations. A PVDF/HFP basecoat with a PVDF/HFP topcoat provides a minor physical barrier to drug elution, and a minimal chemical barrier because the basecoat and topcoat are chemically identical. A topcoat of BMA on a basecoat of EVA/BMA provides a physical barrier because of the compatibility between the EVA/BMA drug matrix and the BMA topcoat chemistries. The BMA topcoat provides a slightly more effective barrier to elution because of the difference in basecoat matrix (EVA/BMA) and topcoat (BMA only) chemistries. The most substantial barrier to the elution of rapamycin, however, is observed with a PVDF/HFP basecoat matrix and a BMA topcoat because of the chemical barrier that results from the incompatible polymer chemistries. Even within the chemical barrier, however, changes in the topcoat thickness or density, still provide additional levels of physical barriers to drug elution, resulting in a coating system that provides both a chemical and a physical barrier to control release of a pharmaceutical compound as indicated in curves 4908, 4910 and 4912.

The idea of utilizing incompatible polymer chemistries in conjunction with varying the thickness of the topcoat in accordance with the present invention takes advantage of what may normally be viewed as a negative aspect of chemical incompatibility to achieve a desired effect. As indicated in curve 4912, the peak elution release at three days is substantially less than fifty percent, whereas the peak elution release at three days for a PVDF/HFP basecoat and a PVDF/HFP topcoat is substantially greater than seventy-five percent as indicated in curve 4902.

Although demonstrated here with specific examples of a PVDF/HFP (sixty-forty weight ratio of VDF:HFP) copolymer and a BMA polymer, the concept would apply to any polymer in the family of fluoropolymers in combination with any polymer in the family of acrylics (poly(alkyl)acrylate and poly(alkyl)meth)acrylate).

Figure 50:
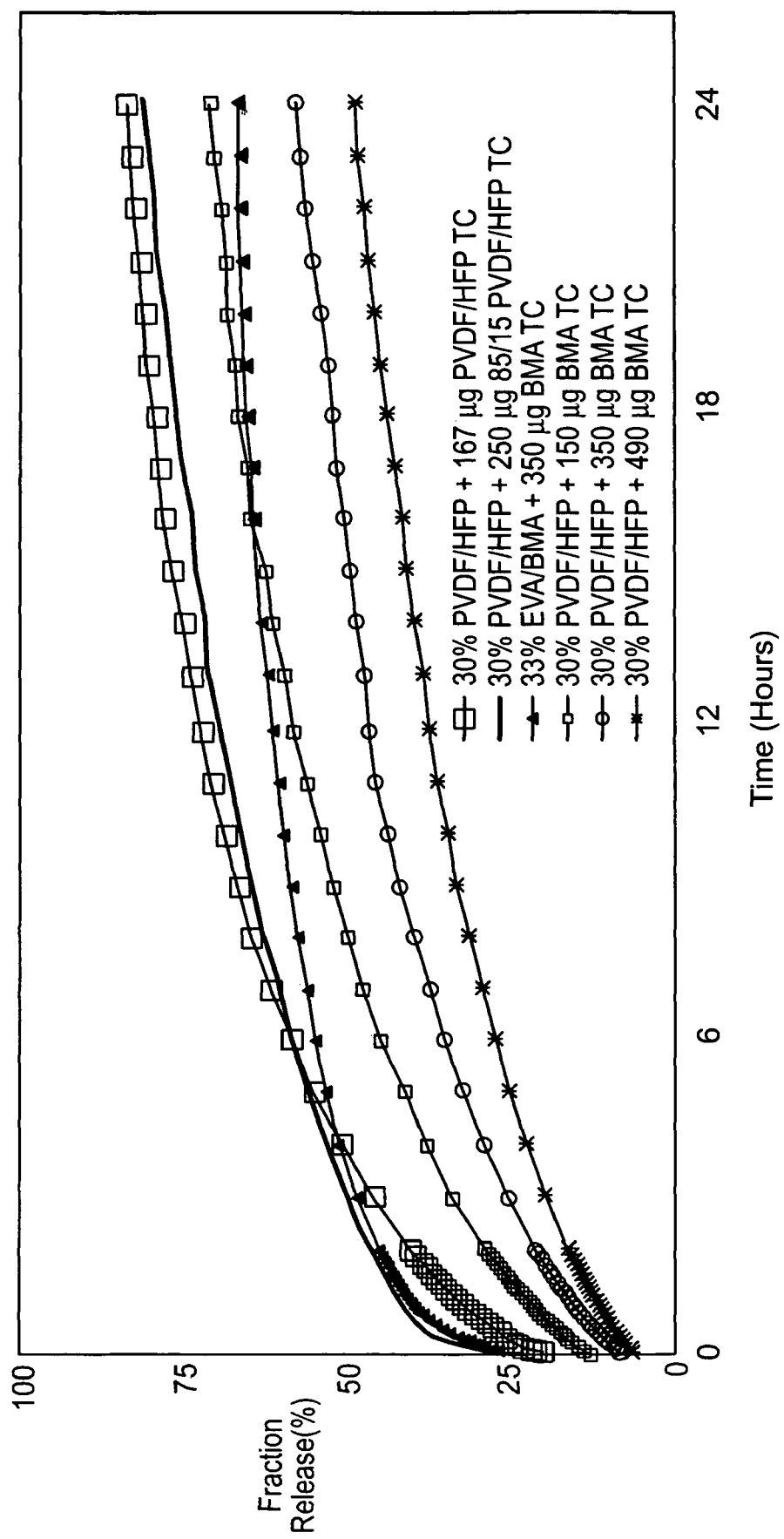
FIG. 50 indicates the fraction or percentage of rapamycin released over time from various polymeric coatings during in vitro testing in accordance with the present invention.

Referring to FIG. 50, there is illustrated in vitro drug release curves for the same fluoropolymer/acrylic coating formulations described above with respect to FIG. 49. In in vitro testing procedures, the stents are exposed to continuous flow of a surfactant media for a period of twenty-four hours. The exposure of the media causes elution of the drug, agent and/or compound (rapamycin in this instance) from the stents. The flow of media is directed through an ultraviolet/visible spectrophotometer, and the concentration of rapamycin eluting from the stent is determined as a function of time. Calculations are made based on the fraction of rapamycin released compared to the total drug content, as determined from a drug content assay on stents from the same lot.

The results from the in vitro testing are similar to the results from the in vivo testing. Essentially, a review of 5002, 5004, 5006, 5008, 5010 and 5012 indicate that once again, the most substantial barrier to the elution of rapamycin is observed with a PVDF/HFP basecoat matrix and a BMA topcoat because of the chemical barrier that results from the incompatible polymer chemistries and the physical barrier provided by the thicker topcoat as shown by curve 5012.

It is also interesting to note that a stent coated with a PVDF/HFP (sixty/forty weight ratio of VDF:HFP) basecoat matrix and a BMA topcoat is more durable than a stent coated with a PVDF/HFP (sixty/forty weight ratio of VDF:HFP) basecoat matrix and a PVDF/HFP (sixty/forty weight ratio of VDF:HFP) topcoat.

The design of a coated implantable medical device that elutes a therapeutic drug, agent and/or compound requires the balancing of a number of design factors. For example, the addition of a coating to an implantable medical device alters the profile of the device which in turn may have an impact on device delivery. More specifically, the addition of a coating on a stent increases the diameter of the stent, which in turn may make delivery more difficult. Accordingly, it may be preferable to minimize the thickness of the coating while increasing the concentration of the therapeutic drug, agent and/or compound. Increasing the concentration of the therapeutic drug, agent and/or compound may increase its elution rate into the surrounding tissue or bloodstream. Increasing the elution rate may in turn deplete the drug, agent and/or compound prematurely. Therefore, the present invention provides a mechanism whereby drug, agent and/or compound concentrations may be increased while maintaining control over the elution rate and maintaining a lower profile. Essentially, the chemical and physical barrier provided by the topcoat in the two layer approach provides a means for increasing drug, agent and/or compound concentrations, if preferable, maintaining a lower profile, if preferable, and maintaining more precise control over elution rates.

In addition, it is important to emphasize the multiple layers; multiple polymer approach offers the advantages of durability, flexibility and lubriciousness that a single layer approach may not be able to provide.

Atherosclerosis is a thickening and hardening of the arteries and is generally believed to be caused by the progressive buildup of fatty substances, for example, cholesterol, cellular waste products, inflammatory cells, calcium and other substances in the inner lining or intima of the arteries. The buildup of these substances may in turn stimulate cells in the walls of the affected arteries to produce additional substances that result in the further buildup of cells.

Atherosclerosis is a slow, complex disease that typically starts in childhood and progresses as the individual ages. The rate of progression may be affected by a number of factors, including blood cholesterol levels, diabetes, obesity, physical inactivity, high blood pressure and tobacco use. This buildup in commonly referred to as plaque and may grow large enough to significantly reduce blood flow through the affected arteries.

Essentially, the deposits of the various substances set forth above, and the proliferation of additional cellular substances or constituents caused thereby, substantially enlarge the intima, which in turn reduces luminal cross-sectional area and decreases the diameter of the affected artery or arteries, which in turn reduces the oxygen supply to one or more organs. The deposits or plaque may also rupture and form blood clots or thrombi that can completely obstruct blood flow in the affected artery or break free and travel, emboli, to another part of the body. If either of these events occurs, the individual may suffer a myocardial infarction if the artery or arteries affected perfuse the heart or a stroke if the artery or arteries affected supply blood to the brain. If the artery or arteries affected supply blood to a limb or appendage, gangrene may result.

As indicated above, conventional wisdom holds that heart attacks, for example, originate from severe blockages created by atherosclerosis. The increase of lipids in the artery or arteries and ensuing tissue reaction lead to a narrowing of the affected artery or arteries, which in turn, may result in angina and eventually coronary occlusion, sudden cardiac death and thrombotic stroke. Relatively recent research, however, is leading to a shift in understanding atherosclerosis. Researchers now believe that at least some coronary artery disease is an inflammatory process, in which inflammation causes plaque buildup or progression and rupture. These plaques which are prone to rupture, commonly referred to as vulnerable plaques, do not block flow in the affected artery or arteries per se, but rather, much like an abscess, they may be ingrained in the arterial wall so that they are difficult to detect. Essentially, these vulnerable plaques cannot be seen by conventional angiography and/or fluoroscopy, and they do not typically cause symptoms such as shortness of breath or pain. Techniques for determining the presence of vulnerable plaques are, however, improving as discussed subsequently.

For a variety of reasons, these so-called vulnerable plaques are more likely to erode or rupture, creating emboli and raw or exposed tissue surfaces that are highly thrombogenic. Accordingly, it is now accepted that the majority of cases of acute myocardial infarction, sudden cardiac death and thrombolitic stroke result from the disruption of vulnerable atherosclerotic plaques leading to thrombosis. Therefore, these vulnerable plaques are more dangerous than other plaques that simply cause pain, and may be responsible for as much as sixty to eighty percent of all heart attacks.

More specifically, unstable or vulnerable plaques are inflammatory vascular lesions that develop in atherosclerotic blood vessels. Vulnerable plaques are characterized by active inflammation, cellular hyperplasia and variable degrees of lumen obstruction. Morphologically, vulnerable plaques comprise a fibrous cap in contact with the lumen of the vessel overlying a core of lipid and cellular material. Vulnerable plaque lesions are not typically obstructive, in contrast to chronic stable plaques that produce ischemic symptoms. For that reason, they are not easily detected.

The hallmark of vulnerable plaques is active inflammation with significant inflammatory cell infiltration, predominantly T-lymphocytes and macrophage, causing the generation of proteolytic enzymes that essentially digest the wall of the fibrous cap thereby inducing plaque instability and eventually plaque rupture. Plaque rupture exposes highly thrombogenic material in the lipid core to flowing blood leading to the rapid development of occlusive thrombi. Ruptured vulnerable plaque, as stated above, is the primary cause of acute coronary and cerebral syndromes. These include unstable angina, myocardial infarction, both Q-wave and non-Q-wave myocardial infarction, cerebral stroke and transient cerebral ischemia. In other words, ruptured vulnerable plaque accounts for a significant percentage of cardiovascular morbidity and mortality.

Given the lack of currently available effective technologies for detecting vulnerable plaque, the treatment of vulnerable plaque is typically initiated only after the plaque has ruptured and clinical symptoms have developed. Detection technologies currently under investigation include refined magnetic resonance imaging, thermal sensors that measure the temperature of the arterial wall on the premise that the inflammatory process generates heat, elasticity sensors, intravascular ultrasound, optical coherence tomography, contrast agents, and near-infrared and infrared light. As better diagnostic methods evolve to identify vulnerable plaque lesions before they rupture, it becomes possible to treat discrete lesions before dangerous clinical symptoms occur. The treatment of vulnerable plaque, however, is preferably as described below.

Essentially, there are two physiologic processes ongoing in active vulnerable plaque, inflammation and lipid metabolism. Inflammation is an ongoing process which includes the inflammation of the fibrous cap and creating a cap vulnerable to rupture. Lipid metabolism is the formation of a molten or active lipid pool or core comprising a paliable, cholesterolemic lipid material susceptible to rupture. The inflammation process is the acute phase and the lipid metabolism is the chronic phase of vulnerable plaque disease.

A stent or other scaffold structure designed to maintain vessel potency and comprising a multilaminate coating architecture, including one or more therapeutic agents, drugs, and/or compounds for treating both the inflammation and lipid metabolism processes, may be utilized to effectively treat vulnerable plaques. In one exemplary embodiment, a stent comprising a coating having a two tier release profile may be utilized to treat both the acute and chronic phases of vulnerable plaque. For example, anti-inflammatory therapeutic agents, such as corticosteroids, non-steroidal anti-inflammatories, acetylsalicyclic acid, acetaminophen and ibuprofen may be incorporated into the coating architecture for "fast release" and shorter overall duration to address the acute phase of vulnerable plaque disease and lipid lowering or lipid modifying agents may be incorporated into the coating architecture for "slow release" and longer overall duration to address the chronic phase of vulnerable plaque disease. The entire stent/drug, agent and/or compound architecture may be released utilizing a variety of non-resorbable or resorbable polymers to control, modulate and/or optimize the delivery profile for optimal physiologic effect. In other words, specific therapeutic drug, agent and/or compound delivery profiles may be utilized in conjunction with the stent to treat all aspects of vulnerable plaques, for example, fast release anti-inflammatory drugs, agents and/or compounds to address the inflammatory rupture of the fibrous cap and slow release lipid lowering or lipid modifying drugs, agents and/or compounds to affect the size and composition of the vulnerable plaque lipid pool.

The stent may comprise any suitable scaffold structure, including balloon expandable stents, constructed from stainless steel or other metal alloys, and/or self-expanding stents, constructed from nitinol or other shape memory metal alloys. Alternately, the stent may be made from non-metallic materials, such as ceramics and/or polymers, which may be biodegradable. The biodegradable stent would serve as a temporary scaffold and eventually dissolve over a period of time raging from days or weeks to months and years. The stent would be mounted on a delivery catheter and delivered percutaneously through the lumen of a blood vessel to the site of the vulnerable plaque lesion as described in detail above with respect to treating restenosis. The stent, as described above, is designed to maintain vessel patency and also provide structural support to the weakened or potentially weakened fibrous cap and prevent it from rupturing. The stent also provides a means for preventing further encroachment by the lesion.

The one or more therapeutic drugs, agents and/or compounds utilized in combination with the stent would preferably prevent neointimal hyperplasia that is commonly encountered in stenting and which could lead to restenosis and device failure as described in detail above. In addition, the same or additional therapeutic drugs, agents and/or compounds would preferably stabilize or passivate the lesion by reducing local inflammation and preventing further erosion of the fibrous cap. The one or more therapeutic drugs, agents and/or compounds may be delivered in a polymer matrix coating applied to the stent struts or embedded into the material forming the stent itself and would release into the vessel wall over a predetermined period of time, preferably utilizing the dual profile release rate as briefly described above.

In treating both restenosis following vascular injury and treating vulnerable plaque, it may be advantageous to provide for the regional delivery of various drugs, agents and/or compounds in addition to the local delivery of various drugs, agents and/or compounds as described herein. The drugs, agents, and/or compounds delivered regionally may be the same as those delivered locally or they may be different. Regional delivery, as used herein, shall mean delivery to an area greater than the area covered by a local delivery device such as those disclosed herein, including stents and other implantable medical devices. For example, an infusion catheter may be utilized to administer a predetermined therapeutic dosage or range of dosages of one or more drugs, agents and/or compounds to a number of sites proximate to the disease site, for example, stenotic or vulnerable plaque lesions. Essentially, the drug or drugs may be administered proximal to the lesion, distal to the lesion, directly into the lesion or any combination thereof. The drug or drugs may be administered in any number of ways, including adventitial injection. The dosage and number of injection sites depends on a number of factors, including the type of drug, agent and/or compound, the diffusion characteristics of the drug, agent and/or compound and the area in the body that is to be treated. In practice, the drug, agent and/or compound is injected into the adventitial tissue proximal and/or distal to the lesion, as well as the adventitial tissue surrounding the lesion, and then distributes axially and longitudinally away from the site of injection.

As set forth herein, drug coated stents may be utilized in the treatment and/or prevention of restenosis and vulnerable plaque. The stents may be coated with any number of drugs or combinations of drugs as described herein. For example, rapamycin alone or in combination, may be locally delivered from a stent or other implantable medical devices. In this exemplary embodiment, the same or different drugs may also be regionally delivered via a catheter-based device. Essentially, the catheter-based device may be utilized to deliver additional quantities of the drug or drugs associated with the local delivery device or completely different drugs. The regional delivery of drugs may be beneficial for a number of reasons, including higher dose quantities and broader coverage areas. In addition, certain drugs may be more efficacious in injectable form rather than dissolved or suspended in a polymeric coating. Also, drug therapies may be tailored to the individual patient.

In addition to rapamycin, other drugs that may be regionally delivered for the treatment of vulnerable plaque include non-steroidal anti-inflammatories such as aspirin and celecoxib, steroidal agents such as estrogen, metabolic agents such as troglitazone and anti-coagulants such as enoxaparin, probucol, hirudin and apo-A1$_{MILANO}$. Accordingly, these drugs may be utilized alone or in combination with rapamycin.

Any number of catheter-based devices may be utilized for regional drug delivery. In one exemplary embodiment, the drug delivery device comprises a microfabricated surgical device for interventional procedures or microneedle. The device is the EndoBionics MicroSyringe™ Infusing Catheter available from EndoBionics, Inc., San Leandros Calif. and may be generally characterized set forth below.

The microneedle is inserted substantially normal to the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel is terminated, and the actuator is controlled to cause the microneedle to be thrust outwardly, substantially perpendicular to the central axis of a vessel, for instance, in which the catheter has been inserted.

Figure 73A:
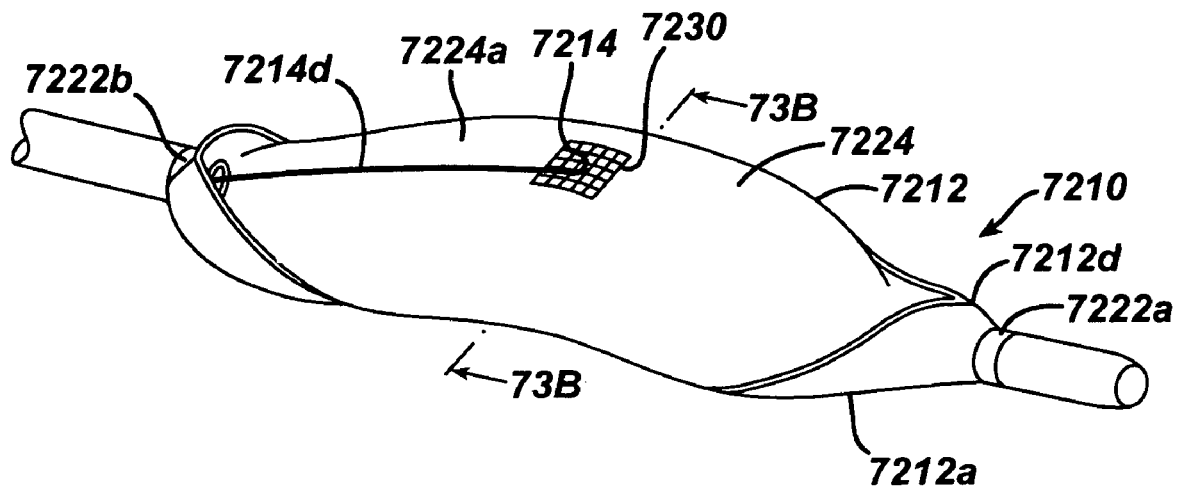
FIG. 73A is a schematic, perspective view of a microfabricated surgical device for interventional procedures in an actuated condition in accordance with the present invention.
Figure 73B:
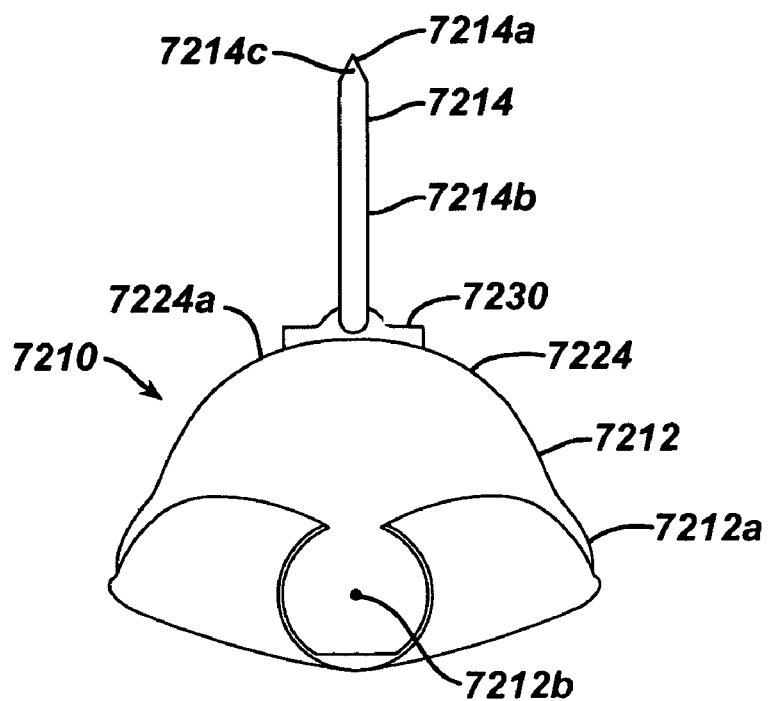
FIG. 73B is a schematic view along line 73B-73B of FIG. 73A.

As shown in FIGS. 72A-73B, a microfabricated surgical device 7210 includes an actuator 7212 having an actuator body 7212a and a central longitudinal axis 7212b. The actuator body more or less forms a C-shaped outline having an opening or slit 7212d extending substantially along its length. A microneedle 7214 is located within the actuator body, as discussed in more detail below, when the actuator is in its unactuated condition (furled state), as illustrated in FIG. 72B. The microneedle is moved outside the actuator body when the actuator is operated to be in its actuated condition (unfurled state), as illustrated in FIG. 73B.

The actuator may be capped at its proximal end 7212e and distal end 7212f by a lead end 7216 and a tip end 7218, respectively, of a therapeutic catheter 7220. The catheter tip end serves as a means of locating the actuator inside a blood vessel by use of a radio opaque coatings or markers. The catheter tip also forms a seal at the distal end 7212f of the actuator. The lead end of the catheter provides the necessary interconnects (fluidic, mechanical, electrical or optical) at the proximal end 7212e of the actuator.

Retaining rings 7222a and 7222b are located at the distal and proximal ends, respectively, of the actuator. The catheter tip is joined to the retaining ring 7222a, while the catheter lead is joined to retaining ring 7222b. The retaining rings are made of a thin, on the order of ten to one hundred microns, substantially rigid material, such as Parylene (types C, D or N), or a metal, for example, aluminum, stainless steel, gold, titanium or tungsten. The retaining rings form a rigid substantially C-shaped structure at each end of the actuator. The catheter may be joined to the retaining rings by, for example, a butt-weld, an ultra-sonic weld, integral polymer encapsulation or an adhesive such as an epoxy.

The actuator body further comprises a central, expandable section 7224 located between retaining rings 7222a and 7222b. The expandable section 7224 includes an interior open area 7226 for rapid expansion when an activating fluid is supplied to that area. The central section 7224 is made of a thin, semi-rigid or rigid, expandable material, such as a polymer, for instance, Parylene (types C, D or N), silicone, polyurethane or polyimide. The central section 7224, upon actuation, is expandable somewhat like a balloon-device.

The central section is capable of withstanding pressures of up to about one-hundred atmospheres upon application of the activating fluid to the open area 7226. The material from which the central section is made of is rigid or semi-rigid in that the central section returns substantially to its original configuration and orientation (the unactuated condition) when the activating fluid is removed from the open area 7226. Thus, in this sense, the central section is very much unlike a balloon which has no inherently stable structure.

The open area 7226 of the actuator is connected to a delivery conduit, tube or fluid pathway 7228 that extends from the catheter's lead end to the actuator's proximal end. The activating fluid is supplied to the open area via the delivery tube.

The delivery tube may be constructed of Teflon® or other inert plastics. The activating fluid may be a saline solution or a radio-opaque dye.

The microneedle 7214 may be located approximately in the middle of the central section 7224. However, as discussed below, this is not necessary, especially when multiple microneedles are used. The microneedle is affixed to an exterior surface 7224a of the central section. The microneedle is affixed to the surface 7224a by an adhesive, such as cyanoacrylate. Alternatively, the microneedle may be joined to the surface 7224a by a metallic or polymer mesh-like structure 7230, which is itself affixed to the surface 7224a by an adhesive. The mesh-like structure may be made of, for instance, steel or nylon.

The microneedle includes a sharp tip 7214a and a shaft 7214b. The microneedle tip can provide an insertion edge or point. The shaft 7214b can be hollow and the tip can have an outlet port 7214c, permitting the injection of a pharmaceutical or drug into a patient. The microneedle, however, does not need to be hollow, as it may be configured like a neural probe to accomplish other tasks.

As shown, the microneedle extends approximately perpendicularly from surface 7224a. Thus, as described, the microneedle will move substantially perpendicularly to an axis of a vessel or artery into which it has been inserted, to allow direct puncture or breach of vascular walls.

The microneedle further includes a pharmaceutical or drug supply conduit, tube or fluid pathway 7214d which places the microneedle in fluid communication with the appropriate fluid interconnect at the catheter lead end. This supply tube may be formed integrally with the shaft 7214b, or it may be formed as a separate piece that is later joined to the shaft by, for example, an adhesive such as an epoxy.

The needle 7214 may be a 30-gauge, or smaller, steel needle. Alternatively, the microneedle may be microfabricated from polymers, other metals, metal alloys or semiconductor materials. The needle, for example, may be made of Parylene, silicon or glass.

Figure 74:
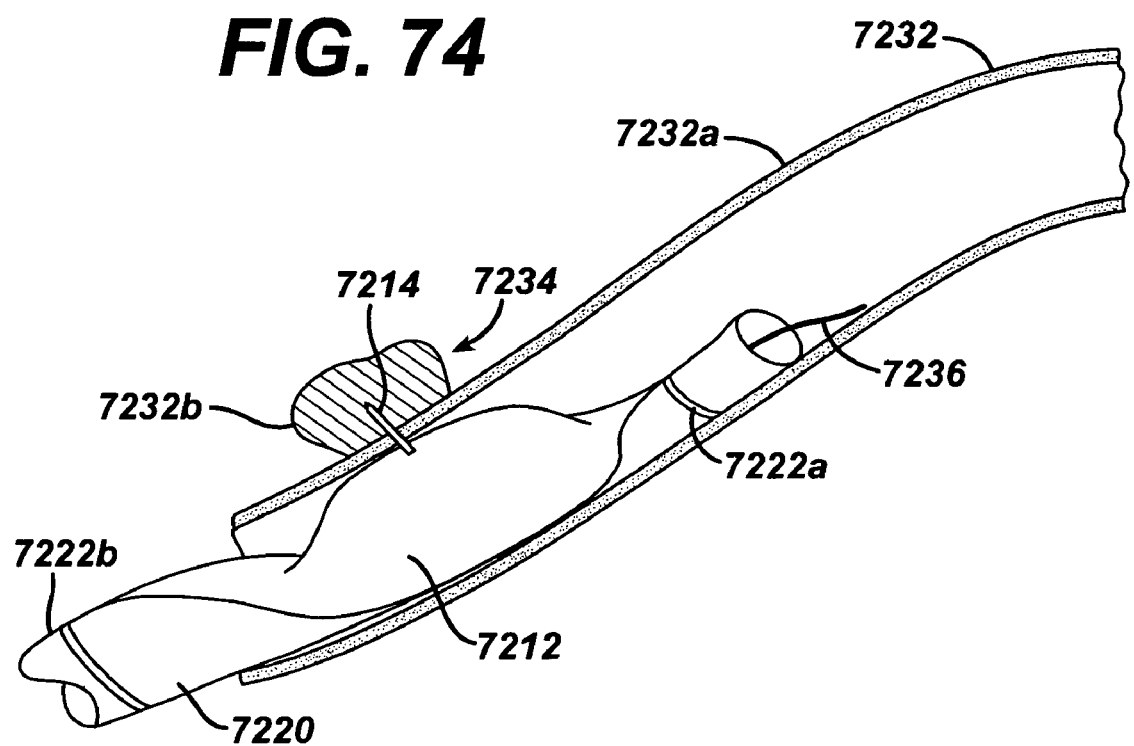
FIG. 74 is a schematic, perspective view of the microfabricated surgical device of the present invention inserted into a patient's vasculature.

The catheter 7220, in use, is inserted through an artery or vein and moved within a patient's vasculature, for instance, a vein 7232, until a specific, targeted region 7234 is reached, as illustrated in FIG. 74. As is well known in catheter-based interventional procedures, the catheter 7220 may follow a guide wire 7236 that has previously been inserted into the patient. Optionally, the catheter 7220 may also follow the path of a previously-inserted guide catheter (not shown) that encompasses the guide wire. In either case, the actuator is hollow and has a low profile and fits over the guide wire.

During maneuvering of the catheter 7220, well-known methods of fluoroscopy or magnetic resonance imaging (MRI) can be used to image the catheter and assist in positioning the actuator 7212 and the microneedle 7214 at the target region. As the catheter is guided inside the patient's body, the microneedle remains unfurled or held inside the actuator body so that no trauma is caused to the vascular walls.

After being positioned at the target region 7234, movement of the catheter is terminated and the activating fluid is supplied to the open area 7226 of the actuator, causing the expandable section 7224 to rapidly unfurl, moving the microneedle 7214 in a substantially perpendicular direction, relative to the longitudinal central axis 7212b of the actuator body 7212a, to puncture a vascular wall 7232a. It may take only between approximately one-hundred milliseconds and two seconds for the microneedle to move from its furled state to its unfurled state.

The ends of the actuator at the retaining rings 7222a and 7222b remain rigidly fixed to the catheter 7220. Thus, they do not deform during actuation. Since the actuator begins as a furled structure, its so-called pregnant shape exists as an unstable buckling mode. This instability, upon actuation, produces a large scale motion of the microneedle approximately perpendicular to the central axis of the actuator body, causing a rapid puncture of the vascular wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle, in fact, travels so quickly and with such force that it can enter perivascular tissue 7232b as well as vascular tissue. Additionally, since the actuator is "parked" or stopped prior to actuation, more precise placement and control over penetration of the vascular wall are obtained.

After actuation of the microneedle and delivery of the pharmaceutical to the target region via the microneedle, the activating fluid is exhausted from the open area 7226 of the actuator, causing the expandable section 7224 to return to its original, furled state. This also causes the microneedle to be withdrawn from the vascular wall. The microneedle, being withdrawn, is once again sheathed by the actuator.

As set forth above, the microneedle or other catheter-based delivery systems may be utilized to deliver one or more drugs, agents and/or compounds, including rapamycin, to the site of atherosclerotic plaque. This type of regional delivery may be utilized alone or in combination with an implantable medical device with the same or different drugs affixed thereto. The one or more drugs, agents and/or compounds are preferably delivered to the adventitial space proximate the lesion.

As described herein, there are a number of advantages to the local or regional delivery of certain drugs, agents and/or compounds via means other than or in addition to delivery from an implantable medical device. However, the efficacy of the drugs, agents and/or compounds may, to a certain extent, depend on the formulation thereof.

It is typically very difficult to create solution dosage forms of water insoluble and lipohilic (having an affinity for and/or tending to combine with lipids) drugs such as rapamycin without resorting to substantial quantities of surfactants, co-solvents and the like. Often times, these excipients (inert substance that acts as a vehicle), such as Tween 20 and 80, Cremophor and polyethylene glycol (PEG) come with varying degrees of toxicity to the surrounding tissue. Accordingly, the use of organic co-solvents such as dimethol sulfoxide (DMSO), N-methylpyrrolidone (NMP) and ethanol need to be minimized to reduce the toxicity of the solvent. Essentially, the key for a liquid formulation of a water insoluble drug is to find a good combination of excipient and co-solvent, and an optimal range of the additives in the final dosage form to balance the improvement of drug solubility and necessary safety margins.

As the outstanding results from clinical trials of recent drug eluting stents such as the Cypher® and Taxus® drug eluting stents demonstrated, a prolonged local high concentration and tissue retention of a potent anti-inflammatory and anti-neoplastic agent released from a stent coating can substantially eliminate the neointimal growth following an angioplasty procedure. Rapamycin, released from the Cypher® stent has consistently demonstrated superior efficacy against restenosis after stent implantation as compared to a bare metal stent. However, there are clinical situations where a non-stent approach for the local delivery or regional delivery may be advantageous, including bifurcated junctions, small arteries and the restenosis of previously implanted stents. Accordingly, there may exist a need for potent therapeutics that only need to be deposited locally or regionally and the drug will exert its pharmacological functions mainly through its good lipophilic nature and long tissue retention property.

A locally or regionally delivered solution of a potent therapeutic agent, such as rapamycin, offers a number of advantages over a systemically delivered agent or an agent delivered via an implantable medical device. For example, a relatively high tissue concentration may be achieved by the direct deposition of the pharmaceutical agent in the arterial wall. Depending on the location of the deposition, a different drug concentration profile may be achieved than through that of a drug eluting stent. In addition, with a locally or regionally delivered solution, there is no need for a permanently implanted device such as a stent, thereby eliminating the potential side affects associated therewith, such as inflammatory reaction and long term tissue damage. It is, however, important to note that the locally or regionally delivered solution may be utilized in combination with drug eluting stents or other coated implantable medical devices. Another advantage of solution or liquid formulations lies in the fact that the adjustment of the excipients in the liquid formulation would readily change the drug distribution and retention profiles. In addition, the liquid formulation may be mixed immediately prior to the injection through a pre-packaged multi-chamber injection device to improve the storage and shelf life of the dosage forms.

In accordance with exemplary embodiments of the present invention, a series of liquid formulations were developed for the local or regional delivery of water insoluble compounds such as sirolimus and its analogs, including CCI-779, ABT-578 and everolimus, through weeping balloons and catheter injection needles. Sirolimus and its analogs are rapamycins, and rapamycin as used herein, includes rapamycin and all analogs, derivatives and congeners that bind FKBP12 and possess the same pharmacologic properties as rapamycin. These liquid formulations increase the apparent solubility of the pharmacologically active but water insoluble compounds by two to four orders of magnitude as compared to the solubility limits of the compounds in water. These liquid formulations rely on the use of a very small amount of organic solvents such as Ethanol (typically less than two percent) and a larger amount of safe amphiphilic (of or relating to a molecule having a polar, water soluble group attached to a non-polar, water insoluble hydration chain) excipients such as polyethylene glycol (PEG 200, PEG 400) and vitamin E TPGS to enhance the solubility of the compounds. These liquid formulations of highly water insoluble compounds are stable and readily flowable at room temperature. Certain excipients, such as Vitamin E TPGS and BHT may be utilized to enhance the storage stability of sirolimus compounds through their anti-oxidation properties.

Table 8, shown below, summarizes the concentrations of the excipient, the co-solvents and the drug for four different liquid formulations in accordance with exemplary embodiments of the present invention. The concentrations of each constituent were determined by liquid chromatography and are presented as weight by volume figures. As may be seen from Table 8, a 4 mg/ml concentration of sirolimus was achieved with an ethanol concentration of two percent, a water concentration of twenty-five percent and a PEG 200 concentration of seventy-five percent. The concentration of ethanol is preferably two or less percent so as to avoid ethanol becoming an active ingredient in the formulation.

TABLE 8

|  | Formulation B1 | Formulation A1 |
| --- | --- | --- |
| Sirolimus conc. (mg/mL) | 1.79 | 1.0 |
| EtOH conc. (%) | 3.83 | 2 |
| H2O conc. (%) | 7.7 | 25 |
| PEG 200 conc. (%) | 88.5 | 73 |
| Sirolimus conc. (mg/mL) | 2.0 | 4 |
| EtOH conc. (%) | 2.0 | 2.0 |
| H2O conc. (%) | 25 | 25 |
| PEG 200 conc. (%) | 75 | 75 |

As set forth above, a liquid formulation comprising 4 mg/ml of sirolimus may be achieved utilizing PEG 200 as the excipient and ethanol and water as the co-solvents. This concentration of sirolimus is about four hundred to about one thousand times higher than the solubility of sirolimus in water. The inclusion of an effective co-solvent, PEG 200, ensures that the high concentration of sirolimus does not start to precipitate out of solution until diluted five to ten fold with water. The high concentration of sirolimus is necessary to maintain an effective and high local concentration of sirolimus after delivery to the site. The liquid formulations are flowable at room temperature and are compatible with a number of delivery devices. Specifically, each of these formulations were successfully injected through an infusion catheter designated by the brand name CRESCENDO™ from Cordis Corporation, Miami, Fla., as described in more detail subsequently, and the EndoBionics Micro Syringe™ Infusion Catheter available from EndoBionics, Inc., San Leandros, Calif., as described in more detail above, in porcine studies.

In another exemplary embodiment, the liquid formulation of sirolimus comprises water and ethanol as co-solvents and Vitamin E TPGS as the excipient. The liquid formulation was created utilizing the following process. Two hundred milligrams of sirolimus and two grams of ethanol were added to a pre-weighed twenty milliliter scintillation vial. The vial was vortexed and sonicated until the sirolimus was completely dissolved. Approximately six hundred milligrams of Vitamin E TPGS was then added to the solution of ethanol and sirolimus. The vial was vortexed again until a clear yellowish solution was obtained. Nitrogen gas was then used to reduce the amount of ethanol in the vial to approximately two hundred twenty-nine milligrams. In a separate vial, three hundred milligrams of Vitamin E TPGS was dissolved in eleven milliliters of purified water while undergoing vortexing. The Vitamin E TPGS and water solution was then added to the first vial containing the sirolimus, Vitamin E TPGS and ethanol. The first vial was then vortexed vigorously and continuously for three minutes. The resulting sirolimus solution was clear with a foam on top. The foam gradually disappeared after sitting at room temperature. An HPLC assay of sirolimus indicated that the sirolimus concentration in the final solution was 15 mg/ml. The final solution had an ethanol concentration of less than two percent, which as stated above is important so as to maintain ethanol as an inactive ingredient. Accordingly, utilizing Vitamin E TPGS as the excipient rather than PEG, resulted in a higher concentration of sirolimus in the final formulation.

Table 9, as shown below, summarizes the composition and visual observations for aqueous formulations of sirolimus utilizing ethanol, Vitamin E TPGS and water at different ratios. The solutions represented by the data contained in Table 9 were generated using essentially the same procedure as described above, except that the ratios between sirolimus and Vitamin E TPGS were varied.

TABLE 9

| Group # | Sirolimus mg | Vitamin E TPGS, mg | Ethanol mg | 13.3 ml water containing Vitamin E TPGS, mg | Observation of final solution |
|---|---|---|---|---|---|
| 1 | 202.7 | 642 | 230 | 320 | Clear |
| 2 | 205.2 | 631 | 260 | 330 | Clear |
| 3 | 201.1 | 618 | 260 | 600 | Clear |
| 4 | 204.1 | 625 | 260 | 590 | Clear |
| 5 | 203.3 | 618 | 250 | 1400 | Hazy to clear, Viscous |
| 6 | 204.5 | 630 | 250 | 1420 | Clear, viscous |

All of the above preparations except for number five remained as stable solutions at both room temperature and under refrigerated condition. The results in Table 9 indicate that, Vitamin E TPGS may be utilized over a wide range of concentrations to increase the solubility of sirolimus in an aqueous solution.

In another exemplary embodiment, a liquid formulation of CCI-779, a sirolimus analog, is prepared utilizing ethanol, Vitamin E TPGS and water. This liquid formulation was made under similar conditions as to that described above. Because of its better solubility in ethanol, only 0.8 grams of ethanol was used to dissolve two hundred milligrams of CCI-779 as opposed to the two grams of sirolimus. After the amount of ethanol was reduced to approximately two hundred thirty milligrams, eleven milliliters of purified water containing three hundred milligrams of Vitamin E TPGS was added to the vial of ethanol and CCI-779. The combined solution was vortexed for three minutes and resulted in a clear solution. An HPLC assay of CCI-779 indicated that the concentration of CCI-779 in the final solution was 15 mg/ml. The concentration of ethanol in the final solution was less than two percent. Accordingly, the results are substantially identical to that achieved for the sirolimus.

As stated above, a number of catheter-based delivery systems may be utilized to deliver the above-described liquid formulations. One such catheter-based system is the CRESCENDO™ infusion catheter. The CRESCENDO™ infusion catheter is indicated for the delivery of solutions, such as heparinized saline and thrombolytic agents selectively to the coronary vasculature. The infusion catheter may also be utilized for the delivery of the liquid formulations, including the liquid solution of sirolimus, described herein. The infusion region includes an area comprised of two inflatable balloons with multiple holes at the catheter's distal tip. The infusion region is continuous with a lumen that extends through the catheter and terminates at a Luer port in the proximal hub. Infusion of solutions is accomplished by hand injection through an infusion port. The catheter also comprises a guidewire lumen and a radiopaque marker band positioned at the center of the infusion region to mark its relative position under fluoroscopy.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An aqueous formulation of a therapeutic agent comprising:
   rapamycin in a pharmaceutically effective dosage;
   ethanol in a residual concentration of about 1.57 percent by weight;
   vitamin E TPGS in an amount of about 6.55 percent by weight; and
   water in an amount of about 90.51 percent by weight, the rapamycin, vitamin E TPGS and water forming a stable aqueous solution, thereby remaining a solution without precipitation, the stable aqueous formulation comprising a final solution of rapamycin in the range from about 4 mg/ml to about 15 mg/ml.

2. The aqueous formulation according to claim 1, wherein the rapamycin is sirolimus.

3. The aqueous formulation according to claim 1, wherein the rapamycin is CCI-779.

* * * * *